US008513398B2

(12) United States Patent
Chau et al.

(10) Patent No.: US 8,513,398 B2

(45) Date of Patent: Aug. 20, 2013

(54) HUMAN PAPILLOMA VIRUS PROBES FOR THE DIAGNOSIS OF CANCER

(75) Inventors: Miu Fun Chau, Santa Barbara, CA (US); Kirsten Bisgaard-Franzen, Birkerød (DK); Jone Lin, Goleta, CA (US); Ole Feldballe Rasmussen, Måløv (DK); Zunde Wang, Santa Barbara, CA (US); Jason Lusk, Carpinteria, CA (US); Martin Lindberg, Copenhagen V (DK); Sienna Yoast, Oak View, CA (US)

(73) Assignee: Dako Denmark A/S, Glostrup (DK)

( * ) Notice: Subject to any disclaimer, the term of this patent is extended or adjusted under 35 U.S.C. 154(b) by 0 days.

(21) Appl. No.: 13/527,489

(22) Filed: Jun. 19, 2012

(65) Prior Publication Data

US 2012/0259105 A1 Oct. 11, 2012

Related U.S. Application Data

(63) Continuation of application No. 10/959,175, filed on Oct. 7, 2004, now Pat. No. 8,221,970.

(60) Provisional application No. 60/543,925, filed on Feb. 13, 2004, provisional application No. 60/509,205, filed on Oct. 7, 2003.

(30) Foreign Application Priority Data

Oct. 7, 2003 (DK) ................................ 2003 01474

(51) Int. Cl.
*C07H 21/04* (2006.01)

(52) U.S. Cl.
USPC ...................................................... 536/24.32

(58) Field of Classification Search
USPC ...................................................... 536/24.32
See application file for complete search history.

(56) References Cited

U.S. PATENT DOCUMENTS

| | | | |
|---|---|---|---|
| 4,302,204 | A | 11/1981 | Wahl et al. |
| 4,886,741 | A | 12/1989 | Schwartz |
| 5,750,340 | A | 5/1998 | Kim et al. |
| 6,218,104 | B1 | 4/2001 | Morris et al. |
| 6,221,623 | B1 | 4/2001 | Smith-McCune et al. |
| 6,656,685 | B2 | 12/2003 | Utermohlen et al. |

FOREIGN PATENT DOCUMENTS

| | | | |
|---|---|---|---|
| EP | 0 524 807 | A1 | 1/1993 |
| EP | 1 201 771 | A2 | 5/2002 |
| EP | 1 302 550 | A1 | 4/2003 |
| WO | WO 89/02934 | A1 | 4/1989 |
| WO | WO 93/04197 | A1 | 3/1993 |
| WO | WO 00/24760 | A1 | 5/2000 |
| WO | WO 01/11361 | A2 | 2/2001 |
| WO | WO 01/37192 | A1 | 5/2001 |
| WO | WO 01/68915 | A1 | 9/2001 |
| WO | WO01/75174 | A2 | 10/2001 |
| WO | WO 02/061139 | A2 | 8/2002 |
| WO | WO 03/057914 | A2 | 7/2003 |
| WO | WO 03/062803 | A2 | 7/2003 |

OTHER PUBLICATIONS

ACS et al., Hypoxia-inducible erythropoietin signaling in squamous dysplasia and squamous cell carcinoma of the uterine cervix and its potential role in cervical carcinogenesis and tumor progression, *Am. J. of Pathology*, 2003, vol. 162(6), 1789-1806.

Altschul et al., Basic local alignment search tool, *J. Mol. Biol.*, 1990, vol. 215, 403-410.

Altschul et al., Gapped BLAST and PSI-BLAST: a new generation of protein database search programs, *Nucleic Acids Research*, 1997, vol. 25(17), 3389-3402.

Ausebel et al., *Current protocols in molecular biology*, John Wiley & Sons, Inc., 1995, vol. 3, Section 2, Section 4, Section 6, Unit 14.7.

Bachtiary et al., Overexpression of hypoxia-inducible factor 1α indicates diminished response to radiotherapy and unfavorable prognosis in patients receiving radical radiotherapy for cervical cancer, *Clin. Cancer Research*, 2003, vol. 9, 2234-2240.

Boehringer Mannheim, *Non-radioactive in situ hybridization application manual*, Germany, 1992, Chapter V.

Denko et al., Epigenetic regulation of gene expression in cervical cancer cells by the tumor microenvironment, *Clin. Cancer Research*, 2000, vol. 6, 480-487.

Ferber et al., Integrations of the hepatitis B virus (HBV) and human papillomavirus (HPV) into the human telomerase reverse transcriptase (hTERT) gene in liver and cervical cancers, *Oncogene*, 2003, vol. 22, 3813-3820.

Höckel et al., Association between tumor hypoxia and malignant progression in advanced cancer of the uterine cervix, *Cancer Research*, 1996, vol. 56(19), 4509-4515.

Kim et al., Expression of cyclooxygenase-1 and-2 associated with expression of VEGF in primary cervical cancer and at metastatic lymph nodes, *Gynecologic Oncology*, 2003, vol. 90, 83-90.

Kohlberger et al., Immunohistochemical expression of laminin-5 in cervical intraepithelial neoplasia, *Gynecologic Oncology*, 2003, vol. 89, 391-394.

Kruse et al., Evaluation of MIB-1-positive cell clusters as a diagnostic marker for cervical intraepithelial neoplasia, *Am. J. of Surgical Pathology*, 2002, vol. 26(11) , 1501-1507.

Myers et al., Optimal alignments in linear space, *Comput. Appl. Biosci.*, 1988, vol. 4(1), 11-17.

Needleman et al., A general method applicable to the search for similarities in the amino acid sequence of two proteins, *J. Mol. Biol.*, 1970, vol. 48, 444-453.

(Continued)

*Primary Examiner* — Kenneth Horlick

(74) *Attorney, Agent, or Firm* — Finnegan, Henderson, Farabow, Garrett & Dunner, L.L.P.

(57) ABSTRACT

In one embodiment, the invention relates to a method of detecting cervical cancer, and other types of cancer, using a combination of at least three genomic clones, or fragments thereof, of high risk Human Papilloma Virus. For example, the invention relates to a composition comprising at least three full length genomic clones, or fragments thereof, of high risk Human Papilloma Viruses.

20 Claims, 51 Drawing Sheets

(56) References Cited

OTHER PUBLICATIONS

Nielson, 2001, Peptide nucleic acid: a versatile tool in genetic diagnostics and molecular biology, *Current Opin. Biotechnol.* vol. 12, 16-20.
Parkin et al., Estimates of the worldwide incidence of 25 major cancers in 1990, *Int. J. Cancer*, 1999, vol. 80, 827-841.
Rakowicz-Szulczynska et al., Inhibition of cancer cell growth by internalized immuno-histone conjugates, *Cancer Biotherapy and Radiopharmaceuticals*, vol. 11(1), 1996, 77-86.
Sambrook et al., *Molecular Cloning: A laboratory manual*, 2nd ed., Cold spring Harbor press, 1989, Section 1.101-104, Chapter 7, Chapter 9, Section 10.6-12, Chapter 11.
Sano et al., Expression status of p16 protein is associated with human papillomavirus oncogenic potential in cervical and genital lesions, *Am J of Pathology*, 1998, vol. 153(6), 1741-1748.
Schulze, Biomedical image processing with morphology-based nonlinear filters, Ph.D dissertation, Univ. Of Texas at Austin, 1994.
Schulze et al., Noice reduction in synthetic aperture radar imagery using a morphology-based nonlinear filter, in *Proc. of DICTA95, Digital Image Computing: Techniques and Applications,* 1995, 661-666.
Sørensen et al., Functionalized LNA (locked nucleic acid): high-affinity hybridization of oligonucleotides containing N-acylated and N-alkylated 2'-amino-LNA monomers, *Chem. Commun*., 2003, vol. 7(17), 2130-2131.
Tatusova et al., BLAST 2 Sequences, a new tool for comparing protein and nucleotide sequences, *FEMS Microbiology Letters*, 1999, vol. 174, 247-250.
Yasmeen et al., E- and A-type cyclins as markers for cancer diagnosis and prognosis, *Expert Rev. Mol. Diagn*., 2003, vol. 3(5), 617-633.
E. Giarnieri et al., “Msh2, Mlh1, Fhit, p53, Bcl-2, and Bax Expression in Invasive and in Situ Squamous Cell Carcinoma of the Uterine Cervix[1]”, Clinical Cancer Research, vol. 6, p. 3600-3606, 2000.
L.G. Roberts, “Machine Perception of Three-Dimensional Solids”, in Optical and Electro-optical Information Processing, Tippet, J.T. (ed.), MIT Press, Cambridge, MA, p. 159-197,1965.
M. Sherman, “Baseline Cytology, Human Papillomavirus Testing, and Risk for Cervical Neoplasia: A 10-Year Cohort Analysis”, Journal of the National Cancer Institute, vol. 95, No. 1, p. 46-52, 2003.
Sobel I., “Neighborhood Coding of Binary Images for Fast Contour Following and General Binary Array Processing,” *Computer Graphics and Image Processing*, 7:127-138 (1987).
Prewitt J.M.S., “Object Enhancement and Extraction,” *Picture Processing and Psychopictorics*, 75-149 (Lipkin B.S. et al. ed., 1970).
Schwarzbacher A.Th. et al., “A Low-Power CMOS Design for RBG to HSI Conversion,” *Irish Machine Vision and Image Processing Conference*, 257, 2001.
M.J. Sworn et al., “Squamous intraepithelial neoplasia in an ovarian cyst, cervical intraepithelial neoplasia, and human papillomavirus,” Human Pathology, 26: 344-347 (1995).
D.C. Swan et al., “A sensitive, type-specific, fluorogenic probe assay for detection of human papillomavirus DNA,” *J. Clin. Microbiol*., 35(4): 886-891 (1997).
Restriction Requirement, mailed Apr. 10, 2007, for U.S. Appl. No. 10/959,175 (15 pages).
Response to Restriction Requirement, filed May 24, 2007, for U.S. Appl. No. 10/959,175 (6 pages).
Restriction Requirement, mailed Aug. 6, 2007, for U.S. Appl. No. 10/959,175 (16 pages).
Response to Second Restriction Requirement, filed Sep. 4, 2007, for U.S. Appl. No. 10/959,175 (6 pages).
Office Communication, mailed Oct. 30, 2007, for U.S. Appl. No. 10/959,175 (2 pages).
Amendment and Response to Restriction Requirement, filed Nov. 29, 2007, for U.S. Appl. No. 10/959,175 (24 pages).
Interview Summary, mailed Dec. 11, 2007, for U.S. Appl. No. 10/959,175 (3 pages).
Non-final Office Action, mailed Feb. 21, 2008, for U.S. Appl. No. 10/959,175 (16 pages).
Amendment and Response under 37 C.F.R. §1.111, filed Jul. 7, 2008, for U.S. Appl. No. 10/959,175 (31 pages).
Final Office Action, mailed Oct. 8, 2008, for U.S. Appl. No. 10/959,175 (10 pages).
Amendment After Final under 37 C.F.R. §1.116, filed Jan. 5, 2009, for U.S. Appl. No. 10/959,175 (31 pages).
Advisory Action, mailed Jan. 23, 2009, for U.S. Appl. No. 10/959,175 (3 pages).
Request for Continued Examination, filed Feb. 10, 2009, for U.S. Appl. No. 10/959,175 (1 page).
Non-final Office Action, mailed Apr. 14, 2009, for U.S. Appl. No. 10/959,175 (9 pages).
Response and Request for Reconsideration under 37 C.F.R. §1.111, filed Jul. 13, 2009, for U.S. Appl. No. 10/959,175 (9 pages).
Non-final Office Action, mailed Sep. 29, 2009, for U.S. Appl. No. 10/959,175 (9 pages).
Amendment and Response to Office Action under 37 C.F.R. §1.111, filed Dec. 1, 2009, for U.S. Appl. No. 10/959,175 (27 pages).
Final Office Action and Interview Summary, mailed Mar. 3, 2010, for U.S. Appl. No. 10/959,175 (12 pages).
Amendment After Final Office Action under 37 C.F.R. §1.116, filed Jun. 2, 2010, for U.S. Appl. No. 10/959,175 (27 pages).
Advisory Action, mailed Jun. 11, 2010, for U.S. Appl. No. 10/959,175 (3 pages).
Request for Continued Examination, filed Jul. 2, 2010, for U.S. Appl. No. 10/959,175 (1 page).
Non-final Office Action, mailed Aug. 12, 2011, for U.S. Appl. No. 10/959,175 (10 pages).
Reply to Office Action, filed Jan. 12, 2012, for U.S. Appl. No. 10/959,175 (29 pages).
Notice of Allowance and Fee(s) Due, mailed Mar. 20, 2012, for U.S. Appl. No. 10/959,175 (9 pages).

HPV 16 ATCC # K02718

```
1 actacaataa ttcatgtata aaactaaggg cgtaaccgaa atcggttgaa ccgaaaccgg
61 ttagtataaa agcagacatt ttatgcacca aaagagaact gcaatgtttc aggacccaca
121 ggagcgaccc agaaagttac cacagttatg cacagagctg caaacaacta tacatgatat
181 aatattagaa tgtgtgtact gcaagcaaca gttactgcga cgtgaggtat atgactttgc
241 ttttcgggat ttatgcatag tatatagaga tgggaatcca tatgctgtat gtgataaatg
301 tttaaagttt tattctaaaa ttagtgagta tagacattat tgttatagtt tgtatggaac
361 aacattagaa cagcaataca acaaaccgtt gtgtgatttg ttaattaggt gtattaactg
421 tcaaaagcca ctgtgtcctg aagaaaagca aagacatctg gacaaaaagc aaagattcca
481 taatataagg ggtcggtgga ccggtcgatg tatgtcttgt tgcagatcat caagaacacg
541 tagagaaacc cagctgtaat catgcatgga gatacaccta cattgcatga atatatgtta
601 gatttgcaac cagagacaac tgatctctac tgttatgagc aattaaatga cagctcagag
661 gaggaggatg aaatagatgg tccagctgga caagcagaac cggacagagc ccattacaat
721 attgtaacct tttgttgcaa gtgtgactct acgcttcggt tgtgcgtaca aagcacacac
781 gtagacattc gtactttgga agacctgtta atgggcacac taggaattgt gtgccccatc
841 tgttctcaga aaccataatc taccatggct gatcctgcag gtaccaatgg ggaagagggt
901 acgggatgta atggatggtt ttatgtagag gctgtagtgg aaaaaaaaac aggggatgct
961 atatcagatg acgagaacga aaatgacagt gatacaggtg aagatttggt agattttata
1021 gtaaatgata atgattattt aacacaggca gaaacagaga cagcacatgc gttgtttact
1081 gcacaggaag caaaacaaca tagagatgca gtacaggttc taaaacgaaa gtatttggta
1141 gtccacttag tgatattagt ggatgtgtag acaataatat tagtcctaga ttaaaagcta
1201 tatgtataga aaaacaaagt agagctgcaa aaaggagatt atttgaaagc gaagacagcg
1261 ggtatggcaa tactgaagtg gaaactcagc agatgttaca ggtagaaggg cgccatgaga
1321 ctgaaacacc atgtagtcag tatagtggtg gaagtggggg tggttgcagt cagtacagta
1381 gtggaagtgg gggagagggt gttagtgaaa gacacactat atgccaaaca ccacttacaa
1441 atattttaaa tgtactaaaa actagtaatg caaaggcagc aatgttagca aaatttaaag
1501 agttatacgg ggtgagtttt tcagaattag taagaccatt taaaagtaat aaatcaacgt
1561 gttgcgattg gtgtattgct gcatttggac ttacacccag tatagctgac agtataaaaa
1621 cactattaca acaatattgt ttatatttac acattcaaag tttagcatgt tcatggggaa
1681 tggttgtgtt actattagta agatataaat gtggaaaaaa tagagaaaca attgaaaaat
1741 tgctgtctaa actattatgt gtgtctccaa tgtgtatgat gatagagcct ccaaaattgc
1801 gtagtacagc agcagcatta tattggtata aaacaggtat atcaaatatt agtgaagtgt
1861 atggagacac gccagaatgg atacaaagac aaacagtatt acaacatagt tttaatgatt
1921 gtacatttga attatcacag atggtacaat gggcctacga taatgacata gtagacgata
1981 gtgaaattgc atataaatat gcacaattgg cagacactaa tagtaatgca agtgcctttc
2041 taaaaagtaa ttcacaggca aaaattgtaa aggattgtgc aacaatgtgt agacattata
2101 aacgagcaga aaaaaaacaa atgagtatga gtcaatggat aaaatataga tgtgataggg
2161 tagatgatgg aggtgattgg aagcaaattg ttatgttttt aaggtatcaa ggtgtagagt
2221 ttatgtcatt tttaactgca ttaaaaagat tttgcaagg catacctaaa aaaaattgca
2281 tattactata tggtgcagct aacacaggta aatcattatt tggtatgagt ttaatgaaat
2341 ttctgcaagg gtctgtaata tgttttgtaa attctaaaag ccatttttgg ttacaaccat
2401 tagcagatgc caaaataggt atgttagatg atgctacagt gccctgttgg aactacatag
2461 atgacaattt aagaaatgca ttggatggaa atttagtttc tatggatgta aagcatagac
2521 cattggtaca actaaaatgc cctccattat taattacatc taacattaat gctggtacag
2581 attctaggtg gccttattta cataatagat tggtggtgtt tacatttcct aatgagtttc
2641 catttgacga aaacggaaat ccagtgtatg agcttaatga taagaactgg aaatcctttt
2701 tctcaaggac gtggtccaga ttaagtttgc acgaggacga ggacaaggaa aacgatggag
2761 actctttgcc aacgtttaaa tgtgtgtcag gacaaaatac taacacatta tgaaaatgat
2821 agtacagacc tacgtgacca tatagactat tggaaacaca tgcgcctaga atgtgctatt
2881 tattacaagg ccagagaaat gggatttaaa catattaacc accaagtggt gccaacactg
2941 gctgtatcaa agaataaagc attacaagca attgaactgc aactaacgtt agaaacaata
3001 tataactcac aatatagtaa tgaaaagtgg acattacaag acgttagcct tgaagtgtat
3061 ttaactgcac caacaggatg tataaaaaaa catggatata cagtggaagt gcagtttgat
3121 ggagacatat gcaatacaat gcattataca aactggacac atatatatat ttgtgaagaa
```

Fig. 1

```
3181 gcatcagtaa ctgtggtaga gggtcaagtt gactattatg gtttatatta tgttcatgaa
3241 ggaatacgaa catattttgt gcagtttaaa gatgatgcag aaaaatatag taaaaataaa
3301 gtatgggaag ttcatgcggg tggtcaggta atattatgtc ctacatctgt gtttagcagc
3361 aacgaagtat cctctcctga aattattagg cagcacttgg ccaaccaccc cgccgcgacc
3421 cataccaaag ccgtcgcctt gggcaccgaa gaaacacaga cgactatcca gcgaccaaga
3481 tcagagccag acaccggaaa cccctgccac accactaagt tgttgcacag agactcagtg
3541 gacagtgctc caatcctcac tgcatttaac agctcacaca aaggacggat taactgtaat
3601 agtaacacta caccccatagt acatttaaaa ggtgatgcta atactttaaa atgtttaaga
3661 tatagattta aaaagcattg tacattgtat actgcagtgt cgtctacatg gcattggaca
3721 ggacataatg taaaacataa aagtgcaatt gttacactta catatgatag tgaatggcaa
3781 cgtgaccaat tttgtctca agttaaaata ccaaaaacta ttacagtgtc tactggattt
3841 atgtctatat gacaaatctt gatactgcat ccacaacatt actggcgtgc tttttgcttt
3901 gctttgtgtg cttttgtgtg tctgcctatt aatacgtccg ctgcttttgt ctgtgtctac
3961 atacacatca ttaataatat tggtattact attgtggata acagcagcct ctgcgtttag
4021 gtgttttatt gtatatatta tatttgttta tataccatta tttttaatac atacacatgc
4081 acgcttttta attacataat gtatatgtac ataatgtaat tgttacatat aattgttgta
4141 taccataact tactattttt tcttttttat tttcatatat aatttttttt tttgtttgtt
4201 tgtttgtttt ttaataaact gttattactt aacaatgcga cacaaacgtt ctgcaaaacg
4261 cacaaaacgt gcatcggcta cccaacttta taaaacatgc aaacaggcag gtacatgtcc
4321 acctgacatt atacctaagg ttgaaggcaa aactattgct gaacaaatat tacaatatgg
4381 aagtatgggt gtattttttg gtgggttagg aattggaaca gggtcgggta caggcggacg
4441 cactgggtat attccattgg gaacaaggcc tcccacagct acagatacac ttgctcctgt
4501 aagacccccct ttaacagtag atcctgtggg cccttctgat ccttctatag tttctttagt
4561 ggaagaaact agttttattg atgctggtgc accaacatct gtaccttcca ttcccccaga
4621 tgtatcagga tttagtatta ctacttcaac tgataccaca cctgctatat tagatattaa
4681 taatactgtt actactgtta ctacacataa taatcccact ttcactgacc catctgtatt
4741 gcagcctcca acacctgcag aaactggagg gcattttaca ctttcatcat ccactattag
4801 tacacataat tatgaagaaa ttcctatgga tacatttatt gttagcacaa accctaacac
4861 agtaactagt agcacaccca taccagggtc tcgcccagtg gcacgcctag gattatatag
4921 tcgcacaaca caacaggtta aagttgtaga ccctgctttt gtaaccactc ccactaaact
4981 tattacatat gataatcctg catatgaagg tatagatgtg gataatacat tatatttttc
5041 tagtaatgat aatagtatta atatagctcc agatcctgac tttttggata tagttgcttt
5101 acataggcca gcattaacct ctaggcgtac tggcattagg tacagtagaa ttggtaataa
5161 acaaacacta cgtactcgta gtggaaaatc tataggtgct aaggtacatt attattatga
5221 tttaagtact attgatcctg cagaagaaat agaattacaa actataacac cttctacata
5281 tactaccact tcacatgcag cctcacctac ttctattaat aatggattat atgatattta
5341 tgcagatgac tttattacag atacttctac aaccccggta ccatctgtac cctctacatc
5401 tttatcaggt tatattcctg caaatacaac aattcctttt ggtggtgcat acaatattcc
5461 tttagtatca ggtcctgata tacccattaa tataactgac caagctcctt cattaattcc
5521 tatagttcca gggtctccac aatatacaat tattgctgat gcaggtgact tttatttaca
5581 tcctagttat tacatgttac gaaaacgacg taaacgttta ccatattttt tttcagatgt
5641 ctctttggct gcctagtgag gccactgtct acttgcctcc tgtcccagta tctaaggttg
5701 taagcacgga tgaatatgtt gcacgcacaa acatatatta tcatgcagga acatccagac
5761 tacttgcagt tggacatccc tatttttccta ttaaaaaacc taacaataac aaaatattag
5821 ttcctaaagt atcaggatta caatacaggg tatttagaat acatttacct gaccccaata
5881 agtttggttt tcctgacacc tcattttata atccagatac acagcggctg gtttgggcct
5941 gtgtaggtgt tgaggtaggt cgtggtcagc cattaggtgt gggcattagt ggccatcctt
6001 tattaaataa attggatgac acagaaaatg ctagtgctta tgcagcaaat gcaggtgtgg
6061 ataatagaga atgtatatct atggattaca aacaaacaca attgtgttta attggttgca
6121 aaccacctat aggggaacac tggggcaaag gatccccatg taccaatgtt gcagtaaatc
6181 caggtgattg tccaccatta gagttaataa acacagttat tcaggatggt gatatggttc
6241 atactggctt tggtgctatg gactttacta cattacaggc taacaaaagt gaagttccac
6301 tggatatttg tacatctatt tgcaaatatc cagattatat taaaatggtg tcagaaccat
6361 atggcgacag cttatttttt tatttacgaa gggaacaaat gtttgttaga catttattta
6421 atagggctgg tactgttggt gaaaatgtac cagacgattt atacattaaa ggctctgggt
```

Fig. 1, cont.

```
6481 ctactgcaaa tttagccagt tcaaattatt ttcctacacc tagtggttct atggttacct
6541 ctgatgccca aatattcaat aaaccttatt ggttacaacg agcacagggc cacaataatg
6601 gcatttgttg ggggtaaccaa ctatttgtta ctgttgttga tactacacgc agtacaaata
6661 tgtcattatg tgctgccata tctacttcag aaactacata taaaaatact aactttaagg
6721 agtacctacg acatggggag gaatatgatt tacagtttat ttttcaactg tgcaaaataa
6781 ccttaactgc agacgttatg acatacatac attctatgaa ttccactatt ttggaggact
6841 ggaattttgg tctacaacct cccccaggag gcacactaga agatacttat aggtttgtaa
6901 cccaggcaat tgcttgtcaa aaacatacac ctccagcacc taaagaagat gatcccctta
6961 aaaaatacac tttttgggaa gtaaatttaa aggaaaagtt ttctgcagac ctagatcagt
7021 ttcctttagg acgcaaattt ttactacaag caggattgaa ggccaaacca aaatttacat
7081 taggaaaacg aaaagctaca cccaccacct catctacctc tacaactgct aaacgcaaaa
7141 aacgtaagct gtaagtattg tatgtatgtt gaattagtgt tgtttgttgt gtatatgttt
7201 gtatgtgctt gtatgtgctt gtaaatatta agttgtatgt gtgtttgtat gtatggtata
7261 ataaacacgt gtgtatgtgt ttttaaatgc ttgtgtaact attgtgtcat gcaacataaa
7321 taaacttatt gtttcaacac ctactaattg tgttgtggtt attcattgta tataaactat
7381 atttgctaca tcctgttttt gttttatata tactatattt tgtagcgcca ggcccatttt
7441 gtagcttcaa ccgaattcgg ttgcatgctt tttggcacaa aatgtgtttt tttaaatagt
7501 tctatgtcag caactatggt ttaaacttgt acgtttcctg cttgccatgc gtgccaaatc
7561 cctgttttcc tgacctgcac tgcttgccaa ccattccatt gtttttttaca ctgcactatg
7621 tgcaactact gaatcactat gtacattgtg tcatataaaa taaatcacta tgcgccaacg
7681 ccttacatac cgctgttagg cacatatttt tggcttgttt taactaacct aattgcatat
7741 ttggcataag gtttaaactt ctaaggccaa ctaaatgtca ccctagttca tacatgaact
7801 gtgtaaaggt tagtcataca ttgttcattt gtaaaactgc acatgggtgt gtgcaaaccg
7861 attttgggtt acacatttac aagcaactta tataataata ctaa
```

Fig. 1, cont.

HPV 18 ATCC # X05015

1 attaatactt ttaacaattg tagtatataa aaaagggagt aaccgaaaac ggtcgggacc
61 gaaaacggtg tatataaaag atgtgagaaa cacaccacaa tactatggcg cgctttgagg
121 atccaacacg gcgaccctac aagctacctg atctgtgcac ggaactgaac acttcactgc
181 aagacataga aataacctgt gtatattgca agacagtatt ggaacttaca gaggtatttg
241 aatttgcatt taaagattta tttgtggtgt atagagacag tataccccat gctgcatgcc
301 ataaatgtat agatttttat tctagaatta gagaattaag acattattca gactctgtgt
361 atggagacac attggaaaaa ctaactaaca ctgggttata caatttatta ataaggtgcc
421 tgcggtgcca gaaaccgttg aatccagcag aaaaacttag acaccttaat gaaaaacgac
481 gatttcacaa catagctggg cactatagag gccagtgcca ttcgtgctgc aaccgagcac
541 gacaggaacg actccaacga cgcagagaaa cacaagtata atattaagta tgcatggacc
601 taaggcaaca ttgcaagaca ttgtattgca tttagagccc caaaatgaaa ttccggttga
661 ccttctatgt cacgagcaat taagcgactc agaggaagaa aacgatgaaa tagatggagt
721 taatcatcaa catttaccag cccgacgagc cgaaccacaa cgtcacacaa tgttgtgtat
781 gtgttgtaag tgtgaagcca gaattgagct agtagtagaa agctcagcag acgaccttcg
841 agcattccag cagctgtttc tgaacaccct gtcctttgtg tgtccgtggt gtgcatccca
901 gcagtaagca acaatggctg atccagaagg tacagacggg gagggcacgg gttgtaacgg
961 ctggttttat gtacaagcta ttgtagacaa aaaaacagga gatgtaatat cagatgacga
1021 ggacgaaaat gcaacagaca cagggtcgga tatggtagat tttattgata cacaaggaac
1081 attttgtgaa caggcagagc tagagacagc acaggcattg ttccatgcgc aggaggtcca
1141 caatgatgca caagtgttgc atgttttaaa acgaaagttt gcaggaggca gcacagaaaa
1201 cagtccatta ggggagcggc tggaggtgga tacagagtta agtccacggt tacaagaaat
1261 atctttaaat agtgggcaga aaaaggcaaa aaggcggctg tttacaatat cagatagtgg
1321 ctatggctgt tctgaagtgg aagcaacaca gattcaggta actacaaatg gcgaacatgg
1381 cggcaatgta tgtagtggcg gcagtacgga ggctatagac aacgggggca cagagggcaa
1441 caacagcagt gtagacggta caagtgacaa tagcaatata gaaaatgtaa atccacaatg
1501 taccatagca caattaaaag acttgttaaa agtaaacaat aaacaaggag ctatgttagc
1561 agtatttaaa gacacatatg ggctatcatt tacagattta gttagaaatt ttaaaagtga
1621 taaaaccacg tgtacagatt gggttacagc tatatttgga gtaaacccaa caatagcaga
1681 aggatttaaa acactaatac agccatttat attatatgcc catattcaat gtctagactg
1741 taaatgggga gtattaatat tagccctgtt gcgttacaaa tgtggtaaga gtagactaac
1801 agttgctaaa ggtttaagta cgttgttaca cgtacctgaa acttgtatgt taattcaacc
1861 accaaaattg cgaagtagtg ttgcagcact atattggtat agaacaggaa tatcaaatat
1921 tagtgaagta atgggagaca cacctgagtg gatacaaaga cttactatta tacaacatgg
1981 aatagatgat agcaattttg atttgtcaga aatggtacaa tgggcatttg ataatgagct
2041 gacagatgaa agcgatatgg catttgaata tgccttatta gcagacagca acagcaatgc
2101 agctgccttt ttaaaaagca attgccaagc taaatattta aaagattgtg ccacaatgtg
2161 caaacattat aggcgagccc aaaaacgaca aatgaatatg tcacagtgga tacgatttag
2221 atgttcaaaa atagatgaag gggagattgg gagaccaata gtgcaattcc tgcgatacca
2281 acaaatagag tttataacat ttttaggagc cttaaaatca tttttaaaag gaacccccaa
2341 aaaaaattgt ttagtatttt gtggaccagc aaatacagga aaatcatatt ttggaatgag
2401 ttttatacac tttatacaag gagcagtaat atcatttgtg aattccacta gtcatttttg
2461 gttggaaccg ttaacagata ctaaggtggc catgttagat gatgcaacga ccacgtgttg
2521 gacatacttt gatacctata tgagaaatgc gttagatggc aatccaataa gtattgatag
2581 aaagcacaaa ccattaatac aactaaaatg tcctccaata ctactaacca caaatataca
2641 tccagcaaag gataatagat ggccatattt agaaagtaga ataacagtat ttgaatttcc
2701 aaatgcattt ccatttgata aaaatggcaa tccagtatat gaaataaatg acaaaaattg
2761 gaaatgtttt tttgaaagga catggtccag attagatttg cacgaggaag aggaagatgc
2821 agacaccgaa ggaaaccctt tcggaacgtt taagttgcgt gcaggacaaa atcatagacc
2881 actatgaaaa tgacagtaaa gacatagaca gccaaataca gtattggcaa ctaatacgtt
2941 gggaaaatgc aatattcttt gcagcaaggg aacatggcat acagacatta aaccaccagg
3001 tggtgccagc ctataacatt tcaaaaagta aagcacataa agctattgaa ctgcaaatgg
3061 ccctacaagg ccttgcacaa agtcgataca aaaccgagga ttggacactg caagacacat
3121 gcgaggaact atggaataca gaacctactc actgctttaa aaaaggtggc caaacagtac
3181 aagtatattt tgatggcaac aaagacaatt gtatgaccta tgtagcatgg gacagtgtgt

Fig. 2

3241 attatatgac tgatgcagga acatgggaca aaaccgctac ctgtgtaagt cacaggggat
3301 tgtattatgt aaaggaaggg tacaacacgt tttatataga atttaaaagt gaatgtgaaa
3361 aatatgggaa cacaggtacg tgggaagtac attttgggaa taatgtaatt gattgtaatg
3421 actctatgtg cagtaccagt gacgacacgg tatccgctac tcagcttgtt aaacagctac
3481 agcacacccc ctcaccgtat tccagcaccg tgtccgtggg caccgcaaag acctacggcc
3541 agacgtcggc tgctacacga cctggacact gtggactcgc ggagaagcag cattgtggac
3601 ctgtcaaccc acttctcggt gcagctacac ctacaggcaa caacaaaaga cggaaactct
3661 gtagtggtaa cactacgcct ataatacatt taaaaggtga cagaaacagt ttaaaatgtt
3721 tacggtacag attgcgaaaa catagcgacc actatagaga tatatcatcc acctggcatt
3781 ggacaggtgc aggcaatgaa aaaacaggaa tactgactgt aacataccat agtgaaacac
3841 aaagaacaaa atttttaaat actgttgcaa ttccagatag tgtacaaata ttggtgggat
3901 acatgacaat gtaatacata tgctgtagta ccaatatgtt atcacttatt tttttatttt
3961 gcttttgtgt atgcatgtat gtgtgctgcc atgtcccgct tttgccatct gtctgtatgt
4021 gtgcgtatgc atgggtattg gtatttgtgt atattgtggt aataacgtcc cctgccacag
4081 cattcacagt atatgtattt tgttttttat tgcccatgtt actattgcat atacatgcta
4141 tattgtcttt acagtaattg tataggttgt tttatacagt gtattgtaca ttgtatattt
4201 tgttttatac cttttatgct ttttgtattt ttgtaataaa agtatggtat cccaccgtgc
4261 cgcacgacgc aaacgggctt cggtaactga cttatataaa acatgtaaac aatctggtac
4321 atgtccacct gatgttgttc ctaaggtgga gggcaccacg ttagcagata aaatattgca
4381 atggtcaagc cttggtatat ttttgggtgg acttggcata ggtactggca gtggtacagg
4441 gggtcgtaca gggtacattc cattgggtgg gcgttccaat acagtggtgg atgttggtcc
4501 tacacgtccc ccagtggtta ttgaacctgt gggccccaca gacccatcta ttgttacatt
4561 aatagaggac tccagtgtgg ttacatcagg tgcacctagg cctacgttta ctggcacgtc
4621 tgggtttgat ataacatctg cgggtacaac tacacctgcg gttttggata tcacaccttc
4681 gtctacctct gtgtctattt ccacaaccaa ttttaccaat cctgcatttt ctgatccgtc
4741 cattattgaa gttccacaaa ctggggaggt ggcaggtaat gtatttgttg gtacccctac
4801 atctggaaca catgggtatg aggaaatacc tttacaaaca tttgcttctt ctggtacggg
4861 ggaggaaccc attagtagta ccccattgcc tactgtgcgg cgtgtagcag gtccccgcct
4921 ttacagtagg gcctaccaac aagtgtcagt ggctaaccct gagtttctta cacgtccatc
4981 ctctttaatt acatatgaca acccggcctt tgagcctgtg gacactacat taacatttga
5041 tcctcgtagt gatgttcctg attcagattt tatggatatt atccgtctac ataggcctgc
5101 tttaacatcc aggcgtggga ctgttcgctt tagtagatta ggtcaacggg caactatgtt
5161 tacccgcagc ggtacacaaa taggtgctag ggttcacttt tatcatgata taagtcctat
5221 tgcaccttcc ccagaatata ttgaactgca gcctttagta tctgccacgg aggacaatga
5281 cttgtttgat atatatgcag atgacatgga ccctgcagtg cctgtaccat cgcgttctac
5341 tacctccttt gcattttta aatattcgcc cactatatct tctgcctctt cctatagtaa
5401 tgtaacggtc cctttaacct cctcttggga tgtgcctgta tacacgggtc ctgatattac
5461 attaccatct actacctctg tatggcccat tgtatcaccc acggcccctg cctctacaca
5521 gtatattggt atacatggta cacattatta tttgtggcca ttatattatt ttattcctaa
5581 gaaacgtaaa cgtgttccct atttttttgc agatggcttt gtggcggcct agtgacaata
5641 ccgtatatct tccacctcct tctgtggcaa gagttgtaaa taccgatgat tatgtgactc
5701 ccacaagcat attttatcat gctggcagct ctagattatt aactgttggt aatccatatt
5761 ttagggttcc tgcaggtggt ggcaataagc aggatattcc taaggtttct gcataccaat
5821 atagagtatt tagggtgcag ttacctgacc caaataaatt tggtttacct gatactagta
5881 tttataatcc tgaaacacaa cgtttagtgt gggcctgtgc tggagtggaa attggccgtg
5941 gtcagccttt aggtgttggc cttagtgggc atccatttta taataaatta gatgacactg
6001 aaagttccca tgccgccacg tctaatgttt ctgaggacgt tagggacaat gtgtctgtag
6061 attataagca gacacagtta tgtattttgg gctgtgcccc tgctattggg gaacactggg
6121 ctaaaggcac tgcttgtaaa tcgcgtcctt tatcacaggg cgattgcccc cctttagaac
6181 ttaaaaacac agttttggaa gatggtgata tggtagatac tggatatggt gccatggact
6241 ttagtacatt gcaagatact aaatgtgagg taccattgga tatttgtcag tctatttgta
6301 aatatcctga ttatttacaa atgtctgcag atccttatgg ggattccatg tttttttgct
6361 tacggcgtga gcagcttttt gctaggcatt tttggaatag agcaggtact atgggtgaca
6421 ctgtgcctca atccttatat attaaaggca caggtatgcc tgcttcacct ggcagctgtg
6481 tgtattctcc ctctccaagt ggctctattg ttacctctga ctcccagttg tttaataaac
6541 catattggtt acataaggca cagggtcata acaatggtgt ttgctggcat aatcaattat

Fig. 2, cont.

```
6601 ttgttactgt ggtagatacc actcccagta ccaatttaac aatatgtgct tctacacagt
6661 ctcctgtacc tgggcaatat gatgctacca aatttaagca gtatagcaga catgttgagg
6721 aatatgattt gcagtttatt tttcagttgt gtactattac tttaactgca gatgttatgt
6781 cctatattca tagtatgaat agcagtattt tagaggattg gaactttggt gttccccccc
6841 ccccaactac tagtttggtg gatacatatc gttttgtaca atctgttgct attacctgtc
6901 aaaaggatgc tgcaccggct gaaaataagg atccctatga taagttaaag ttttggaatg
6961 tggatttaaa ggaaaagttt tctttagact tagatcaata tccccttgga cgtaaatttt
7021 tggttcaggc tggattgcgt cgcaagccca ccataggccc tcgcaaacgt tctgctccat
7081 ctgccactac gtcttctaaa cctgccaagc gtgtgcgtgt acgtgccagg aagtaatatg
7141 tgtgtgtgta tatatatata catctattgt tgtgtttgta tgtcctgtgt ttgtgtttgt
7201 tgtatgattg cattgtatgg tatgtatggt tgttgttgta tgttgtatgt tactatattt
7261 gttggtatgt ggcattaaat aaaatatgtt ttgtggttct gtgtgttatg tggttgcgcc
7321 ctagtgagta acaactgtat ttgtgtttgt ggtatgggtg ttgcttgttg ggctatatat
7381 tgtcctgtat ttcaagttat aaaactgcac accttacagc atccatttta tcctacaatc
7441 ctccattttg ctgtgcaacc gatttcggtt gcctttggct tatgtctgtg gttttctgca
7501 caatacagta cgctggcact attgcaaact ttaatctttt gggcactgct cctacatatt
7561 ttgaacaatt ggcgcgcctc tttggcgcat ataaggcgca cctggtatta gtcattttcc
7621 tgtccaggtg cgctacaaca attgcttgca taactatatc cactccctaa gtaataaaac
7681 tgcttttagg cacatatttt agtttgtttt tacttaagct aattgcatac ttggcttgta
7741 caactacttt catgtccaac attctgtcta cccttaacat gaactataat atgactaagc
7801 tgtgcataca tagtttatgc aaccgaaata ggttgggcag cacatactat acttttc
```

Fig. 2, cont.

HPV 11 ATCC # M14119

1 cttaataaca atcttagttt aaaaaagagg agggaccgaa aacggttcaa ccgaaaacgg
61 ttatatataa accagcccaa aaaattagca gacgaggcat tatggaaagt aaagatgcct
121 ccacgtctgc aacatctata gaccagttgt gcaagacgtt taatctttct ttgcacactc
181 tgcaaattca gtgcgtgttt tgcaggaatg cactgaccac cgcagagata tatgcatatg
241 cctataagaa cctaaaggtt gtgtggcgag acaactttcc ctttgcagcg tgtgcctgtt
301 gcttagaact gcaagggaaa attaaccaat atagacactt taattatgct gcatatgcac
361 ctacagtaga agaagaaacc aatgaagata ttttaaaagt gttaattcgt tgttacctgt
421 gtcacaagcc gttgtgtgaa atagaaaaac taaagcacat attgggaaag gcacgcttca
481 taaaactaaa taaccagtgg aagggtcgtt gcttacactg ctggacaaca tgcatggaag
541 acttgttacc ctaaaggata tagtactaga cctgcagcct cctgaccctg tagggttaca
601 ttgctatgag caattagaag acagctcaga agatgaggtg gacaaggtgg acaaacaaga
661 cgcacaacct ttaacacaac attaccaaat actgacctgt tgctgtggat gtgacagcaa
721 cgtccgactg gttgtggagt gcacagacgg agacatcaga caactacaag acctttttgct
781 gggcacacta aatattgtgt gtcccatctg cgcaccaaaa ccataacaag gatggcggac
841 gattcaggta cagaaaatga ggggtcgggg tgtacaggat ggtttatggt agaagccata
901 gtagagcaca ctacaggtac acaaatatca gaagatgagg aagaggaggt ggaggacagt
961 gggtatgaca tggtggactt tattgatgac aggcatatta cacaaaattc tgtggaagca
1021 caggcattgt ttaataggca ggaggcggat gctcattatg cgactgtgca ggacctaaaa
1081 cgaaagtatt taggcagtcc atatgtaagt cctataagca atgtagctaa tgcagtagaa
1141 agtgagataa gtccacggtt agacgccatt aaacttacaa cacagccaaa aaaggtaaag
1201 cgacggctgt ttgaaacacg ggaattaacg gacagtggat atggctattc tgaagtggaa
1261 gctgcaacgc aggtagagaa acatggcgac ccggaaaatg gggagatgg tcaggaaagg
1321 gacacaggga gggacataga gggtgagggg gtggaacata gagaggcgga agcagtagac
1381 gacagcaccc gagagcatgc agacacatca ggaatattag aattactaaa atgtaaggat
1441 atacgatcta cattacatgg taagtttaaa gactgctttg ggctgtcatt tgttgattta
1501 attaggccat ttaaaagtga tagaaccaca tgtgccgatt gggtggttgc aggatttggt
1561 atacatcata gcatagcaga tgcatttcaa aagttaattg agccattaag tttatatgca
1621 catatacaat ggcttacaaa tgcatgggga atggtactat tagtattaat aaggtttaaa
1681 gtaaataaga gcagatgtac cgtggcacgt acattaggta cgttattaaa tatacctgaa
1741 aatcacatgt taattgagcc tcctaaaata caaagtggcg tacgagccct gtattggttt
1801 aggacaggca tttcaaatgc aagtacagtt ataggggagg cgccggaatg gataacgcgc
1861 cagaccgtta ttgaacatag tttggctgac agtcaattta aattaactga aatggtgcag
1921 tgggcatatg ataatgatat ttgtgaagaa agtgagatag catttgaata tgcacagcgt
1981 ggagactttg actccaatgc aagggccttt ttaaatagta atatgcaggc taaatatgta
2041 aaagattgtg caattatgtg cagacattat aaacatgcag aaatgaaaaa gatgtctatt
2101 aaacaatgga ttaagtatag ggtactaaa gttgacagtg taggtaactg gaagccaatt
2161 gtgcagtttc taagacatca aaacatagaa tttattccat ttttaagcaa actaaaatta
2221 tggctgcacg gaacgcccaa aaaaaattgt atagccattg tagggccacc tgacactggg
2281 aagtcgtgct tttgcatgag tttaattaag tttttggggg gaacagttat tagttatgtt
2341 aattcctgca gccatttctg gctacagcca ctaacggatg caaaagtggc attattggat
2401 gatgccacac aaccatgttg gacatatatg gatacatata tgagaaacct attagatggt
2461 aatcctatga gcatagatag aaaacataga gcattaacat taattaagtg tccaccgcta
2521 ctggttacat caaatataga cattagcaaa gaggagaaat acaaatattt acatagtaga
2581 gttaccacat ttacatttcc aaatccattc cccttgaca gaaatgggaa tgcagtatat
2641 gaactatcag atgcaaactg gaaatgtttc tttgaaagac tgtcgtccag cctagacatt
2701 gaggattcag aggacgagga agatggaagc aatagccaag cgtttagatg cgtgccagga
2761 tcagttgtta gaactttatg aagaaaacag tattgatata cacaaacaca ttatgcattg
2821 gaaatgcata cgattggaaa gtgtattact acacaaagca aaacaaatgg gcctgagcca
2881 catcgggtta caagtagtac caccattaac tgtgtcagag actaaaggac ataatgctat
2941 tgaaatgcaa atgcatttag aatccttagc aaaaactcag tatggtgtgg aaccttggac
3001 attacaggac accagttatg aaatgtggct aacaccaccc aaacggtgct ttaaaaaaca
3061 gggaaatact gtggaggtaa aatttgatgg ctgtgaagac aatgtaatgg agtatgtggt
3121 atggacacat atatacctgc aggacaacga ctcatgggta aaagtaacta gttccgtaga
3181 tgccaagggc atatattata catgtggaca atttaaaaca tattatgtaa attttaataa

Fig. 3

```
3241 agaggcacaa aagtatggta gtaccaatca ttgggaagta tgttatggca gcacagttat
3301 atgttctcct gcatctgtat ctagcactgt acgagaagta tccattgctg aacctactac
3361 atacaccccc gcacagacca ccgcccctac agtgtccgcc tgcaccacgg aagacggcgt
3421 gtcggcgccg cctaggaagc gagcacgtgg accgtccact aacaacaccc tgtgtgtggc
3481 caacatcaga tccgtggaca gtacaatcaa caacatcgtc actgacaatt acaacaagca
3541 ccaaagaagg aacaactgtc acagtgcagc tacgcctata gtgcaactgc aaggtgattc
3601 caattgttta aaatgtttta gatatagact gaatgacaaa tataaacatt tgtttgaatt
3661 agcatcttca acgtggcatt gggcctcacc tgaggcacca cataaaaatg caattgtaac
3721 attaacatat agcagtgagg aacaacgtca gcaatttttta aacagtgtaa aaataccacc
3781 caccattagg cataaggtgg ggtttatgtc attacattta ttgtaaccat tacacctgta
3841 tatatgtata tgtgtacata acatacgtgt atggaggtag tgcctgtaca aattgctgca
3901 gcaacaacta caacattgat attgcctgtt gttattgcat ttgcagtatg tattcttagt
3961 attgtactta taatattaat atctgatttt gtagtatata catctgtgct ggtactaaca
4021 cttcttttat atttgctttt gtggctttta ttaacaaccc ctttgcaatt ctttttacta
4081 acactgtgtg tgtgctattt tcctgccttt tatatacaca tatacattgt gcaaacgcaa
4141 caataatggt gatgttaacc tgtcacttaa atgatggtga tacatggttg tttctgtggt
4201 tgtttactgc atttgttgta gctgtacttg gattgttgtt actacattac agggctgtac
4261 atggtactga aaaaactaaa tgtgctaagt gtaaatcaaa ccgcaatact actgtggatt
4321 atgtgtatat gtcacatggt gataatggag attatgtgta catgaactag agtaaacctt
4381 ttttatacag tgtgtggtgt acgttagtta tatataatga aacctagggc acgcagacgt
4441 aaacgtgcgt cagccacaca actatatcaa acatgcaagg ccactggtac atgtcccccca
4501 gatgtaattc ctaaagttga acatactact attgcagatc aaatattaaa atggggaagc
4561 ttaggggttt tttttggtgg gttaggtatt ggtacagggg ctggtagtgg cggtcgtgca
4621 gggtatatac ccttgggaag ctctcccaag cctgctatta ctgggggggcc agcagcacgt
4681 ccgccagtgc ttgtggagcc tgttgcccct tccgatccct ccattgtgtc cttaattgag
4741 gagtctgcta ttattaatgc tggtgcacct gaggtggtac cccctacaca gggtggcttt
4801 actataacat catctgaatc gactacacct gctattttag atgtgtctgt taccaatcac
4861 actaccacta gtgtgtttca aaatcccctg tttacagaac cgtctgtaat acagccccaa
4921 ccacctgtgg aggccagtgg tcacatactt atatctgccc caacaataac atcccaacat
4981 gtagaagaca ttccactaga cacttttgtt gtatcctcta gtgatagtgg acctacatcc
5041 agtactcctc ttcctcgtgc ttttcctcgg cctcgggtgg gtttgtatag tcgtgcctta
5101 cagcaggtac aggttacgga ccccgcgttt ttgtccacgc cacagcgatt ggtaacttat
5161 gacaaccctg tctatgaagg agaagatgta agtttacaat ttacccatga gtctatccac
5221 aatgcacctg atgaagcatt tatggatatt attagactac atagaccagc tataacgtcc
5281 agacggggtc ttgtgcgttt tagtcgcatt gggcaacggg ggtccatgta cacacgcagt
5341 ggacaacata taggtgcccg catacattat tttcaggaca tttcaccagt tacacaagct
5401 gcagaggaaa tagaactgca ccctctagtg gctgcagaaa atgacacgtt tgatatttat
5461 gctgaaccat ttgaccctat ccctgacccct gtccaacatt ctgttacaca gtcttatctt
5521 acctccacac ctaataccct ttcacaatcg tggggtaata ccacagtccc attgtcaatc
5581 cctagtgact ggtttgtgca gtctgggcct gacataactt ttcctactgc atctatggga
5641 acacccttta gtcctgtaac tcctgcttta cctacaggcc ctgtttttat tacaggttct
5701 gacttctatt tgcatcctac atggtacttt gcacgcagac gccgtaaacg tattccctta
5761 ttttttacag atgtggcggc ctagcgacag cacagtatat gtgcctcctc ccaaccctgt
5821 atccaaggtt gttgccacgg atgcgtatgt taaacgcacc aacatatttt atcatgccag
5881 cagttctaga ctccttgctg tgggacatcc atattactct atcaaaaaag ttaacaaaac
5941 agttgtacca aaggtgtctg gatatcaata tagagtgttt aaggtagtgt tgccagatcc
6001 taacaagttt gcattacctg attcatccct gtttgacccc actacacagc gtttagtatg
6061 ggcgtgcaca gggttggagg taggcagggg tcaacctta ggcgttggtg ttagtgggca
6121 tccattgcta aacaaatatg atgatgtaga aaatagtggt gggtatggtg gtaatcctgg
6181 tcaggataat agggttaatg taggtatgga ttataaacaa acccagctat gtatggtggg
6241 ctgtgctcca ccgttaggtg aacattgggg taagggtaca caatgttcaa atacctctgt
6301 acaaaatggt gactgccccc cgttggaact tattaccagt gttatacagg atggggacat
6361 ggttgataca ggctttggtg ctatgaattt tgcagactta caaaccaata aatcggatgt
6421 tccccttgat atttgtggaa ctgtctgcaa atatcctgat tatttgcaaa tggctgcaga
6481 cccttatggt gataggttgt ttttttattt gcgaaaggaa caaatgtttg ctagacactt
6541 ttttaatagg gccggtactg tgggggaacc tgtgcctgat gacctgttgg taaaaggggg
```

Fig. 3, cont.

```
6601 taataacaga tcatctgtag ctagtagtat ttatgtacat acacctagtg gctcattggt
6661 gtcttcagag gctcaattat ttaataaacc atattggctt caaaaggctc agggacataa
6721 caatggtatt tgctggggaa accacttgtt tgttactgtg gtagatacca cacgcagtac
6781 aaatatgaca ctatgtgcat ctgtgtctaa atctgctaca tacactaatt cagattataa
6841 ggaatacatg cgccatgtgg aggagtttga tttacagttt atttttcaat tgtgtagcat
6901 tacattatct gcagaagtca tggcctatat acacacaatg aatccttctg ttttggagga
6961 ctggaacttt ggtttatcgc ctccaccaaa tggtacactg gaggatactt atagatatgt
7021 acagtcacag gccattacct gtcagaaacc cacacctgaa aaagaaaaac aggatcccta
7081 taaggatatg agtttttggg aggttaactt aaaagaaaag ttttcaagtg aattagatca
7141 gtttcccctt ggacgtaagt tttattgca aagtggatat cgaggacgga cgtctgctcg
7201 tacaggtata aagcgcccag ctgtgtctaa gccctctaca gcccccaaac gaaaacgtac
7261 caaaaccaaa aagtaatata tgtgtgtcag tgtgttgtgt tatttatatg ttgttgtagt
7321 gtgtatatgt ttcttgtatt gtgtatatgt gtatatgttt gtgtatatgt gtatgttatg
7381 tatgttatgt tgttatgtat gtttgtgtgt ttagtgtgtg tatatatttg tggaatgtgt
7441 atgtatgttt ttgtgcaata aacaattatt atgtgtgtcc tgttacaccc agtgactaag
7501 ttgtgttttg cacgcgccgt ttgtgttgcc ttcatattat attatatata tttgtaatat
7561 acctatacta tgttaccccc ccccacttgc aaccgttttc ggttgccctt acatacactt
7621 acctcaaatt tgttataacg tgttttgtac taatcccata tgttgtgtgc caaggtacat
7681 attgccctgc caagtatctt gccaacaaca cacctggcca gggcgcggta ttgcatgact
7741 aatgtacaat aaacctgtcg gtttgtacaa tgttgtggat tgcagccaaa ggttaaaagc
7801 atttttggct tctagctgaa catttttgta cccttagtat attatgcaca atacccacaa
7861 aatgagtaac ctaaggtcac acacctgcaa ccggtttcgg ttacccacac cctacatatt
7921 tccttcttat a
```

Fig. 3, cont.

HPV 51 ATCC # M62877

1 aacaattatc ttgtaaaaac tagggtgtaa ccgaaaaggg ttatgaccga aaacggtgca
61 tataaaagtg cagtggtaaa agtatagaag aacaccatgt tcgaagacaa gagggaaaga
121 ccacgaacgc tgcatgaatt atgtgaagct ttgaacgttt ctatgcacaa tatacaggta
181 gtgtgtgtgt attgtaaaaa ggaattatgt agagcagatg tatataatgt agcatttact
241 gaaattaaga ttgtatatag ggataataat ccatatgcag tatgcaaaca atgtttactg
301 ttttattcaa aaattagaga gtatagacgt tatagcaggt ctgtgtatgg tactacatta
361 gaggcaatta ctaaaaaaag cttatatgat ttatcgataa ggtgtcatag atgtcaaaga
421 ccacttgggc ctgaagaaaa gcaaaaattg gtggacgaaa aaaaaaggtt ccatgaaata
481 gcgggacgtt ggacggggca atgcgctaat tgctggcaac gtacacgaca acgtaacgaa
541 acccaagtgt aataaagcca tgcgtggtaa tgtaccacaa ttaaaagatg tagtattgca
601 tttaacacca cagactgaaa ttgacttgca atgctacgag caatttgaca gctcagagga
661 ggaggatgaa gtagataata tgcgtgacca gctaccagaa agacgggctg gacaggctac
721 gtgttacaga attgaagctc cgtgttgcag gtgttcaagt gtagtacaac tggcagtgga
781 aagcagtgga gacacccttc gcgttgtaca gcagatgtta atgggcgaac taagcctggt
841 ttgcccgtgt tgtgcgaaca actagcaacg gcgatggact gtgaaggtac agaggatgag
901 ggggcggggt gtaatgggtg gtttttttgtt gaagcaatag tagaaaaaaa aacaggagat
961 aatgtttcgg atgatgagga tgaaaatgca gatgatacag gatctgattt aataaacttt
1021 atagatagtg aaactagtat ttgcagtcag gcggaacagg agacagcacg ggcgttgttt
1081 caggcccaag aattacaggc aaacaaagag gctgtgcatc agttaaaacg aaagtttcta
1141 gtcagcccgc gaagcagccc attaggagac attacaaatc aaaacaacac acacagccat
1201 agtcaggcaa acgagtcaca agttaaaagg agattactgg acagttatcc ggacagcgga
1261 tatggcaata cacaagtgga aactgtggaa gcaacgttgc aggtagatgg gcaacatggc
1321 ggttcacaga acagtgtgtg tagtagcggg gggggcagtg ttatggatgt ggaaacaaca
1381 gaaagctgtg caaatgtaga actaaacagt atatgtgaag tattaaaaag cagtaatgca
1441 aaagcaacgt taatggcaaa atttaaagag ttgtatggta ttagttataa tgagttggta
1501 cgggtgttta aaagtgataa aacatgttgt atagattggg tttgtgcatt gtttggcgtt
1561 tccccaatgg tagcagaaaa tttaaaaaca ctaattaagc cattttgcat gtactaccat
1621 atacaatgtt tatcatgtga ttggggcacc attgtattaa tgctaattag gttttcatgt
1681 gcaaaaaaca gaacaacaat tgctaagtgt ttaagtacat tagtaaatat cccacaatca
1741 caaatgttta tagaaccacc aaaattacgt agtacacctg tggcattata tttttataga
1801 acaggcatat caaacattag caatacatat ggagagacac ctgaatggat tacacgacaa
1861 acgcaactac aacatagttt tgaggatagt acctttgaat tatcacaaat ggtgcaatgg
1921 gcatttgacc atgaagtatt agatgatagt gaaatagcat ttcattatgc acaattagca
1981 gatatagata gtaatgctgc agcgttttta aagagtaatt gccaagcaaa atatgtaaaa
2041 gattgtggga ccatggcacg gcattacaaa cgagcacaaa gaaaatcatt atctatgtca
2101 gcctggataa ggtatagatg tgatagagca aaggatggag gcaactggag agaaattgct
2161 aaatttttaa gatatcaagg tgtaaacttt atgtccttta ttcaaatgtt taaacagttt
2221 ttaaaaggaa caccaaaaca caattgcata gtcatatatg gcccaccaaa cacaggcaag
2281 tcattatttg caatgagcct aatgaagttt atgcaagggt ccattatttc atatgtaaac
2341 tctggtagtc atttttggtt acagccacta gaggatgcta aaatagcatt gttagatgat
2401 gctacgtatg ggtgttggac atatattgat cagtatttaa gaaacttttt agatggtaat
2461 ccatgtagta tagatagaaa acataggagt ttaatacaat tagtatgtcc accattacta
2521 ataacgtcaa acataaatcc acaagaggat gcaaacctaa tgtatttaca tacaagggta
2581 acagtattaa agtttttaaa tacatttcca tttgataaca atgggaatgc tgtgtataca
2641 ttgaatgatg aaaattggaa aaattttttt tccaccacat ggtccagatt agatttggag
2701 gaggaagagg acaaagaaaa tggagacccc atgccaccgt ttaaatgtgt gccaggagaa
2761 aatactagac tgttatgaac tggacagtga taaattagta gatcaaatta actattggac
2821 attgttacga tatgaagctg ctatgtttta tgcagcacgg gaaagaaact tacgaacaat
2881 caatcaccag gtagtaccag caacaacagt atcaaaacaa aaggcctgtc aagcaattga
2941 aatgcacatg gccttacaat cgcttaacaa atcagactat aacatggaac catggacaat
3001 gcgggagaca tgttatgaac tatggtgtgt ggctcccaag caatgtttca aaaagggggg
3061 cataactgta acagttatat ttgatggaaa taaggacaat gcaatggact atacaagctg
3121 gaaatttata tatatatatg ataatgataa gtgggtaaag acaaatggaa atgtggacta

Fig. 4

```
3181 tacgggtata tattacactg taaattcaaa aaaagaatat tatgtacagt ttaaagatga
3241 agccaaaata tatggggcac aacagtggga ggtctatatg tatggtactg taataacatg
3301 tcctgaatat gtatctagta cctgcagcga cgcgttatcc actactacaa ctgttgaaca
3361 actatcaaac accccaacga ccaatcccct taccacctgc gtgggcgcca aagaagccca
3421 gacacaacag cgaaaacgac agcgacttac tgagcccgac tcctccacaa tctccccact
3481 gtccgtggac aatacaaaca accaaataca ctgtggaagt ggaagcacta acactggagg
3541 gcaccaaagt gcaactcaga ctgcgtttat agtgcattta aaaggtgata caaattgttt
3601 aaaatgtttt agatacagat ttacaaaaca caaagggtta tataaaaacg tatcctcaac
3661 ctggcattgg accagtaata ctaaaacagg cattgttacc attgtgtttg acagtgcaca
3721 tcaacgggaa acatttataa aaaccattaa agtaccccca agtgtaacac tgtcattggg
3781 aattatgaca ctgtaactag tgtaatatat gtattgtaca tatatactgt cacaagccaa
3841 tatgtgctgc taattgtata gacatattgt aaccattgca gtgtttatta ttttgctatt
3901 tgtgctttgc ttgtgtgtgt gtcttgtgtt gtgttgtttg ttgccgctac tgctgtccca
3961 atacgtgttt gcagctgcct tattattaat tttatgtttt tggtttgttg ttgcaacatc
4021 ccaattaact acattttttg tatatttgat ttttttttac ttaccttgtt tacttttaca
4081 tctatataca tttttacttt tgcaataaac ttgttatatt tttgtgatta aatatggtgg
4141 ctacacgtgc acggcgtcgg aagcgagcat ctgtaacaca attatattct acatgcaaag
4201 ctgctggtac atgtcctcct gatgttgtga ataaggttga aggtactaca ttggccgata
4261 aaatattaca gtggagtggg ttgggtatat ttttgggtgg cctaggtatt ggtactgggt
4321 ctggatctgg ggggcgtact ggatatatcc ctttaggtgg tggggtcgc ccaggcgtgg
4381 tggatattgc tcctgcaagg ccacctatta taattgacct atggcaccat actgaacctt
4441 ctatagtaaa tttggttgag gactctagta ttattcagtc tgggtctcct atacctacct
4501 ttactggtac cgatggcttt gaaattactt catcttccac aacaacccct gctgtgttgg
4561 acatcacccc atctgctggt actgtacatg tttctagtac taacattgaa aatcctttat
4621 atattgaacc tccatccatt gaggctccac aatctggaga agtgtcagat atatatttac
4681 tagtacacta ctctggtact catgggtatg aagaaatacc tatggaagtg tttgcatcca
4741 atgtcagtac tggtactgaa cctattagca gcacacctac tccagggggtt agtcgcatag
4801 ctgctccccg cttgtatagt aagtcctaca cacaggttaa agttacaaat cctgatttta
4861 ttagtaagcc atccacattt gttacattta ataatcctgc ttttgagcct attgacacat
4921 ccataacttt tgaggaacct gatgctgttg cacctgatcc tgattttctg gatattatta
4981 cactgcaccg ccctgccctt acatctcgta gaggcacagt acgctttagt aggttaggtc
5041 aaaaggccac catgcgcact cgtagtggca aacaaattgg tgctcgtgta cattattatc
5101 atgatattag tagaattgca ccagctgatg aacttgaaat gcagccttta ctttcacctt
5161 ctaataatta tagttatgac atttatgctg atttagatga agctgaaaca ggttttatac
5221 agcccacaca caccacacct atgtcacact cctctttgtc taggcagttg ccctccttat
5281 cttcatctat gtcttcatct tatgcaaatg ttactattcc attttcaact acatattctg
5341 ttcctattca tacagggcct gatgtggtat tgcccacatc tcctacagta tggccttatg
5401 ttccccacac ttccattgac accaagcatt ctattgttat actaggtggg gattactatt
5461 tgtggcccta tacacattta ctacgcaaac gccgtaaacg tataccctat ttttttacag
5521 atggcattgt ggcgcactaa tgacagcaag gtgtatttgc cacctgcacc tgtgtctcga
5581 attgtgaata cagaagaata tatcacacgc accggcatat attactatgc aggcagttcc
5641 agactaataa cattaggaca tccctatttt ccaataccta aaacctcaac gcgtgctgct
5701 attcctaaag tatctgcatt tcaatacagg gtatttaggg tacagttacc agatcctaac
5761 aagtttggac tcccggatcc aaatttatat aatccagaca cagataggtt ggtgtggggt
5821 tgtgtgggcg ttgaggtggg cagaggacag ccccttggtg ttggccttag tggtcatccc
5881 ttatttaata aatatgatga cacagaaaat tcacgcatag caaatggcaa tgcacaacaa
5941 gatgttagag ataacacatc tgttgacaac aaacagactc agttatgtat aataggctgt
6001 gctccaccta ttggggaaca ctggggtatt ggcactacat gcaaaaacac acctgtacct
6061 ccaggagact gcccccccct ggaacttgta tcctctgtca ttcaggatgg cgatatgatt
6121 gatacagggt ttggagctat ggatttcgct gccctacagg ccaccaaatc agacgtccct
6181 ttggatattt cacagtctgt ttgtaaatat cctgattatt taaaaatgtc tgcagacaca
6241 tatggtaatt ccatgttttt tcatttacgc agggagcaaa tctttgctag gcactattat
6301 aataaacttg taggtgttgg ggaagacatt cctaacgatt attatattaa gggtagtggt
6361 aatggccgtg accctataga aagttatata tactctgcta ctcccagtgg gtctatgata
6421 acatctgatt ctcaaatttt taataagcct tattggctcc accgtgcgca gggtcacaat
6481 aatggcattt gctggaacaa tcagcttttt attacctgtg ttgatactac cagaagtaca
```

Fig. 4, cont.

```
6541 aatttaacta ttagcactgc cactgctgcg gtttccccaa catttactcc aagtaacttt
6601 aagcaatata ttaggcatgg ggaagagtat gaattgcaat ttatttttca attatgtaaa
6661 attactttaa ctacagaggt aatggcttat ttacacacaa tggatcctac cattcttgaa
6721 cagtggaatt ttggattaac attacctccg tctgctagtt tggaggatgc atataggttt
6781 gttagaaatg cagctactag ctgtcaaaag gacacccctc cacaggctaa gccagatcct
6841 ttggccaaat ataaattttg ggatgttgat ttaaaggaac gattttcttt agatttagac
6901 caatttgcat tgggtcgcaa gtttttgttg caggttggcg tacaacgcaa gcccagacca
6961 ggccttaaac gcccggcctc atcggcatcc tcttcctctt cctcttcagc caaacgtaaa
7021 cgtgttaaaa agtaatgtat gttagttttt gtatgcttgt gcacactgtt gtatgcctgt
7081 atgtatatgt ttgtgtatgt actgtatgtg tttttgtgtg tgtgtgtgtt gttgttcctg
7141 tatgtatgag ttatgtatgt ttattattaa taaactatgt ggtgtgtgtg tgtgtgtttt
7201 tgcatgactg catttgtatg acatgtacgg gtgtatgtgg gtattacatt atccccgtag
7261 gtcaagggtg gtgtttcggt ggcgtcccta ttgccctacc catttttttgc agcacaacag
7321 tttatatttg tgctatttag ttatactttg tagcttccat tttgttacag ctgcagccat
7381 tttgagtgca accgatttcg gttcgtgtac ttttagtata tttgccaagt tttaaaccac
7441 aactgccagt tgtttttggc ataaaccatc atttttttat gacatagtgc atacatccgc
7501 ccgcccacgc cttgtacttg gcgcgcctta ccggcgctag tcatacaacc tattagtcat
7561 ttgtacttta acaattgttg gcacactgtt ttccgcccta taataattta actgcttata
7621 ggcatgtatt ttttggcata ttttatctta ctaattgcat agttggcagg tcaaatacta
7681 tgtttttagt gccaagtttc tatcctactt ataaaccatc ttactcatat gcaggtgtgc
7741 tacacaaatg tgttacctaa ccgatttgtg ttctgcctat gcttgcaaca tttttttctta
7801 taacattt
```

Fig. 4, cont.

HPV 58 ATCC # D90400

1 ctaaactata atgccaaatc ttgtaaaaac tagggtgtaa ccgaaaacgg tctgaccgaa
61 accggtgcat atataaagca gacatttttt ggtaggctac tgcaggacta tgttccagga
121 cgcagaggag aaaccacgga cattgcatga tttgtgtcag gcgttggaga catctgtgca
181 tgaaatcgaa ttgaaatgcg ttgaatgcaa aaagactttg cagcgatctg aggtatatga
241 ctttgtattt gcagatttaa gaatagtgta tagagatgga aatccatttg cagtatgtaa
301 agtgtgctta cgattgctat ctaaaataag tgagtataga cattataatt attcgctata
361 tggagacaca ttagaacaaa cactaaaaaa gtgtttaaat gaaatattaa ttagatgtat
421 tatttgtcaa agaccattgt gtccacaaga aaaaaaaagg catgtggatt taaacaaaag
481 gtttcataat atttcgggtc gttggacagg gcgctgtgca gtgtgttgga gacccccgacg
541 tagacaaaca caagtgtaac ctgtaacaac gccatgagag gaaacaaccc aacgctaaga
601 gaatatattt tagatttaca tcctgaacca actgacctat tctgctatga gcaattatgt
661 gacagctcag acgaggatga aataggcttg gacgggccag atggacaagc acaaccggcc
721 acagctaatt actacattgt aacttgttgt tacacttgtg gcaccacggt tcgtttgtgt
781 atcaacagta caacaaccga cgtacgaacc ctacagcagc tgcttatggg cacatgtacc
841 attgtgtgcc ctagctgtgc acagcaataa acaccatctg caatggatga ccctgaaggt
901 acaaacgggg taggggcggg ctgtactggc tggtttgagg tagaagcggt aatagaacga
961 agaacaggag ataatatttc agatgatgag gacgaaacag cagacgatag tggtacagat
1021 ttaatagagt ttatagatga ttcagtacaa agtactacac aggcagaagc agaggcagcc
1081 cgagcgttgt ttaatgtaca ggaaggggtg gacgatataa atgctgtgtg tgcactaaaa
1141 cgaaagtttg cagcatgctc agaaagtgct gtagaggact gtgtggaccg ggctgcaaat
1201 gtgtgtgtat cgtggaaata taaaaataaa gaatgcacac acagaaaacg aaaaattatt
1261 gagctagaag acagcggata tggcaatact gaagtggaaa ctgagcagat ggcacaccag
1321 gtagaaagcc aaaatggcga cgcagactta aatgactcgg agtctagtgg ggtgggggct
1381 agttcagatg taagcagtga aacggatgta gacagttgta atactgttcc attacaaaat
1441 attagtaata ttctacataa cagtaatact aaagcaacgc tattatataa attcaaagaa
1501 gcttatggag taagttttat ggaattagtt agaccattta aaagtgataa aacaagctgt
1561 acagattggt gtataacagg gtatggaata agtccctccg tagcagaaag tttaaaagta
1621 ctaattaaac agcacagtat atatacacac ctacaatgtt taacgtgtga cagaggaatt
1681 atattattat tgttaattag atttaaatgt agcaaaaata gattaactgt ggcaaaatta
1741 atgagtaatt tactatcaat tcctgaaaca tgtatgatta tcgagccacc aaaattacga
1801 agtcaagcat gtgccttata ttggtttaga acagcaatgt caaatataag tgatgtgcaa
1861 gggacaacac cagaatggat agatagatta acagtgttac agcatagctt taatgatgat
1921 atatttgatt taagtgaaat gatacaatgg gcatatgata atgacattac agatgatagt
1981 gacattgcat ataaatatgc acagttagca gatgttaata gtaatgcagc agcattttta
2041 agaagcaatg cacaagcaaa aatagtaaaa gactgtggcg ttatgtgcag acattataaa
2101 agagcagaaa agcgtggtat gacaatggga caatggatac aaagtaggtg tgaaaaaaca
2161 aatgatggag gtaattggag accaatagta caatttttaa gatatcaaaa tattgaattt
2221 acagcatttt tagttgcatt taaacagttt ttacaaggtg taccaaaaaa aagttgtatg
2281 ttactgtgtg gcccagcaaa tacagggaaa tcatattttg gaatgagttt aatacatttt
2341 ttaaaaggat gcattatttc atatgtaaat tccaaaagtc atttttggtt gcagccatta
2401 tcagatgcta aactaggtat gatagatgat gtaacagcca taagctggac atatatagat
2461 gattatatga gaaatgcatt agatggtaac gacatttcaa tagatgtaaa acatagggca
2521 ttagtacaat taaaatgtcc accattaata attacctcaa atacaaatgc aggcaaagat
2581 tcacgatggc catatttgca cagtagacta acagtatttg aatttaacaa tccatttcca
2641 tttgatgcaa atggtaatcc agtgtataaa ataaatgatg aaaattggaa atccttttttc
2701 tcaaggacgt ggtgcaaatt aggcttaata gaggaagagg acaaggaaaa cgatggagga
2761 aatatcagca cgtttaagtg cagtgcagga caaaatccta gacatatacg aagctgataa
2821 aaatgattta acatcacaaa ttgaacattg gaaactaata cgcatggagt gtgctataat
2881 gtatacagcc agacaaatgg gaatatcaca tttgtgccac caggtggtgc cgtcattggt
2941 agcatcaaag actaaagcgt ttcaagtaat tgaactgcaa atggcattag agacattaaa
3001 tgcatcacca tataaaacag atgaatggac attgcaacaa acaagcttag aagtgtggtt
3061 atcagagcca caaaaatgct ttaaaaaaaa aggcataaca gtaactgtac aatatgacaa
3121 tgataaagca aacacaatgg attatacaaa ttggagtgaa atatatatta ttgaggaaac

Fig. 5

3181 aacatgtact ttggtagcag gagaagttga ctatgtgggg ttgtattata tacatggcaa
3241 tgaaaagacg tattttaaat attttaaaga ggatgcaaaa aagtactcta aaacacaatt
3301 atgggaggta catgtgggta gtcgggtaat tgtatgtcct acatctatac ctagtgatca
3361 aatatccact actgaaactg ctgacccaaa gaccaccgag gccaccaaca acgaaagtac
3421 acaggggaca aagcgacgac gactcgattt accagactcc agagacaaca cccagtactc
3481 cacaaagtat acagactgcg ccgtggacag tagaccacga ggaggaggac tacacagtac
3541 aactaactgt acatacaaag ggcggaacgt gtgtagttct aaagtttcac ctatcgtgca
3601 tttaaaaggt gacccaaata gtttaaaatg tttaagatat agattaaaac catttaaaga
3661 cttatactgt aatatgtcat ccacatggca ttggaccagt gatgacaaag gtgacaaagt
3721 aggaattgtt actgtaacat acacaacgga aacacaacga caactgtttt taaacactgt
3781 taaaatacca cccactgtgc aaataagtac tggtgttatg tcattgtaat tgtattgtac
3841 aattactgta tgtaaaccac aagccaatat gtgctgctaa gtgtatatac aatgatatta
3901 cctattttg ttgtttgttt tatactgttt ttatgcttgt gcattttttt gcggccattg
3961 gtgctatcta tttctatata tgcttggttg ctggtgttgg tgttgctgct ttgggtgtct
4021 gtggggtcgg ctctacgaat tttttctgt tacttaatat ttttatatat accaatgatg
4081 tgtattaatt ttcatgcaca atacttaacc caacaagact aactgtatac tggttctgca
4141 catggtggta tggtattgta aatatttact gttgtgtgtg ttgtttttat tatttttata
4201 catttactaa taaatacttt tatattttta gcactgtctt attatgagac acaaacggtc
4261 tacaaggcgc aagcgtgcat ctgctacaca actttaccaa acatgcaagg cctcaggcac
4321 ctgcccacct gatgttatac ccaaagttga aggcactact atagcagatc aaatattacg
4381 atatggtagc ttaggggtgt tttttggagg tttaggcatt ggtacagggt cgggtacagg
4441 tggcaggact ggatatgtgc cccttggtag taccccaccg tctgaggcta tacctttaca
4501 gcccatacgt cccccagtta ccgttgatac tgtggggcct ttggattctt ctattgtatc
4561 tttaatagag gaatctagtt ttatagacgc cggtgcacca gccccatcaa ttcccactcc
4621 atctggtttt gatattacca cctctgcaga tactacacct gcaatactta atgtttcctc
4681 tattggagaa tcatctatac aaactgtttc tacacattta aatccctcct ttactgagcc
4741 atccgtactc cgccctcctg cacctgcaga ggcctctgga catttaatat tttcctctcc
4801 tactgttagc acacatagtt atgaaaacat accaatggat acctttgtta tttctactga
4861 cagtggcaat gtcacgtcta gcacacccat tccagggtct cgccctgtgg cacgccttgg
4921 tttatacagt cgcaacaccc aacaagttaa ggttgttgac cctgcttttt taacatctcc
4981 tcatagactt gtaacatatg ataatccagc atttgaaggc tttaaccctg aggacacatt
5041 gcagtttcaa catagtgaca tatcgcctgc tcctgatcct gattttctag atattgttgc
5101 attacacaga cctgcattaa cctctcgcag ggtactgta cgttatagta gggttgggca
5161 aaaggctaca cttcgtactc gcagtggaaa gcaaataggg gctaaagtac attactacca
5221 agacttaagt cccatacagc ctgtccagga acaggtacaa cagcagcaac aatttgaatt
5281 acaatcttta aatacttctg tttctcccta tagtattaat gatggacttt atgatattta
5341 tgctgacgat gctgatacta tacatgattt tcagagtcct ctgcactcac atacgtcctt
5401 tgccaccaca cgtaccagta atgtgtccat accattaaat actggatttg acactcctct
5461 tgtgtcattg gaacctggtc cagacattgc atcttctgta acatctatgt ctagtccatt
5521 tattcctata tctccactaa ctcctttaa taccataatt gtggatggtg ctgattttat
5581 gttgcaccct agctatttta ttttgcgtcg cagacgtaaa cgttttccat atttttttgc
5641 agatgtccgt gtggcggcct agtgaggcca ctgtgtacct gcctcctgtg cctgtgtcta
5701 aggttgtaag cactgatgaa tatgtgtcac gcacaagcat ttattattat gctggcagtt
5761 ccagactttt ggctgttggc aatccatatt tttccatcaa aagtcccaat aacaataaaa
5821 aagtattagt tcccaaggta tcaggcttac agtatagggt ctttagggtg cgtttacctg
5881 atcccaataa atttggtttt cctgatacat ctttttataa ccctgataca caacgtttgg
5941 tctgggcatg tgtaggcctt gaaataggta ggggacagcc attgggtgtt ggcgtaagtg
6001 gtcatcctta tttaaataaa tttgatgaca ctgaaaccag taacagatat cccgcacagc
6061 cagggtctga taacagggaa tgcttatcta tggattataa acaaacacaa ttatgtttaa
6121 ttggctgtaa acctcccact ggtgagcatt ggggtaaagg tgttgcctgt aacaataatg
6181 cagctgctac tgattgtcct ccattggaac tttttaattc tattattgag gatggtgaca
6241 tggtagatac agggtttgga tgcatggact ttggtacatt gcaggctaat aaaagtgatg
6301 tgcctattga tatttgtaac agtacatgca aatatccaga ttatttaaaa atggccagtg
6361 aaccttatgg ggatagtttg ttcttttttc ttagacgtga gcagatgttt gttagacact
6421 tttttaatag ggctggaaaa cttggcgagg ctgtcccgga tgacctttat attaaagggt
6481 ccggtaatac tgcagttatc caaagtagtg catttttttcc aactcctagt ggctctatag

Fig. 5, cont.

```
6541 ttacctcaga atcacaatta tttaataagc cttattggct acagcgtgca caaggtcata
6601 acaatggcat ttgctggggc aatcagttat ttgttaccgt ggttgatacc actcgtagca
6661 ctaatatgac attatgcact gaagtaacta aggaaggtac atataaaaat gataatttta
6721 aggaatatgt acgtcatgtt gaagaatatg acttacagtt tgtttttcag ctttgcaaaa
6781 ttacactaac tgcagagata atgacatata tacatactat ggattccaat attttggagg
6841 actggcaatt tggtttaaca cctcctccgt ctgccagttt acaggacaca tatagatttg
6901 ttacctccca ggctattact tgccaaaaaa cagcaccccc taaagaaaag gaagatccat
6961 taaataaata tacttttttgg gaggttaact taaaggaaaa gttttctgca gatctagatc
7021 agtttccttt gggacgaaag tttttattac aatcaggcct taaagcaaag cccagactaa
7081 aacgttcggc ccctactacc cgtgcaccat ccaccaaacg caaaaaggtt aaaaaataat
7141 tgttgtggta cttacactat tttattatac atgtttgttt gttttatgta tgtgttgtct
7201 gtttgtttat gtttgtgtat atgttgtatg tgttatgtgt catgtttgtg tacatgttct
7261 atgtccttgt cagtttcctg tttctgtata tatgtaataa actattgtgt gtattgtaaa
7321 ctatttgtat tgtttgggtg tatctatgag taaggtgctg tccctaaatt gccctacccct
7381 gccctgccta ttatgcatac ctatgtaata gtatttgtat gatatgtatt ttatagtttt
7441 taacagtact gcctccattt tactttacct ccattttgtg catgtaaccg atttcggttg
7501 ctggcacaaa cgtgtttttt ttaaactaca atttaaacaa tacagttaat cctttccctt
7561 cctgcactgc ttttgcctat acttgcatat gtgactcata tatacatgca gtgcagttgc
7621 aaaatgttta attatactca tagtttaaac atgcttatag gcacatattt taacttactt
7681 tcaatgctta agtgcagttt tggcttgcac aatagtttgt tatgccaaac tatgtcttgt
7741 aaaagtgact cactaacatt tattgccagg tgtggactaa ccgttttggg tcacattgtt
7801 catgtttcaa cattttatat aata
```

Fig. 5, cont.

HPV 56 ATCC # x74483

```
1 gaaagtttca atcatacttt tatatattgg gagtgaccga aaagggttta agaccgaaaa
61 cggtacatat aaaaggcagc ttattctgtg tggacatatc catggagcca caattcaaca
121 atccacagga acgtccacga agcctgcacc acttgagtga ggtattagaa ataccttttaa
181 ttgatcttag attatcatgt gtatattgca aaaaagaact aacacgtgct gaggtatata
241 attttgcatg cactgaatta aaattagtgt atagggatga ttttccttat gcagtgtgca
301 gagtatgttt attgttttat agtaaagtta gaaaatatag gtattatgac tattcagtgt
361 atggagctac actagaaagt ataactaaaa aacagttatg tgatttatta ataaggtgct
421 acagatgtca aagtccgtta actccggagg aaaagcaatt gcattgtgac agaaaaagac
481 gatttcatct aatagcacat ggttggaccg ggtcatgttt ggggtgctgg agacaaacat
541 ctagagaacc tagagaatct acagtataat catgcatggt aaagtaccaa cgctgcaaga
601 cgttgtatta gaactaacac ctcaaacaga aattgaccta cagtgcaatg agcaattgga
661 cagctcagag gatgaggatg aggatgaagt agaccatttg caggagcggc cacagcaagc
721 tagacaagct aaacaacata cgtgttacct aatacacgta ccttgttgtg agtgtaagtt
781 tgtggtgcag ttggacattc agagtaccaa agaggacctg cgtgttgtac aacagctgct
841 tatgggtgcg ttaacagtaa cgtgcccact ctgcgcatca agtaactaac tgcaatggcg
901 tcacctgaag gtacagatgg ggaggggaag ggatgttgtg gatggtttga agtagaggca
961 attgtagaaa aaaaaacagg agataaaata tcagatgatg aaagtgacga ggaggatgaa
1021 atagatacag atttagatgg atttatagac gattcatata tacaaaatat acaggcagac
1081 gcagaaacag tcaacaattg ttgcaagtac aaacagcaca tgcagataaa cagacgttgc
1141 aaaaactaaa acgaaagtat atagctagtc cattaaggga tattagtaat cagcaaactg
1201 tgtgccggga aggagtaaaa cggaggctta ttttatcaga cctacaagac agcgggtatg
1261 gcaatacatt ggaaactctg gaaacaccag aacaggtaga tgaagaggta cagggacgtg
1321 ggtgcgggaa tacacaaaat ggaggctcac aaaacagtac ctatagtaac aatagtgagg
1381 actctgtaat acatatggat attgatagaa acaatgaaac gccaacacaa caattgcagg
1441 acttgtttaa aagtagcaat ttacaaggta aattatatta taaatttaaa gaagtgtatg
1501 gtattccatt ttcagaattg gtgcgtacgt ttaaaagtga tagtacatgt tgcaatgatt
1561 ggatatgtgc tatatttggt gttaatgaaa cattagccga ggcactaaaa actataataa
1621 aaccacactg tatgtattat catatgcaat gtttaacatg tacatggggg gttatagtaa
1681 tgatgctaat tagatataca tgtggcaaaa acagaaaaac aattgcaaaa gcattaagct
1741 caatattaaa tgtaccacag gagcaaatgt taattcaacc accaaaaata cgaagtcctg
1801 ctgtagcttt atatttttat aaaacagcaa tgtcaaatat tagtgatgtg tatggagaca
1861 caccagaatg gatacaaaga caaacacaat tgcaacacag tttacaggat agtcaatttg
1921 aattatctaa aatggtgcag tgggcatttg ataatgaagt aacagatgat agccaaattg
1981 cgtttcaata tgcacaatta gcagatgtag acagcaatgc acaagccttt ttaaaaagca
2041 atatgcaggc aaaatatgta aaggattgtg gaataatgtg tagacattat aaaagggcac
2101 aacagcaaca aatgaatatg tgccagtgga taaagcacat atgtagtaaa acagatgaag
2161 gggtgattg gaaacccatt gtacaatttt taagatatca aggggtcgat ttcatttcat
2221 ttctaagtta ctttaaatta tttctacaag gaacacctaa acataactgt ttggtacttt
2281 gtggaccgcc aaatacaggt aaatcatgct ttgctatgag tcttataaag tttttcaag
2341 ggtctgtcat ttcatttgtg aattcacaaa gccacttttg gttgcagcca ttagacaatg
2401 ctaaacttgg gttgttggat gatgcaacag aaatatgttg gaaatatata gacgattatt
2461 taaggaattt ggtagatgga aatcctataa gtttagatag aaaacataaa caattagtac
2521 aaataaaatg tccaccatta ctaattacaa ccaatataaa tcctatgcta gatgctaaat
2581 tacgatattt acacagtaga atgttagtgt ttcagtttca aaatccattt ccattagata
2641 ataatggtaa tcctgtatat gaattaagta atgtaaactg gaaatgtttc tttacaagga
2701 cgtggtccag attaaatttg gataacgacg aggacaaaga aaacaatgga gacgctttcc
2761 caacgtttaa atgcgtgcca gaacaaaata ctagactgtt ttgaaaaaag atagtagatg
2821 tattgcagat catatagaat attggaaagc tgtgcgacat gaaaatgtgc tatactataa
2881 agcaagagaa aatgacatta ctgtactaaa ccaccagatg gtgccttgtt tacaagtatg
2941 taaagcaaaa gcatgtagtg caatagaagt gcaaatagca ctggaatcat taagtacaac
3001 aatatataac aatgaagagt ggacattaag agacacatgc gaggaactat ggcttactga
3061 acctaaaaaa tgctttaaaa aagaaggaca acatatagaa gtatggtttg atggtagtaa
3121 aaacaattgt atgcaatatg tagcctggaa atatatatat tacaatggag attgtgggtg
3181 gcaaaaagtg tgttctgggg tagactatag aggtatatat tatgtacatg atggccacaa
3241 aacatactac acagactttg aacaagaggc caaaaaattt gggtgtaaaa acatatggga
```

Fig. 17

```
3301 agtacatatg gaaaatgaga gtatttattg tcctgactct gtgtctagta cctgtagata
3361 caacgtatcc cctgttgaaa ctgttaacga atacaacacc cacaagacca ccaccaccac
3421 ctccacgtcc gtgggcaacc aagacgccgc agtatcccac agaccaggaa aacgacccag
3481 actacgggaa tcagaatttg actcctccag agagtcccac gcaaagtgtg tcacaacaca
3541 cacacacatc agcgacacag acaataccga cagtagaagt agaagtatca acaacaacaa
3601 ccaccctggt gataagacta cgcctgtagt acatttaaaa ggtgaaccta acagattaaa
3661 atgttgtaga tatcgatttc aaaaatataa aacattgttt gtggatgtaa catcaacata
3721 tcattggaca agtacagaca ataaaaatta tagcataatt acaattatat ataaggatga
3781 aacacaacga aacagctttt taagtcatgt aaaaattcca gtagtgtaca ggttagtttg
3841 ggacaaatga gtttttccata aagtgctgta tatattgtat atacatttgt gttattgtaa
3901 cacacaaata cgtgaagtgt acctgccata cattgctgct acgcatatat attgcaacca
3961 ttgatttttg tgttattggt gtgtttgcgc tttgcttttg tgtttgtttg cttgtgtgtc
4021 atgttgtccc gcttttgcta tctgcctctg tgttttccag ttgtatatta ttaataatat
4081 tgttttggtt tgttatagcc acatcctttt ttaatacatt tataatattt ttgatatttt
4141 tttactgtcc tgtgctgtgt atatatttac atgctttgtg gataataaat aatatgtaaa
4201 tgtagtagta ctgttactac tatggttgcc caccgtgcca cacgacgcaa acgcgcatct
4261 gcaacacaac tatataaaac atgtaagttg tctggtacat gtccagagga tgttgttaat
4321 aaaatagagc aaaaaacatg ggctgataaa atattgcaat ggggaagttt atttacatat
4381 tttggaggcc ttggcattgg tacaggaact gggtctgggg gtcgtgcagg ctatgttcca
4441 ttggggtcta ggccttccac aatagttgat gtaactccgg cgcgaccacc tattgttgtg
4501 gaatccgtag ggcctacaga cccttccatt gttacattag ttgaggagtc cagtgttata
4561 gaatctggtg cagggattcc taattttact gggtctgggg gatttgaaat tacatcctca
4621 tcaacaacta cacctgccgt gttggatatt acaccaacct ctagtactgt acatgtcagt
4681 agtacccata taaccaatcc gttatttatt gatcccccctg ttattgaggc cccacaaaca
4741 ggcgaggtgt ctggcaatat tttaattagc acacccacat ctggtataca tagctatgaa
4801 gaaataccta tgcaaacatt tgctgttcac ggttctggta cagaacctat tagtagtact
4861 cctattccag gctttaggcg tattgcagct cctagattat atagaaaagc atttcagcag
4921 gttaaggtaa ctgaccctgc atttcttgat agacctgcaa cattagtatc tgctgataat
4981 ccacttttttg aaggtactga cacatcttta gctttttctc cgtcgggtgt ggctcctgac
5041 cctgatttta tgaatatagt agcattacat aggcctgcat ttactacacg taggggtggt
5101 gtacgtttta gtaggcttgg cagaaaggct actatacaaa cacgtagagg cacacaaata
5161 ggtgcccgtg tgcattatta ttatgatata agtcctattg cacaggctga ggaaattgaa
5221 atgcagccat tattgtctgc aaataattca tttgatggcc tatatgatat ttatgcaaat
5281 atagatgatg aagcacctgg tttgtctagc cagtcagttg ctacaccttc tgcacactta
5341 cctataaagc cttccacatt gtcttttgct agtaacacca ctaatgtaac tgcccccttta
5401 ggtaatgtgt gggaaacacc attttattca ggtcctgaca tagtgttgcc tacaggcccc
5461 agtacgtggc cctttgttcc tcagtctcct tatgatgtta cccatgatgt atatatacag
5521 ggatcctcct ttgcattatg gcctgtgtat ttttttagac gtaggcgccg taaacgtatt
5581 ccctattttt ttgcagatgg cgacgtggcg gcctagtgaa aataaggtgt atctacctcc
5641 aacacctgtt tcaaaggttg tggcaacgga ttcctatgta aaacgcacta gtatatttta
5701 tcatgcaggc agttcacgat tgcttgccgt aggacatccc tattactctg tgactaagga
5761 caataccaaa acaaacattc ccaaagttag tgcatatcaa tatagggtat ttagggtacg
5821 gttgcccgac cctaataagt ttgggcttcc agatactaat atttataatc cggaccagga
5881 acggttagtg tgggcatgtg taggtttgga ggtaggccgc ggacagcctt taggtgctgg
5941 gctaagtggc catccattgt ttaataggct ggatgatact gaaagttcca atttagcaaa
6001 taataatgtt atagaagata gtagggacaa tatatcagtt gatggcaagc aaacacagtt
6061 gtgtattgtt ggatgtactc ccgctatggg tgaacattgg actaaaggtg ctgtgtgtaa
6121 gtccacacaa gttaccacag ggactgccc gcctcttgca ttaattaata cacctataga
6181 ggatggggac atgatagaca caggatttgg cgctatggac tttaaggtgt tgcaggaatc
6241 taaggctgag gtacctttag acattgtaca atccacctgt aaatatcctg actatttaaa
6301 aatgtctgca gatgcctatg gtgattctat gtggttttac ttacgcaggg aacaattatt
6361 tgccagacat tattttaata gggctggtaa agttggggaa acaataacctg cagagttata
6421 tttaaagggt agcaatggta gagaaccccc tccgagttct gtatatgttg ctacgcctag
6481 tgggtctatg attacgtctg aggcacagtt atttaataaa ccttattggt tgcaacgtgc
6541 ccaaggccat aataatggca tttgctgggg taatcaatta tttgttactg tagtagatac
6601 tactagaagt actaacatga ctattagtac tgctacagaa cagttaagta aatatgatgc
6661 acgaaaaatt aatcagtacc ttagacatgt ggaggaatat gaattacaat ttgtttttca
6721 attatgcaaa attactttgt ctgcagaggt tatggcatat ttacataata tgaatgctaa
```

Fig. 17, cont.

```
6781 cctactggag gactggaata ttgggttatc cccgccagtg gccaccagcc tagaagataa
6841 atatagatat gttagaagca cagctataac atgtcaacgg gaacagccac caacagaaaa
6901 acaggaccca ttagctaaat ataaattttg ggatgttaac ttacaggaca gtttttctac
6961 agacctggat caatttccac tgggtagaaa atttttaatg caactgggca ctaggtcaaa
7021 gcctgctgta gctacctcta aaaagcgatc tgctcctacc tccacctcta caccagcaaa
7081 acgtaaaagg cggtagtgtg ttgttgtgtg tttgtgtaac tgtgtttgtg tgttgtatat
7141 atggtatgtt tgtgtatgtg ctttatttta tactttgtat gtgtatgttg tgtttgtgta
7201 aatgtttgtg tgaaatgttt gtgtgtgtat tcattgtatg tatgactgta tatatgtgta
7261 atgtttgtgt gtctgtaata aacatgaatg agtgctttta cgcgtggttg cataaactaa
7321 ggtgtgtcat tattgtggct tttgttttgt aagttattgt gtacagtgta ctatgtgtat
7381 tgtgcataca tatatatacc ataacatact ccatttttgtt gtttttccgc cattttgtac
7441 atgcaaccga attcggttgc atggcctagt gccattattt aaactaaaag gaattcggtt
7501 gcatggccta gtgccattat ttaaaccaaa aggccctttt cagcagaaca gttaatcctt
7561 tggcatattg ccgtttcctg tgttttatac ttgaattatg tacagtaccg caccctgtat
7621 tactcacagg tactatgact gccaactatg cttttatctg catactttag tgctgttggg
7681 cacacatttt tatacatgtg tctgcaactt tggtgttttg gcttgcagaa tacactatgt
7741 aggccaagta tctgtcagta tctgttttgc aaacatgtaa catacaatta ctcatttttt
7801 aaaaccgttt acggtcgtgc aaaaacaggt ttcttttaat tgtt
```

Fig. 17, cont.

HPV 66 ATCC # U31794

1 gaaagtttca atcatacttt attatattgg gagtaaccga aatgggttta ggaccgaaaa
61 cggtacatat aaaaggcagc ctgttgtgcc tgtagatatc catggattcc atattcagca
121 atacacagga acgtccacga agcctgcacc atctgagcga ggtattacaa atacctttac
181 ttgatcttag attatcatgt gtatactgca aaaaggaact tacaagttta gagctatata
241 ggtttgcatg tattgagtta aaactagtat atagaaacaa ttggccatat gcagtatgta
301 gggtatgttt attgttttat agtaaggtta gaaaatatag gtactataaa tattcagtgt
361 atggggcaac attagaaagt ataactaaaa aacagttatc tgatttatca ataaggtgct
421 accgatgtca atgtccgtta acaccggagg aaaaacaatt gcactgtgaa cataaaagac
481 gatttcatta tatagcatat gcatggaccg ggtcatgttt gcagtgttgg agacatacga
541 gtagacaagc tacagaatct acagtataac catgcatggt aaagtaccaa cgttgcaaga
601 ggttatatta gaacttgcac cgcaaacgga aattgaccta caatgcaatg agcaattgga
661 cagctcagag gatgaggatg aggatgaaat agaccatttg ctggagcggc cacagcaagc
721 tagacaagct gaacaacata agtgttacct aattcacgta ccttgttgta agtgtgagtt
781 ggtggtgcag ttggacattc agagtaccaa agaggagcta cgtgtggtac aacagctgct
841 tatgggtgcg ttaacagtaa cgtgcccact ctgcgcatca tctaaataac tgcaatggca
901 tcacctgaag gtacagatgg ggaggggatg ggatgttgtg gatggtttca ggtagaagca
961 attgtagaaa gaaaaacggg ggatacaata tcagatgatg aaagcgagga ggagaatgaa
1021 acagatacag atgtagatgg atttatagac aatacactta taaacaatac acaggaagac
1081 agggagacag ctcaacaatt attgcaagta caaacagcac atgcagatgc acagacgttg
1141 caaaaactaa aacgaaagta tataggtagt cccttaagtg atattagtaa tcagcaaact
1201 gtgtaccgag aggaagtaaa acgaaggcta atattatcag aagacagcgg gtatggcaat
1261 acattggaaa cattggaaac atcacaacag gtagaatacg aaaagggaaa tgggtgcggg
1321 agctcacaaa atggaggctc gcaaaacagt aattgtagtg agcactcggt atcaaatatg
1381 gatatagata caaatatgga aacaccaaca caccaattgc aggaactatt taaaagtagt
1441 aacgtacaag gaagattaca ttttaaattt aaagaagtgt atggagtgcc atatacagag
1501 ttggtgcgaa catttaaaag cgatagtaca tgttgtaacg attggatatg tgcaatattt
1561 ggcgttaatg aaacattagc agaggcgtta aaaactatac taaaaccaca atgtgtgtac
1621 tatcatatgc aatgcttaac atgttcatgg ggagtaattg taatgatgct aattagatat
1681 atatgtggaa aaaatagaaa aacaattaca aaatcgctaa gctcaatttt aaatgtacca
1741 caagagcaaa tgttaattca accaccaaaa ctacgaagtc ctgctgtagc attatatttt
1801 tataaaacag caatgtcaaa tattagtgag gtgtatgggg aaacaccaga atggatacaa
1861 agacagacac aattgcaaca cagtttacaa gacaatcaat ttgaattgtc taaaatggta
1921 cagtgggcat ttgataatga agtaacagat gatagccaaa ttgccttttt atatgcacaa
1981 ctagcagaca tagatagcaa tgcacaagca tttttaaaaa gtaatatgca agcaaaatat
2041 gtaaaggatt gtggaataat gtgtagacat tacaaaaggg cacagcaaca gcaaatgaat
2101 atgtgccagt ggataaagca tatatgtagt aaagtagatg aagggggtga ttggaaaccc
2161 attgtgcaat ttttacgata tcaaggggtc gacttcattt catttttaag ttattttaaa
2221 ttatttttac aaggaacgcc taaacataat tgtttggtac tgtgtggacc accaaataca
2281 ggtaaatcat gttttgctat gagccttata aatttttcc aagggtcagt catttcattt
2341 gttaattcac aaagccactt ttggttacag ccactagaca atgccaaatt aggtttgctg
2401 gatgatgcaa cagatacgtg ttggagatac atagatgatt atctaagaaa tttattagat
2461 gggaatccca taagtttaga taggaaacat aaacaattag tacaaataaa atgtcctcca
2521 gttattatta caactaatgt aaatcctatg caagatgcaa aattaagata tttacacagt
2581 agaatttcag tgtttaagtt tgaaaatcca tttccattag ataacaatgg taatcctgtg
2641 tatgaattaa gtaatgtaaa ttggaaatgt tttttgaaa ggacatggtc cagattaaat
2701 ttggataacg acgaggacaa agaaaacaat ggagactcta tcccaacgtt tagatgcgtg
2761 ccagaacaaa atactagact gttatgaaaa agatagtaaa tgcattatag atcacataga
2821 ctattggaaa gctgtacgac atgaatatgt attatattat aaagcaagag aaaatgacat
2881 taatgtacta aaccaccaga tggtgccctc tttacaagtg tgtaaagcaa aagcatgtag
2941 tgcaatagaa ttacaaatag cactggaagc aataagtaac acaatatata aaaatgaaga
3001 gtggacatta cgtgatacat gtgatgaact gtggcgcacg gagcctaaaa actgttttaa
3061 aaaagaagga caacacatag aagtgtggtt tgatggtaac aaaaataatt gtatggaata
3121 tgtggtgtgg aaatttatat attataatgg agagtgtggg tggtgtaaag tgtcatcagg
3181 ggtggattac agaggcatat attatatgca tgatggccac aaaacatatt acacagactt
3241 tgaacaggag gccaaaaaat atgggtgtac aaacatatgg gaagtacata tggaaaccga

Fig. 18

```
3301 gagtatttac tgtcctgact ctgtgtctag tacctgtaga tacaacgtac cccctgttga
3361 gactgttaac gaatacaaca accacaggac caccaccacc gcctccacct ttgtgggcgc
3421 ccaagacgcc gcggtatccc acagaccagg aaaacgaccc agagcaagtg aatcagaacc
3481 tgactcctcc agagagtcct acgcacactg tgtcacaaca gacacagaca tcagtaacaa
3541 cgccaacagt agaagtccac gtatcaacac acaaagccac tgtggtgata aaactacgcc
3601 tgtaatccat ttaaaaggtg aagctaatag attaaagtgt tgtagataca gatttcaaaa
3661 atataaaaca ttatttacag atgtaacaac aacatatcat tggacaagta cagataataa
3721 agacagtagt attattacaa tatatatataa agatgaaaca caacggaca cctttttaaa
3781 tgttgtaaaa ataccaccta gtgtacaggt tattttggga caaatgagtt gtccataaag
3841 tgttgtatat attgtatata catatgtgtt attgtaacac tggtacaggt gaagtgtaat
3901 tgccatacat tgctgctaag catatatatt gcacccatta attgtatttg gtatattatg
3961 tgttattgta acactgggaa aggtaacgtg taatcgccat atattgcaac cattgatttt
4021 tgtgtaattt gtgtgtttgc gctttgcttt tgtgtttgtc tgtgtgtgtg ccattttgtc
4081 ccgcttttgc tatctgcatc tttatttaca agttgtctta tactaattat tttattttgg
4141 tttgttgtgg ctacatcatt ttttgatact tttatactgt ttttactatt tttttatata
4201 cctacactgt gtatatattg ccatgctttg tggttaataa accatttgta acagtagtaa
4261 tttttgctac tatggttgcc caccgtgcca cacgacgcaa acgcgcatct gccacacaat
4321 tatataaaac atgcaaatta tctggtacat gtcctgagga tgttattaat aaggtggagc
4381 aaaaaacatg ggctgatagg attttacaat ggggaagttt atttacatat tttgggggc
4441 ttggcattgg tactgggtct gggtcgggtg gtcgggcggg ctatgttccc ttaggctcta
4501 ggccttctac tatagttgat gtcactcctg cacgaccacc tattgtggtg gagtcagttg
4561 ggcctacaga tccttctatt gttacactgg tagaagaatc tagtgttatt aactcagggg
4621 ctggtgttcc caattttact gggtcagggg gatttgaagt tacatcctct tccacaacca
4681 cacctgctgt gttggatatt acacccacat ctagtactgt acatgtaagt agtactacta
4741 taacaaaccc actatatatt gatcctccag taattgaggc tccacaaact ggagaggtat
4801 ctggtaatat tttgattagc actcctacat ctggaataca tagctatgag gaaataccta
4861 tgcaaacatt tgctatacac ggtactggca acgaacctat tagtagtacc cctattccag
4921 gttttagacg ccttgctgct cccaggttat atagtagggc ttttcagcag gttagggtca
4981 ctgacccagc atttttggac aaccccacaa cattaatatc tgctgataat cctgtttttg
5041 aaggtgctga cacaacgttg acctttctc cctcgggtgt ggctcctgat cctgatttta
5101 tggatatagt tgcattacat aggcctgcat ttactacacg tagaacaggt gtgcgtttta
5161 gtaggctagg caaaaaggct accatgcaaa cacgtagggg tacgcaaata ggtgctcgtg
5221 tgcattatta ttatgatata agtcctattg cacaggctga tgaaattgaa atgcagccat
5281 tattgtctac agacaattca tttgatggcc tatatgatat ttatgcaaat attgatgatg
5341 aggcacccat ttcatttcgt cagtctggtg ctacaccttc tgcacaatta cctattaaac
5401 cttctacatt atcctttgct agtaacacag ctaatgttac tgcccctttg ggaaatgttt
5461 gggaaacacc attttattca ggtcctgata tagttttacc tacaggcccc agtacttggc
5521 ccttcgtacc tcagtctcct tctgatgtta cacatgatgt atatatacag ggagctacat
5581 ttgcactatg gcctgtatat ttttttaaac gtaggcgccg taaacgtatt ccctattttt
5641 ttgcagatgg cgatgtggcg gcctagtgac aataaggtgt acctacctcc aacacctgtt
5701 tcaaaggttg tggcaacgga tacatatgta aaacgtacca gtatatttta tcatgcaggt
5761 agctctaggt tgcttgctgt tggccatcct tattactctg tttccaaatc tggtaccaaa
5821 acaaacatcc ctaaagttag tgcatatcag tatagagtgt ttagggtacg gttgcctgat
5881 cctaataagt ttggccttcc tgatccatct ttctataatc ctgaccagga acgtttggta
5941 tgggcctgtg taggtttgga ggtaggccga ggtcaacctt taggtgctgg gttaagtggt
6001 catccattat ttaataggct ggatgacact gaggtctcta atttagcagg taataatgtt
6061 atagaagata gccgggacaa tatatctgtt gattgtaaac aaacccagtt atgtattgtg
6121 ggatgtgcac cagcattagg ggaacattgg actaagggcg cggtgtgtaa gtctacacca
6181 ggtaatacag gggattgtcc acctcttgca ttagttaata ccccgataga ggacggtgac
6241 atggtggaca ccgggtttgg tgcaatggac tttaagctat tacaggaatc aaaggctgag
6301 gtgccattgg acattgtaca atctacatgt aaatatcctg attatttaaa aatgtctgca
6361 gatgcctatg ggggattctat gtggttttac ttacgcaggg aacaattgtt tgccagacat
6421 tactttaata gggcaggtaa tgttggggaa gccattccta cagatttgta ttggaagggt
6481 ggcaatggca gggaccctcc tcccagttct gtatatgttg ctactcctag tgggtccatg
6541 attacctctg aggcccaatt atttaataaa ccttattggt tgcaacgtgc acagggccat
6601 aataatggca tatgctgggg taatcaggta tttgttactg ttgtggatac taccagaagc
6661 accaacatga ctattaatgc agctaaaagc acattaacta aatatgatgc ccgtgaaatc
6721 aatcaatacc ttcgccatgt ggaggaatat gaactacagt ttgtgtttca actttgtaaa
```

Fig. 18, cont.

```
6781 ataaccttaa ctgcagaagt tatggcatat ttgcataata tgaataatac tttattagac
6841 gattggaata ttggcttatc cccaccagtt gcaactagct tagaggataa atataggtat
6901 attaaaagca cagctattac atgtcagagg gaacagcccc ctgcagaaaa gcaggatccc
6961 ctggctaaat ataagttttg ggaagttaat ttacaggaca gcttttctgc agacctggat
7021 cagtttcctt tgggtagaaa atttttaatg caactaggcc ctagaccccc tagacccaag
7081 gctagtgtat ctgcctctaa aaggcgggcg gctcctacct cttcctcttc ttcaccagct
7141 aaacgtaaaa aacgatagtt gtgtgttgtg tgttgtatgt attgtatggt tgtgcttgta
7201 ctgtatgttt ttgtgtatgt ttatgtattt tataattgtg tatgtgctat gtgtatgtat
7261 gactgtatgt atgtgtaatg ttttgtgtgt atgtaataaa catgcatggt tacttttacg
7321 cgtggttgca taaactaagg tgcggtagta tccttgggca gtgtgtgtca ggttaggtgg
7381 tgttccttac tgtttaatgt tatattaaat aggttgtttg tatgcactat agtaacacac
7441 caaactccat tttagtgctg tacgccattt tatgcatgca accgaattcg gttgcctagc
7501 cttttgtcct tatttaaacc caaaacgact tttcagcaaa acagttaatc ctttggcata
7561 ttgccgtttc ctgttgtatg attcaggtat gtacactgcc ttaccctgta ttactcacct
7621 gtatttctgt gccaactatg cttttatctg catactttgg cgctgttggg catatgtttt
7681 tatgcaggtg tttgcaatat attttgttgg cgtgtagccc ttattgtata agccaagtat
7741 ctgtcttgca aatatgtaac catatactta ctcattttac aaaaccgttt acggtcgtgc
7801 taaaacaggt ttcttttaat tgtt
```

Fig. 18, cont.

HPV 73 ATCC # x94165

1 actataatgt actattaaaa aaaagggtgt aaccgaaaac ggtttcaacc gaaatcggtg
61 catataaaag taggaaagca aaaaacgcta cagattggga aatgctgttt cccaattcag
121 aagaacgacc atacaagcta caagcgttat gtgacgaagt gaatatttct atacatgata
181 taaacctgga ctgtgtgttt tgccaacgtg gactgtacag atctgaggta tatgattttg
241 catttagtga tttgtgtatt gtatatagaa aggataaacc atatggtgta tgtcaaccgt
301 gtttaaaatt ttattctaaa attagagagt ataggcgata tagacaatca gtatatggca
361 ctacgttaga aaatttaact aacaaacagt tatgtaatat tttaataagg tgcggaaaat
421 gccaaaaacc attatgtcca ctggaaaagc aaaagcatgt agatgaaaaa aaacggtttc
481 atcaaatagc agaacagtgg accggacgct gtacacggtg ctggagacca tctgcaactg
541 tggtgtaaga tgcatggaaa aaaaacaacc ttgcaggaca ttactttaga cctgaaacca
601 acaaccgaaa ttgaccttac atgttacgag tcattggaca actcagagga tgaggatgaa
661 acagacagcc atctagacag acaagctgaa cgagagtgtt acagaatagt tactgactgc
721 acgaagtgtc agtgcacagt atgccttgcc attgaaagca acaaagctga tttaagagtg
781 atagaagagt tgcttatggg tacactaggt attgtgtgcc ccaactgttc cagaaaccta
841 taaaagaaga tggctgattc aggtaattgg gaagggaggt gtacgggatg gtttaatgta
901 gaagccattg tagaaagaaa aacaggggat ccaattccag aggatgaaaa ttatgatgga
961 ggggatacag atgagtcgga aatgggggat tttattgata atgcacatat accaaatata
1021 tatgcacaac aggaaattgc acaggcattg tatcagtcac agcaagcaaa tgcagacaat
1081 gaggctatac gtgttctaaa acgaaagttt acaggtagtc ctggcggtag cccagatatg
1141 aaaagagatg aattcataga caaacagctt agtccacaaa taaatgtatt gtcaataagt
1201 agcggtagaa gtacatctaa acgaagactg tttgaggagc aggacagtgg atatggcaat
1261 actgaagtgg aaacttacga gacagaggta ccgggacttg ggcaggggt agggtgttta
1321 caaaatgtta atgaagaagg caaccaaatt gtgtcgccac gtgaaagcag tagtgggtcc
1381 agtagcattt caaatatgga tatagaaaca gagagcacac ctataacaga tattacaaat
1441 ttattacaaa ggaataatgc aaaagcagca ttgctagcaa aatttaaaga agtatatggg
1501 ttaagttata tggaattagt tagaccatat aaaagtgata aaacacattg ccaagattgg
1561 gtgtgtgctg tgtttggtgt aataccctca cttgcagaaa gtttaaaatc cttactaaca
1621 cagtattgta tgtatataca tttgcagtgt ttaacatgta catggggcat aatagtgtta
1681 gtattagtaa gatttaagtg caataaaaat agactaacag tgcaaaaatt attaagtagt
1741 ttattaaatg taacacaaga acgcatgtta attgaacctc caagactacg aagtacacca
1801 tgtgcattat attggtatag aactagttta tcaaatatta gtgaaatagt aggagacaca
1861 cctgagtgga ttaaaagaca aacgttagtg cagcatagtt tagatgatag tcaatttgac
1921 ctatctcaaa tgatacagtg ggcatttgat aatgatataa cagacgactg tgaaatagca
1981 tataaatatg cattattagg caatgtagac agtaatgcag ctgcattttt aaaaagtaat
2041 gcacaagcaa aatatgtaaa agactgtggt acaatgtgca gacattataa agcagcagaa
2101 cgtaaacaaa tgtcaatggc acaatggata caacatagat gtgatttaac taatgatggt
2161 ggtaattgga aagatattgt gctattccta agatatcaaa atgtagaatt tatgcctttt
2221 ttaattacat taaaacaatt tttaaaaggt attcccaaac aaaactgtat agtattatat
2281 ggaccgccag atacaggaaa atcacatttt ggaatgagtt taattaaatt tatacaaggt
2341 gtagttattt cgtatgtaaa ttcaactagt cattttggt tatcaccctt agctgatgca
2401 aaaatggcat tattagatga tgcaacacct ggatgctgga cgtacataga caaatattta
2461 agaaatgcat tagatggtaa tcctatatgt ttagatagaa aacataaaaa tttattacaa
2521 gttaaatgcc ctccattact gataacatca aatacaaatc ctaaagcaga tgatacttgg
2581 aaatatttac atagtagaat taaggtgttt actttttaa atccatttcc atttgacagt
2641 aatgggaacc cactatacca acttactaat gaaaactgga aagcattttt tacaaaaacg
2701 tggtcaaaac tagatttaac agaggacgac gacaaggaaa atgatggaga cactgtgcaa
2761 acgtttaagt gcgtgtcagg acgcaatcct agaactgtat gaacgtgaca gtgtacacct
2821 aagtgatcat attgatcatt ggaaacacgt gcgacatgaa aatgtattat tacataaagc
2881 acgtgaaatg ggactgcaaa ctgttaacaa tcaagcggtg ccaagccttg cagtatcacg
2941 atccaaaggg tataatgcaa ttgaaatgca aatagcacta gaaagtttaa atgaatcttt
3001 gtataacaca gaggaatgga cattgcaaca tacaagttgg gaactgtggg ttacagaacc
3061 taaacaatgt tttaaaaagg atggaaaaac agtagaggtt agatatgact gtgaaaagga
3121 caatagcatg caatatgtat tttggacaca tatatattgt tggtatgaag gggggtgggc
3181 aaaggtaggt agcaaaatag attataatgg tatatattat gaaacagatg atgaggaaaa
3241 ggtatactat acaagatttg atacagatgc aaaacggtac ggggtaaaag gcatatggga

Fig. 19

```
3301 agtacatatg ggtggtcagg taatatgttg tgctcctgta tctagcgcct gtgaagtatc
3361 cattcctgaa attgttaacc cactgcacac cacaaccacc aacaccacca ccacctgcac
3421 caacgttgac accggtgtgc catcacggaa acggcaaaga cagtgtgact cggaccagag
3481 gcccctggat tgtttgcata acctacatcc caccacagag tcctgtaccc agtgtactac
3541 acataatgtt gcgccaatag tgcatttaaa aggtgacaaa aacagcttaa aatgttttag
3601 atatagattg cataaaggct attcacattt atttaaaaat gtaacaacaa catggcattg
3661 gaccaatact acaaatagta aatgtggtgt aataacatta atgtttacaa ctgtattgca
3721 acaacaacat tttttacaac atgtaaaaat accacaaact attgtagtta catcaggata
3781 catgtctttg taacattggt tacacagtat atatgattct ttgtatattt gtatttttgt
3841 tttgtgttgg cttttgtttg tgcttgtgtg tgtcgcttgc agtgtctgtg tatatttacc
3901 catggttatt ggtattgatt ataataacct ttatacatgt atcacaatca ttgttaaaag
3961 tatttttttt atatgttttg gtattttata ttcctatggc acttgtacat taccatgcta
4021 cattacaaat aacataaaca attttacata tataataaac tgcctaatat ttttagtgta
4081 ccatgcgtcg caagcgtgac acacacatac gaaaaaaacg tgcatctgca acacaattat
4141 ataaaacatg taaacaagca ggtacgtgcc ctcctgatgt aattcccaag gttgaaggta
4201 gtactatagc tgataatata ttaaaatatg gtagtattgg agtttttttt gggggattgg
4261 gaataggtag tgggtctgga tcaggggggc gtactggata cgttccatta tctacaggca
4321 caccatctaa accagttgaa attccattac aacctatacg accatcagtt gttacgtctg
4381 ttgggccttc agattcttct attgtttcat tagtggaaga atcaagtttt atagagtcag
4441 gtatacctgg tcctacatct atagtgcctt ctacttcagg gtttgatatt acaacttctg
4501 taaacagtac acctgctatt atagatgtat ctgctattag tgatactaca caaatatctg
4561 ttacaacatt taaaaatcca acctttactg acccatctgt gttgcaacct cctccaccct
4621 tagaagcctc tggcagactt ttattttcaa atgacactgt aactacccat tcatatgaaa
4681 atatacctct tgacacattt gtagttacaa cagaccacaa tagtattgtt agtagtacgc
4741 ccatcccagg gaggcaacct gctgcacgct taggattata tggacgtgca atacaacagg
4801 ttaaggttgt agaccctgcg tttttaacta cgcctacacg tttagtaaca tatgacaacc
4861 ctgcctttga aggcctgcag gatacaacat tagagtttca gcacagtgac ttgcataatg
4921 ctcctgattc tgatttttta gatattgtaa aattacatag gcctgcttta acctctagaa
4981 aaacaggcat acgtgttagt agattgggac aacgtgcaac actttctact agaagtggca
5041 aacgtatagg tgctaaagta catttttatc atgatataag tcctatacct actaatgata
5101 ttgaaatgca acctttagtt acaccacaaa cacctagtat agtaactggt agtagtatta
5161 atgatgggtt atatgatgtg tttttagaca atgatgtaga agagactgta ctacaacaaa
5221 catatacacc tacaagtata catagtaata gtttagttag tagtgatatt tctactgcaa
5281 ctgcaaatac aactattcct tttagtactg ggttagacac acatcctggt ccagatattg
5341 ctttaccact accttctaca gaaactattt ttacaccaat agtgccatta cagcctgctg
5401 gtcctatata tatttatggg tcaggtttta tattacaccc tagttattat ttgttaaagc
5461 gcaaacgtaa acgtctgtca tattctttta cagatgtggc gacctactga tgcaaaggta
5521 tacctgcccc ctgtgtctgt gtctaaggtt gtaagcacag atgaatatgt aacaagaaca
5581 aatatatatt attatgcagg tagcacacgt ttgttggctg tgggacaccc atattttcct
5641 atcaaggatt ctcaaaaacg taaaaccata gttcctaaag tttcaggttt gcaatacagg
5701 gtgtttaggc ttcgtttacc agatcctaat aaatttggat ttccagatgc atccttttat
5761 aatcctgata aggagcgcct agtatgggcc tgttctggtg tggaggttgg acgtggacaa
5821 ccccttaggta taggtactag tggcaatcca tttatgaata aattagatga tactgaaaat
5881 gctcctaaat acattgctgg acaaaaataca gatggtagag aatgtatgtc agtggattat
5941 aaacaaacac agttgtgtat tttaggttgt aggcctccct taggggaaca ttggggtcca
6001 ggcacgccat gtacttcaca aactgttaat actggtgatt gtccccccact ggaattaaag
6061 aacacccccta tacaggatgg tgatatgata gatgttggct ttggagccat ggattttaaa
6121 gctttacaag caaataaaag tgatgtacct attgatattt ctaacactac ctgtaaatac
6181 ccagattatt taggcatggc tgctgatccc tatggtgatt ccatgtggtt ttatcttcgt
6241 agggaacaaa tgtttgttcg acacttattt aacagggctg gtgataccgg tgataaaatc
6301 ccagatgacc taatgattaa aggcacaggc aatactgcaa caccatccag ttgtgttttt
6361 tatcctacac ctagtggttc catggtttct tcagatgcac agttgtttaa taaaccttat
6421 tggttgcaaa aggcacaggg acaaaataat ggtatttgtt ggcataatca attatttttta
6481 actgttgtag atactactag aagcactaat tttctgtat gtgtaggtac acaggctagt
6541 agctctacta caacgtatgc caactctaat tttaaggaat atttaagaca tgcagaagag
6601 tttgatttac agtttgtttt tcagttatgt aaaattagtt taactactga ggtaatgaca
6661 tatatacatt ctatgaattc tactatattg gaagagtgga attttggtct taccccacca
6721 ccgtcaggta ctttagagga aacatataga tatgtaacat cacaggctat tagttgccaa
```

Fig. 19, cont.

```
6781 cgtcctcaac ctcctaaaga aacagaggac ccatatgcca agctatcctt ttgggatgta
6841 gatcttaagg aaaagttttc tgcagaatta gaccagtttc ctttgggaag aaaattttta
6901 ttacaacttg gtatgcgtgc acgtcctaag ttacaagctt ctaaacgttc tgcatctgct
6961 accacaagtg ccacacctaa gaaaaaacgt gctaaacgta tttaataagt gtaatgtgta
7021 tgtgttgttt gttgtatgtt acatgtgttt tgtatgtttg tttgttgtat gttaactgtt
7081 tactaatact gtgtgtatgt ttatgtacat gtgtataact gtttgtttat atatatgtat
7141 gtatttgtgt gtatgtgtat gtgtatgtgt atgtgtagta atgtttgtat gtatgtttaa
7201 taaagtttat atgtgtgttg tgtgggtggt ttacttgact actgtgcttc cattttgtat
7261 agtcgccatt ttacatgcat taaggtaaaa agggcaaccg atttcggttg cacagtaaaa
7321 catgttttaa tgtgttttgc tgttgtagca aaatagttgt actgtttttg gcttcctgca
7381 ggcaacttgg cagggtttgt ttccttaaca tgttcatccc acgcaaggtt ataaaggtaa
7441 aaggcgccac ctggcagtta ctcatttgtc tgcaattatt taaacaatgt cttgcacaca
7501 cattttttac ccaccctatc ataaaattgc ttttaagcac atacctatac tatgtacaca
7561 gtgtactctt ggcagaacat tgttttttaa atgccaagta attgttttat aaatgagtaa
7621 taacgtgtta ctcatactgc acctaaaaag ttaaacctat ttggatcaca caaatgccaa
7681 tttatttctt attacaaata
```

Fig. 19, cont.

HPV 70 ATCC # U21941

1 cttataacat tttacaatca taatttaaaa aaagggaggc accgaaaacg gtcacgaccg
61 aaaacggtgt atataaaacc atgcaaaagt tgcttgccca tacggaatgg cgcgatttcc
121 caatcctgca gaacggccat acaaattgcc tgacctgtgc acggcgctgg acactacatt
181 gcacgacatt acaatagact gtgtctattg taaaacacag ctacagcaaa cagaggtata
241 tgaatttgca tttagtgatt tatttatagt atatagaaac ggggagccat atgctgcatg
301 ccaaaaatgt attaaatttc atgctaaagt aagggaacta cggcattatt cgaactcggt
361 gtatgcaaca actttggaaa gcataactaa taccaagtta tataatttat caataaggtg
421 catgagttgc ctgaaaccat tgtgtccagc agaaaaatta aggcatgtta ataccaaaag
481 aagatttcac caaatagcag gaagctatac aggacagtgc cgacactgct ggaccagcaa
541 ccgggaggac cgcagacgta tacgaagaga aacacaagta taaatataaa tatgcatgga
601 ccacggccga cattgcaaga gattgtttta gatttatatc catacaatga aatacagccg
661 gtcgaccttg tatgtcacga gcaattagaa gattcagaca atgaaacaga tgaacccgac
721 catgtagtta atcaccaaca acaactacta gccagacggg aagaaccaca gcgtcacaaa
781 atacagtgta tgtgttgtaa gtgtaatact acactgcact tagtagtaga agcctcacaa
841 gagaacctgc gatctctact gcagctgttt atggagacac tgtcatttgt gtgtccctgg
901 tgtgcatcgg gaacccagta acctgcaatg gccaattgtg aaggtacaga tggggatggg
961 tcgggatgta acggatggtt cctagtacag gcaatagtag ataaacaaac gggcgacact
1021 gtgtcagagg acgaggacga aaatgcaaca gatacaggtt cagacttggc agactttatt
1081 gatgatacta cagatatttg tgtacaggca gagcgcgaga cagcacaggt actgtataat
1141 atgcaagagg cccaaaggga tgcacaatca gtgcgtgcct taaaacgaaa gtatggaggg
1201 agcaatctaa ataaaagtcc ttgtgcaaaa ccgccaggcg tacataggga acaaagggta
1261 acactacaag agctcccggt aaacatatgc aataaacagg caagaacaaa cgtgtattca
1321 gtaccagaca gcggctatgg caatatggaa gtggaaacag ctgaagtgga ggtaactgta
1381 gtaaataata caaatgggga agaggaaggg gaaaatggcg gggaaaatgg cggcagcata
1441 cgggaggagt gcagtagtgt agacagtgct attgatagtg agaatcaaga tccacagtca
1501 cctactgcac agctaaaaac agtattacag gctaataacc aaaaagccat actactatca
1561 caatttaaac acacatatgg attagcattt aacgacctgg tacgtacatt taaaagtgat
1621 aaaaccatat gtactgactg ggtagcagca atatgtggag taaatcccac catagcagaa
1681 ggctttaaaa cactaattca gccatatgcg ttatatacac atatacagtg tttggatacc
1741 aaatatggag tgtatatact actattaatt agatataaat gtggaaaaaa caggataaca
1801 gtaggcaaag gattaagtaa attattacat gtgccagaaa gttgtatgct aattgaacca
1861 cctaaattgc gtagccctgt tgcagcactg tattggtata gaactggaat gtctaatata
1921 agtgaagtgt caggtactac gccagaatgg atacagcgat taacagtaat acagcatgga
1981 atagatgaca gtgtatttga cctgtctgat atggtacaat gggcatttga taatgatgta
2041 acagaagaca gtgacatagc atatggatat gcattattag cagatagtaa tagtaatgct
2101 gcagcatttt taaaaagtaa ctgccaggca aaatatgtac gcgactgtgc tacaatgtgc
2161 agacattata aaagggcaca aaaaaaacaa atgactatgg cgcaatggat taggtttaga
2221 tgtgataaat gtgacgatgg gggcgactgg cgaccaatag tgcaatttct aaggtatcaa
2281 ggggtagaat ttataacctt tttgtgtgca tttaaggagt ttttaaaggg caccccaaag
2341 aaaaattgca tagtaataca gggaccacca aacacaggca agtcatactt ttgtatgagt
2401 ttaatgcact ttttacaagg tacagtaatt tcatatgtaa attccactag tcattttttgg
2461 ttagagccac ttgcagatgc aaaggtagca atgttggatg atgccacagg cacatgctgg
2521 tcatatttcg atacgtatat gagaaatgca ttagatggaa atcctataag ccttgacaga
2581 aaacatagac atttaataca aattaagtgt ccacccatat taataacatc caataccaat
2641 cctgtagagg aaaataggtg gccataccta actagcagac taacagtgtt tacatttcct
2701 aatgcattcc catttgacca aaacaggaat ccagtgtaca caatcaataa taaaaactgg
2761 aaaagttttt tccaaaagac ttggtgcaaa ttagacttgc agcaggacga ggatgaagga
2821 gacaatgatg gaaacactat cccaacgttt aaatgcgtta caggagaaaa tactagaaca
2881 ttatgaacag gacagtaaac taatatatga tcaaatcaat tattggaaat atgtgcgact
2941 ggaaaatgca atattttatg cagcacggga acgtggcatg catactatag accaccaggt
3001 ggtgccacca ggcactactt caaaagcaaa agcatatcaa gctattgaac tgcagatggc
3061 cctagagagc cttgcacaaa ctgactttaa taaagaggag tggacattaa aggacacaag
3121 taatgaaatg tggcagacaa agccaaaaca atgttttaaa aaaaaaggtg ttacagtgga
3181 ggtgtggtac gatggaaaca aggacaattc tatgcattat gtagtgtggg gagcaatata
3241 ttataaaaca catacagaca cgtggtgtaa aacagaaggg tatgtggatt actggggtat

Fig. 20

```
3301 atattatgtg cacgagcagc ataagacata ttatgaagtg tttaagcagg atgcacaaat
3361 gtatgggact agcggaaaat gggaagtgca ttgtaatggc aacataattc attgtcctga
3421 ctctatgtac agtaccagtg acgacacagt acccactact gagcttactg cagaactaca
3481 acacaccacc ccggcccata ccgccgcaac aaccccatgc accaaaaaaa ctaagtcggc
3541 gccgtcttgc aagtgtggag tctccagacc ctcagaaaca gacggagtgt tcgtggacct
3601 tgttacaagt aaaggctgca acaaacgacg gcaccagtgt tgtggtgaca ctacacctat
3661 agtgcattta aaaggtgaca aaaatggttt aaagtgtctt aggtatcgat tgcgaaaatt
3721 taattcattg tatgaaaata tttcatgtac ttggcattgg ataggggca agggaagtaa
3781 acatacaggt atactaactg taacatatac tactgaagca caacgccaaa aatttttgga
3841 aactgttaga attccaccta gtgtacatgt atctgtggga tatatgacat tgtaacagca
3901 catgctgtat gtatattgta tacatatcaa tgattgcatt ggtgtttttg gtgtggtttg
3961 ctgtatgctt atatatatgt tgcagtgtcc cgcttttgcc gtctgtgcat ttgtgtgcgt
4021 atatgtggct acttttattt gtgtttattg ttgtacatac cacaccattg caaatgtttt
4081 gtatatattt actatttttt atattgccta tgtggttttt acacatcctt tcagtatatg
4141 cttaagttgt gttgctgcat agtgtattgt acattacttg tttttacatt tatattgtac
4201 caataaacat ggtttctagc cgtgcgtcca ggcgtaagcg tgcatctgca acagacatat
4261 ataaaacctg caagcaatca ggcacatgtc cgcctgatgt tgttaataag gtggagggta
4321 ccacactggc tgataggttt ttacaatggg ctagtttagg tatttttttg ggtggtttgg
4381 gaatcggtac gggtactggt actgggggcc gcacagggta cattcctttg gggggtaggc
4441 ctagtacagt tgtagatgtt acccctgcac gtcctcctgt ggttatagaa cctgtaggac
4501 ctacagaacc ttctattgtt cagttggtag aggaatctag tgttgtttcc tctggtacac
4561 ccatccctac ttttacaggc acatctgggt ttgaaattac atcttctgca accacaacac
4621 ctgctgtatt agatattacc cctgcttctg ggtctgttca aattagtacc actagttata
4681 ccaatcctgc atttgctgat ccatcgttaa ttgaggttcc acaaacaggt gaggtgtcag
4741 gcaatatatt tgttactact ccaacatctg gaacacatgg atatgaagaa attcctatgc
4801 aggtttttgc ctcacatgga acaggcacag aacctattag tagtactcct gttcctggtg
4861 ttagtcgtgt ggcaggccca cgtttatata gtagggccta tcatcaggtt cgtgttaata
4921 attttgattt tgtaacccgc ccttcatctt ttgtaacatt tgacaatcca gcttttgagc
4981 ctggtgatac atccttaaca tttgaacctg ctgacacagc tcctgatcca gattttctgg
5041 acattgttcg tttacatcgg cctgctttaa cctcacgacg cggaacagta cgctttagta
5101 ggcttggtaa aaaggccaca atgtttaccc ggcggggtac acaaattggg gcacaggttc
5161 attattatca tgatattagt aacattactg caacagaaga cattgagatg caacctttac
5221 ttacctctga atctacagat ggtttatatg atatatatgc agatgcagat atagataatg
5281 caatgttaca tactacttct catacaggtt ctacaggacc taggtcccat ctttcatttc
5341 cttctatacc ttctacagtg tctacaaaat atagtaatac aaccattcca tttactactt
5401 cttgggacat acctgtaacc actggccctg acatagtttt acctactgca tcccccaatt
5461 tgccctttgt ccctcctaca tctatagata ccacagttgc aatagccatt cagggctcca
5521 attattattt attgccttta ttatattatt ttctaaagaa acgtaaacgt attccctatt
5581 tttttacaga tggctttgtg gcggtctagt gacaacacgg tgtatttgcc accccccttct
5641 gtggcgaagg ttgtcaatac agatgattat gtaacacgta caggcatata ttattatgct
5701 ggaagctctc gcttattaac agtagggcat ccttatttta aggtacctgt aaatggtggc
5761 cgcaagcagg aaatacctaa ggtgtctgca tatcagtata gggtatttag ggtatcccta
5821 cctgatccta ataagtttgg ccttccggat ccttcccttt ataatcctga cacacaacgc
5881 ctggtatggg cctgtatagg tgtggaaatt ggtagaggcc agccattggg cgttggcgtt
5941 agtggacatc ctttatataa tagattggat gatactgaaa attctcattt ttcctctgct
6001 gttagtacac aggacagtag ggacaatgtg tctgtggact ataagcaaac acagttatgt
6061 attataggct gtgttcctgc tatgggagag cactgggcta agggcaaggc ctgtaagtcc
6121 actcaacagg gcgattgtcc accattagaa ttagttaata ctgcaattga ggatggcgat
6181 atgatagata caggctatgg tgccatggac tttcgtacat tgcaggaaac caaaagtgag
6241 gtaccactag atatttgcca atccgtgtgt aaatatcctg attatttgca gatgtctgct
6301 gatgtatatg gggacagtat gtttttttgt ttgcgcaagg aacagttgtt tgccaggcac
6361 ttttggaata gaggtggcat ggtgggcgac acaatacctt cagagttata tattaaaggc
6421 acggatatac gtgagcgtcc tggtactcat gtatattccc cttccccaag tggctctatg
6481 gtctcttctg attcccagtt gtttaataag ccctattggt tgcataaggc ccagggacac
6541 aataatggca tttgttggca taaccagttg tttattactg tggtggacac tacacgtagt
6601 actaatttta cattgtctgc ctgcaccgaa acggccatac ctgctgtata tagccctaca
6661 aagtttaagg aatatactag gcatgtggag gaatatgatt tacaatttat atttcaattg
6721 tgtactatca cattaactgc tgacgttatg gcctacatcc atactatgaa tcctgcaatt
```

Fig. 20, cont.

```
6781 ttggacaatt ggaatatagg agttacccct ccaccatctg caagcttggt ggacacgtat
6841 aggtatttac aatcagcagc tatagcatgt caaaaggatg ctcctacacc tgaaaaaaag
6901 gatccctatg acgatttaaa attttggaat gttgatttaa aggaaaagtt tagtacagaa
6961 ctagatcagt ttcctttggg gcgcaaattt ttactacagg taggggctcg cagacgtcct
7021 actataggcc ctcgcaaacg ccctgcgtca gctaaatcgt cttcctcagc ctctaaacac
7081 aaacggaaac gtgtgtccaa gtaatgtatg tatgttgtat gctgtgtatt attgtactat
7141 tacatatttg tgtttttatg ttgtatgctt gcacactgtt tacatatttg tgtttgtatg
7201 ttgtatgctt gcacactgta ctgtatatgt ttgtcctggt acatatttgt ggttgtatgt
7261 gtatatgttg cgtgctatgt gtatgtttta gaagtatgtg tgtatgtatg tttttgttaa
7321 taaagtatgt atggaggttt catttgtggt tgcaccctgt gactaaggtg ttgtccctgt
7381 tttacatata ataggagtgt gattacccaac atttcctaca taattttatg ccctacccta
7441 aggtgtgtgt ataccatttg tagtttatac atttatattt tatagtgggt tacctgtata
7501 cagcaacggc cattttgtgt gaaaccgttt tcggttgcat ttggctttgt accatcagtt
7561 acccttataa accttttgta tcagcaaaaa catgtcctgt aacctaagtt cacctacata
7621 cttggcacta ctaacagttt tagtggcgca cctacactta gtcatcatcc tgtccaggtg
7681 cactacaaca atgctttggc aaccttatgc acctccaccc tgtctaataa agtgctttta
7741 ggcatgtatt ttacctgttt ttacttacct aagagcatag ttggcctgta taacagcttt
7801 tacatccaag aatgtgtcgt ttggtgcaag ttatattttg tgactaatat ttttacagac
7861 ctgtgtgcaa ccgaaatagg ttgggcagac attcctatac tttta
```

Fig. 20, cont.

| | |
|---|---|
| +1 | 0 |
| 0 | -1 |

Gx

| | |
|---|---|
| 0 | +1 |
| -1 | 0 |

| | | |
|---|---|---|
| 6 | 2 | 0 |
| 3 | 97 | 4 |
| 19 | 3 | 10 |

Fig. 28

| | | |
|---|---|---|
| | | |
| | 4 | |
| | | |

Fig. 29

HUMAN PAPILLOMA VIRUS PROBES FOR THE DIAGNOSIS OF CANCER

This application is a divisional of U.S. patent application Ser. No. 10/959,175, filed Oct. 7, 2004, now U.S. Pat. No. 8,221,970 B2, which claims the benefit under 35 U.S.C. §119(e) of U.S. Provisional Application No. 60/509,205, filed on Oct. 7, 2003, and U.S. Provisional Application No. 60/543,925, filed on Feb. 13, 2004, all of which are hereby incorporated by reference. This application also claims the benefit of priority under 35 U.S.C. §119 to Danish Patent Application No. DK PA 2003 01474.

SEQUENCE LISTING

The instant application contains a Sequence Listing which has been submitted in ASCII format via EFS-Web and is hereby incorporated by reference in its entirety. Said ASCII copy, created on Jun. 19, 2012, is named 9138_14_01_SeqList.txt and is 94,208 bytes in size.

In one embodiment, the invention relates generally to methods of diagnosing cancer or the risk of developing cancer. For example, the invention relates to compositions useful in the diagnosis of cancer or the risk of developing cancer. In one embodiment, the invention relates to methods of diagnosing cervical cancer or the risk of developing cervical cancer.

Cervical cancer is the third most common cancer among women worldwide, preceded only by breast and colorectal cancer. Approximately 371,200 new cases of cervical cancer occur every year, accounting for 10% of all cases of cancer in women (Parkin et al., 1999, *Int. J. Cancer* 80(6):827).

Cytological assays, such as the Papanicolaou (PAP) smear, have traditionally been used in the diagnosis of cervical cancer. A standard PAP smear involves sampling the uterine cervix with a spatula or cytobrush and smearing the cells directly on a slide for staining and light microscopy. The microscopic examination is a tedious process, and requires a cytotechnologist to visually scrutinize all the fields within a slide to detect often few aberrant cells in a specimen. Detection, based on altered cell morphology is subjective and positive samples are often missed.

More recently, testing for cervical cancer has been done using ThinPrep® (Cytyc, Boxborough, Mass.) or SurePath® (Tripath, Burlington, N.C.). These techniques involve placing cell samples directly into a preservative solution. The solution is then used to prepare monolayer slides for staining. The monolayer slides are easier to read. The sensitivity of these assays is still low, with an accurate detection rate in the range of 50-80% of all positive specimens. Thus, a need exists to develop more accurate screening methods for diagnosing subjects having cervical cancer, as well as those at risk for developing cervical cancer. Papilloma viruses have been implicated in the etiology of cervical cancer, thus detection of the presence of a papilloma virus can provide a more objective way to diagnose cervical cancer.

Papilloma viruses are a group of small DNA viruses that in some cases induce warts in higher vertebrates, including humans. Human papilloma virus (HPV) is sexually transmitted, infecting over a million people per year in the United States (WO/0024760). HPV infection can result in genital warts. Persistent high risk HPV infection can result in cancer, such as cervical cancer (Knipe et al., 2001, *Fundamental Virology Fourth Edition*, Lippincott Williams and Wilkins, Philadelphia, Pa.). Papilloma viruses have also been associated with other types of cancer, e.g., epidemodysplasia verruciforms, colon cancer, cancers of the head, neck and mouth (Baron, S. eds., *Medical Microbiology*, 1996, University of Texas Medical Branch, Galveston, Tex.).

There are more than 90 HPV types. HPV types are classified according to the risk associated with the development of cervical cancer. Fifteen types are classified as high-risk. They include HPV types 16, 18, 31, 33, 35, 39, 45, 51, 52, 56, 58, 59, 68, 73 and 82. Three types are classified as probable high risk. They are HPV types 26, 53, and 66. Those with little associated risk of developing cervical cancer include HPV types 6, 11, 41, 42, 43, 44, 54, 61, 70, 72 and 81. High risk HPV types are detected in more than 99% of all cervical cancers.

In one embodiment, the inventors have determined that a single cellular sample can be used to screen for more than one marker for cancer, e.g., cervical cancer. In one embodiment, the present invention provides for a sensitive and specific method for the early detection of any cancer that is characterized by the presence of an HR-HPV infection, e.g., cervical cancer, colon cancer, by providing a method of detecting cancer markers. The method uses probes, comprising full length genomic clones, or fragments thereof, of HPV. The probes may be combined with other means of detecting cancer, e.g., a pap smear, thus ensuring both specificity and sensitivity in the detection of cancer.

In one embodiment, the invention provides a new method of detecting cancer, or the risk of developing cancer, e.g., cervical cancer, comprising performing at least two assays to detect cancer on one sample on a single platform, e.g., a microscope slide. Thus, in one embodiment, cervical cells are placed on a microscope slide and HPV is detected in the sample and the sample is stained for a pap smear. As an example, HPV detection can be done by in situ hybridization using a cocktail of nucleic acid probes that are specific to at least 14 HR-HPV types. In another embodiment, the method can include an assay which detects at least one protein marker for cancer combined with at least one other assay for the detection of cancer, e.g., a PAP stain or in situ hybridization using nucleic acid probes which are specific to at least 14 HR-HPV types, or an additional protein marker. The invention contemplates any combination of assays and particularly where more than one detection method is used on a single sample.

In one embodiment, the invention provides a new method of detecting cancer, or the risk of developing cancer, e.g., cervical cancer, comprising contacting one sample on a single platform, e.g., a microscope slide, with a cocktail of nucleic acid probes which can hybridize to at least 14 HR-HPV types.

In other embodiments, the invention provides an automated method of analyzing a sample for markers that indicate the presence of cancer, or the risk of developing cancer, e.g., cervical cancer. The automated method comprises creating a digital image of a sample that has been contacted with at least two molecules capable of detecting markers for cancer, e.g., a cocktail of nucleic acid probes which hybridize to at least 14 HR-HPVs and a pap stain, saving the digital image to a digital media, such as a computer hard drive or CD, analyzing the digital image using an algorithm which detects and quantifies the molecules used to detect the markers which indicate the presence of cancer, and creating a report which contains information relating to the identification and quantification of markers for cancer.

In other embodiments, the invention provides an automated method of analyzing a sample for markers that indicate the presence of cancer, or the risk of developing cancer, e.g., cervical cancer. The automated method comprises creating a digital image of a sample that has been contacted with a cocktail of nucleic acid probes which hybridize to at least 14

HR-HPVs, saving the digital image to a digital media, such as a computer hard drive or CD, analyzing the digital image using an algorithm which detects and quantifies the molecules used to detect the markers which indicate the presence of cancer, and creating a report which contains information relating to the identification and quantification of markers for cancer.

In other embodiments, the invention provides a new composition useful for the detection of cancer, or the risk of developing cancer, e.g., cervical cancer, comprising a cocktail of nucleic acid probes which specifically hybridize to nucleic acid sequences encoded by HR-HPV genomic DNA. In some embodiments, the nucleic acid probe can hybridize to at least 14 HR-HPV types.

In one embodiment, the invention provides a method of detecting markers for cervical cancer in a subject comprising:

a) obtaining a sample comprising cervical cells from the subject;

b) contacting the sample with a probe comprising, a nucleic acid molecule substantially identical to a full length genomic clone of human papilloma virus 16 (FIG. 1) (SEQ ID NO: 1); and, a nucleic acid molecule substantially identical to a full length genomic clone of human papilloma virus 18 (FIG. 2) (SEQ ID NO: 2); and, a nucleic acid molecule substantially identical to a full length genomic clone of human papilloma virus 51 (FIG. 4) (SEQ ID NO: 4) under conditions such that the probe hybridizes to human papilloma virus nucleic acid contained in the sample; wherein hybridization of the probe to the sample indicates the presence of cervical cancer or the risk of developing cervical cancer. In some embodiments, the probe comprises SEQ ID NO: 1, or a fragment thereof, SEQ ID NO: 2, or a fragment thereof, and SEQ ID NO: 4, or a fragment thereof.

The invention provides a composition comprising a nucleic acid molecule substantially identical to a full length genomic clone of human papilloma virus 16 (FIG. 1) (SEQ ID NO: 1); and, a nucleic acid molecule substantially identical to a full length genomic clone of human papilloma virus 18 (FIG. 2) (SEQ ID NO: 2); and, a nucleic acid molecule substantially identical to a full length genomic clone of human papilloma virus 51 (FIG. 4) (SEQ ID NO: 4); and at least one of the following: a nucleic acid molecule substantially identical to a full length genomic clone of human papilloma virus 11 (FIG. 3) (SEQ ID NO: 3); a nucleic acid molecule substantially identical to a full length genomic clone of human papilloma virus 58 (FIG. 5) (SEQ ID NO: 5); a nucleic acid molecule substantially identical to a full length genomic clone of human papilloma virus 56 (FIG. 17) (SEQ ID NO: 6); a nucleic acid molecule substantially identical to a full length genomic clone of human papilloma virus 66 (FIG. 18) (SEQ ID NO: 7); a nucleic acid molecule substantially identical to a full length genomic clone of human papilloma virus 73 (FIG. 19) (SEQ ID NO: 8); a nucleic acid molecule substantially identical to a full length genomic clone of human papilloma virus 70 (FIG. 20) (SEQ ID NO: 9); a molecule that binds to a protein marker for cancer, e.g., c-Myc, Cox-2, HIF-1α, telomerase markers, such as hTERT, hTR, and other telomerase associated proteins; an extra-cellular matrix marker, such as, Laminin; a proliferation marker, such as, Ki-67 or Histone H3; a cell cycle marker, such as, Cyclin E or, P63, $p16^{INK4a}$; or apoptosis markers, such as Bax, or Bcl-2.

In some embodiments, the invention provides for a composition comprising SEQ ID NO: 1, or a fragment thereof, SEQ ID NO: 2, or a fragment thereof, and SEQ ID NO: 4, or a fragment thereof and at least one of the following: SEQ ID NO: 3, or a fragment thereof; SEQ ID NO: 5, or a fragment thereof; SEQ ID NO: 6, or a fragment thereof; SEQ ID NO: 7, or a fragment thereof; SEQ ID NO: 8, or a fragment thereof; SEQ ID NO: 9, or a fragment thereof; a molecule that binds to a protein marker for cancer, e.g., c-Myc, Cox-2, HIF-1α, telomerase markers, such as hTERT, hTR, and other telomerase associated proteins; an extra-cellular matrix marker, such as, Laminin; a proliferation marker, such as, Ki-67 or Histone H3; a cell cycle marker, such as, Cyclin E, P63 or $p16^{INK4a}$; or apoptosis markers, such as Bax, or Bcl-2.

It is to be understood that both the foregoing general description and the following detailed description are exemplary and explanatory only and are not restrictive of the invention, as claimed.

BRIEF DESCRIPTION OF THE DRAWINGS

FIG. 1 depicts the DNA sequence of the full length genomic clone of HR HPV 16 (SEQ ID NO: 1).

FIG. 2 depicts the DNA sequence of the full length genomic clone of HR HPV 18 (SEQ ID NO: 2).

FIG. 3 depicts the DNA sequence of the full length genomic clone of HPV 11 (SEQ ID NO: 3).

FIG. 4 depicts the DNA sequence of the full length genomic clone of HR HPV 51 (SEQ ID NO: 4).

FIG. 5 depicts the DNA sequence of the full length genomic clone of HR HPV 58 (SEQ ID NO: 5).

FIG. 17 depicts the DNA sequence of the full length genomic clone of HR HPV 56 (SEQ ID NO: 6).

FIG. 18 depicts the DNA sequence of the full length genomic clone of HPV 66 (SEQ ID NO: 7).

FIG. 19 depicts the DNA sequence of the full length genomic clone of HR HPV 73 (SEQ ID NO: 8).

FIG. 20 depicts the DNA sequence of the full length genomic clone of HPV 70 (SEQ ID NO: 9).

FIG. 27 depicts a pair of 2×2 convolution kernels.

FIGS. 28 and 29 depict an example of median filtering of a single 3×3 window.

DESCRIPTION OF THE EMBODIMENTS

A. Definitions

Figure 6:
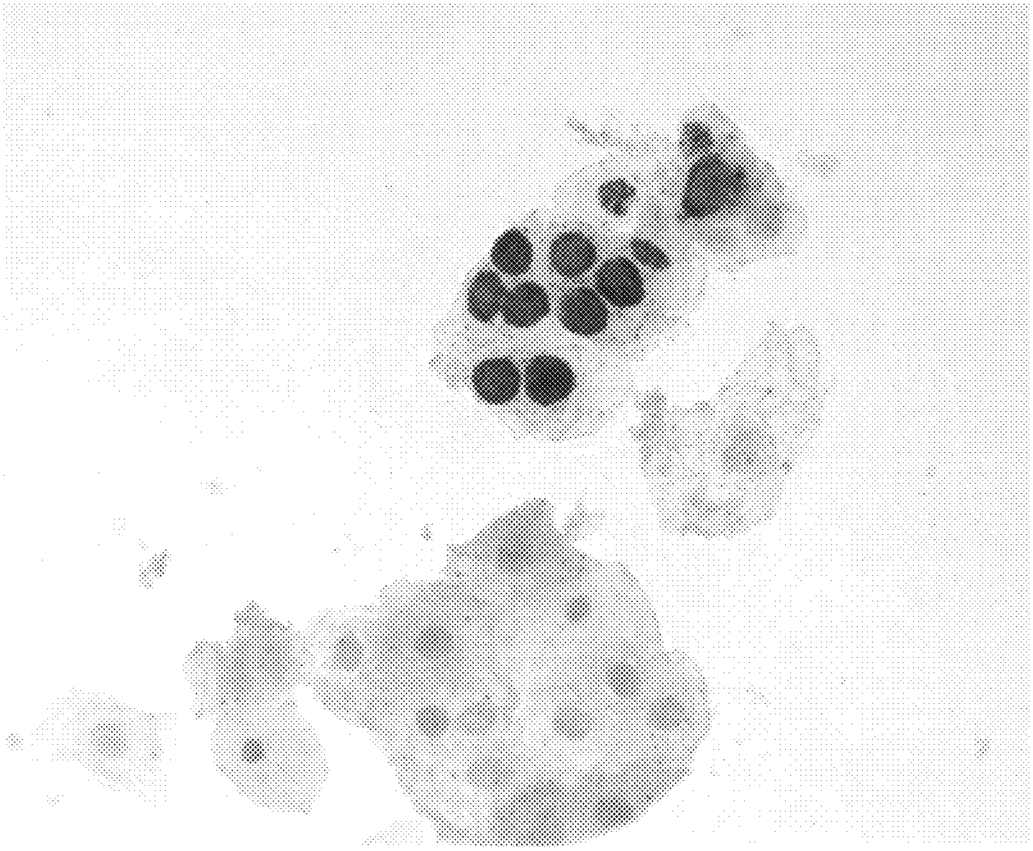
FIG. 6 depicts in situ hybridization (ISH) with an HPV probe cocktail on a cytology sample prepared by the Thin Prep® method (HPV positive sample). HPV positive dysplastic cells displayed brown nuclear staining (400× magnification).
Figure 7:
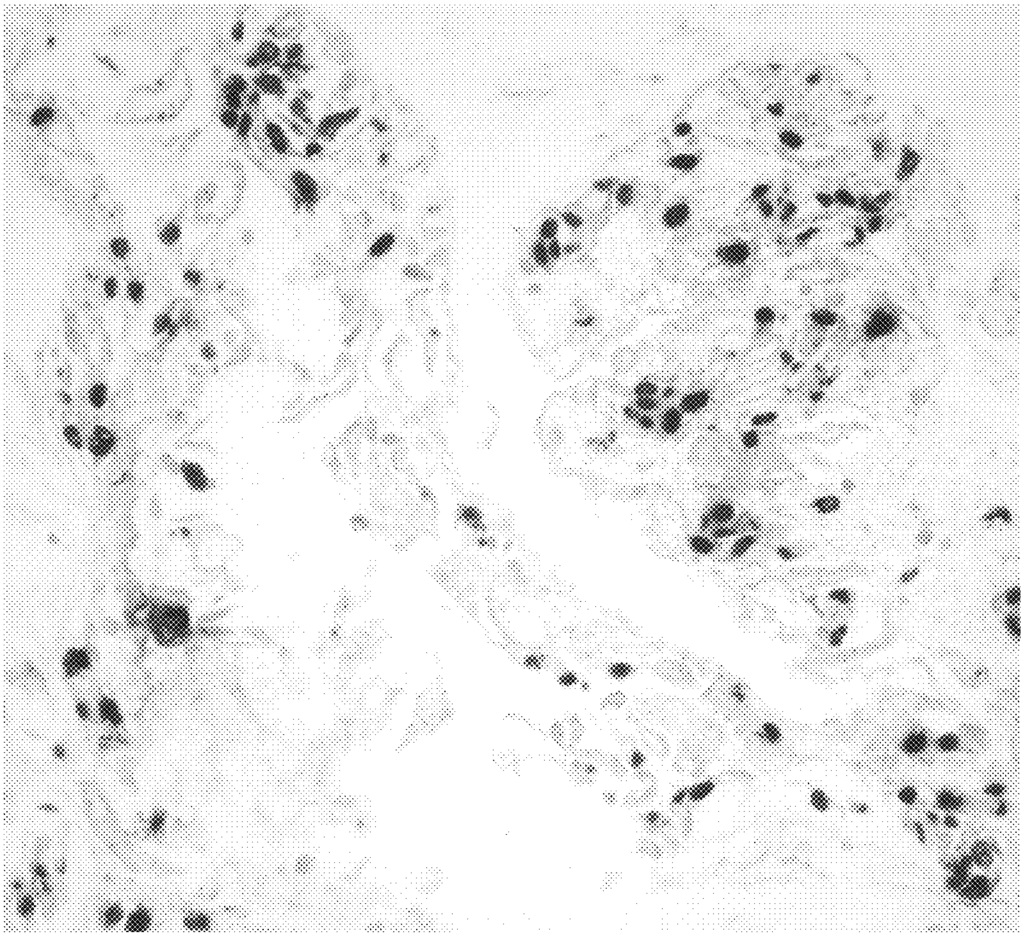
FIG. 7 depicts ISH with an HPV probe cocktail on a cervical biopsy sample that was HPV 16 positive. The HPV probe hybridized to HPV 16 positive cells in the cervical epithelium as demonstrated by brown nuclear staining (200× magnification).
Figure 8:
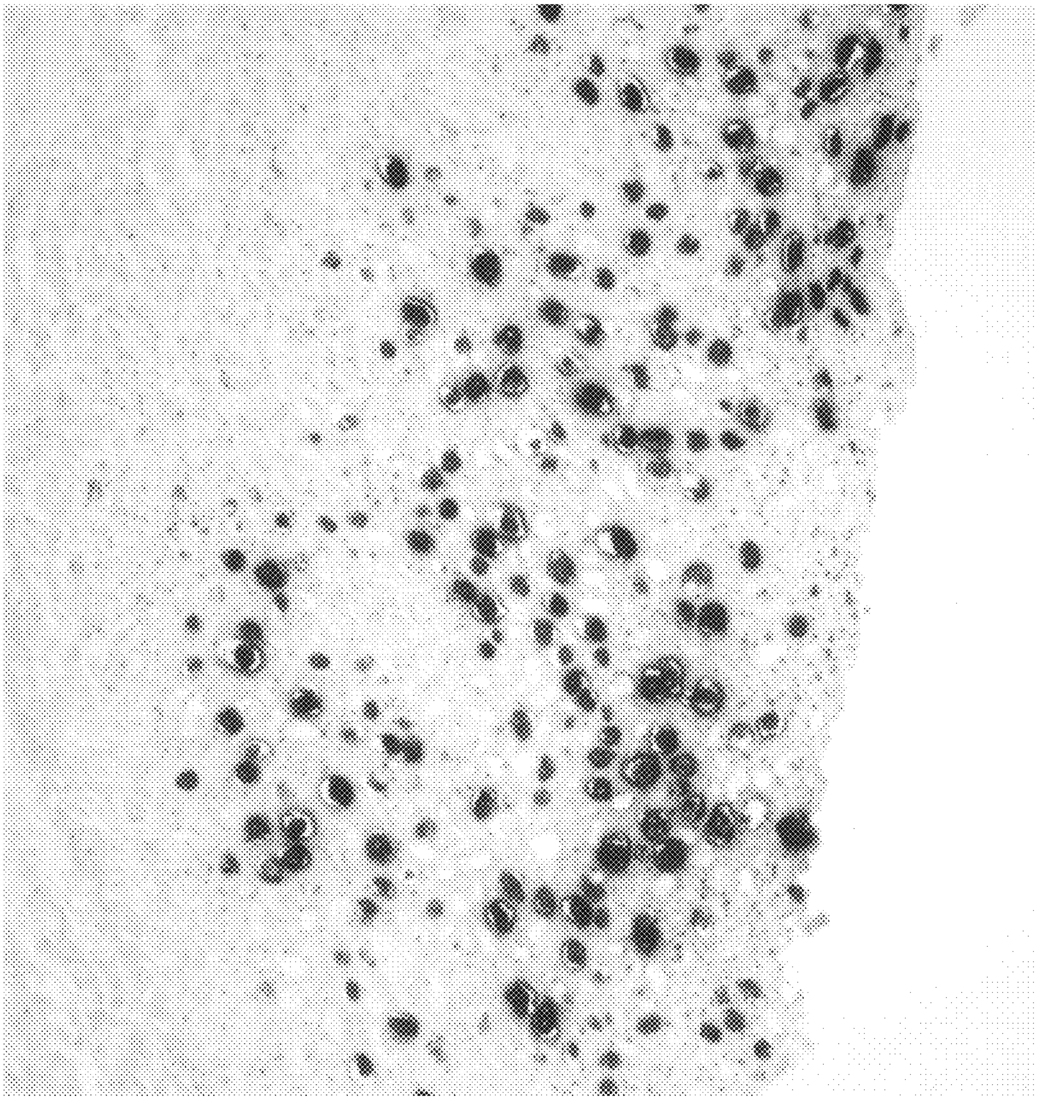
FIG. 8 depicts ISH with an HPV probe cocktail on a cervical biopsy sample that was HPV 18 positive. The HPV probe hybridized to HPV 18 positive cells in the cervical epithelium as demonstrated by brown nuclear staining (200× magnification).
Figure 9:
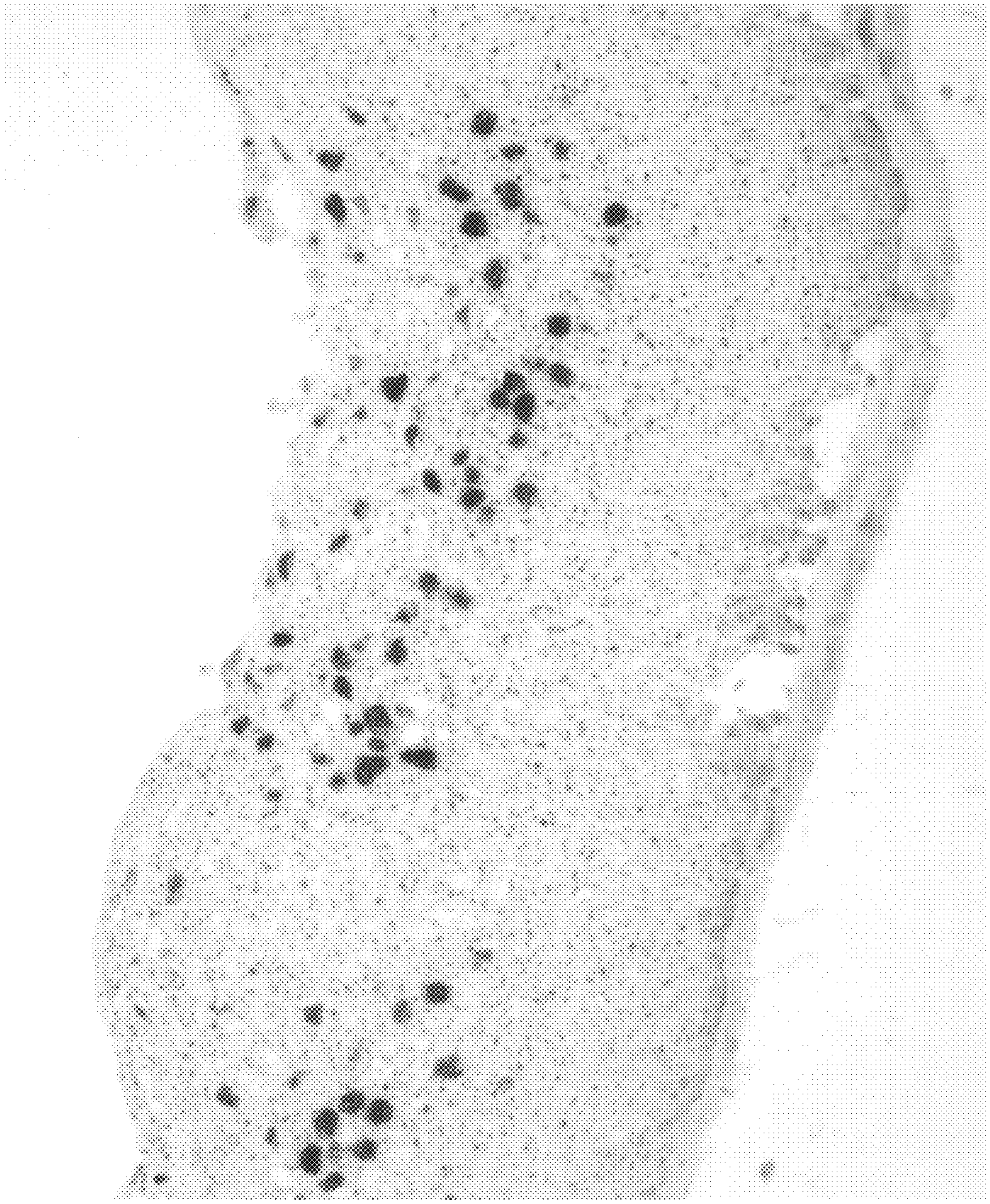
FIG. 9 depicts ISH with an HPV probe cocktail on a cervical biopsy sample that was HPV 31 positive. The HPV probe hybridized to HPV 31 positive cells in the cervical epithelium as demonstrated by brown nuclear staining (200× magnification).
Figure 10:
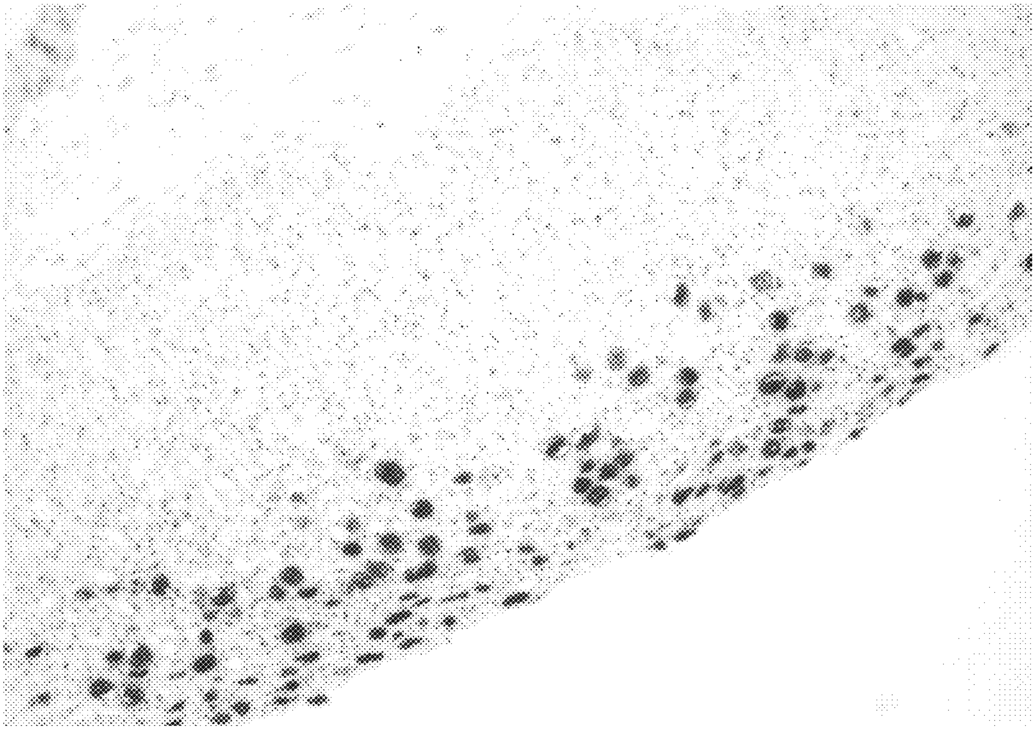
FIG. 10 depicts ISH with an HPV probe cocktail on a cervical biopsy sample that was HPV 33 positive. The HPV probe hybridized to HPV 33 positive cells in the cervical epithelium as demonstrated by brown nuclear staining (200× magnification).
Figure 11:
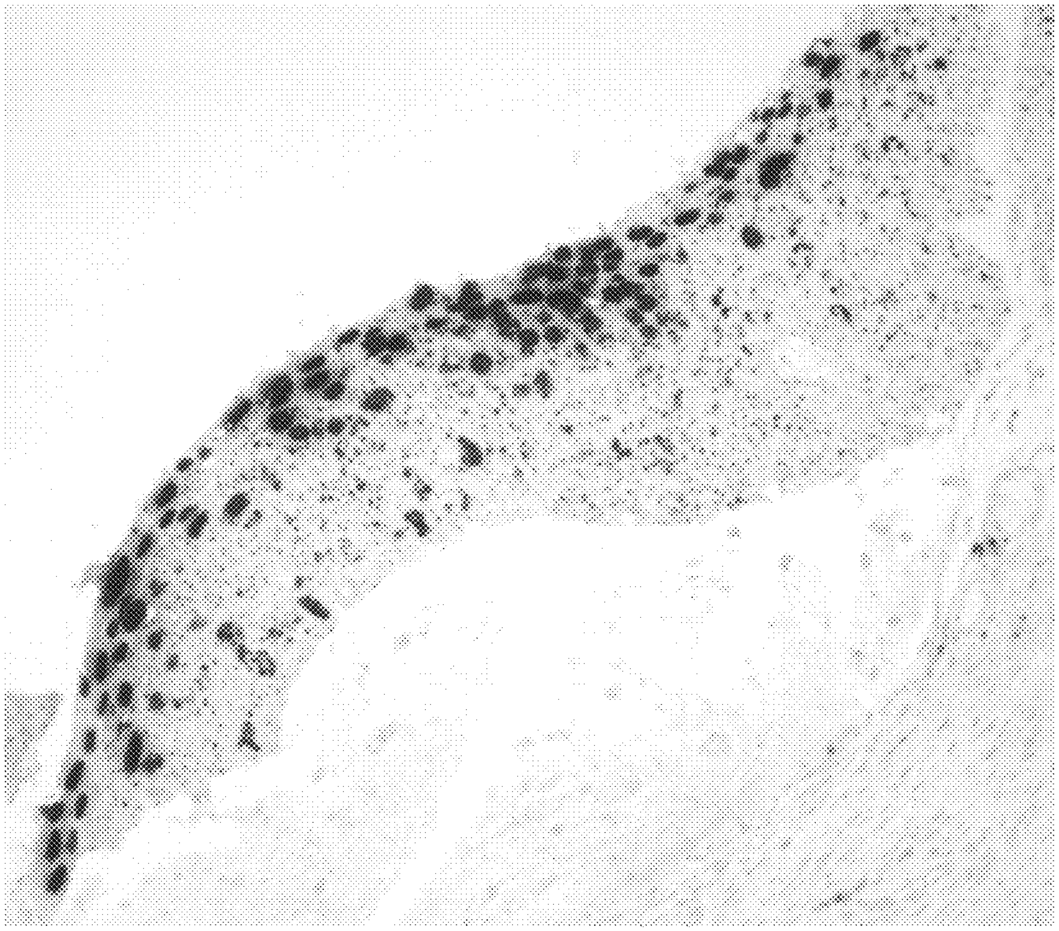
FIG. 11 depicts ISH with an HPV probe cocktail on a cervical biopsy sample that was HPV 51 positive. The HPV probe hybridized to HPV 51 positive cells in the cervical epithelium as demonstrated by brown nuclear staining. (200× magnification).
Figure 12:
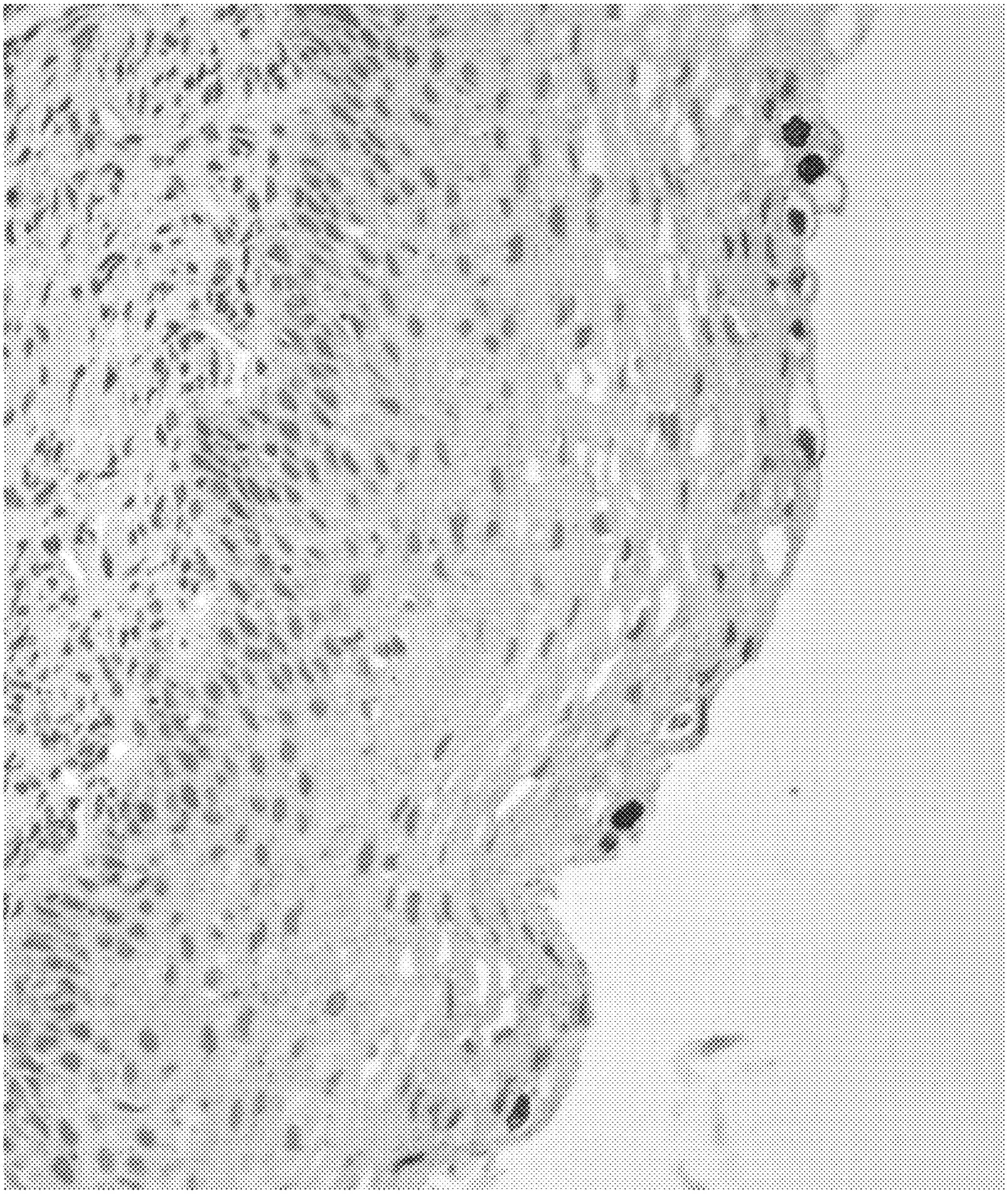
FIG. 12 depicts ISH with an HPV probe cocktail on a cervical biopsy sample that was HPV 52 positive. The HPV probe hybridized to HPV 52 positive cells in the cervical epithelium as demonstrated by brown nuclear staining. (200× magnification).

Antibody, as used herein, means an immunoglobulin or a part thereof, and encompasses any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, an Fab, $F(ab')_2$, Fv, scFv.

Biological information, as used herein, means the type of cell, the predicted cell size, etc.

Cell cycle markers, as used herein, refers to any protein that is involved in the regulation of the cell cycle, including cell cycle checkpoints (for surveillance of the cell cycle process) and cell cycle transition, e.g., entry from one phase of the cell cycle to the next. Examples include activating proteins such as cyclins, kinases, and cyclin dependent kinase inhibitors, e.g., $p16^{INK4a}$.

Cervical cancer, as used herein, means any cancer or cancerous lesion associated with cervical tissue or cervical cells and includes precursors to cervical cancer, e.g., atypical squamous cell of undetermined significance (ASCUS), dysplasia also known as cervical intraepithelial neoplasia (CIN) or squamous intraepithelial lesion (LSIL/HSIL).

As used herein HPV-related cancer relates to any cancer or cancerous lesion, including pre-stages thereof, associated with HPV-infection, e.g. cervical cancer, colon cancer, oral cancer, head and neck cancer, anal cancer, lung cancer, and gastric cancer.

As used herein, all cancer or cancerous lesions include pre-stages thereof.

Chromatic information, as used herein, means the color may be described in different color space, such as hue-saturation-illumination (HSI).

Detectable substance, as used herein, refers to any compound which when attached to a marker contained within a sample, permits recognition of the presence of this marker. The compound can comprise, for example, a radioactive molecule, a fluorescent molecule, a hapten, a carrier, an enzyme, an intervening molecule such as biotin, or a dye.

Digital media, as used herein, includes any material capable of storing a digital signal, e.g., a computer hard drive, a compact disc (CD).

Extra-cellular matrix marker, as used herein, refers to molecules associated with the extra-cellular matrix. The extra-cellular matrix is comprised of collagen fibers, proteoglycans, and multiadhesive matrix proteins. The extra-cellular matrix helps to organize cells into tissues and helps to coordinate cellular function. It provides a route for cellular migration and molecules within the matrix activate signal transduction pathways that induce cell proliferation. Example of extra-cellular matrix markers include laminins, fibronectins and collagens.

HPV-related cancer markers as used herein include markers associated with the cell cycle, e.g. cell cycle regulatory proteins.

As used herein, cancer markers used for e.g. cervical cancer, colon cancer, anal cancer, gastric cancer, oral cancer, neck and head cancer, lung cancer, are cancer markers associated with cancer, cancerous lesions, and pre-stages thereof known in the art as well as disclosed herein. Examples are extra cellular matrix markers, proliferation markers, telomerase markers or telomerase associated markers, cell cycle associated markers, apoptosis markers, c-Myc, Cox-2, HIF-1α

Genomic clone, as used herein, refers to a nucleic acid sequence derived from the genome of a human papilloma virus. Also included within the definition of genomic clone are sequences that are substantially identical to the genome of a human papilloma virus. A full-length genomic clone means the complete nucleic acid sequence encoding a human papilloma virus, or sequences which are substantially identical to the complete nucleic acid sequence encoding a human papilloma virus. The sequence can be derived using any recombinant DNA technology, e.g., PCR, or can be isolated from cultured virus.

Geometric information, as used herein, means the size and shape of a cell.

High resolution, as used herein, means an image with at least 50,000 pixels.

HSI Color Space, as used herein, describes color pixels in terms of hue, saturation, and illumination.

Image resolution reduction, as used herein, means reducing the number of pixels in an image, e.g., from 50,000 pixels per inch to 25,000 pixels per inch to enhance processing time.

Label, as used herein, means an antibody or a probe.

Pre-determined object, as used herein, refers to a way to define expected object characteristics such as color, shape, and size.

Probe, as used herein, refers to at least one nucleic acid molecule or a nucleic acid analog which can hybridize, e.g., by complementary base pairing, under specified conditions, to another nucleic acid molecule, e.g., a portion of an HPV genome. A probe could be selected from the group of: DNA, RNA, LNA or PNA. As used herein this would also include mixtures thereof.

Proliferation marker, as used herein, refers to any protein that promotes cell division or the assembly of control mechanisms of the cell cycle. It can also refer to any protein that characterizes the proliferation status of a cell. A cell can be at an active, retarded or arrested state of proliferation. Examples include Ki-67, Histone H3 and cdc25.

Sample, as used herein, means a suitable quantity of cells or tissue, e.g., cervical cells, or cervical tissue, for testing for the presence of cancer, e.g., cervical cancer or any HPV-related cancer. The sample can take the form of a biopsy, a smear, or a swab containing cells.

Segmentation, as used herein, means the process of dividing an image into a number of individual objects or contiguous regions, differentiating them from each other and the image background.

Solid support, as used herein, means any three dimensional, non-liquid, surface upon which a sample is placed. The solid support can be comprised of any suitable material, e.g., glass, plastic. Examples of a solid support include a microscope slide, a chip, a micro-array, a bead, and a microtiter plate.

Subject, as used herein, means a human, having, or suspected of having, cancer.

Substantially identical, as used herein, means that two or more nucleic acid sequences, are at least 50% identical, at least 60% identical, at least 70% identical, at least 80% identical, at least 90% identical, at least 95% identical, at least 99% identical, at least 99.9% identical, when compared and aligned for maximum correspondence as measured by either visual inspection or by using one of the algorithms described below. Substantially identical sequences are typically considered to be homologous. Substantial identity may exist over a region of the sequences that is at least 50 residues in length, at least 100 residues in length, at least 150 residues in length, or over the full length of the sequences to be compared. Two sequences can be substantially identical where at least one of the sequences has at least one nucleotide substitution, at least one nucleotide addition, or at least one nucleotide deletion. Percent identity between two nucleic acid sequences may be determined by standard alignment algorithms such as, for example, Basic Local Alignment Tool (BLAST) described in Altschul et al. 1990, *J. Mol. Biol.,* 215:403-410 (hereby incorporated by reference); the algorithm of Needleman et al. 1970, *J. Mol. Biol.,* 48:444-453; the algorithm of Meyers et al. 1988, *Comput. Appl. Biosci.,* 4:11-17 (hereby incorporated by reference); or Tatusova et al. 1999, *FEMS Microbiol. Lett.,* 174:247-250 (hereby incorporated by reference). Such algorithms are incorporated into the BLASTN, BLASTP and "BLAST 2 Sequences" programs (see www.ncbi.nlm.nih.gov/BLAST). When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. Percent identity between two nucleic acids may also be determined using commercially available software such as Vector NTI Suite (Invitrogen, Carlsbad, Calif.).

Topological information, as used herein, refers to how cells are organized and related to each other. For example, a membrane surrounds a nucleus or a group of cells clustered together, etc.

B. Human Papilloma Virus Probes

Persistent infection of cervical epithelia with high risk human papilloma virus (HR HPV) can lead to cancer, such as cervical cancer, colon cancer, anal cancer, gastric cancer, oral cancer, neck and head cancer, lung cancer, etc. Detection of HR HPV can thus be used to screen for any cancer or risk for developing cancer, particularly any HR HPV related cancer such as cervical cancer, colon cancer, anal cancer, gastric cancer, oral cancer, neck and head cancer, lung cancer, etc. The invention, in one embodiment, is based in part on the discovery that certain HR HPVs share significant sequence homology throughout their genome. Thus, probes derived from HR-HPV types will crossreact with other HR-HPV types. Accordingly, the invention, in one embodiment, provides for a cocktail of nucleic acid molecules, i.e., probes, comprised of HR HPV genomic clones, e.g., DNA, or fragments thereof, which have a high degree of homology to HR HPV types. HR HPV type 16, 18 and 51, share significant homology with 14 of the 15 known HR HPV types. These include HR HPV types 16, 18, 31, 33, 35, 39, 45, 51, 52, 56, 58, 59, 68, and 82. HR HPV 16 share more than 70% homology with HR HPV types 31, 33, 35, 52, and 58. HR HPV 18 share more than 70% homology with HR HPV types 39, 45, 59, and 68 and 60% homology with HPV type 56. Type 51 shares more than 70% homology with HR types 26 and 82 and 60% homology with HR HPV 56.

In some embodiments, the invention provides a composition comprising a full length genomic clone of HR HPV types 16, 18 and 51. In other embodiments, the invention provides a composition comprising a full length genomic clones of HR HPV types 16, 18 and 51, and at least one full length genomic clone, or fragment thereof, of HR HPV types 56 and 58. In some embodiments, the invention provides for a composition comprising a full length genomic clones of HR HPV types 16, 18 and 51 and at least one probe that is substantially identical to a full length genomic clone, or fragment thereof, of HR HPV types 56, 58, 66, and 73.

In some embodiments, the invention also provides for at least one probe, which hybridizes to at least one low risk HPV type, comprising at least one of the following: a nucleic acid molecule, comprising a full length genomic clone of HPV 11 (SEQ ID NO: 3), or fragment thereof, or a nucleic acid molecule substantially identical to SEQ ID NO: 3, or a full length genomic clone of HPV 70 (SEQ ID NO: 9), or fragment thereof, or a nucleic acid molecule substantially identical to SEQ ID NO: 9 (a low risk probe), or a mixture thereof.

In some embodiments, the low risk probe can be a blocking probe, i.e., a probe that prevents the HR-HPV specific probes contained in the nucleic acid cocktail from hybridizing with low risk HPV. Thus, in one embodiment, the blocking probe is not labeled with a detectable substance. In another embodiment, the low risk probe is labeled with a detectable substance that is different from the detectable substance used to label the HR-HPV nucleic acid probe so that low risk HPV and HR HPV can both be detected.

In some embodiments, the invention provides for a cocktail comprising genomic clone fragments of HR HPV. The genomic clone fragments can include fragments comprising nucleic acids from HR HPV types 16, 18 and 51 and optionally, at least one genomic clone fragment comprising nucleic acids from HR HPV types 56, 58, 66 and 73. In some embodiments, the fragment of HR HPV 56 comprises at least 10 nucleotides. In other embodiments, the fragments can be any length so long as they hybridize to at least 14 HR HPV types, e.g., HR HPV types 16, 18, 31, 33, 35, 39, 45, 51, 52, 56, 58, 59, 68 and 82, when combined in a nucleic acid cocktail comprising at least one other probe. The full length genomic clones, or fragments thereof, also include nucleic acid sequences which are substantially identical to the full length genomic clones or fragments thereof.

In some embodiments, fragments of the full length HR HPV genomic clones or LR HPV genomic clones may be any fragment of the full length genomic clone generated after enzymatic cleavage, such as DNase I cleavage, of the full length genomic clone is disclosed in the present invention. Such fragments are usually in a range of about 10-500 bp, such as about 10, 20, 30, 40, 50, 60, 70, 80, 90, 100, 200, 300, 400, or about 500 bp.

In some embodiments, fragments thereof is any fragment of the full length genomic HPV clone, such as 20, 30, 40, 50, 60, 70, 80, 90, 95, or even 99% of full length.

In some embodiments, the probe is comprised of DNA. In other embodiments, the probe is comprised of RNA. In yet other embodiments, the probe is comprised of a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments the probe is comprised of locked nucleic acids (LNA) (Sorenson et al. 2003, *Chem. Commun.* 7(17):2130).

In some embodiments, the HR HPV probes hybridize to a target sequence in a sample, e.g., a nucleic acid sequence encoding the HR HPV genome, under specific conditions of stringency. As used herein, the term "hybridization under stringent conditions," is intended to describe conditions for hybridization and washes under which nucleotide sequences that are significantly identical or homologous to each other remain complementarily bound to each other. The conditions are such that sequences at least about 70%, more preferably at least about 80%, at least about 85-90% identical remain bound to each other. The percent identity is determined as described in Altschul et al. (1997) *Nucleic Acids Res.* 25:3389-3402 (hereby incorporated by reference).

Specified conditions of stringency are known in the art and can be found in Current Protocols in Molecular Biology, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual, 2nd ed.* Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at about 65-70° C. or hybridization in 4×SSC plus 50% formamide at about 42-50° C., followed by one or more washes in 1×SSC, at about 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the HR HPV probes hybridize to a target sequence in a sample, e.g., a nucleic acid sequence encoding the HR HPV genome, under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual,* 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the HR HPV probes hybridize to a target sequence in a sample, e.g., a nucleic acid sequence encoding the HR HPV genome, under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×$10^6$ CPM probe is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

The invention contemplates that the hybridization reaction can be automated. The slides will be automatically processed in a well controlled environment for the following steps: deparaffinization or conditioning, pre-treatment to provide probe access to the target, addition of the probe to the sample, denaturation of the probe and the target, hybridization of the probe to the target, stringency wash, and signal detection steps.

The invention contemplates that the antibody binding reaction, for detecting protein markers for cancer, can be automated. The slides will be automatically processed in a well controlled environment for the following steps: deparaffinization or conditioning, pre-treatment to provide antibody access to the target, addition of the antibody to the sample, and signal detection steps. Wash steps are included between each step.

C. HR HPV Probe Labels

The invention also provides for HR HPV probes which are labeled with a detectable substance. The detectable substance may be directly linked to the HR HPV probe, e.g., by a covalent or non-covalent bond. The detectable substance may be linked to the HP HPV probe indirectly, e.g., through an intervening molecule such as strepavidin or biotin. The detectable substance, for example, may be a fluorescent material, a dye, a chemiluminescent material, a bioluminescent material or a radioactive material, e.g., tritium, $^{32}$P. The detectable substance can take the form of any suitable molecule, e.g., an enzyme, a hapten, biotin.

Examples of fluorescent detectable substances include fluorescein isothiocyanate, rhodamine, phycoerythrin, phycocyanin, allophycocyanin, o-phthaldehyde and fluorescamine. When the fluorescently labeled substance is exposed to light of the proper wave length, its presence can then be detected due to fluorescence. Other fluorescent substances include fluorescence emitting metals such as $^{152}$Eu, or others of the lanthanide series. Fluorescent substances can be detected directly or indirectly using a hapten.

Examples of chemiluminescent substances include luminol, isoluminol, theromatic acridinium ester, imidazole, acridinium salt and oxalate ester. Examples of bioluminescent compounds for purposes of labeling include, luciferin, luciferase and aequorin.

In another embodiment, the detectable substance may be an enzyme. Catalysis of the enzyme substrate can result in a color change. The enzyme may be, for example, horseradish peroxidase, or alkaline phosphatase. Other additional detectable substances include, for example, digoxigenin, DNP and biotin.

Peroxidase, and phosphatase enzymes are naturally present in human tissues. These enzymes are called endogenous enzymes. When performing immuno-histo-chemistry (IHC) or in situ hybridization (ISH) it is important to distinguish between the endogenous enzymes and the enzymes added as part of the IHC or ISH label, otherwise the endogenous enzymes will react with the chromogenic substrate producing a color which cannot be distinguished from a true positive result. Generally, the endogenous enzymes are suppressed or blocked before performing the IHC or ISH stain. Reagents have been developed that can be applied to the tissues to block either endogenous peroxidase or endogenous alkaline phosphatase. Accordingly, the invention contemplates a method of performing IHC or ISH using either peroxidase or phosphatase which relies on a single reagent that can block both enzymes simultaneously. In one embodiment, the method for performing multi-staining in tissue or cell samples comprises simultaneously blocking endogenous expression of both peroxidase and alkaline phosphatase enzymes by applying a single blocking reagent. In certain specific embodiments the single blocking agent comprises the following: a chelating agent and hydrogen peroxide, where the reaction occurs at a pH <2.

D. Cellular Markers for Cancer

Combining detection of protein markers for cancer, such as any HPV-related cancer, e.g., cervical cancer, colon cancer, anal cancer, gastric cancer, oral cancer, neck and head cancer, lung cancer, etc., with the HR HPV probes, and optionally the LR HPV probes, described above in methods of detecting cancer in a subject may increase both the specificity and the sensitivity of the method of detecting cancer, such as any HPV-related cancer, e.g., cervical cancer, colon cancer, anal cancer, gastric cancer, oral cancer, neck and head cancer, lung cancer, e.t.c. Combining detection of more than one protein marker for cancer in methods of detecting cancer, such as any HPV-related cancer, e.g., cervical cancer, colon cancer, anal cancer, gastric cancer, oral cancer, neck and head cancer, lung cancer, etc., may increase both the specificity and the sensitivity of the method of detecting cancer. Numerous markers for cancer, such as HPV-related cancer, e.g. cervical cancer, colon cancer, etc., have been described. Said markers for cancer may be detected by contacting a sample with a label that binds to the marker, e.g., an antibody or a probe. Examples of markers to detect cancer, such as any HPV-related cancer, e.g. cervical cancer, colon cancer, anal cancer, gastric cancer, oral cancer, neck and head cancer, lung cancer, etc., are given below.

The p16$^{INK4a}$ protein is a cyclin-dependent kinase inhibitor that decelerates the cell cycle. Recent studies have indicated that p16$^{INK4a}$ expression is influenced by the status of Rb expression. p16$^{INK4a}$ overexpression has been demonstrated in cervical cancer because of the functional inactivation of the retinoblastoma protein by the HPV E7 protein (Sano et al. 1998, *American Journal of Pathology,* 153:1741). Accordingly, the invention provides for screening for p16$^{INK4a}$ expression as a means of detecting cervical cancer. In some embodiments, detection of p16$^{INK4a}$ is combined with detection of at least one other marker for cervical cancer, e.g., the presence of HR HPV. The p16$^{INK4a}$ marker will sometimes detect a small fraction of metaplastic and columnar cells resulting in a false positive signal. This problem is alleviated by combining p16$^{INK4a}$ with a second marker which ensures the desired specificity and sensitivity.

Laminin 5 is an attachment protein for epithelial cells. Studies indicate that its expression is increased in the cytoplasm and basement membrane of cervical epithelium and expression correlates with the grade of dysplasia. (Kohlberger et al. 2003, *Gynecology Oncology,* 89:391). Accordingly, the invention provides for screening for Laminin 5 expression as a means of detecting cervical cancer. In some embodiments, detection of Laminin 5 is combined with detection of at least one other marker for cervical cancer, e.g., the presence of HR HPV.

Cox-2 expression has been found to correlate with lymph node metastasis and parametrial invasion in cervical cancer (Kim et al. 2003, *Gynecology Oncology,* 90:83). Accordingly, the invention provides for screening for Cox-2 expression as a means of detecting cervical cancer. In some embodiments, detection of Cox-2 is combined with detection of at least one other marker for cervical cancer, e.g., the presence of HR HPV.

Certain tumors, including squamous cell carcinoma of the uterine cervix, with low oxygen tension respond poorly to chemotherapy, radiotherapy or even surgery (Hockel, 1996, *Cancer Res* 56:4509). Several genes responsive to stresses of the microenvironment, such as low oxygen, have been identified (Denko, 2000, *Clin Cancer Res* 6:480). Tissue hypoxia is indicated by the expression of Hypoxia-inducible Factor 1a (HIF-1α). In cervical cancer the over expression has been found to be associated with diminished tumor response to radiotherapy (Bachtiary, 2003 *Clin Cancer Res* 9:2234). Furthermore, HIF-1α expression is increased in dysplasia compared to benign epithelia. Focal HIF-1α expression is seen near necrotic areas in invasive squamous cell carcinomas and correlates with the spatial distribution. (Acs, G 2003 *Am J Pathol* 162:1789). Thus, HIF-1α expression is a cellular marker for cervical cancer. Accordingly, the invention provides for screening for HIF-1α as a means of detecting cervical cancer. In some embodiments, detection of HIF-1α is combined with detection of at least one other marker for cervical cancer, e.g., the presence of HR HPV.

Other markers for cervical cancer include hTERT (Ferber et al. 2003, *Oncogene* 22:3813), Ki-67 (Kruse et al. 2002, *Am. J. Surg. Pathol.,* 26:1501), cyclin E (Yasmeen et al. 2003, *Expert Rev. Mol. Diagn.* 3(5):617) and histone H3 (Rakowicz-Szulczynska, et al. 1996, *Cancer Biother. Radiopharm.* 11:77). Accordingly, the invention provides for screening for hTERT expression as a means of detecting cervical cancer. In some embodiments, detection of hTERT is combined with detection of at least one other marker for cervical cancer, e.g., the presence of HR HPV. The invention also provides for screening for Ki-67 expression as a means of detecting cancer, such as any HPV-related cancer, e.g. cervical cancer, colon cancer, anal cancer, gastric cancer, oral cancer, neck and head cancer, lung cancer, e.t.c. In some embodiments, detection of Ki-67 is combined with detection of at least one other marker for cervical cancer, e.g., the presence of HR HPV. The invention also provides for screening for histone H3 expression as a means of detecting cervical cancer. In some embodiments, detection of histone H3 is combined with the detection of at least one other marker for cervical cancer, e.g., the presence of HR HPV.

PAP smears are commonly used to detect cervical cancer. A PAP smear involves applying cervical cells to a slide, staining the cells and examining the cells by light microscopy. Altered cell morphology indicates dysplasia or neoplasia. The invention thus provides for pap screening as a means of detecting cervical cancer. In some embodiments, a PAP smear is combined with detection of at least one other marker for cervical cancer, e.g., the presence of HR HPV.

E. Compositions for Detecting Cancer Markers

The invention discloses a probe composition for detection of cancer markers. The composition comprises a nucleic acid molecule substantially identical to a full length genomic clone of human papilloma virus 16 (SEQ ID NO: 1), or a fragment thereof, or a nucleic acid molecule substantially identical to SEQ ID NO: 1; and a nucleic acid molecule substantially identical to a full length genomic clone of human papilloma virus 18, (SEQ ID NO: 2), or a fragment thereof, or a nucleic acid molecule substantially identical to SEQ ID NO: 2; and a nucleic acid molecule substantially identical to a full length genomic clone of human papilloma virus 51 (SEQ ID NO: 4), or a fragment thereof or a nucleic acid molecule substantially identical to SEQ ID NO: 4.

In other embodiments, the composition further comprises at least one of:

a) a nucleic acid molecule substantially identical to a full length genomic clone of human papilloma virus 11 (SEQ ID NO: 3), or fragments thereof, or a nucleic acid molecule substantially identical to SEQ ID NO: 3;

b) a nucleic acid molecule substantially identical to a full length genomic clone of human papilloma virus 58 (SEQ ID NO: 5), or fragments thereof, or a nucleic acid molecule substantially identical to SEQ ID NO: 5;

c) a nucleic acid molecule substantially identical to a full length genomic clone of human papilloma virus 66 (SEQ ID NO: 7), or a fragment thereof, or a nucleic acid molecule substantially identical to SEQ ID NO: 7;

d) a nucleic acid molecule substantially identical to a full length genomic clone of human papilloma virus 73 (SEQ ID NO: 8), or a fragment thereof, or a nucleic acid molecule substantially identical to SEQ ID NO: 8;

e) a nucleic acid molecule substantially identical to a full length genomic clone of human papilloma virus 70 (SEQ ID NO: 9), or a fragment thereof, or a nucleic acid molecule substantially identical to SEQ ID NO: 9;

f) a nucleic acid molecule substantially identical to a full length genomic clone of human papilloma virus 56 (SEQ ID NO: 6), or a fragment thereof, or a nucleic acid molecule substantially identical to SEQ ID NO: 6.

Further embodiments of the invention include compositions wherein the nucleic acid is comprised of DNA, RNA, LNA or PNA. In these embodiments the sequence of the nitrogenous bases comprising the composition are the same as or substantially the same as the sequences recited infra.

In further embodiments, the composition further comprises at least one additional molecule that binds at least one protein marker for cancer or that binds at least one additional nucleic acid encoding a protein marker for cancer.

Further embodiments of the invention may include compositions wherein the at least one protein marker for cancer is chosen from p16$^{INK4a}$ P63, c-Myc, Cox-2, HIF-1α, a telomerase markers, a telomerase associated protein; an extra-cellular matrix marker; a proliferation marker; a cell cycle marker; or an apoptosis marker.

Still further embodiments of the invention may include compositions wherein the molecule that binds the at least one protein marker for cancer is an antibody.

Still further embodiments of the invention may include compositions wherein the molecule that binds the at least one further nucleic acid encoding a protein marker for cancer is a nucleic acid.

Still further embodiments of the invention may include compositions wherein the nucleic acid encodes a protein chosen from p16$^{INK4a}$, P63, c-Myc, Cox-2, HIF-1α, a telomerase markers, a telomerase associated protein; an extra-cellular matrix marker; a proliferation marker; a cell cycle marker; or an apoptosis marker.

Still further embodiments of the invention may include compositions wherein the nucleic acid molecules are labeled with a detectable substance.

Still further embodiments of the invention may include compositions wherein the detectable substance is covalently linked to the nucleic acid molecule.

Still further embodiments of the invention may include compositions wherein the detectable substance is linked to an intervening molecule.

Still further embodiments of the invention may include compositions wherein the intervening molecule is biotin.

Still further embodiments of the invention may include compositions wherein the intervening molecule is streptavidin.

Still further embodiments of the invention may include compositions wherein the detectable substance is chosen from a fluorescent material, a chemiluminescent material, a bioluminescent material, an enzyme, and a radioactive material.

In yet other embodiments, the composition further comprises a molecule, which hybridizes to at least one low risk HPV type.

Other embodiments of the invention may include compositions wherein the molecule that hybridizes to said low risk HPV type is a nucleic acid molecule.

Still other embodiments of the invention may include compositions wherein the nucleic acid molecule is a nucleic acid substantially identical to a full length genomic clone of a low risk HPV type, or fragment thereof.

Still other embodiments of the invention may include compositions wherein the low risk HPV type is HPV 11 or HPV 70.

Still other embodiments of the invention may include compositions wherein the nucleic acid molecule is comprised of DNA, RNA, LNA or PNA.

Still other embodiments of the invention may include compositions wherein the nucleic acid that hybridizes to the low risk HPV types is not labeled with a detectable substance.

Still other embodiments of the invention may include compositions wherein the nucleic acid that hybridizes to the low risk HPV types is labeled with a detectable substance that is different from the detectable substance used to label the nucleic acid molecule which hybridizes to the HR-HPV.

Still other embodiments of the invention may include compositions wherein the detectable substance is chosen from a fluorescent material, a chemiluminescent material, a bioluminescent material, an enzyme and a radioactive material.

Still other embodiments of the invention may include compositions wherein the detectable substance is covalently linked to the nucleic acid which blocks probe hybridization to the low risk HPV types.

Still other embodiments of the invention may include compositions wherein the detectable substance is linked to an intervening molecule.

Still other embodiments of the invention may include compositions wherein the intervening molecule is biotin.

Still other embodiments of the invention may include compositions wherein the intervening molecule is streptavidin.

Still other embodiments of the invention may include compositions wherein the cancer markers detected are cervical cancer markers.

Still other embodiments of the invention may include compositions wherein the cancer markers detected are colon cancer markers.

Still other embodiments of the invention may include compositions wherein the cancer markers detected are anal cancer markers.

Still other embodiments of the invention may include compositions wherein the cancer markers detected are markers for HPV-related cancers.

In yet other embodiments, the composition further comprises a low molecular weight dextran sulfate.

Still other embodiments of the invention may include compositions wherein the dextran sulfate has a molecular weight range of about 25,000-75,000.

Still other embodiments of the invention may include compositions wherein the dextran sulfate has a molecular weight of about 35,000-50,000.

Still other embodiments of the invention may include compositions wherein the low molecular weight dextran sulfate is in a range of about 5-15 wt./vol. %.

Still other embodiments of the invention may include compositions wherein the low molecular weight dextran sulfate is in about 10 wt./vol. %.

Also contemplated is a kit for detecting at least one marker associated with cancer comprising the following reagent: a) a probe composition according to the present invention.

In other embodiments, the kit further comprises at least one of the following;

b) reagents for performing a PAP stain
c) reagents, e.g., an antibody or nucleic acid probe, for the detection of at least one of the following protein markers: c-Myc, Cox-2, HIF-1α, Histone H3, a telomerase marker, a telomerase associated protein; an extra-cellular matrix marker; a proliferation marker; a cell cycle marker; or an apoptosis marker.
d) reagents for the detection of other cellular markers associated with the progression of cancer or risk of progression of cancer.
e) reagent for the detection of antibodies or probes,
f) at least one sample for carrying out a positive control reaction for at least one of the above markers,
g) at least one container, and
h) instructions for performing an assay to detect cancer markers in a sample.

F. Methods for Detecting Markers for Cancer

The invention discloses a method for detecting markers for cancer in a subject. The method comprises a) obtaining a sample comprising cells from the subject;
b) contacting the sample with a composition as described above, comprising a nucleic acid molecule substantially identical to a full length genomic clone of human papilloma virus 16 (SEQ ID NO: 1), or a fragment thereof, or a nucleic acid molecule substantially identical to SEQ ID NO: 1; and a nucleic acid molecule substantially identical to a full length genomic clone of human papilloma virus 18, (SEQ ID NO: 2), or a fragment thereof, or a nucleic acid molecule substantially identical to SEQ ID NO: 2; and a nucleic acid molecule substantially identical to a full length genomic clone of human papilloma virus 51 (SEQ ID NO: 4), or a fragment thereof or a nucleic acid molecule substantially identical to SEQ ID NO: 4, under conditions such that the nucleic acid molecules hybridizes to a human papilloma virus (HPV) nucleic acid contained in the sample thereby forming at least one nucleic acid-HPV hybridization complex, and
c) detecting said nucleic acid-HPV hybridization complex, wherein hybridization of the nucleic acid molecules to the sample indicates the presence of cancer or the risk of developing cancer.

In further embodiments, the method further comprises contacting the sample with a probe comprising a nucleic acid molecule, comprising at least one of:

a) a nucleic acid molecule substantially identical to a full length genomic clone of human papilloma virus 56 (SEQ ID NO: 6), or a fragment thereof, or a nucleic acid molecule substantially identical to SEQ ID NO:6;

b) a nucleic acid molecule substantially identical to a full length genomic clone of human papilloma virus 58 (SEQ ID NO: 5), or a fragment thereof, or a nucleic acid molecule substantially identical to SEQ ID NO:5;

c) a nucleic acid molecule substantially identical to a full length genomic clone of human papilloma virus 66 (SEQ ID NO: 7), or a fragment thereof, or a nucleic acid molecule substantially identical to SEQ ID NO:7;

d) a nucleic acid molecule substantially identical to a full length genomic clone of human papilloma virus 73 (SEQ ID NO: 8), or a fragment thereof, or a nucleic acid molecule substantially identical to SEQ ID NO:8, under conditions such that the probe hybridizes to a human papilloma virus nucleic acid contained in the sample; and wherein hybridization of the probe to the sample indicates the presence of cervical cancer or the risk of developing cervical cancer.

Other embodiments of the invention may include methods wherein the conditions permitting the nucleic acid probe to hybridize to the human papilloma virus nucleic acid contained in the sample are high stringency conditions.

Other embodiments of the invention may include methods wherein the conditions permitting the nucleic acid probe to hybridize to the human papilloma virus nucleic acid contained in the sample are moderate stringency conditions.

Other embodiments of the invention may include methods wherein the conditions permitting the probe to hybridize to the human papilloma virus nucleic acid contained in the sample are low stringency conditions.

Other embodiments of the invention may include methods wherein the conditions permitting the probe to hybridize to the human papilloma virus nucleic acid contained in the sample include a hybridization buffer comprising 50% formamide, 0.3 M NaCl, and at least one non-specific DNA molecule.

In other embodiments, the invention provides a method for detecting markers for cancer in a subject further comprising contacting the sample with at least one molecule that hybridizes to at least one low risk HPV type.

Other embodiments of the invention may include methods wherein the at least one molecule is a nucleic acid molecule.

Other embodiments of the invention may include methods wherein the nucleic acid molecule is a full length genomic clone of a low risk HPV type, or fragment thereof; or a molecule which is substantially identical to a full length genomic clone of a low risk HPV type, or fragment thereof.

Other embodiments of the invention may include methods wherein the low risk HPV type is HPV 11 or HPV 70.

Other embodiments of the invention may include methods wherein the nucleic acid molecule is comprised of DNA, RNA, LNA or PNA.

In other embodiments, the method further comprises contacting the sample with at least one other agent that can detect cancer.

Other embodiments of the invention may include methods wherein the cancer is cervical cancer.

Other embodiments of the invention may include methods wherein the cancer is colon cancer.

Other embodiments of the invention may include methods wherein the cancer is a HPV-related cancer.

Other embodiments of the invention may include methods wherein the at least one other agent is a stain used in a PAP smear.

Other embodiments of the invention may include methods wherein the stain is Papanicolaou stain.

Other embodiments of the invention may include methods wherein the at least one other agent is an agent which binds to a protein marker for cancer or a nucleic acid encoding a protein marker for cancer.

Other embodiments of the invention may include methods wherein the agent that binds a protein marker is an antibody.

Other embodiments of the invention may include methods wherein the agent is an agent that binds to a protein marker for cervical cancer or a nucleic acid encoding a protein marker for cervical cancer.

Other embodiments of the invention may include methods wherein the agent is an agent that binds to a protein marker for HPV-related cancer or a nucleic acid encoding a protein marker for HPV-related cancer.

Other embodiments of the invention may include methods wherein the protein marker for cancer is chosen from $p16^{INK4a}$ P63, c-Myc, Cox-2, HIF-1α, a telomerase markers, a telomerase associated protein; an extra-cellular matrix marker; a proliferation marker; a cell cycle marker; or an apoptosis marker.

Other embodiments of the invention may include methods wherein the sample is a cytology sample comprising cells.

Other embodiments of the invention may include methods wherein the sample is a histology sample comprising cells.

Other embodiments of the invention may include methods wherein the sample is provided on a solid support.

Other embodiments of the invention may include methods wherein the solid support is chosen from a microscope slide, a bead, a micro-array and a chip.

Other embodiments of the invention may include methods wherein the sample is placed in solution and the cells comprised in the sample are lysed before the sample is applied to the solid support.

Other embodiments of the invention may include methods wherein the sample is screened for cancer by flow cytometry.

The invention also discloses a method of detecting markers for cancer in a subject comprising a) obtaining a sample comprising cells from the subject, b) placing the sample on a solid support, c) detecting HR-HPV in the sample from step b) by using the probe composition as described above, d) performing a PAP stain on the same sample from step b) wherein the presence of HR-HPV and an abnormal PAP smear indicates the presence of cervical cancer or the risk of developing cancer.

Other embodiments of the invention may include methods wherein the sample is a cervical cancer sample and the cells comprised in the sample cervical cells.

Other embodiments of the invention may include methods wherein the sample is a colon cancer sample and the cells comprised in the sample colon cells.

Other embodiments of the invention may include methods wherein the sample is a HPV-related cancer sample, and the cells comprised in the sample HPV-infected cells.

Other embodiments of the invention may include methods wherein the detecting the HR-HPV in the sample is done by in situ hybridization of a nucleic acid probe specific to HR-HPV.

Other embodiments of the invention may include methods wherein the nucleic acid probe specific to HR-HPV detects at least 14 HR-HPV types.

The methods described above may be automated methods. Automated methods are further described in detail below.

G. A Composition Binding at Least Two Protein Markers

The invention also provides a composition comprising at least one molecule that binds at least two protein markers for cancer, or at least two nucleic acids encoding protein markers for cancer, or a combination of at least one protein marker and at least one nucleic acid encoding a protein marker for cancer.

Other embodiments of the invention include compositions wherein the at least two protein markers for cancer are chosen from: c-Myc, Cox-2, HIF-1α, Histone H3, a telomerase marker, a telomerase associated protein; an extra-cellular matrix marker; a proliferation marker; a cell cycle marker; an apoptosis marker, and HR HPV.

Other embodiments of the invention include compositions wherein the markers for cancer are markers for HPV-related cancer.

Other embodiments of the invention include compositions wherein the markers for cancer are markers for cervical cancer.

H. A Method for Detection and Quantitation of at Least Two Markers for Cancer

The invention further provides a method for detection and quantitation of at least two markers for cancer comprising: a) preparing a cytology sample on a solid support, b) staining the sample of a) with at least two markers for cancer using the composition described above, c) detecting the at least two markers for cancer, d) quantifying the at least two markers for cancer.

Other embodiments of the invention include methods wherein the cancer is HPV-related cancer.

Other embodiments of the invention include methods wherein the cancer is cervical cancer.

Other embodiments of the invention include methods wherein the cancer is colon cancer.

Other embodiments of the invention include methods wherein the markers for cancer are detected using at least one reagent chosen from an antibody, a nucleic acid molecule, and a PAP stain.

Other embodiments of the invention include methods wherein at least two markers for cancer are stained where the markers are chosen from a PAP stain, c-Myc, Cox-2, HIF-1α, Histone H3, a telomerase marker, a telomerase associated protein; an extra-cellular matrix marker; a proliferation marker; a cell cycle marker; or an apoptosis marker, and HR-HPV.

In other embodiments, the method may be automated.

I. A Method for Detecting Markers for Cancer

The present invention also discloses a method for detecting markers for cancer in a subject comprising a) obtaining a sample comprising cells from the subject;
b) contacting the sample with a composition binding at least two markers, comprising at least two molecules that bind to at least two protein markers for cancer under conditions such that the at least two molecules bind to the at least two protein markers for cancer in the sample; wherein binding of the two molecules to the sample indicates the presence of cancer or the risk of developing cancer.

Other embodiments of the invention include methods wherein the cancer is HPV-related cancer.

Other embodiments of the invention include methods wherein the cancer is cervical cancer.

Other embodiments of the invention include methods wherein the protein markers for cancer are chosen from c-Myc, Cox-2, HIF-1α, Histone H3, a telomerase marker, a telomerase associated protein; an extra-cellular matrix marker; a proliferation marker; a cell cycle marker; HR HPV, or an apoptosis marker.

Other embodiments of the invention include methods wherein the sample is contained on a single solid support.

Other embodiments of the invention include methods where the single solid support is a microscope slide.

In other embodiments method further comprises contacting the sample with PAP stain, wherein an abnormal PAP stain and binding of the at least two molecules to the sample indicates the presence of cancer or the risk of developing cancer.

J. Platforms for Detecting Cancer

Any platform known in the art can be used to screen samples in the methods of the invention for the detection of cancer, such as any HPV-related cancer, e.g., cervical cancer, colon cancer, anal cancer, gastric cancer, oral cancer, neck and head cancer, lung cancer, etc. In some embodiments, the method involves placing a sample on a solid support. In some embodiments, a label is placed on a solid support, e.g., an antibody, a probe. Examples of solid supports include a microscope slide, a chip, a bead, a micro titer plate, or a micro array. In these embodiments, the samples can be examined and analyzed manually, e.g., using a light microscope or the samples can be analyzed by a computer using a computer program which detects parameters associated with cervical cancer, as described infra in section F. In other embodiments, the method of the invention involves analyzing a sample in solution. The sample can be analyzed using flow cytometry. Flow cytometry can also be used to analyze a sample when the sample is provided on a bead.

K. Computer Analysis for Detecting Cancer in a Sample

In some embodiments the invention provides for an automated method of analyzing a sample for markers which indicate the presence of cancer, or the risk of developing cancer. Thus any of the methods described infra may further comprise a) creating a digital image of a sample
b) saving the digital image to a digital media,
c) analyzing the digital image using an algorithm which detects and quantifies molecules used to detect markers which indicate the presence of cancer or the risk of developing cancer, and
d) creating a report which contains information relating to the identification and quantification of markers for cancer.

In one embodiment the saved digital image is a high resolution image, and step c) analyzing the digital image comprises a) reducing the image resolution by sub sampling the high resolution digital image to create a second low resolution digital image;
b) analyzing the low resolution digital image to locate potential objects of interest within the low resolution image;
c) mapping potential objects of interest back onto the high resolution image;

d) analyzing each mapped object within the high resolution image to compile a list of descriptive statistics that describe each object; and e) comparing the descriptive statistics for each object to an object definition to determine the likelihood that the described object is a nuclei.

The method may further comprise analyzing the low resolution digital image comprises segmenting the low resolution digital image in HSI color space based on staining and counter staining colors; and detecting the edge of the cells to separate cells from background.

The method may also include smoothing the image.

Analyzing each mapped object within the high resolution image may comprise classifying the objects (cells) based on chromatic, geometric, topological and biological information; and collecting statistics by using the original image to gather chromatic, geometric and topological information.

When some objects are cells the method further comprises filtering the cells based on chromatic, geometric, topological and biological information by comparing the object descriptive statistics to a pre-determined object definition to determine the probability that the cell fits the acceptance criteria and that the cell is captured by the filter; storing the results for additional analysis.

The method may be executed using a computer controlled software algorithm.

The computer controlled software algorithm for performing image analysis of high resolution microscopic digital images of cells containing nuclei comprises the following steps:

a) analyzing a saved high resolution digital image, said digital image saved as multiple gigabytes;

b) sub sampling the high resolution digital image to create a second low resolution digital image;

c) analyzing the low resolution digital image to locate potential objects of interest within the low resolution image;

d) mapping potential objects of interest back onto the high resolution image;

e) analyzing each mapped object within the high resolution image to generate a list of descriptive statistics that describe each object; and f) comparing the descriptive statistics for each object to an object definition to determine the likelihood that the described object is a nuclei.

The image analysis algorithm step c) comprises the analysis of the low resolution digital image to locate potential objects of interest in the low resolution image may comprise the following steps:

a) reducing image resolution;

b) smoothing the image;

c) segmenting the image in HSI color space;

d) detecting the edges of objects.

The image analysis algorithm step e), comprises analyzing each mapped object, comprising classifying the object based on chromatic, geometric, topological and biological information;

collecting statistics by using the original image to gather chromatic, geometric and topological information.

The collected statistics for a mapped object within the high resolution image may include:

a) contour length; b) size; c) symmetry; d) compactness; e) topology; f) color; g) saturation; and h) intensity The collected statistics for the whole image or the regions of interest within the high resolution image include:

a) total number of objects in each categories; b) average and mean intensity; c) average size; and d) topology.

Figure 15:
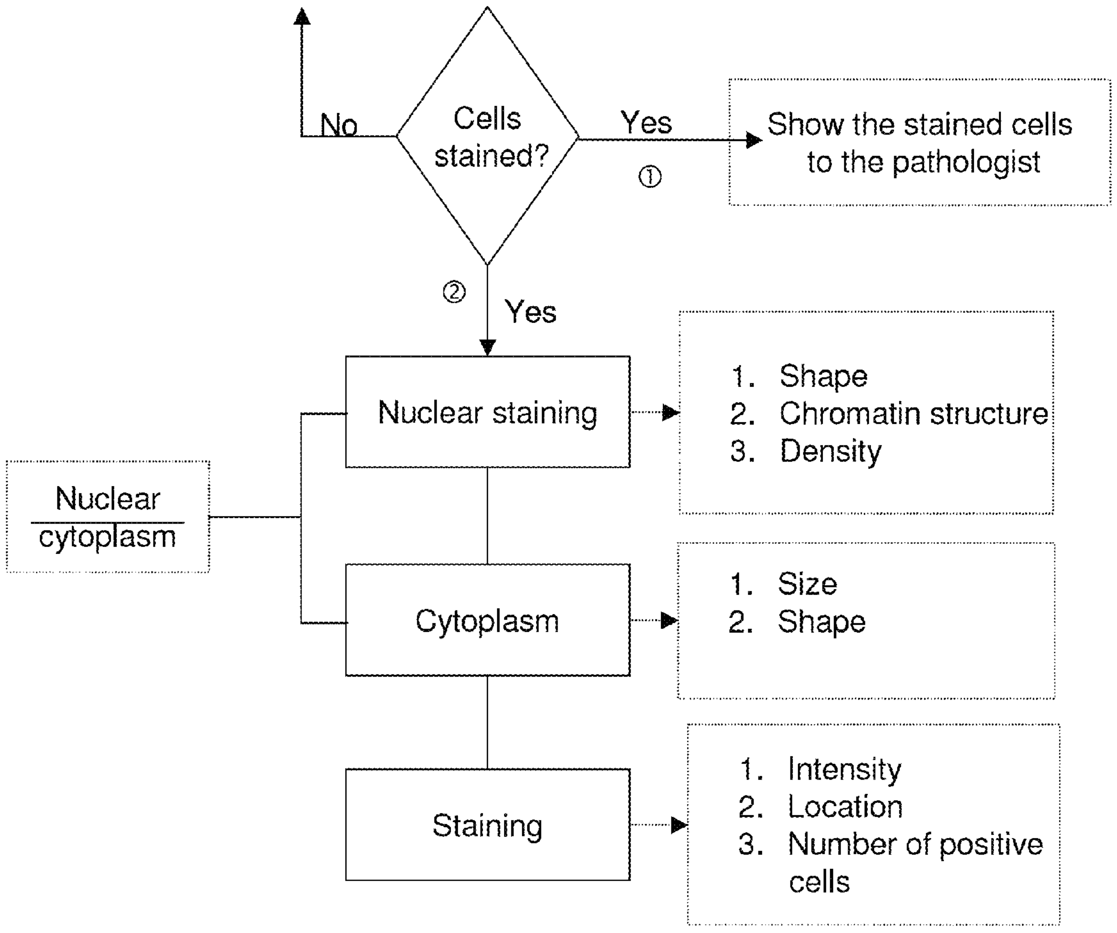
FIG. 15 is a flow chart depicting the parameters considered in an automated analysis of a sample for the presence of cervical cancer.

In one embodiment, the invention provides a computer program, which can analyze a sample on a solid support, e.g., a microscope slide, for the presence of cancer, e.g., cervical cancer. (FIG. 15). For example, the program may analyze stained cells digitally for the detection of cervical cancer and can be run on a personal computer with a Pentium processor. The program considers the nuclear cytoplasm ratio by analyzing the shape of the nucleus, the chromatin structure and the density of the nucleus. The cytoplasm is analyzed for size and shape. The staining pattern is analyzed for the number of positively stained cells, the intensity of the stain and the location of the stain. A preferred embodiment of a system for using a program according to the invention is defined below:

System Architecture of a Preferred Embodiment

The above mentioned computer program is preferably carried out using a system as described herein. The design of the system is based on a multi-tiered architecture. The image FIG. 23 used as an example is acquired using a ScanScope™ (a line scanner for scanning microscope slides) (Aperio Technologies, Vista, Calif.). The ScanScope™ may be connected to another computer, which serves as an image repository through a 1 Gb network connection. The object lens may be a Nikon Plan Apo 20× with a numerical aperture value of 0.75 and the CCD camera model is L301 KC line scan camera from Basler. The computer used to store and serve image may have the following specifications:

| | |
|---|---|
| Motherboard | Intel |
| CPU | Pentium 4 2.6 GHz |
| RAM | 2 GB |
| Hard Drive | 250 GB |

Program Steps

Figure 16:
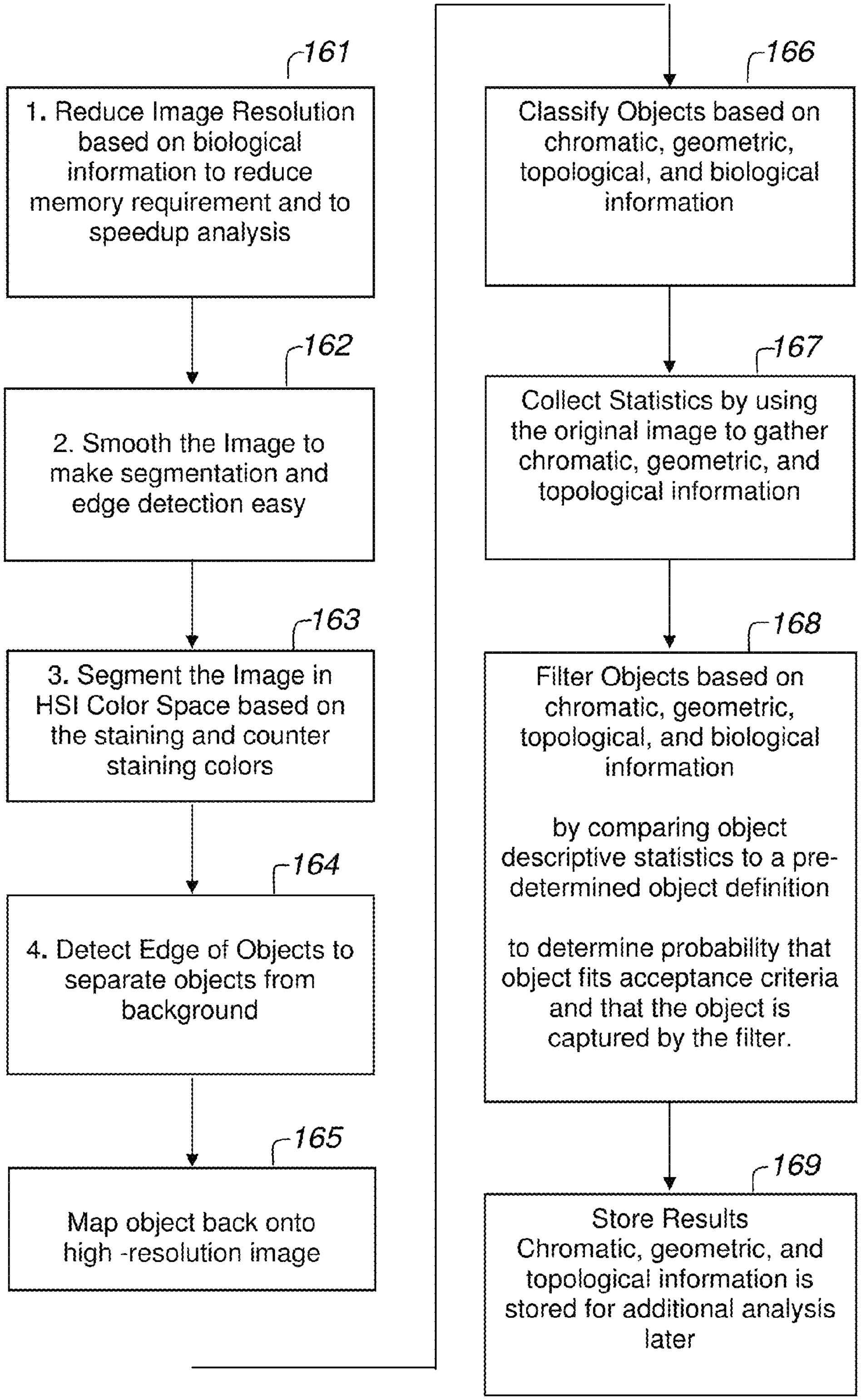
FIG. 16 is a flow chart depicting the steps performed in an automated analysis of sample for the detection of cervical cancer.

In one embodiment, the steps of the program are described in FIG. 16. In this embodiment, the steps include reducing the image resolution to enhance efficiency of the analysis (161); smoothing (162) the image to permit segmentation and edge detection; segmenting (163) the image in HSI color space based on staining and counter staining colors;

detecting (164) the edge of cells to separate cells from background; [through detection of high rate of change in HSA]

mapping (165) the cells back into the high resolution image;

classifying (166) the cells based on chromatic, geometric, topological and biological information;

collecting (167) statistics by using the original image to gather chromatic, geometric and topological information;

filtering (168) the cells based on chromatic, geometric, topological and biological information by comparing the object descriptive statistics to a pre-determined object definition to determine the probability that the object fits the acceptance criteria and that the cell is captured by the filter;

storing (169) the results, e.g., chromatic, geometric and topological information is stored for additional analysis.

Figure 23:
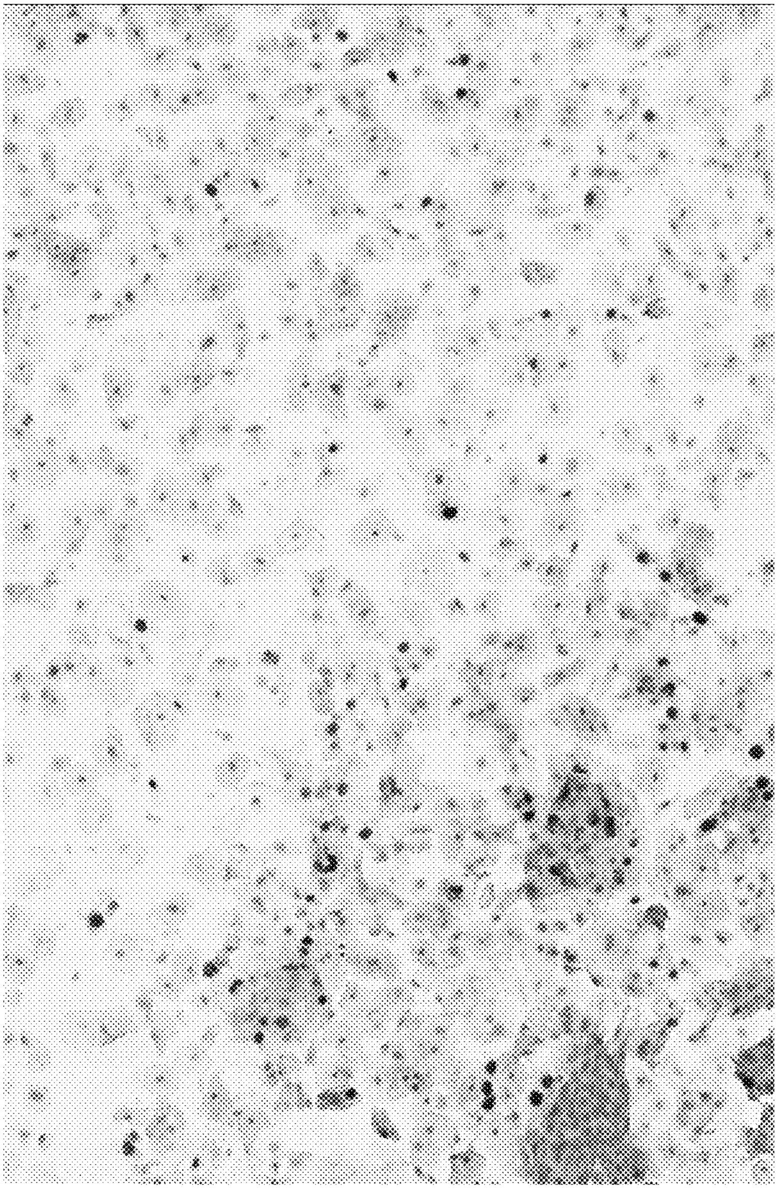
FIG. 23 depicts the image of a sample acquired using ScanScope™.

In one embodiment the digital image may be created using a high resolution, e.g. 0.46 micron per pixel. If the type of cells, which are the target of the actual analysis, generally are expected to have a size of 8 micron then the image of the target would cover about 16 pixels per line. The algorithm according to the present invention, in general, does not require this full resolution for object detection and thus the image may be reduced to a lower resolution, such as e.g. a resolution of about 4 micron per pixel. Consequently, the memory requirement is greatly reduced. FIG. 23 is an example of such an image. The actual reduction chosen for a specific sample will depend on the biologic information available for this sample, i.e. the type and size of cells to be looked for. If those cells are big a great reduction may be applied; otherwise in case of small cells no reduction or only a small reduction may apply.

Figure 24:
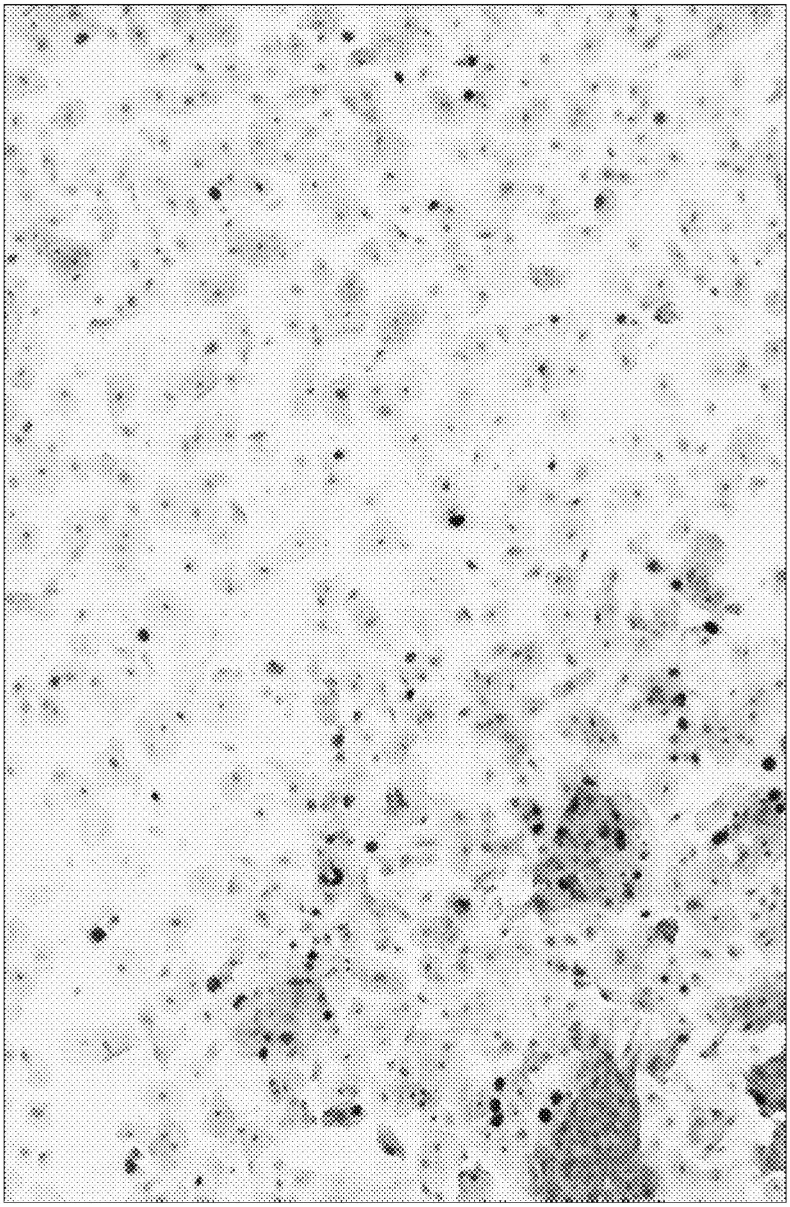
FIG. 24 was obtained after use of "median blur" on the image in FIG. 23.

The smoothing is carried out in order to remove or blur irrelevant items. The smoothing is recommended in view of the fact that images obtained through scanning slides, especially with high resolution, may contain small pixels due to dust, optical aberration, stain background, and compression that are not normally perceived by the human eye. These artifacts may interfere the algorithm in the later stages. A smoothing operation maybe used to remove these minor artifacts. As an example, a "median blur" may be used on the preceding image to obtain the image shown in FIG. 24. Other filters such as Mean of Least Variance (MLV)[3] and Mean of Coefficient of Variation (MCV)[4] may also be used.

Figures 27, 28, 29:
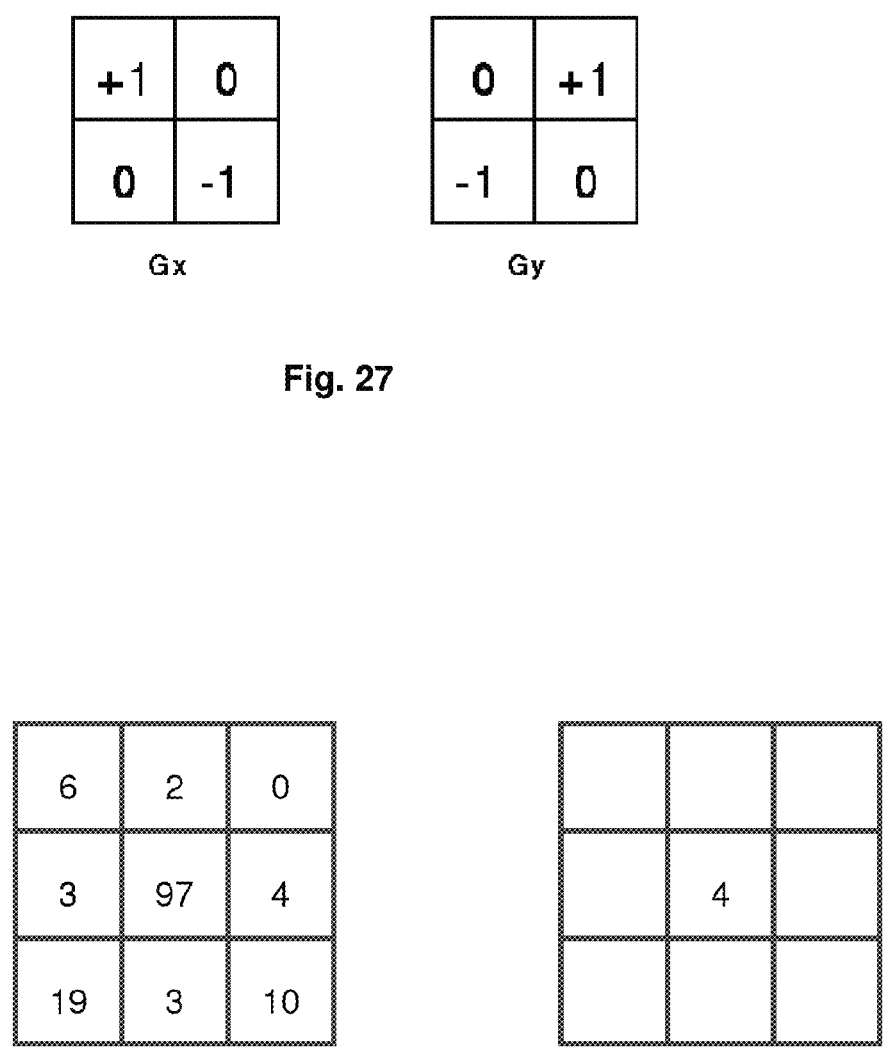

Median filter is a type of spatial filter that uses a sliding-window. It replaces the center value in the window with the median of all pixel value in the window. An example of median filtering of a single 3×3 window of values is shown in FIGS. 28, 29 where the center pixel of value 97 is under consideration.

When sorted in order, the numbers appear in the following sequence: 0, 2, 3, 3, 4, 6, 10, 15, 97, where 4 is selected to replace 97 as the pixel value.

This illustrates one of the celebrated features of the median filter: its ability to remove 'impulse' noise. The median filter is also recognized to be edge-preserving based on the fact it will preserve step edges without blurring.

Figure 25:
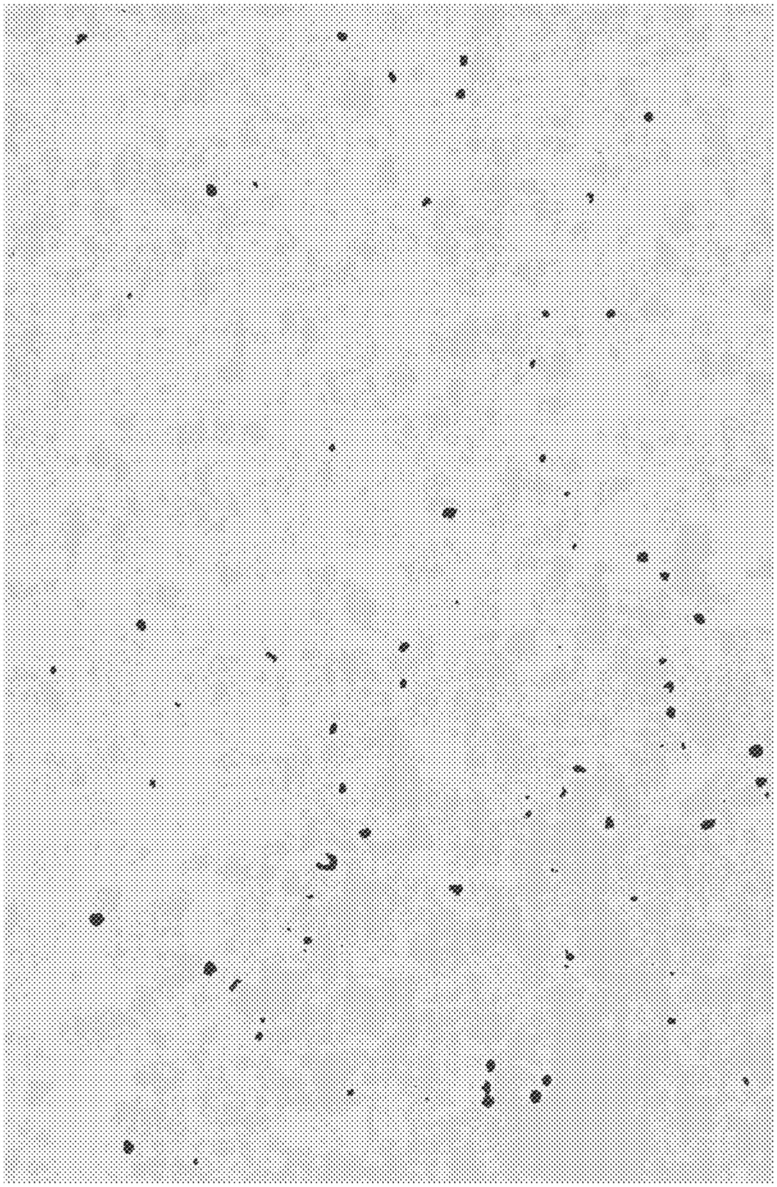
FIG. 25 depicts the image of FIG. 23 transformed from RGB space into HIS space.

Segmenting:

Segmentation is the process of dividing an image into meaningful regions. In the context of histological image processing, it means separating the object of interest from the image background. Segmentation is carried out by converting the image from RGB color space to HSI color space. This process is well known, see, e.g., Rafael Gonzalez, Richard Woods, *Digital Image Processing, $2^{nd}$* Edition. [1][2]: The segmented image is shown in FIG. 25.

To cleanly detect the edges in order to extract objects from the image, color segmentation may be used to separate out background and desired biological objects. The human eye, viewing the slides, does not perceive red-green-blue components, but hue, saturation, and brightness. (This is explained in details in Rafael Gonzalez, Richard Woods, Digital Image Processing, $2^{nd}$ Edition.). Since the original images are acquired and represented in RGB color space, the image may be transformed into HSI color space. As an example, shown in FIG. 25, the image was transformed from RGB space into HSI space and then partitioned into regions. Such transformation may be carried out by use of the following algorithm:

| Kender's Algorithm for Faster Computation of HUE: | Saturation: |
|---|---|
| if ((R > B) and ((G > B)<br>$\text{hue} = \frac{\pi}{3} + \arctan\left(\frac{\sqrt{3}\times(R-G)}{R-B+G-B}\right)$ | saturation =<br>$1 - \frac{3\times\min(R, G, B)}{R+G+B}$ |
| | Intensity: |
| else if (G > R)<br>$\text{hue} = \pi + \arctan\left(\frac{\sqrt{3}\times(B-G)}{B-R+G-R}\right)$ | $\text{intensity} = \frac{R+G+B}{3}$ |

-continued else if (B > G)

$$\text{hue} = \frac{5\times\pi}{3} + \arctan\left(\frac{\sqrt{3}\times(R-B)}{R-G+B-G}\right)$$

else if (R > B)
hue = 0
else
'achromatic'

An example of such implementation in Java is given infra.

Detect Edge of Objects to Separate Objects from Background

Figure 26:
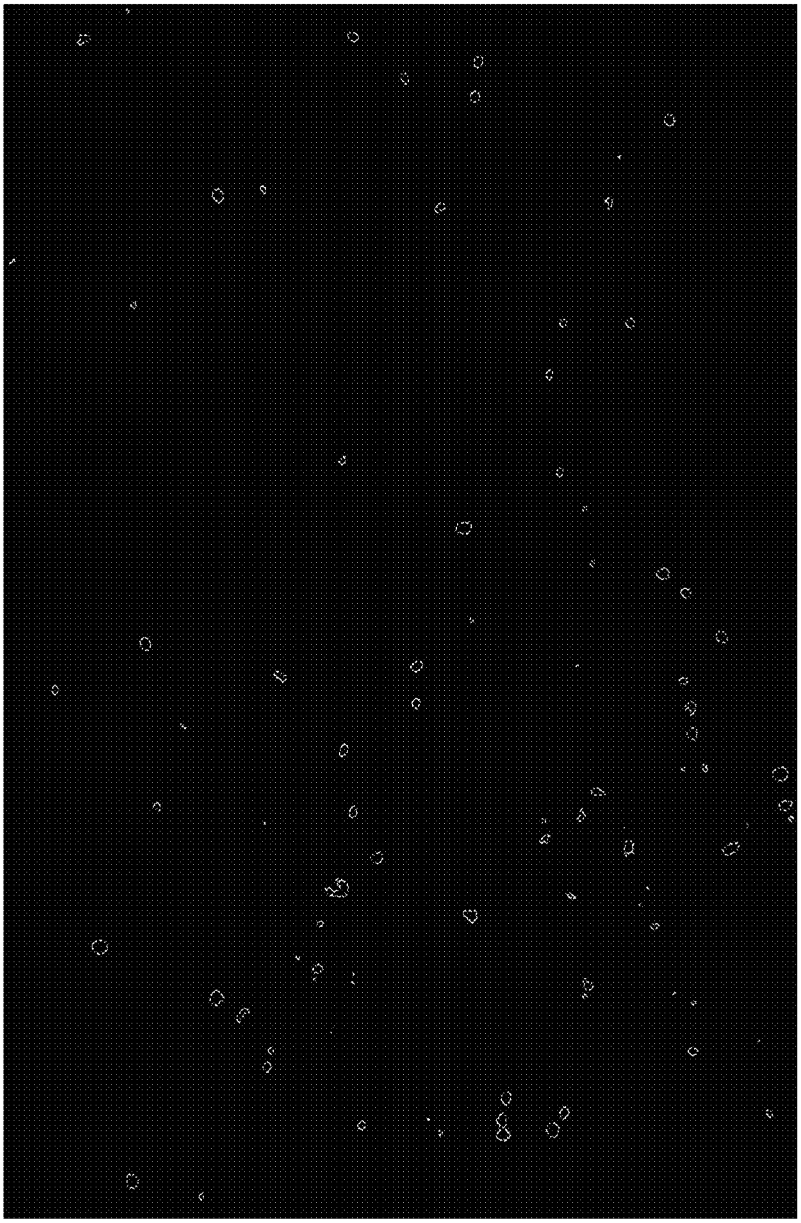
FIG. 26 depicts the image in FIG. 25 after a Roberts Cross edge detection operation.

The object may first be described in terms of its edge Then we may use it to derive other information such as chromatic information or topological information. As an example, the image in FIG. 26 is obtained by passing the preceding image shown in FIG. 25 through the Roberts Cross edge detection operation. Edge detection attempts to determine whether an edge passes through or near to a given pixel. This can be done by examining the rate of change of intensity near the pixel. A sharp change of intensity or hue is an indication of an edge. Works by Roberts (1965), Sobel, (Davis, 1975) and Prewitt (1970) are typical of approach. The example given above, uses the Robert Cross operator which performs a quick 2-dimensional spatial gradient measurement on an image. One way to implement this is to use a pair of 2×2 convolution kernels as show in FIG. 27: The kennel can be applied separately to the source image and produce two gradient measurement corresponding to two orientations. The absolute magnitude of the gradient at each point is defined as:

$$|G| = \sqrt{Gx^2 + Gy^2}$$

Or as an approximation:

$$|G| = |Gx| + |Gy|$$

Map Object Back onto High-Resolution Image

The edge of the objects identified in previous step is in a lower resolution image space compared to the original image. At this stage, a simple linear translation between the coordinate system in the low resolution image of FIG. 26 and the coordinate system in the stored high resolution image is used for mapping the cells back into the high resolution image.

In the following steps the cells are classified based on chromatic, geometric, topological and biological information; and statistics are collected by using the original image to gather chromatic, geometric and topological information; Further the cells are filtered based on chromatic, geometric, topological and biological information by comparing the object descriptive statistics to a pre-determined object definition to determine the probability that the object fits the acceptance criteria and that the cell is captured by the filter. Finally the results, e.g., chromatic, geometric and topological information a restored for additional analysis.

Each of the image processes mentioned above are well-known and described in the literature, see, e.g.,

[1] Rafael Gonzalez, Richard Woods, *Digital Image Processing,* 2nd Edition.

[2] A. Th. Schwarzbacher, P. A. Comiskey, and J. B. Foley, *A Low-Power CMSO Design for RBG to HSI Conversion.* Dublin Institute of Technology, Dublin, Ireland, Trinity College, Dublin, Ireland, Dun Logahire Institute of Technology, Dublin, Ireland. *Biomedical Image Processing with Morphology-Based Nonlinear Filters*

[3] Mark Allen Schulze, University of Texas at Austin, 1994

[4] Mark A. Schulze and Qing X. Wu, *Noise Reduction in Synthetic Aperture Radar Imagery Using a Morphology-Based Nonlinear Filter*, Landcare Research New Zealand Wellington, New Zealand, 1995.

The invention provides, In certain embodiments, combinations of the various processes as described infra.

The algorithm is specifically developed, for example, for use in the automated method of analyzing a sample for markers which indicate the presence of cancer, or the risk of developing cancer, for executing a method of the invention.

Converting RGB to HIS in a Java Method

```
public static int RGBtoHSI(int rgb)
{
   double h = 0, s = 0, l = 0; // initialize HSI value
   // extract RGB values
   int r = (rgb & 0x00FF0000) >> 16;
   int g = (rgb & 0x0000FF00) >> 8;
   int b = (rgb & 0X000000FF);
   // Calculate maximum, and minimum of the RGB component values
   int max, min;
   if (r>g && r>b) {
      max = r;
      min = Math.min(g,b);
   } else {
      if (g>b) {
         max = g;
         min = Math.min(r,b);
      } else {
         max = b;
         min = Math.min(r,g);
      }
   }
   // Compute intensity Value, normalized between 0-255
   i =Math.round(((float)max/255)*100);
   if (i==0) return (int)(((int)h << 16) + ((int)s << 8) + (int)i);
   // No intensity - Colour is black
   // Compute Saturation Value, normalized between 0-255
   if (max==min) return (int)(((int)h << 16) + ((int)s << 8) + (int)i);
   // No saturation - Colour is grey
   s = Math.round((((float)max/255) –
   ((flost)min/255))/((flost)max/255)*100);
   // Compute Hue Value, normalized between 0-255
   double d_hue = Math.acos((0.5*((r–g)+(r–b)))/
   (Math.sqrt(Math.pow((r–g),2)+(r–b)*(g–b))));
   if (b>g) d_hue = (2*Math.PI)– d_hue;
   d_hue = Math.toDegrees(d_hue);
   h = Math.round(Math.round(d_hue));
   return (int)(((int)h << 16) + ((int)s << 8) + (int)i);
}
```

L. Kits

In one embodiment, the invention provides for a kit comprising one or more nucleic acid probes which may hybridize to at least 14 HR HPV types, e.g., 16, 18, 31, 33, 35, 39, 45, 51, 52, 56, 58, 59, 68, and 82. The probes may include genomic clones, or fragments thereof, of HR HPV 16, 18 and 51. Optionally, the kit may further comprise at least one of the following: a nucleic acid probe comprising HPV 11, or fragment thereof; HR HPV 56, or fragment thereof; or HR HPV 58, or fragment thereof; or HR HPV 66, or fragment thereof; or HR HPV 70, or fragment thereof; or HR HPV 73, or fragment thereof. Of course nucleic acid probes comprised of nucleic acid sequences substantially identical to genomic clones of any of the HR-HPV or low risk HPV types described above can also be included in the kit. The probe hybridization conditions may include any of the conditions described herein. Optionally, the kit may further comprise a pap stain for performing a pap smear or a reagent to detect a marker for cancer, such as any HPV-related cancer, e.g., c-Myc, Cox-2, HIF-1α, telomerase markers, such as hTERT, hTR, and other telomerase associated proteins; an extra-cellular matrix marker, such as, Laminin 5; a proliferation marker, such as, Ki-67 or Histone H3; a cell cycle marker, such as, Cyclin E, P63 or $p16^{INK4a}$; or apoptosis markers, such as Bax, or Bcl-2. The molecule can be a protein, e.g. an antibody, or a nucleic acid. In another embodiment, the kit comprises at least 2 molecules that may detect a marker for cancer e.g., c-Myc, Cox-2, HIF-1α, telomerase markers, such as hTERT, hTR, or other telomerase associated proteins; an extra-cellular matrix marker, such as, Laminin 5; a proliferation marker, such as, Ki-67 or Histone H3; a cell cycle marker, such as, Cyclin E, p63 or $p16^{INK4a}$; or apoptosis markers, such as Bax, or Bcl-2. In yet another embodiment, the kit can comprises at least one molecules which can detect a marker for cancer, such as HPV-related cancer marker, e.g., c-Myc, Cox-2, HIF-1α, telomerase markers, such as hTERT, hTR, and other telomerase associated proteins; an extra-cellular matrix marker, such as, Laminin 5; a proliferation marker, such as, Ki-67 or Histone H3; a cell cycle marker, such as, Cyclin E, p63 or $p16^{INK4a}$; or apoptosis markers, such as Bax, or Bcl-2 and a pap stain.

Optionally, the kit may further comprise instructions for using the probes or the molecules used to detect the protein markers for cancer. The kit may further comprise at least one container for each of the components.

M. Dextran Sulfates

For in situ hybridization (ISH), the rate of hybridization is dependent on many factors, including probe concentration and hybridization buffer used. The use of dextran sulfate in ISH has been described (see, e.g., U.S. Pat. Nos. 4,886,741, 5,750,340; WO 02/061139; U.S. application Ser. No. 09/772, 123). Dextran sulfate is strongly hydrated in solution so it will exclude other macromolecules (e.g., a DNA probe) from the water and in effect "concentrate" the probe. This apparent increase in the concentration of the probe may accelerate the hybridization rate. Typically, high molecular weight (e.g. 500,000 dalton) dextran sulfate is used in the hybridization buffer at a concentration of 5-20% (weight to volume ratio) to achieve the desired acceleration rate for hybridization.

One problem associated with the "effective" increase in probe concentration due to the presence of high molecular weight dextran sulfate is an increase in nonspecific background staining. To address this problem, dextran sulfate of high molecular weight (450,000-550,000) and low molecular weight (35,000 to 50,000) were compared in ISH buffers. It was found that high molecular weight dextran sulfate generates higher nonspecific background on certain tissues than low molecular weight dextran sulfate. No decrease in signal intensity (inferring a similar accelerated hybridization rate) was observed, thus demonstrating that the volume exclusion effect of high and low molecular weight dextran sulfate is very similar.

The invention thus relates to a method of using low molecular weight dextran sulfate in ISH. The use of low molecular weight dextran sulfate in the hybridization buffer may decrease the non-specific background staining in an ISH sample, compared to an ISH sample in which high molecular weight dextran sulfate is used in the hybridization buffer (e.g. 500,000-550,000 daltons). In some embodiments of the invention the low molecular weight of dextran sulfate is in the range of 16,000-500,000 daltons. In other embodiments of the invention it is in the range of 25,000-75,000, or even in the range of 35,000-50,000 daltons.

Examples of hybridization buffers are disclosed herein, as well as in Current Protocols in Molecular Biology, Volume 3, Unit 14.7 "In situ hybridization and detection using nonisotopic probes". (Ausubel F M. et al. 1995, John Wiley & Sons, USA, incorporated herein by reference), and in Nonradioactive In Situ Hybridization Application Manual. Chapter V, (Published by Boehringer Mannheim, Germany, 1992, incorporated herein by reference).

The concentration of low molecular weight dextran sulfate may be 5-15%, such as 5, 6, 7, 8, 9, 10, 11, 12, 13, 14, or 15% weight per volume. In one embodiment, 10% of low molecular weight dextran sulfate is used.

In certain embodiments the invention relates to a method of detecting cancer, such as any HPV-related cancer, e.g., cervical cancer, colon cancer, anal cancer, gastric cancer, oral cancer, neck and head cancer, lung cancer, etc., by ISH using a hybridization buffer comprised of low molecular weight dextran sulfate. The cancer may be any cancer, such as any HPV-related cancer, e.g., cervical cancer, colon cancer, anal cancer, gastric cancer, oral cancer, neck and head cancer, lung cancer, e.t.c and the ISH may be performed using a nucleic acid probe cocktail which specifically hybridizes to nucleic acid sequences encoded by HR-HPV genomic DNA and optionally detecting at least one other marker for cancer, e.g., cervical cancer (e.g. a pap smear or a protein associated with cancer such as $p16^{INK4a}$).

The invention also relates to a composition useful for detecting cancer, such as any HPV-related cancer, e.g., cervical cancer, colon cancer, anal cancer, gastric cancer, oral cancer, neck and head cancer, lung cancer, etc. comprising a nucleic acid probe cocktail which specifically hybridizes to nucleic acid sequences encoded by HR-HPV genomic DNA and a hybridization buffer comprised of low molecular weight dextran sulfate. The composition may further comprise at least one other agent for detecting cancer, such as any HPV-related cancer, e.g., cervical cancer, colon cancer, anal cancer, gastric cancer, oral cancer, neck and head cancer, lung cancer, etc., such as a PAP stain.

The invention also relates to an automated method of detecting cancer by ISH using a hybridization buffer comprised of low molecular weight dextran sulfate. The low molecular weight dextran may provide for lower viscosity which may allow easier probe dispensation thus enhancing the efficiency of the automated detection. The cancer may be cervical cancer and the ISH may be performed using a nucleic acid probe cocktail which specifically hybridizes to nucleic acid sequences encoded by HR-HPV genomic DNA and optionally detecting at least one other marker for cancer, e.g., cervical cancer (e.g. a PAP smear or a protein associated with cancer, e.g. $p16^{INK4a}$).

The invention thus provides for a nucleic acid hybridization buffer for in situ hybridization comprising a low molecular weight dextran sulfate.

Further embodiments of the invention include a hybridization buffer wherein dextran sulfate has a molecular weight range of about 25,000-75,000.

Further embodiments of the invention include a hybridization buffer wherein the dextran sulfate has a molecular weight of about 35,000-50,000.

Further embodiments of the invention include a hybridization buffer wherein the low molecular weight dextran sulfate is in a range of about 5-15 wt./vol. %.

EXAMPLES

Example 1

Labeling of HPV Clones

Three full length HPV clones were selected based upon homology with other high risk HPV types. Full-length HPV 16 (7.9 kb) (SEQ ID NO: 1) was cloned into pGEM3Z vector (Promega). Full length HPV 18 (7.9 kb) (SEQ ID NO: 2) was cloned into pBR322 vector. Full length HPV 51 (7.8 kb) (SEQ ID NO: 4) was cloned into pUC13 vector (*J. Virology* 62:1452, GenBank accession number M62877). Full length HPV 58 (7.8 kb) (SEQ ID NO: 5) was cloned into pCRBluntII vector (Invitrogen, Carlsbad, Calif.)

Full-length HPV 16, 18, and 51 clones were mixed together in equal proportions. The pooled clones were treated with DNAase I in the same reaction tube to obtain fragments ranging from 50 to 500 bp in length.

The DNAase reaction was carried out in a buffer containing 50 mM Tris, pH 7.2, 10 mM MgSO4, 0.1 mM DTT, and 50 ug/mL acetylated BSA. DNA was added to the buffer at a final concentration of 0.5 μg/μl and equilibrated at 37° C. for 15 minutes. DNAase I was added at a final concentration of 0.05 mU/μL (diluted from a 2 mU/μL stock in a 50% glycerol, 20 mM Tris-HCl, pH 7.5, and 1 mM MgCl buffer) and the reaction was incubated at 37° C. for 20-40 minutes. The reaction was stopped by heating at 75° C. for 15 minutes.

1.5 μL of the DNAase reaction was then loaded in a 6% TBE/Urea denaturing gel and electrophoresed together with a low molecular weight marker to assess the extent of DNAasing. The gel was then stained with Ethidium Bromide (0.1 ug/mL) and visualized under UV. Optimal incubation time with DNAase I was one that gave a DNA smear from 50-500 bp.

The DNAase I digested DNA was then purified by ethanol precipitation using ammonium acetate according to the method of Sambrook et al. 1989, *Molecular Cloning: A Laboratory Manual,* 2 ed., Cold Spring Harbor Laboratory Press: Cold Spring Harbor, N.Y.). The precipitated DNA was resuspended in 10 mM Tris, pH 8.0 and 1 mM EDTA (TE) at a final concentration of 0.1 mg/mL and stored at −20° C. for long-term storage.

After treatment with DNAase I the plasmids were labeled with psoralen-biotin (Schleicher and Schuell, Keene, N.H.). The labeling reaction was carried out in a 96 well microtiter plate in an optimal volume of 100 μL per well. Psoralen-biotin intercalates into DNA and forms covalent bonds with the DNA upon UV irradiation.

A U-bottom 96 well microtiter plate was placed on ice. Fifty micrograms of plasmid treated with DNAase I was added to a sterile screw-capped microfuge tube at a concentration of 0.1 ug/uL (in 500 μL) and boiled for 10 minutes to denature the DNA. The microfuge tube was quickly put into an ice slurry after boiling and was kept on ice for 10 minutes to prevent reannealing of the denatured DNA. 52.6 μL of Psoralen-biotin (at a concentration of 0.25 μg/μL) was added to the denatured DNA in the microfuge tube. The labeling mixture was vortexed and then quickly spun down. The mixture was then aliquoted into the wells of the microtiter plate at a volume of 100 μL per well. A long-wave UV lamp (365 nM) was placed directly on top of the wells containing the labeling mixture and turned on for an hour. After UV irradiation, the labeling mixture was then pipetted and pooled into a polypropylene tube for N-butanol extraction. The wells of the microtiter plate were rinsed with 50 μL TE per well and the TE was added to the polypropylene tube.

Unincorporated psoralen-biotin was removed by several rounds of n-butanol extraction. Two volumes of water-saturated n-butanol were added to the labeling mixture and vortexed. The tube was then centrifuged at 1000 rpm for 5 minutes in a Beckman table-top centrifuge (Beckman, Fullerton, Calif.). The extracted labeling mixture (bottom phase) was transferred to a new tube. This procedure was repeated once. The residual n-butanol was removed by the addition of two volumes of ether. The tube was vortexed and spun down as described above. The final labeling mixture was transferred to a new tube and stored at −20° C.

The concentration of the labeled HPV probe cocktail was measured by spectrophometry at 260 nM using a Beckman model number DU640 (Beckman, Fullerton, Calif.). Labeling efficiency of DNA varies. The optimal DNA concentration to be used is determined by in situ hybridization (ISH) on histology samples.

Example 2

In Situ Hybridization (ISH) Using Cytology Samples

Monolayer cervical cytology samples prepared using either ThinPrep® (Cytyc, Boxborough, Mass.) or SurePath® (Tripath, Burlington, N.C.) were stored in 95% ethanol before use. To prepare the slides for in situ hybridization the slides were soaked in 50% ethanol for 30 minutes and then mildly fixed in 10% neutral buffered formalin for 20 minutes. The slides were rinsed in reagent water several times to remove residual neutral buffered formalin and then pre-treated with a ready-to-use proteolytic enzyme (DakoCytomation, Carpinteria, Calif.) for 7 minutes at room temperature. After rinsing in reagent water several times, the slides were incubated in 0.3% $H_2O^2$/methanol for 5 minutes to remove endogenous peroxidase activity.

The slides were then rinsed in reagent water several times and excess water was removed from the sample leaving behind a very thin film of moisture. The HPV probe cocktail labeled with biotin (described in Example 1) was added to the slides at a concentration of 1.8-4 ng/μl in hybridization buffer (DakoCytomation Carpinteria, Calif.) In some cases, HPV 11 DNA treated with DNAase I, but not labeled with biotin, was added at a concentration of 0.02-0.5 ng/μl) to prevent the probes from recognizing HPV11, if present. A glass coverslip was applied to each slide. The probe and the sample DNA were then denatured at 90-95° C. for 5 minutes and the slides were then incubated at 37° C. overnight (12-18 hours) in a moist chamber.

After hybridization, the coverslips were removed by soaking the slides in TBST buffer (50 mM Tris, pH 7.6, 0.3 M NaCl, 0.01% Tween). The slides were then incubated in a 0.1×SSC stringent wash buffer at 48-52° C. for 30 minutes. Signal amplification and detection were performed at room temperature using the DAKO GenPoint™ detection system following manufacturer's instructions (DakoCytomation, Carpinteria, Calif.). Briefly, the slides were incubated with the primary streptavidin horse radish peroxidase (SA-HRP) for 30 minutes followed by a 15 minute incubation with biotinyl tyramide (signal amplification.) (DakoCytomation, Carpinteria, Calif.) The slides were incubated with a secondary SA-HRP for 15 minutes, followed by a 5 minute incubation with 3,3'-diaminobenzidine (DAB) substrate. Between each reagent step the slides were soaked in TBST for 3 minutes and this was repeated 3 times. The slides were counterstained with Hematoxylin (1 minute) (DakoCytomation, CA). A coverslip was applied and mounted in an aqueous mounting medium. Cells infected with high risk HPV types stained brown (DAB precipitate) in the nuclei. The stain pattern took the form of a punctate pattern (HPV integration into the human genome) or a diffuse signal within the entire nuclei (episomal copies of HPV) (FIG. 6).

Example 3

In Situ Hybridization Using Histology Samples

Formalin fixed paraffin embedded (FFPE) cervical biopsies were deparaffinized and rehydrated before use. For deparaffinization, the slides were soaked in Xylene or Histoclear (National Diagnostics, Atlanta, Ga.) for 5 minutes. This step was repeated twice. The sample was re-hydrated by placing it in 2 changes of 99% ethanol and 3 changes of 95% ethanol, 1 minute each. The slides were rinsed in reagent water several times before pre-treatment. For pre-treatment, the slides were incubated in 0.8% pepsin in 0.2N HCl at 37° C. for 10-15 minutes or with a ready-to-use proteinase K for 15-30 minutes at room temperature. After rinsing in reagent water several times, the slides were then incubated in 0.3% $H_2O^2$/methanol for 20 minutes to remove endogenous peroxidase activity.

Denaturation, hybridization, signal amplification and detection were as described above in Example 2.

Example 4

In Situ Hybridization Using Cytology Samples Followed by PAP Staining

In situ hybridization was as described above in Example 2.

After the DAB step of ISH, the slides were processed for PAP staining. The slides were soaked in 70% reagent alcohol, 50% reagent alcohol, and distilled water for 1 minute each. They were then stained with Hematoxylin (Richard-Allan Scientific, Kalamazoo, Mich.) for 45 seconds. After 2 rinses for 15 seconds each in distilled water, the slides were soaked in 0.025% glacial acetic acid (clarifier) for 30 seconds. The slides were then rinsed in distilled water for 30 seconds and soaked in bluing agent (10 mg LiCarb/L) (Richard-Allan Scientific, SC) for 30 seconds. The slides were then dehydrated by placing them in 50% reagent alcohol and 95% reagent alcohol for 30 seconds each. The slides were soaked in Richard-Allan cytology stain for 1 minute (Richard-Allan, Kalamazoo, Mich.). The slides were further dehydrated by placing them in 2 changes of 95% reagent alcohol and 3 changes of 100% reagent alcohol, for 30 seconds each. The slides were mounted in permanent mounting medium after 3 changes of xylene for 1, 1, and 3 minutes, respectively.

Example 5

In Situ Hybridization Using Another HPV Probe Mix

Full length HPV clone 66 (7.8 kb) (SEQ ID NO: 7) and/or HPV clone 73 (7.7 kb) (SEQ ID NO: 8) are added to the probe mixture containing full length HPV clones 16, 18, 51, and 58. The probe mixture is DNAased and labeled as described in Example 1. In some cases, HPV 11 DNA (SEQ ID NO: 3) and/or HPV 70 DNA (SEQ ID NO: 9) treated with DNAase I, but not labeled with biotin, is added at a concentration of 0.02-0.5 ng/μl to prevent the probes from recognizing HPV 11 and 70, respectively, if present.

In situ hybridization of the above probe mix is performed using cytology samples as described in Example 2, using histology samples as described in Example 3, and using cytology samples followed by PAP staining as described in Example 4.

Figure 13:
FIGS. 13*a* and 13*b* depict ISH with an HPV probe cocktail a) without the addition of unlabeled HPV 11 DNA (Full-length clone) and b) with the addition of unlabeled HPV 11 DNA (Full-length clone) on cervical biopsy sample that was HPV 11 positive. Unlabeled HPV 11 DNA blocked the cross-hybridization to HPV 11 positive cells in the cervical epithelium as demonstrated by the reduction of brown nuclear staining in FIG. 13*b* (compare to 13*a*) (40× magnification).
Figure 13:
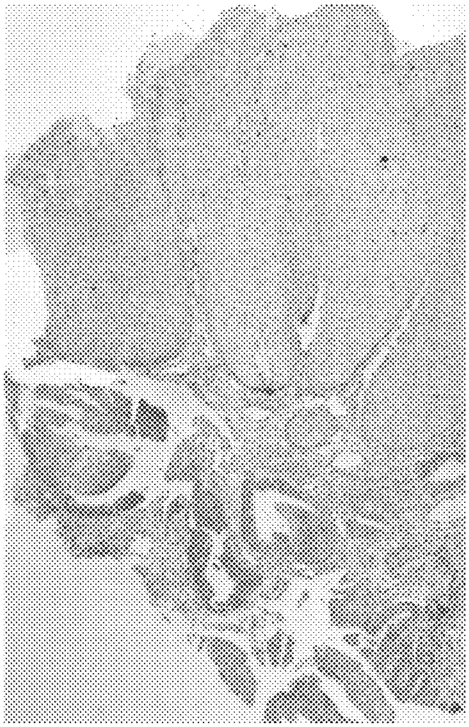
Figure 14:
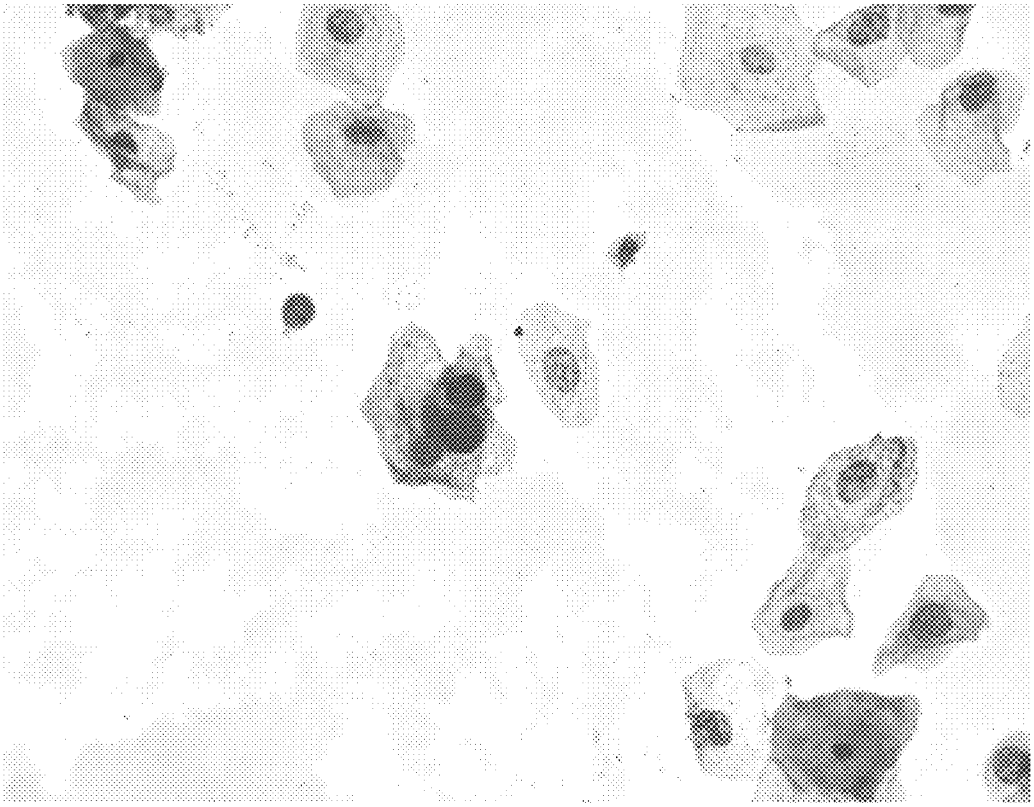
FIG. 14 depicts ISH with an HPV probe cocktail on a cytology sample prepared by the Thin Prep® method followed by PAP staining (HPV positive sample). HPV positive dysplastic cells displayed brown nuclear staining. Cells were also PAP stained (400× magnification).

The probe cocktail containing full length HPV types 16, 18, and 51 was labeled with biotin and tested by in situ hybridization described above on histology samples (FIGS. 7-14) and cytology samples (FIG. 6). The probe was able to cross-hybridize to high risk types 16, 18, 31, 33, 51, and 52 (FIGS. 7-12). In situ hybridization was also performed with the addition of unlabeled HPV 11 clone in the probe cocktail to block cross-hybridization to low risk HPV (FIGS. 13*a* and 13*b*). A cytology sample was counterstained with PAP stain after ISH with the HPV probe cocktail (FIG. 14).

Example 6

Immunocytochemical Detection of High Risk HPV and the Over Expression of p16$^{INK4a}$ in Samples of the Uterine Cervix for Identification of Pre-Neoplastic/Neoplastic Cells Merckofix® (Merck, Whitehouse Station, N.J.) cytological smears of the cervix uteri are prepared using ThinPrep® (Cytyc, Boxborough, Mass.) (liquid based cytology samples). The smears are immunochemically stained using high risk HPV (HR HPV) DNA probes as described in Example 2 and an antibody specific for p16$^{INK4a}$.

To rehydrate and remove the PEG film produced by the fixation, liquid based cytological samples are incubated in ethanol (50%) for 10 minutes and then transferred to distilled water. The smears are incubated in 4% neutral buffered formalin for 5 minutes and rinsed in distilled water and then transferred to washing buffer (50 mM Tris-HCl, 150 mM NaCl, 0.05% Tween 20, pH 7.6) for a minimum of 30 seconds. Antigen retrieval is carried out in 10 mM citrate buffer (pH 6.0). The cytological preparations are heated in a water bath for 40 minutes at 95-98° C. and then allowed to cool to room temperature for 20 minutes in the washing buffer.

After antigen retrieval the smears are rinsed twice in wash buffer (2 times, 5 minutes). To avoid endogenous peroxidase activity the smears are incubated in 3 hydrogen peroxide for 5 minutes followed by three washings in wash buffer for 5 minutes. To avoid endogenous biotin the smears are incubated in 0.1% avidin (X0590, DakoCytomation, Carpinteria, Calif.) for 10 min., followed by three washings in wash buffer for 1 min each. The smears are then incubated in 0.01% Biotin (X0590, DakoCytomation, Carpinteria, Calif.) for 10 min, followed by one washing in wash buffer and three washings in distilled water for 1 min each. Fifteen microliters of the hybridization probe is applied to each smear and a cover slip is applied to the smear. The probes and the HPV target DNA are denaturated by placing the smear with the cover slip in a Hybridizer (DakoCytomation) at 92° C. for five minutes. The smears are kept in the hybridizer for hybridization at 37° C. and incubated over night. After hybridization, the cover slips are removed from the smear by immersing the smears in wash buffer at room temperature and rinsing three times. Samples are thoroughly washed for 30 minutes at 48° C., under stringent conditions, using DakoCytomation code no. K0620. The smears are rinsed in wash buffer 3 times for 1 min. The smears are incubated with primary antibody for 30 min at room temperature. The primary antibody is mouse anti human p16$^{INK4a}$ antibody at a concentration of 3.48 μg/mL (clone E6H4) in 250 μl. The smears are rinsed with wash buffer and washed 2 times for 5 minutes. Excess buffer is tapped off and the smears are incubated for 30 minutes at room temperature with goat anto mouse/AP (code no D0486, DakoCytomation, Glostrup, DK) diluted 1:50. The smears are washed 3 times for 5 minutes in wash buffer. The smears are incubated for 30 minutes in primary streptavidin-HRP (DakoCytomation, Carpinteria, Calif.) diluted 1:3 in primary Streptavidin-HRP diluent (DakoCytomation, Carpinteria, Calif.). The smears are washed 3 times for 5 minutes in wash buffer. Biotinyl tyramide amplification reagent (DakoCytomation, Carpinteria, Calif.) is applied to the smears and incubated at room temperature for 15 minutes. The smears are washed in 3 times for 5 minutes in wash buffer. The smears are incubated with secondary streptavidin-HRP (DakoCytomation, Carpinteria, Calif.) for 15 minutes and then washed 3 times for 5 minutes in wash buffer. The chromogenic reaction is performed with di-amino-benzidine (DAB) where DAB chromogen concentrate is diluted 1:50 in DAB chromogen dilution buffer (DakoCytomation, Carpinteria, Calif.) and incubated 5 minutes at room temperature. The DAB reaction is stopped by washing the smears several times in distilled water and then placing the smears in wash buffer. Thereafter, the smears are incubated with Permanent Red Substrate Chromogen (code No K0640, DakoCytomation, Carpinteria, Calif.) for 10 minutes at room temperature. The smears are washed several times for a minimum of 10 minutes in distilled water before counterstaining with hematoxylin and mounted.

The microscopic examination of the cytological smears reveals, that cells positive for expression of p16$^{INK4a}$ and HR HPV only may be found in samples that may microscopically be identified as containing pre-neoplastic/neoplastic cells.

Cells that are stained by the p16$^{INK4a}$ specific reaction, but which are not stained by the HR HPV probe reaction are either metaplastic, of endometrial origin or contain an HR HPV type not detected by the probe cocktail.

Samples containing cells that react only with a specific HR HPV probe and not with the p16$^{INK4a}$ antibody are classified as samples having a risk for being malignant. Double stained cells that are reactive with both the HR HPV probe and p16$^{INK4a}$ antibody are pre-neoplastic/neoplastic cells.

Figure 30:
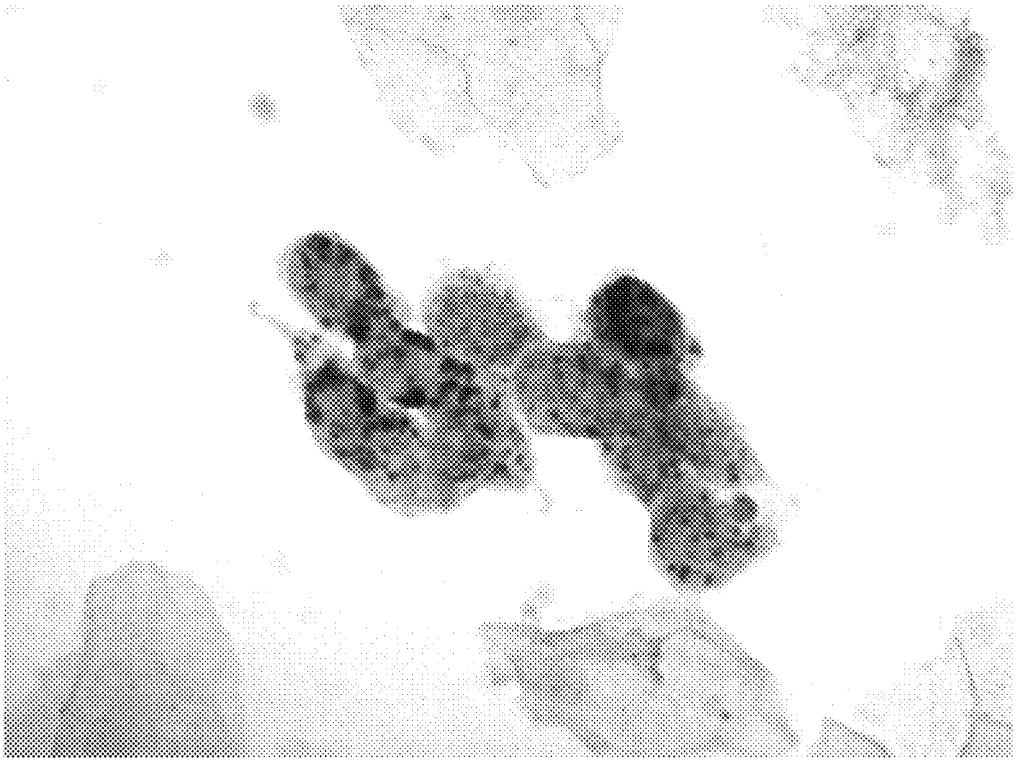
FIG. 30 depicts in situ hybridization with an HPV probe cocktail on a liquid based cytological sample of the cervix uteri in combination with immunostaining of $p16^{INK4a}$ expression. The HPV probe hybridized to HPV positive cells is demonstrated by brown nuclear staining. The $p16^{INK4a}$ antibody reacting with cells positive for expression of $p16^{INK4a}$ is demonstrated by red nuclear and cytoplasmic staining. (400× magnification).

The results show that this method allows for the specific identification of samples that contain pre-neoplastic/neoplastic cells having persistent HR HPV infection and samples that contain other cells infected with HR HPV virus having a risk for malignancy. Furthermore, double staining of the cells with reagents specific for HR HPV and p16$^{INK4a}$ permits discrimination of pre-neoplastic/neoplastic cells from metaplastic cells. It also permits identification of cells infected with HR HPV which are at risk for being malignant. The results are shown in FIG. 30.

Example 7

Immunocytochemical Detection of HR HPV and of Laminin 5 in Samples of the Uterine Cervix for Identification of Pre-Neoplastic/Neoplastic Cells with Invasive Capacity The procedure described above in Example 6, for staining and fixing the cells is followed in this example as well, except that the smears are incubated with a different primary antibody. A mouse anti human Laminin 5 antibody is used at a concentration of 13.3 μg/mL (clone 4G1). Incubation is for 30 minutes at room temperature.

Examination of the stained smears by light microscopy reveals that cells positive for expression of Laminin 5 and HR HPV are pre-neoplastic/neoplastic cells with invasive capacity.

Cells that only react with specific HR HPV probes and not with Laminin 5 antibody are classified as at risk for malignancy or malignant.

Figure 31:
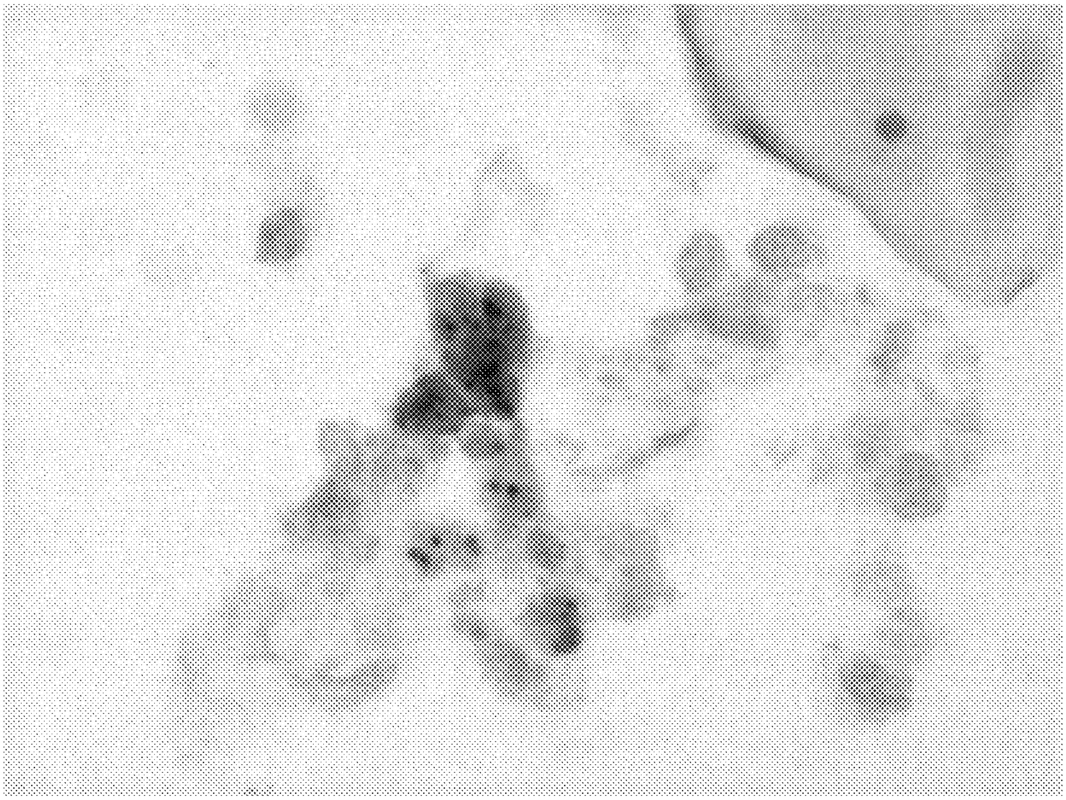
FIG. 31 depicts in situ hybridization with an HPV probe cocktail on a liquid based cytological sample of the cervix uteri in combination with immunostaining of Laminin 5 expression. The HPV probe hybridized to HPV positive cells is demonstrated by brown nuclear staining. The Laminin 5 antibody reacting with cells positive for expression of Laminin 5 is demonstrated by red cytoplasmic staining. (400× magnification).

The assay provides a method for the discrimination of pre-neoplastic/neoplastic cells from normal cervical cells and identify cells with invasive capacity. The results are shown in FIG. 31.

Example 8

Immunocytochemical Detection of Laminin 5 and the Over Expression of p16$^{INK4a}$ in Samples of the Uterine Cervix for Identification of Pre-Neoplastic/Neoplastic Cells with Invasive Capacity Merckofix® (Merck, Whitehouse Station, N.J.) cytological smears (liquid based smears) of the cervix uteri are immunochemically stained using an antibody specific for Laminin 5 and an antibody specific for p16$^{INK4a}$.

The following protocol is used to stain the cells. To rehydrate and remove the PEG film produced by the fixation, liquid based cytological samples are incubated in ethanol (50%) for 10 minutes and then rinsed in distilled water and then transferred to washing buffer (50 mM Tris-HCl, 150 mM NaCl, 0.05% Tween 20, pH 7.6) for a minimum of 30 seconds. Antigen retrieval is carried out in 10 mM citrate buffer (pH 6.0) where the smears are heated in a water bath for 40 minutes at 95-98° C. and afterwards are allowed to cool to room temperature for 20 minutes in the antigen retrieval buffer. The smears are incubated with a mixture of primary antibodies. The primary antibodies are mouse anti human p16$^{INK4a}$, at a concentration of 3.48 μg/mL (clone E6H4) and rabbit anti human Laminin 5, at a concentration of 14.5 μg/mL in a volume of 250 μl for 30 minutes at room temperature. Smears are then rinsed with washing buffer and placed in a fresh wash buffer for 5 minutes.

Excess buffer is tapped off and each slide is incubated with 250 μl of visualization reagent comprising Goat anti mouse EnVision/HRP (vial 3 from code no. K5338, DakoCytomation, Glostrup, DK) and Goat anti Rabbit/AP diluted 1:50 (code no. D0487, DakoCytomation, Carpinteria, Calif.) and then incubated for 30 minutes at room temperature. Samples are washed 3 times for 5 minutes in wash buffer. The samples are then incubated for 5 minutes with the chromogenic substrate DAB (DakoCytomation, Carpinteria, Calif.). The DAB reaction is stopped by washing the smears several times in distilled water and then placed in wash buffer. The smears are then incubated with Permanent Red Substrate Chromogen (code no. K0640, DakoCytomation, Carpinteria, Calif.) for 10 minutes at room temperature and then washed several times in distilled water. The samples are then counterstained with hematoxylin and mounted.

Figure 32:
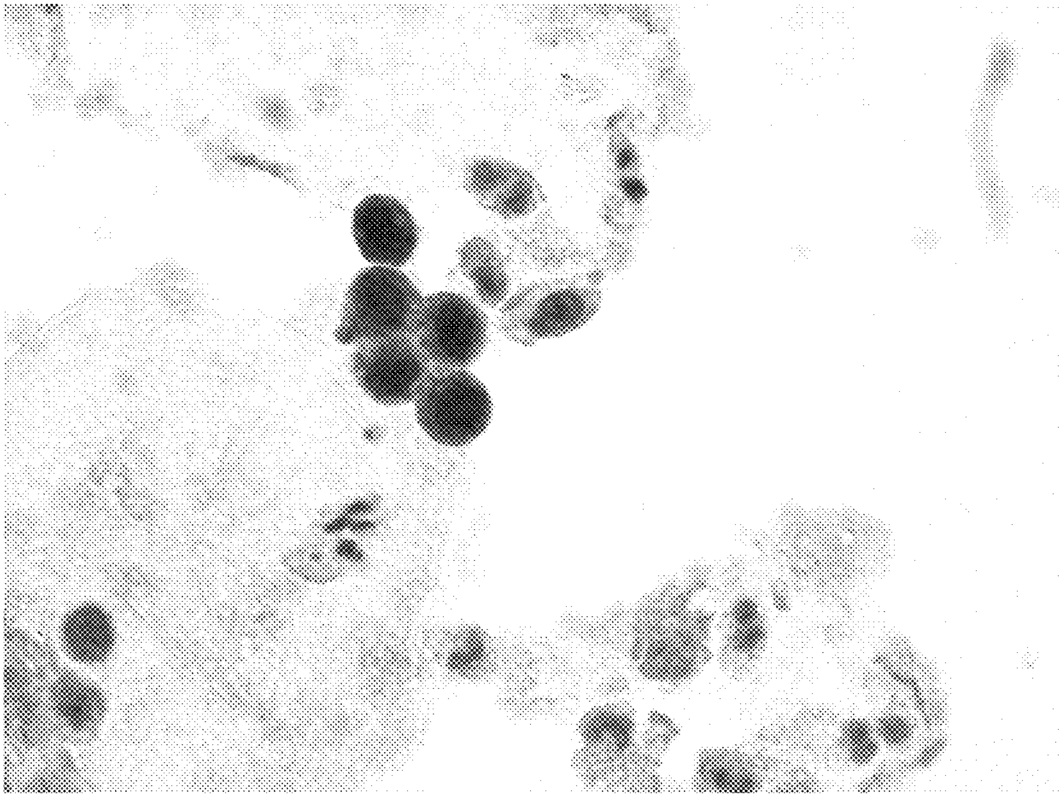
FIG. 32 depicts immunostaining of $p16^{INK4a}$ and Laminin 5 expression on a liquid based cytological sample of the cervix uteri. The $p16^{INK4a}$ antibody reacting with cells positive for expression of $p16^{INK4a}$ is demonstrated by brown nuclear and cytoplasmic staining. The Laminin 5 antibody reacting with cells positive for expression of Laminin 5 is demonstrated by red cytoplasmic staining. (200× magnification).

The microscopic examination of the stained smears reveals that cells positive for expression of Laminin 5 and p16$^{INK4a}$ may only be found in samples that can be microscopically identified as containing pre-neoplastic/neoplastic cells. The results show that this method identifies pre-neoplastic/neoplastic cells with invasive capacity. The results are shown in FIG. 32.

Example 9

Immunocytochemical Detection of HR HPV and Laminin 5 in Sections of Formalin Fixed, Paraffin Embedded Tissue Samples with Diagnosed Colon Cancer This procedure provides a method to diagnose colon cancer.

Sections of formalin fixed paraffin embedded tissue samples from a patient diagnosed with colon cancer are immunochemically stained using the DNA HR HPV probes, as described in Example 2, and an antibody specific for Laminin 5.

Tissue sections are rehydrated by incubating in xylene and graded ethanol, rinsed in distilled water and then transferred to washing buffer (50 mM Tris-HCl, 150 mM NaCl, 0.05% Tween 20, pH 7.6) for a minimum of 30 seconds. Antigen retrieval is carried out in 10 mM citrate buffer (pH 6.0). The slides are heated in a water bath for 40 minutes at 95-98° C. and then allowed to cool to room temperature for 20 minutes in washing buffer.

The sections are then incubated with Proteinase K (DakoCytomation, Carpinteria, Calif.) diluted 1:50 or 1:100 in TBS buffer and incubated for 4-5 minutes at room temperature. After incubation the slides are rinsed twice in wash buffer for 5 minutes per rinse. To avoid endogenous peroxidase activity the sections are incubated in 3% hydrogen peroxide for 5 minutes. The samples are then washed twice for 5 minutes per wash in wash buffer. To avoid endogenous biotin the sections are incubated in 0.1% avidin (X0590, DakoCytomation, Carpinteria, Calif.) for 10 minutes, followed by three washings in wash buffer for 1 min each. The sections are then incubated in 0.01% biotin (X0590, DakoCytomation, Carpinteria, Calif.) for 10 min, followed by three washings in wash buffer for 1 min each. Fifteen microliters of the hybridization probe is applied to each section and a cover slip is applied to the section. The probe and the HPV target DNA are denaturated by placing the section in a Hybridizer (DakoCytomation) at 92° C. for five minutes. The sections are kept in the Hybridizer for hybridization at 37° C. over night. After hybridization the cover slips are removed from the slide by immersing the slides in wash buffer at room temperature and rinsing three times for 1 minute each. Sections are washed under stringent conditions for 30 minutes at 48-52° C. using a prepared wash buffer (DakoCytomation, Carpinteria, Calif.). Then the sections are rinsed in 3× wash buffer for 1 min each.

The sections are incubated with the primary antibody, mouse anti human Laminin 5, at a concentration of 13.3 μg/mL (clone 4G1), for 30 minutes at room temperature. The method for staining and washing the samples described in Example 7 is followed.

Examination of the slides by light microscopy reveals that cells which are positive for expression of Laminin 5 and HR HPV are found only in samples with pre-neoplastic/neoplastic lesions. The results show that this method allows for the specific identification of samples having persistent HR HPV infection containing pre-neoplastic/neoplastic cells with invasive capacity.

Example 10

Automated Immunocytochemical Detection of HR HPV and the Over Expression of p16$^{INK4a}$ in Samples of the Uterine Cervix for Identification of Pre-Neoplastic/Neoplastic Cells The method for staining and washing the samples described in Example 7 is followed.

The remaining steps are automated and performed under the control of a computer program. An Autostainer instrument (DakoCytomation, Carpinteria, Calif.) is used and a program for "HPV and p16$^{INK4a}$" on cytological smears is run. Staining reagents vials are placed in the Autostainer rack according to the computer generated reagent layout map showed on the screen. The smears are loaded onto the instrument according to the computer generated slides layout map. An algorithm comprising the following steps is run:

"Rinse—300 mL primary antibody, mouse anti human p16$^{INK4a}$ antibody 3.48 μg/mL (clone E6H4), 30 minutes—rinse—8 minutes washing buffer (50 mM Tris-HCL, 150 mM NaCl, 0.05% Tween 20, pH 7.6)—300 mL visualization reagent goat anti mouse (DakoCytomation, Carpinteria, Calif.), 30 minutes—rinse—8 minutes TBST—rinse—primary streptavidin-HRP (DakoCytomation, Carpinteria, Calif.) diluted 1:3 in primary Streptavidin-HRP diluent (DakoCytomation, Carpinteria, Calif.), 30 minutes—rinse 8 minutes TBST—rinse 8 minutes TBST—rinse—biotinyl tyramide amplification reagent (DakoCytomation, Carpinteria, Calif.) 15 minutes—rinse 8 minutes TBST—rinse 8 minutes TBST—secondary streptavidin-HRP (DakoCytomation, Carpinteria, Calif.), 15 minutes—rinse 8 minutes TBST—rinse 8 minutes TBST—rinse 5 minutes—300 μL DAB chromogen concentrate is diluted 1:50 in DAB chromogen dilution (DakoCytomation, Carpinteria, Calif.), 5 minutes—rinse.

The smears are placed manually in Permanent Red Substrate Chromogen (DakoCytomation, Carpinteria, Calif.) for 10 minutes followed by several washings in distilled water. Finally, the smears are counterstained with hematoxylin and mounted.

Samples containing cells that react only with a specific HR HPV probe and not with the $p16^{INK4a}$ antibody are classified as samples having a risk for being malignant. Double stained cells that are reactive with both the HR HPV probe and $p16^{INK4a}$ antibody are pre-neoplastic/neoplastic.

Figure 33:
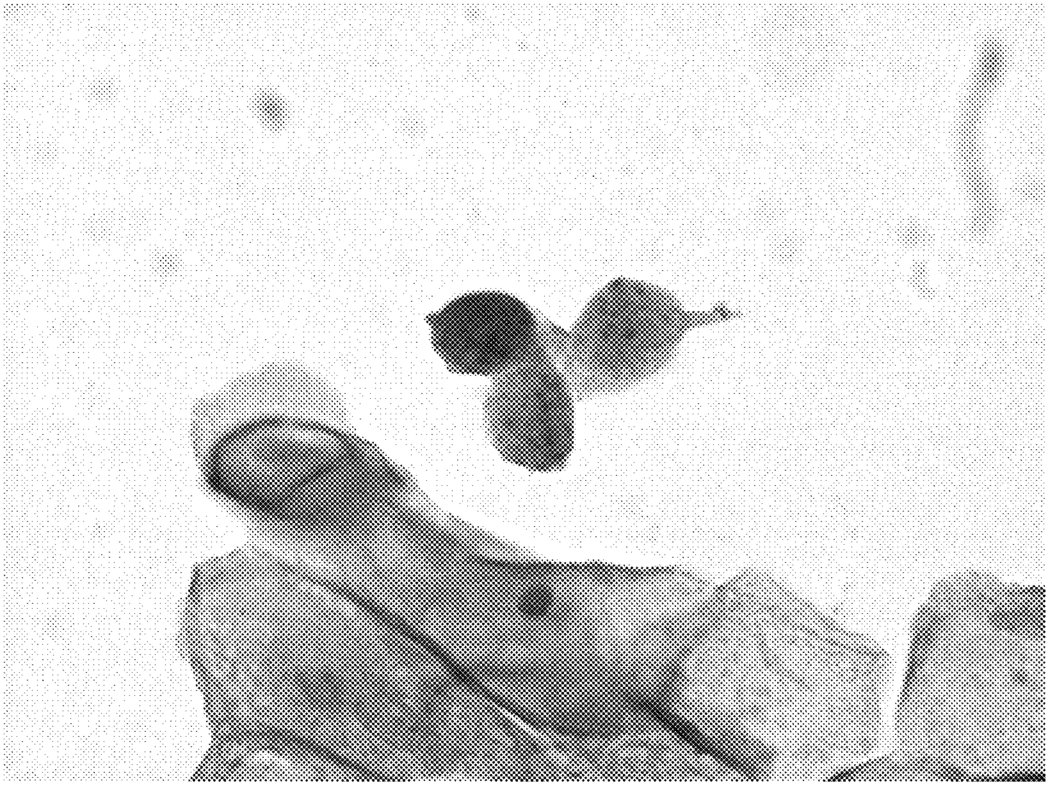
FIG. 33 depicts in situ hybridization with an HPV probe cocktail on a liquid based cytological sample of the cervix uteri in combination with immunostaining of $p16^{INK4a}$ expression, performed with automated immunocytochemical detection. The HPV probe hybridized to HPV positive cells is demonstrated by brown nuclear staining. The $p16^{INK4a}$ antibody reacting with cells positive for expression of $p16^{INK4a}$ is demonstrated by red nuclear and cytoplasmic staining. (400× magnification).

The results show that this method allows for the specific identification of samples that contain pre-neoplastic/neoplastic cells having persistent HR HPV infection and samples that contain other cells infected with HR HPV virus having a risk for malignancy. Furthermore, double staining of the cells with reagents specific for HR HPV and $p16^{INK4a}$ permits discrimination of pre-neoplastic/neoplastic cells from metaplastic cells. It also permits identification of cells infected with HR HPV which are at risk for being malignant. The results are shown in FIG. 33.

Example 11

Immunocytochemical Detection of HR HPV and Laminin 5 and of the Over-Expression of $p16^{INK4a}$ in Samples of the Uterine Cervix for Identification of Pre-Neoplastic/Neoplastic Cells In this experiment, cells are stained for HR HPV and both $p16^{INK4a}$ and Laminin 5. It is not necessary to distinguish between cells staining positive for Laminin 5 or $p16^{INK4a}$. A positive result for either in combination with a positive HR HPV will be indicative of pre-neoplastic/neoplastic cells.

Merckofix® (Merck, Whitehouse Station, N.J.) cytological smears of the cervix uteri are prepared using ThinPrep® (Cytyc, Boxborough, Mass.) (liquid based cytology samples). The samples are immunochemically stained using DNA HR HPV probes, as described in Example 2, an antibody specific for $p16^{INK4a}$ and antibody specific for Laminin 5.

The method for staining and washing the samples described in Example 7 is followed with an antibody to $p16^{INK4a}$ and an antibody to Laminin 5.

The samples are incubated with a mixture of primary antibodies, including mouse anti human $p16^{INK4a}$, at a concentration of 3.48 μg/mL (clone E6H4) and mouse anti human Laminin 5, at a concentration of 13.3 μg/mL (clone 4G1) for 30 minutes at room temperature.

The microscopic examination of the cytological smears reveals, that cells positive for expression of Laminin 5 or $p16^{INK4a}$ and HR HPV are found only in samples that may microscopically be identified as being pre-neoplastic or neoplastic.

Samples that contain cells reacting with only a specific HR HPV probe and not with the Laminin 5 or $p16^{INK4}$a antibodies are classified as samples having a risk of being malignant. Triple stained cells that are reactive with both the HR HPV probe and Laminin 5/$p16^{INK4a}$ antibody are pre-neoplastic/neoplastic cells.

Figure 34:
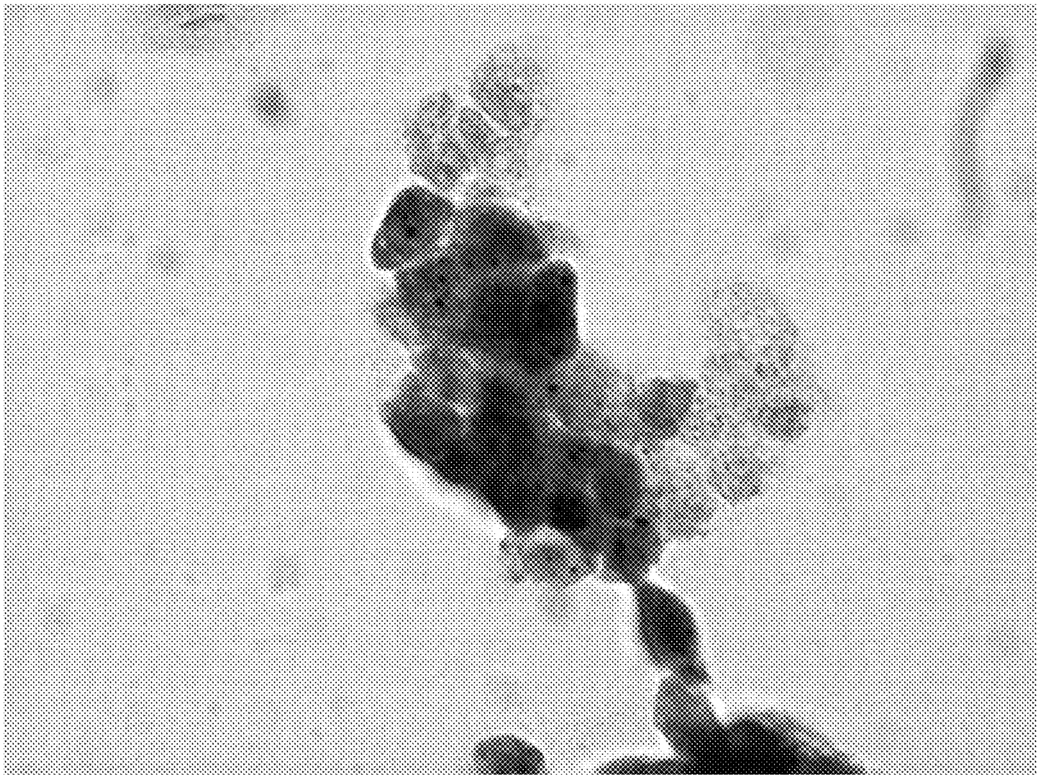
FIG. 34 depicts in situ hybridization with an HPV probe cocktail on a liquid based cytological sample of the cervix uteri in combination with immunostaining of $p16^{INK4a}$ and Laminin 5 expression. The HPV probe hybridized to HPV positive cells is demonstrated by brown nuclear staining. The $p16^{INK4a}$ and Laminin 5 antibodies reacting with cells positive for expression of $p16^{INK4a}$ and Laminin 5 are demonstrated by red nuclear and cytoplasmic staining. (400× magnification).

Triple staining of cells with reagents specific for HR HPV and Laminin 5/$p16^{INK4a}$ allows for discrimination of pre-neoplastic/neoplastic cells from metaplastic cells as well as cells infected with HR HPV having a risk for being malignant. The results are shown in FIG. 34.

Example 12

Detection of Pre-Neoplastic/Neoplastic Lesions Using a Ki-67 Antibody and HR-HPV Probes The procedure described in Example 7, for fixing and staining of the cells is followed in this example as well, except that the smears are incubated with a different primary antibody. A mouse anti human Ki-67 (DakoCytomation, Carpinteria, Calif., clone MIB-1) at a concentration of 0.8 μg/ml is used. Samples are Incubated for 30 minutes at room temperature.

Figure 35:
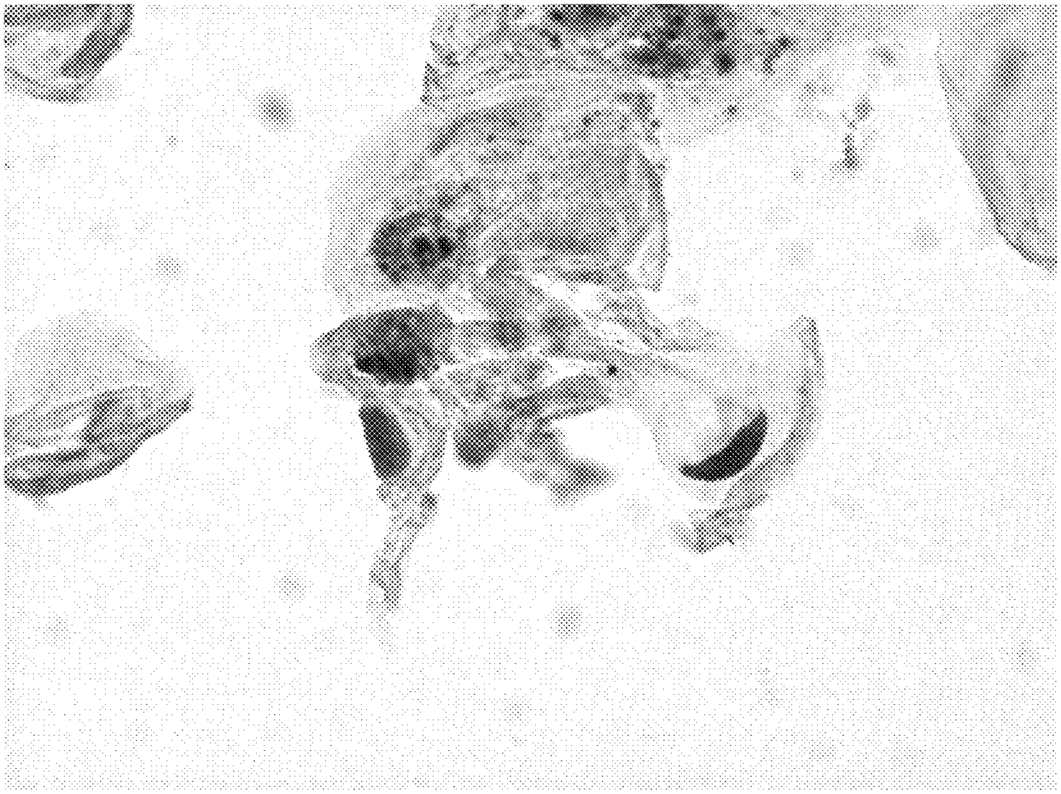
FIG. 35 depicts in situ hybridization with an HPV probe cocktail on a liquid based cytological sample of the cervix uteri in combination with immunostaining of Ki-67 overexpression. The HPV probe hybridized to HPV positive cells is demonstrated by brown nuclear staining. The Ki-67 antibody reacting with cells positive for expression of Ki-67 is demonstrated by red nuclear staining. (400× magnification).

Examination of the stained slides by light microscopy reveals that cells that are positive for expression of Ki-67 and HR HPV are found in samples with pre-neoplastic/neoplastic lesions. The results are shown in FIG. 35.

Example 13

Detection of Pre-Neoplastic/Neoplastic Lesions Using a Cyclin E Antibody and HR-HPV Probes The procedure described in Example 9, for pretreatment of tissue section and staining of the cells is followed in this example as well, except that the tissue samples from a patient diagnosed with cervical cancer is used and incubated with a different primary antibody. A mouse anti human cyclin E antibody (Novocastra Laboratories, Newcastle upon Tyne, clone 13A), diluted 1:25 is used. Samples are incubated for 30 minutes at room temperature.

Examination of the stained slides by light microscopy reveals that cells that are positive for expression of cyclin E and HR HPV are found in samples that with pre-neoplastic/neoplastic lesions.

Example 14

Detection of Pre-Neoplastic/Neoplastic Lesions Using a Cox-2 Antibody and HR-HPV Probes The procedure described in Example 9, for pretreatment of tissue section and staining of the cells is followed in this example as well, except that the tissue samples from a patient diagnosed with colon cancer is used and incubated with a different primary antibody. A mouse anti human Cox-2 antibody (DakoCytomation, Carpinteria, Calif., clone CX-294) diluted to a concentration of 4.9 μg/mL is used. The samples are incubated for 30 minutes at room temperature.

Examination of the stained slides by light microscopy reveals that cells that are positive for expression of Cox-2 and HR HPV are found in samples that are diagnosed with colon cancer.

Example 15

In Situ Hybridization (ISH) Using a Probe Diluted in Hybridization Buffer Containing LMW Dextran Sulfate on Histology Samples In Situ hybridization was performed as described above in Example 3. The only difference is that in some slides 10% LMW dextran sulfate (35,000 to 50,000) (USB Corporation, Cleveland, Ohio or MP Biochemicals, Aurora, Ohio) was used instead of 10% HMW dextran sulfate (450,000 to 550,000) (Sigma, St. Louis, Mo.) in the hybridization buffer described.

Figure 21:
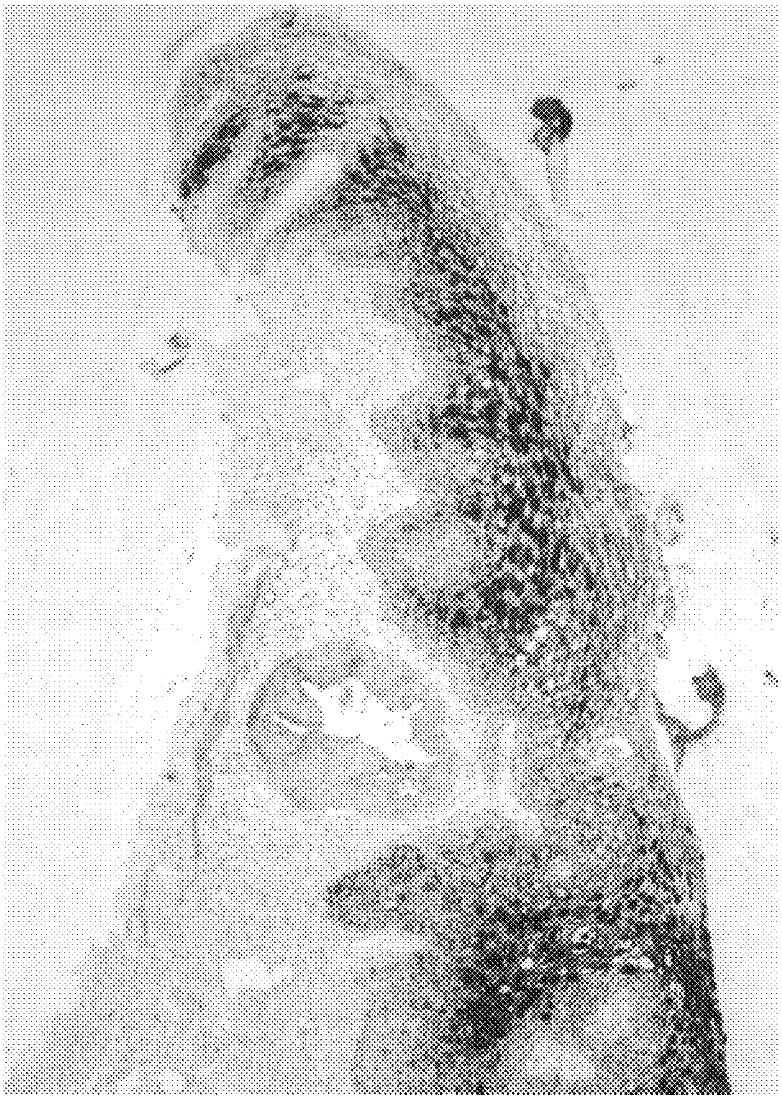
FIG. 21 depicts ISH with an HPV probe cocktail in hybridization buffer containing HMW dextran sulfate on a cervical biopsy sample that was HPV 31 positive. The HPV probe hybridized to HPV 31 positive cells in the cervical epithelium as demonstrated by brown nuclear staining, however, non-specific background brown staining was also apparent (200× magnification).
Figure 22:
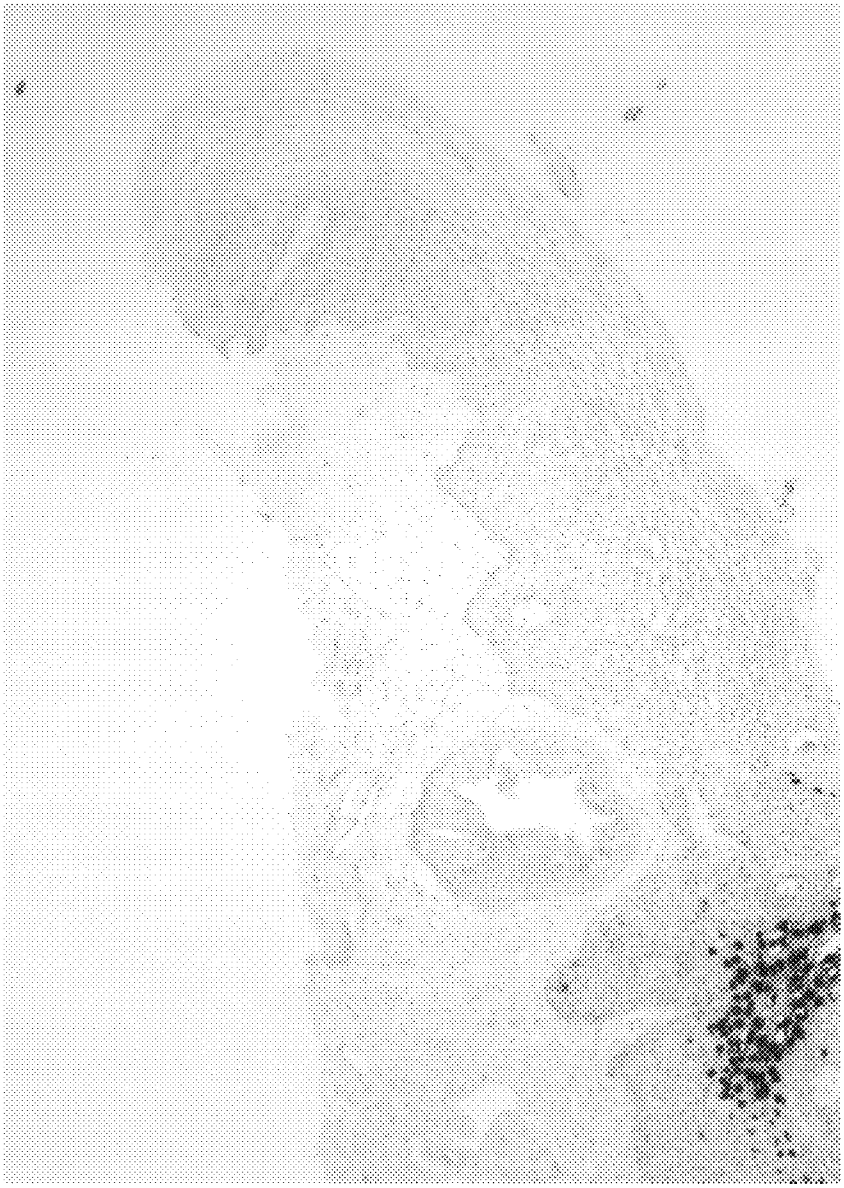
FIG. 22 depicts ISH with an HPV probe cocktail in hybridization buffer containing LMW dextran sulfate on a cervical biopsy sample that was HPV 31 positive. The HPV probe hybridized to HPV 31 positive cells in the cervical epithelium as demonstrated by brown nuclear staining, however, no non-specific background brown staining was apparent with the use of LMW dextran sulfate (200× magnification).

Slides stained with the probe in hybridization buffer containing HMW dextran sulfate showed non-specific background staining. In contrast, the non-specific background staining was removed when LMW dextran sulfate was used. (FIGS. 21 and 22).

Example 16

In Situ Hybridization (ISH) Using Probe Diluted in Hybridization Buffer Containing LMW Dextran Sulfate on Cytology Samples In Situ hybridization was performed as described above in Example 2. The only difference is that in some slides 10% LMW dextran sulfate (35,000 to 50,000) (USB Corporation, Cleveland, Ohio or MP Biochemicals, Aurora, Ohio) was used instead of 10% HMW dextran sulfate (450,000 to 550, 000) (Sigma, St. Louis, Mo.) in the hybridization buffer described.

Slides stained with the probe in hybridization buffer containing HMW dextran sulfate gave similar positive result as slides stained with the probe in hybridization buffer containing LMW dextran sulfate.

Example 17

Immunohistochemical Detection of Expression of Cox-2 and Laminin-5 in Cervical Samples Formalin-fixed paraffin embedded (FFPE) cervical biopsies were deparaffinized and rehydrated before use. For deparaffinization, the slides were soaked in Histoclear (National Diagnostics, Atlanta, Calif.) for five minutes. This step was repeated once. The samples were rehydrated by placing in two changes of 99% ethanol, three minutes each, and 2 changes of 95% ethanol, three minutes each. The slides were then rinsed in reagent water before pre-treatment. For pre-treatment, Target Retrival Solution (TRS), pH 9, (DakoCytomation, code S 2367), was first diluted 1:10 in 180 mL of reagent water. The TRS was pre-warmed to 95° C. in a 97° C. water bath. The samples were incubated at 95° C. for 20 minutes in the TRS and then cooled at room temperature for 20 minutes. After rinsing the slides three times in reagent water the slides were put in 3% $H_2O_2$ for five minutes to remove endogenous peroxidase activity. After rinsing in reagent water, the slides were incubated in 0.05M Tris-HCl, pH 7.6, 0.15M NaCl (TBS) buffer for five minutes.

Primary antibody was applied after excess water was removed from the sample. Cox-2 (DakoCytomation, code M3617) diluted at 1:200 and Laminin-5 (DakoCytomation, code M7262) diluted at 1:25, were combined. Mouse IGg1 (DakoCytomation, code X0931) diluted at 1:50, was used as a negative control. Antibody dilutions were prepared using Antibody Diluent (DakoCytomation, code S0809). The slides were incubated at room temperature in a humid chamber for 30 minutes. The samples were then rinsed with TBS buffer and placed in fresh TBS for five minutes. Excess buffer was removed and Envision®+Labelled Polymer, HRP (DakoCytomation, code K4001) was applied. The slides were incubated at room temperature in a humid chamber for 30 minutes. The samples were then rinsed with TBS buffer and placed in fresh TBS for five minutes. The slides were next incubated for 10 minutes with chromogenic substrate DAB+ (DakoCytomation, Code K3468) in a humid chamber. After rinsing the slides three times in reagent water, they were counterstained with hematoxylin and mounted.

Examination of the stained samples by light microscopy revealed that the expression of Laminin 5 and Cox-2 is minimal in normal cervical samples but increases in high grade intra-epithelial lesions, squamous carcinoma, and adenocarcinoma.

Example 18

Detection of Human Telomerase and Histone H3 Expression by In Situ Hybridization Using Cervical Samples Formalin-fixed paraffin embedded (FFPE) cervical tissues or cells (HeLa) were deparaffinized and rehydrated before use. For deparaffinization, the slides were soaked in Xylene or Histoclear (National Diagnostics, Atlanta, Ga.) for 5 minutes. This step was repeated once. The sample was re-hydrated by placing it in 2 changes of 99% ethanol and 3 changes of 95% ethanol, 1 minute each. The slides were rinsed in reagent water several times before pre-treatment. For pre-treatment, Target Retrival Solution (TRS) (DakoCytomation, code S1700) was pre-warmed to 95° C. in a 97° C. water bath. The samples were incubated at 95° C. for 40 minutes in the TRS and then cooled at room temperature for 20 minutes. For cervical tissues, an additional incubation of 20 minutes in 0.005% pepsin at room temperature was performed. After rinsing in reagent water several times, the slides were then incubated in 3% $H_2O_2$ for 5 minutes to remove endogenous peroxidase activity.

A cocktail probe targeting the RNA component of the human telomerase complex and mRNA of Histone H3 was used. Fifteen microliters of the probe was applied to each sample and a cover slip was applied. The samples were transferred to a humid chamber for hybridization at 37° C. and incubated for 2 hours. After hybridization, the cover slips were removed from the slides by immersing the slides in wash buffer at room temperature. Samples were thoroughly washed for 30 minutes at 52-55° C., under stringent conditions, using stringent wash buffer diluted 1:50 in water (DakoCytomation, code S3500). The samples were rinsed in wash buffer 3 times. The samples were incubated for 30 minutes in anti-FITC/HRP diluted 1:100 in anti-FITC/HRP diluent (DakoCytomation, code K0618) and then washed 3 times for 5 minutes in wash buffer. Fluoresyl tyramide amplification reagent (DakoCytomation, code K0618) was applied to the samples and incubated at room temperature for 15 minutes. The samples were washed 3 times for 5 minutes in wash buffer. The samples were incubated with anti-fluorescein/HRP (DakoCytomation, code no. K0618) for 15 minutes and then washed 3 times for 5 minutes in wash buffer. The chromogenic reaction was performed with di-amino-benzidine (DAB) where DAB chromogen concentrate was diluted 1:50 in DAB chromogen dilution buffer (DakoCytomation, code K0618) and incubated for 5 minutes at room temperature. After rinsing the slides three times in reagent water, they were counterstained with hematoxylin and mounted.

Examination of the stained samples by light microscopy revealed that the expression pattern of Histone H3 mRNA is cytoplasmic and the RNA component of telomerase is nuclear. The 2 markers gave strong staining in HeLa cells. In cervical tissues, both markers gave staining in proliferating cells.

Example 19

Detection of HR-HPV and the Overexpression of $p16^{INK4a}$ in Samples of the Uterine Cervix in Combination with Pap Staining for Identification of Pre-Neoplastic/Neoplastic Cells The procedure described in example 6 for pretreatment and staining of cells is followed. After the DAB step, the slides are processed for PAP staining, as described in example 4.

The microscopic examination of the cytological smears reveals, that cells that are stained by the $p16^{INK4a}$ specific reaction and not stained by the HR HPV probe reaction, are either metaplastic, of endometrial origin, or contain an HR HPV type not detected by the probe cocktail, as can be morphologically identified by the Pap staining.

The results show that this method allows for the specific identification of samples that contain pre-neoplastic/neoplastic cells having persistent HR HPV infection and samples that contain other cells infected with HR HPV virus having a risk for malignancy. Furthermore, double staining of the cells with reagents specific for HR HPV and $p16^{INK4a}$ permits discrimination of pre-neoplastic/neoplastic cells from metaplastic cells. It also permits identification of cells infected with HR HPV which are at risk for being malignant.

Example 20

Immunocytochemical Detection of Ki-67 and Laminin 5, and the Overexpression of $p16^{INK4a}$ and Cyclin E in Samples of the Uterine Cervix for Identification of Pre-Neoplastic/Neoplastic Cells with Invasive Capacity The procedure described in example 8 for pretreatment and staining of cells is followed, except that the smears are incubated with a antibody mixture containing antibody to $p16^{INK4a}$, antibody to Cyclin E, and two additional antibodies. Mouse anti human $p16^{INK4a}$ antibody (isotype IgG2a) is used at a concentration of 3.48 μg/ml (clone E6H4), and Mouse anti human Cyclin E antibody (Novocastra Laboratories, Newcastle upon Tyne) (isotype IgG2a) diluted 1:25 is used. A mouse anti human Ki-67 antibody (clone MIB1) (isotype IgG1) is used at a concentration of 0.8 μg/mL and a rabbit anti human Laminin 5 antibody is used at a concentration of 14.5 μg/mL.

The smears are incubated with a mixture of all four primary antibodies and incubation time is for 30 min at room temperature.

Visualization of $p16^{INK4a}$ and Cyclin E is performed using goat anti mouse IgG2a/FITC (Jackson ImmunoResearch, PA). Visualization of Ki-67 is performed using goat anti mouse IgG1/Rhodamine (Jackson ImmunoResearch, PA). Visualization of Laminin 5 is performed using goat anti rabbit IgG/AMCA (Jackson ImmunoResearch, PA). The smears are incubated with a mixture of all three secondary antibodies and incubation time is for 30 min at room temperature.

The smears are counterstained with DAPI (1 μg/ml) in antifade solution (Vectashield, Vector Laboratories, CA).

The microscopic evaluation of the stained smears with a fluorescent microscope equipped with the corresponding filters reveals, that cells positive for expression of $p16^{INK4a}$/Cyclin E, Ki-67 and Laminin 5 may only be found in samples that can be microscopically identified as pre-neoplastic/neoplastic cells with invasive capacity. The detection of both $p16^{INK4a}$ and Cyclin E increases the sensitivity for identification of pre-neoplastic/neoplastic cells. Cells only positive for Ki-67 can be identified as proliferating cells. Cells only positive for $p16^{INK4a}$/Cyclin E and not for Ki-67 or Laminin 5 can be identified as metaplastic cells.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

We claim:

1. A composition comprising a combination of nucleic acid probes consisting essentially of:

at least one first nucleic acid probe comprising a fragment of 10-500 consecutive bp from human papilloma virus 16 (SEQ ID NO: 1), which probe is capable of hybridizing to SEQ ID NO: 1 under low stringency conditions, at least one second nucleic acid probe comprising a fragment of 10-500 consecutive bp from human papilloma virus 18 (SEQ ID NO: 2), which probe is capable of hybridizing to SEQ ID NO: 2 under low stringency conditions, and at least one third nucleic acid probe comprising a fragment of 10-500 consecutive bp from human papilloma virus 51 (SEQ ID NO: 4), which probe is capable of hybridizing to SEQ ID NO: 4 under low stringency conditions;

wherein the combination of nucleic acid probes is capable of hybridizing to at least 14 high risk HPV types, and wherein at least one nucleic acid probe chosen from the first, second or third nucleic acid probes is capable of hybridizing to a human papilloma virus (HPV) nucleic acid contained in a sample thereby forming at least one nucleic acid-HPV hybridization complex, and wherein hybridization of the at least one nucleic acid probe to the sample indicates the presence of cancer or the risk of developing cancer.

2. The composition of claim 1, wherein the nucleic acid probes comprise DNA, RNA, LNA or PNA.

3. The composition of claim 1, wherein the nucleic acid probes are labeled with a detectable substance.

4. The composition of claim 1, further comprising a hybridization buffer comprising a low molecular weight dextran sulfate.

5. The composition of claim 4, wherein the low molecular weight dextran sulfate is present in an amount ranging from 5-15 wt/vol %.

6. The composition of claim 1, wherein the fragments of 10-500 consecutive bp are 10, 20, 30, 40, 50, 60, 70, 80, 90, 100, 200, 300, 400, or 500 bp in length.

7. The composition of claim 1, wherein the at least one first, at least one second, and at least one third nucleic acid probes are present in equal proportions in the combination.

8. The composition of claim 1, wherein the composition further comprises materials for performing a PAP stain of a sample.

9. A composition comprising:

(a) a combination of nucleic acid probes consisting essentially of:

at least one first nucleic acid probe comprising a fragment of 10-500 consecutive bp from human papilloma virus 16 (SEQ ID NO: 1), which probe is capable of hybridizing to SEQ ID NO: 1 under low stringency conditions, at least one second nucleic acid probe comprising a fragment of 10-500 consecutive bp from human papilloma virus 18 (SEQ ID NO: 2), which probe is capable of hybridizing to SEQ ID NO: 2 under low stringency conditions, and at least one third nucleic acid probe comprising a fragment of 10-500 consecutive bp from human papilloma virus 51 (SEQ ID NO: 4), which probe is capable of hybridizing to SEQ ID NO: 4 under low stringency conditions;

wherein the combination of the first, second, and third nucleic acid probes is capable of hybridizing to at least 14 high risk HPV types, and wherein at least one nucleic acid probe chosen from the first, second or third nucleic acid probes is capable of hybridizing to a human papilloma virus (HPV) nucleic acid contained in a sample thereby forming at least one nucleic acid-HPV hybridization complex, and wherein hybridization of the at least one nucleic acid probe to the sample indicates the presence of cancer or the risk of developing cancer; and further comprising (b) at least one further nucleic acid probe that is capable of hybridizing to at least one low risk HPV type, and/or at least one molecule that is capable of hybridizing to at least one marker for cancer.

10. The composition of claim 9, comprising at least one further nucleic acid probe that is capable of hybridizing to at least one low risk HPV type, wherein the further nucleic acid probe is substantially identical to a full length genomic clone of a low risk HPV type, or fragment thereof.

11. The composition of claim 10, wherein the low risk HPV type is HPV 11 or HPV 70.

12. The composition of claim 9 wherein the nucleic acid probes comprise DNA, RNA, LNA or PNA.

13. The composition of claim 9, wherein the first, second, and third nucleic acid probes are labeled with a detectable substance.

14. The composition of claim 9, wherein the fragments of 10-500 consecutive bp are 10, 20, 30, 40, 50, 60, 70, 80, 90, 100, 200, 300, 400, or 500 bp in length.

15. The composition of claim 9, wherein the at least one first, at least one second, and at least one third nucleic acid probes are present in equal proportions in the combination.

16. The composition of claim 9, wherein the composition further comprises materials for performing a PAP stain of a sample.

17. The composition of claim 9, comprising at least one further nucleic acid probe that is capable of hybridizing to at least one low risk HPV type, wherein the further nucleic acid probe is not labeled with a detectable substance.

18. The composition of claim 13, comprising at least one further nucleic acid probe that is capable of hybridizing to at least one low risk HPV type, wherein the further nucleic acid probe is labeled with a detectable substance that is different from the detectable substance used to label the first, second, and third nucleic acid probes.

19. The composition of claim 9, comprising at least one molecule that is capable of hybridizing to at least one marker for cancer, wherein the molecule is capable of hybridizing to a cervical, colon, anal, or HPV-related cancer marker.

20. The composition of claim 9, comprising at least one molecule that is capable of hybridizing to at least one marker for cancer, wherein the molecule is an antibody.

* * * * *

SEQUENCE LISTING

```
<160> NUMBER OF SEQ ID NOS: 9

<210> SEQ ID NO 1
<211> LENGTH: 7904
<212> TYPE: DNA
<213> ORGANISM: Homo sapiens

<400> SEQUENCE: 1

actacaataa ttcatgtata aaactaaggg cgtaaccgaa atcggttgaa ccgaaaccgg      60

ttagtataaa agcagacatt ttatgcacca aaagagaact gcaatgtttc aggacccaca     120

ggagcgaccc agaaagttac cacagttatg cacagagctg caaacaacta tacatgatat     180

aatattagaa tgtgtgtact gcaagcaaca gttactgcga cgtgaggtat atgactttgc     240

ttttcgggat ttatgcatag tatatagaga tgggaatcca tatgctgtat gtgataaatg     300
```

-continued

```
tttaaagttt tattctaaaa ttagtgagta tagacattat tgttatagtt tgtatggaac    360
aacattagaa cagcaataca acaaaccgtt gtgtgatttg ttaattaggt gtattaactg    420
tcaaaagcca ctgtgtcctg aagaaaagca aagacatctg gacaaaaagc aaagattcca    480
taatataagg ggtcggtgga ccggtcgatg tatgtcttgt tgcagatcat caagaacacg    540
tagagaaacc cagctgtaat catgcatgga gatacaccta cattgcatga atatatgtta    600
gatttgcaac cagagacaac tgatctctac tgttatgagc aattaaatga cagctcagag    660
gaggaggatg aaatagatgg tccagctgga caagcagaac cggacagagc ccattacaat    720
attgtaacct tttgttgcaa gtgtgactct acgcttcggt tgtgcgtaca aagcacacac    780
gtagacattc gtactttgga agacctgtta atgggcacac taggaattgt gtgccccatc    840
tgttctcaga aaccataatc taccatggct gatcctgcag gtaccaatgg ggaagagggt    900
acgggatgta atggatggtt ttatgtagag gctgtagtgg aaaaaaaaac aggggatgct    960
atatcagatg acgagaacga aaatgacagt gatacaggtg aagatttggt agattttata   1020
gtaaatgata atgattattt aacacaggca gaaacagaga cagcacatgc gttgtttact   1080
gcacaggaag caaaacaaca tagagatgca gtacaggttc taaaacgaaa gtatttggta   1140
gtccacttag tgatattagt ggatgtgtag acaataatat tagtcctaga ttaaaagcta   1200
tatgtataga aaaacaaagt agagctgcaa aaaggagatt atttgaaagc gaagacagcg   1260
ggtatggcaa tactgaagtg gaaactcagc agatgttaca ggtagaaggg cgccatgaga   1320
ctgaaacacc atgtagtcag tatagtggtg gaagtggggg tggttgcagt cagtacagta   1380
gtggaagtgg gggagagggt gttagtgaaa gacacactat atgccaaaca ccacttacaa   1440
atattttaaa tgtactaaaa actagtaatg caaaggcagc aatgttagca aaatttaaag   1500
agttatacgg ggtgagtttt tcagaattag taagaccatt taaaagtaat aaatcaacgt   1560
gttgcgattg gtgtattgct gcatttggac ttacacccag tatagctgac agtataaaaa   1620
cactattaca acaatattgt ttatatttac acattcaaag tttagcatgt tcatggggaa   1680
tggttgtgtt actattagta agatataaat gtggaaaaaa tagagaaaca attgaaaaat   1740
tgctgtctaa actattatgt gtgtctccaa tgtgtatgat gatagagcct ccaaaattgc   1800
gtagtacagc agcagcatta tattggtata aaacaggtat atcaaatatt agtgaagtgt   1860
atggagacac gccagaatgg atacaaagac aaacagtatt acaacatagt tttaatgatt   1920
gtacatttga attatcacag atggtacaat gggcctacga taatgacata gtagacgata   1980
gtgaaattgc atataaatat gcacaattgg cagacactaa tagtaatgca agtgcctttc   2040
taaaaagtaa ttcacaggca aaaattgtaa aggattgtgc aacaatgtgt agacattata   2100
aacgagcaga aaaaaaacaa atgagtatga gtcaatggat aaaatataga tgtgataggg   2160
tagatgatgg aggtgattgg aagcaaattg ttatgttttt aaggtatcaa ggtgtagagt   2220
ttatgtcatt tttaactgca ttaaaaagat tttgcaaggg catacctaaa aaaaattgca   2280
tattactata tggtgcagct aacacaggta aatcattatt tggtatgagt ttaatgaaat   2340
ttctgcaagg gtctgtaata tgttttgtaa attctaaaag ccatttttgg ttacaaccat   2400
tagcagatgc caaaataggt atgttagatg atgctacagt gccctgttgg aactacatag   2460
atgacaattt aagaaatgca ttggatggaa atttagtttc tatggatgta aagcatagac   2520
cattggtaca actaaaatgc cctccattat taattacatc taacattaat gctggtacag   2580
attctaggtg gccttattta cataatagat tggtggtgtt tacatttcct aatgagtttc   2640
catttgacga aaacggaaat ccagtgtatg agcttaatga taagaactgg aaatcctttt   2700
```

-continued

```
tctcaaggac gtggtccaga ttaagtttgc acgaggacga ggacaaggaa aacgatggag   2760
actctttgcc aacgtttaaa tgtgtgtcag gacaaaatac taacacatta tgaaaatgat   2820
agtacagacc tacgtgacca tatagactat tggaaacaca tgcgcctaga atgtgctatt   2880
tattacaagg ccagagaaat gggatttaaa catattaacc accaagtggt gccaacactg   2940
gctgtatcaa agaataaagc attacaagca attgaactgc aactaacgtt agaaacaata   3000
tataactcac aatatagtaa tgaaaagtgg acattacaag acgttagcct tgaagtgtat   3060
ttaactgcac caacaggatg tataaaaaaa catggatata cagtggaagt gcagtttgat   3120
ggagacatat gcaatacaat gcattataca aactggacac atatatatat ttgtgaagaa   3180
gcatcagtaa ctgtggtaga gggtcaagtt gactattatg gtttatatta tgttcatgaa   3240
ggaatacgaa catattttgt gcagtttaaa gatgatgcag aaaaatatag taaaaataaa   3300
gtatgggaag ttcatgcggg tggtcaggta atattatgtc ctacatctgt gtttagcagc   3360
aacgaagtat cctctcctga aattattagg cagcacttgg ccaaccaccc cgccgcgacc   3420
cataccaaag ccgtcgcctt gggcaccgaa gaaacacaga cgactatcca gcgaccaaga   3480
tcagagccag acaccggaaa cccctgccac accactaagt tgttgcacag agactcagtg   3540
gacagtgctc caatcctcac tgcatttaac agctcacaca aaggacggat taactgtaat   3600
agtaacacta cacccatagt acatttaaaa ggtgatgcta atactttaaa atgtttaaga   3660
tatagattta aaaagcattg tacattgtat actgcagtgt cgtctacatg gcattggaca   3720
ggacataatg taaaacataa aagtgcaatt gttacactta catatgatag tgaatggcaa   3780
cgtgaccaat tttgtctcaa agttaaaata ccaaaaacta ttacagtgtc tactggattt   3840
atgtctatat gacaaatctt gatactgcat ccacaacatt actggcgtgc tttttgcttt   3900
gctttgtgtg cttttgtgtg tctgcctatt aatacgtccg ctgcttttgt ctgtgtctac   3960
atacacatca ttaataatat tggtattact attgtggata acagcagcct ctgcgtttag   4020
gtgttttatt gtatatatta tatttgttta tataccatta tttttaatac atacacatgc   4080
acgcttttta attacataat gtatatgtac ataatgtaat tgttacatat aattgttgta   4140
taccataact tactattttt tctttttttat tttcatatat aatttttttt tttgtttgtt   4200
tgtttgtttt ttaataaact gttattactt aacaatgcga cacaaacgtt ctgcaaaacg   4260
cacaaaacgt gcatcggcta cccaacttta taaaacatgc aaacaggcag gtacatgtcc   4320
acctgacatt atacctaagg ttgaaggcaa aactattgct gaacaaatat tacaatatgg   4380
aagtatgggt gtattttttg gtgggttagg aattggaaca gggtcgggta caggcggacg   4440
cactgggtat attccattgg gaacaaggcc tcccacagct acagatacac ttgctcctgt   4500
aagacccccct ttaacagtag atcctgtggg cccttctgat ccttctatag tttctttagt   4560
ggaagaaact agttttattg atgctggtgc accaacatct gtaccttcca ttcccccaga   4620
tgtatcagga tttagtatta ctacttcaac tgataccaca cctgctatat tagatattaa   4680
taatactgtt actactgtta ctacacataa taatcccact ttcactgacc catctgtatt   4740
gcagcctcca acacctgcag aaactggagg gcattttaca ctttcatcat ccactattag   4800
tacacataat tatgaagaaa ttcctatgga tacatttatt gttagcacaa accctaacac   4860
agtaactagt agcacaccca taccagggtc tcgcccagtg gcacgcctag gattatatag   4920
tcgcacaaca caacaggtta aagttgtaga ccctgctttt gtaaccactc ccactaaact   4980
tattacatat gataatcctg catatgaagg tatagatgtg gataatacat tatatttttc   5040
tagtaatgat aatagtatta atatagctcc agatcctgac tttttggata tagttgcttt   5100
```

-continued

```
acataggcca gcattaacct ctaggcgtac tggcattagg tacagtagaa ttggtaataa   5160
acaaacacta cgtactcgta gtggaaaatc tataggtgct aaggtacatt attattatga   5220
tttaagtact attgatcctg cagaagaaat agaattacaa actataacac cttctacata   5280
tactaccact tcacatgcag cctcacctac ttctattaat aatggattat atgatattta   5340
tgcagatgac tttattacag atacttctac aaccccggta ccatctgtac cctctacatc   5400
tttatcaggt tatattcctg caaatacaac aattcctttt ggtggtgcat acaatattcc   5460
tttagtatca ggtcctgata tacccattaa tataactgac caagctcctt cattaattcc   5520
tatagttcca gggtctccac aatatacaat tattgctgat gcaggtgact tttatttaca   5580
tcctagttat tacatgttac gaaaacgacg taaacgttta ccatattttt tttcagatgt   5640
ctctttggct gcctagtgag gccactgtct acttgcctcc tgtcccagta tctaaggttg   5700
taagcacgga tgaatatgtt gcacgcacaa acatatatta tcatgcagga acatccagac   5760
tacttgcagt tggacatccc tattttccta ttaaaaaacc taacaataac aaaatattag   5820
ttcctaaagt atcaggatta caatacaggg tatttagaat acatttacct gaccccaata   5880
agtttggttt tcctgacacc tcattttata atccagatac acagcggctg gtttgggcct   5940
gtgtaggtgt tgaggtaggt cgtggtcagc cattaggtgt gggcattagt ggccatcctt   6000
tattaaataa attggatgac acagaaaatg ctagtgctta tgcagcaaat gcaggtgtgg   6060
ataatagaga atgtatatct atggattaca aacaaacaca attgtgttta attggttgca   6120
aaccacctat aggggaacac tggggcaaag gatccccatg taccaatgtt gcagtaaatc   6180
caggtgattg tccaccatta gagttaataa acacagttat tcaggatggt gatatggttc   6240
atactggctt tggtgctatg gactttacta cattacaggc taacaaaagt gaagttccac   6300
tggatatttg tacatctatt tgcaaatatc cagattatat taaaatggtg tcagaaccat   6360
atggcgacag cttatttttt tatttacgaa gggaacaaat gtttgttaga catttattta   6420
atagggctgg tactgttggt gaaaatgtac cagacgattt atacattaaa ggctctgggt   6480
ctactgcaaa tttagccagt tcaaattatt ttcctacacc tagtggttct atggttacct   6540
ctgatgccca aatattcaat aaaccttatt ggttacaacg agcacagggc cacaataatg   6600
gcatttgttg ggtaaccaa ctatttgtta ctgttgttga tactacacgc agtacaaata   6660
tgtcattatg tgctgccata tctacttcag aaactacata taaaaatact aactttaagg   6720
agtacctacg acatggggag gaatatgatt tacagtttat ttttcaactg tgcaaaataa   6780
ccttaactgc agacgttatg acatacatac attctatgaa ttccactatt ttggaggact   6840
ggaattttgg tctacaacct cccccaggag gcacactaga agatacttat aggtttgtaa   6900
cccaggcaat tgcttgtcaa aaacatacac ctccagcacc taaagaagat gatcccctta   6960
aaaaatacac tttttgggaa gtaaatttaa aggaaaagtt ttctgcagac ctagatcagt   7020
ttcctttagg acgcaaattt ttactacaag caggattgaa ggccaaacca aaatttacat   7080
taggaaaacg aaaagctaca cccaccacct catctacctc tacaactgct aaacgcaaaa   7140
aacgtaagct gtaagtattg tatgtatgtt gaattagtgt tgtttgttgt gtatatgttt   7200
gtatgtgctt gtatgtgctt gtaaatatta agttgtatgt gtgtttgtat gtatggtata   7260
ataaacacgt gtgtatgtgt ttttaaatgc ttgtgtaact attgtgtcat gcaacataaa   7320
taaacttatt gtttcaacac ctactaattg tgttgtggtt attcattgta tataaactat   7380
atttgctaca tcctgttttt gttttatata tactatattt tgtagcgcca ggcccatttt   7440
gtagcttcaa ccgaattcgg ttgcatgctt tttggcacaa aatgtgtttt tttaaatagt   7500
```

-continued

```
tctatgtcag caactatggt ttaaacttgt acgtttcctg cttgccatgc gtgccaaatc   7560

cctgttttcc tgacctgcac tgcttgccaa ccattccatt gtttttttaca ctgcactatg   7620

tgcaactact gaatcactat gtacattgtg tcatataaaa taaatcacta tgcgccaacg   7680

ccttacatac cgctgttagg cacatatttt tggcttgttt taactaacct aattgcatat   7740

ttggcataag gtttaaactt ctaaggccaa ctaaatgtca ccctagttca tacatgaact   7800

gtgtaaaggt tagtcataca ttgttcattt gtaaaactgc acatgggtgt gtgcaaaccg   7860

attttgggtt acacatttac aagcaactta tataataata ctaa                    7904
```

<210> SEQ ID NO 2
<211> LENGTH: 7857
<212> TYPE: DNA
<213> ORGANISM: Homo sapiens

<400> SEQUENCE: 2

```
attaatactt ttaacaattg tagtatataa aaaagggagt aaccgaaaac ggtcgggacc     60

gaaaacggtg tatataaaag atgtgagaaa cacaccacaa tactatggcg cgctttgagg    120

atccaacacg gcgaccctac aagctacctg atctgtgcac ggaactgaac acttcactgc    180

aagacataga aataacctgt gtatattgca agacagtatt ggaacttaca gaggtatttg    240

aatttgcatt taaagattta tttgtggtgt atagagacag tataccccat gctgcatgcc    300

ataaatgtat agatttttat tctagaatta gagaattaag acattattca gactctgtgt    360

atggagacac attggaaaaa ctaactaaca ctgggttata caatttatta ataaggtgcc    420

tgcggtgcca gaaaccgttg aatccagcag aaaaacttag acaccttaat gaaaaacgac    480

gatttcacaa catagctggg cactatagag gccagtgcca ttcgtgctgc aaccgagcac    540

gacaggaacg actccaacga cgcagagaaa cacaagtata atattaagta tgcatggacc    600

taaggcaaca ttgcaagaca ttgtattgca tttagagccc caaaatgaaa ttccggttga    660

ccttctatgt cacgagcaat taagcgactc agaggaagaa aacgatgaaa tagatggagt    720

taatcatcaa catttaccag cccgacgagc cgaaccacaa cgtcacacaa tgttgtgtat    780

gtgttgtaag tgtgaagcca gaattgagct agtagtagaa agctcagcag acgaccttcg    840

agcattccag cagctgtttc tgaacaccct gtcctttgtg tgtccgtggt gtgcatccca    900

gcagtaagca acaatggctg atccagaagg tacagacggg gagggcacgg gttgtaacgg    960

ctggttttat gtacaagcta ttgtagacaa aaaaacagga gatgtaatat cagatgacga   1020

ggacgaaaat gcaacagaca cagggtcgga tatggtagat tttattgata cacaaggaac   1080

attttgtgaa caggcagagc tagagacagc acaggcattg ttccatgcgc aggaggtcca   1140

caatgatgca caagtgttgc atgttttaaa acgaaagttt gcaggaggca gcacagaaaa   1200

cagtccatta ggggagcggc tggaggtgga tacagagtta agtccacggt tacaagaaat   1260

atctttaaat agtgggcaga aaaaggcaaa aaggcggctg tttacaatat cagatagtgg   1320

ctatggctgt tctgaagtgg aagcaacaca gattcaggta actacaaatg gcgaacatgg   1380

cggcaatgta tgtagtggcg gcagtacgga ggctatagac aacgggggca cagagggcaa   1440

caacagcagt gtagacggta caagtgacaa tagcaatata gaaaatgtaa atccacaatg   1500

taccatagca caattaaaag acttgttaaa agtaaacaat aaacaaggag ctatgttagc   1560

agtatttaaa gacacatatg ggctatcatt tacagattta gttagaaatt ttaaaagtga   1620

taaaaccacg tgtacagatt gggttacagc tatatttgga gtaaacccaa caatagcaga   1680

aggatttaaa acactaatac agccatttat attatatgcc catattcaat gtctagactg   1740
```

-continued

```
taaatgggga gtattaatat tagccctgtt gcgttacaaa tgtggtaaga gtagactaac   1800
agttgctaaa ggtttaagta cgttgttaca cgtacctgaa acttgtatgt taattcaacc   1860
accaaaattg cgaagtagtg ttgcagcact atattggtat agaacaggaa tatcaaatat   1920
tagtgaagta atgggagaca cacctgagtg gatacaaaga cttactatta tacaacatgg   1980
aatagatgat agcaattttg atttgtcaga aatggtacaa tgggcatttg ataatgagct   2040
gacagatgaa agcgatatgg catttgaata tgccttatta gcagacagca acagcaatgc   2100
agctgccttt ttaaaaagca attgccaagc taaatattta aaagattgtg ccacaatgtg   2160
caaacattat aggcgagccc aaaaacgaca aatgaatatg tcacagtgga tacgatttag   2220
atgttcaaaa atagatgaag ggggagattg gagaccaata gtgcaattcc tgcgatacca   2280
acaaatagag tttataacat ttttaggagc cttaaaatca tttttaaaag gaacccccaa   2340
aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaaccctt tcggaacgtt taagttgcgt gcaggacaaa atcatagacc   2880
actatgaaaa tgacagtaaa gacatagaca gccaaataca gtattggcaa ctaatacgtt   2940
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
ccctacaagg ccttgcacaa agtcgataca aaaccgagga ttggacactg caagacacat   3120
gcgaggaact atggaataca gaacctactc actgctttaa aaaaggtggc caaacagtac   3180
aagtatattt tgatggcaac aaagacaatt gtatgaccta tgtagcatgg gacagtgtgt   3240
attatatgac tgatgcagga acatgggaca aaaccgctac ctgtgtaagt cacaggggat   3300
tgtattatgt aaaggaaggg tacaacacgt tttatataga atttaaaagt gaatgtgaaa   3360
aatatgggaa cacaggtacg tgggaagtac attttgggaa taatgtaatt gattgtaatg   3420
actctatgtg cagtaccagt gacgacacgg tatccgctac tcagcttgtt aaacagctac   3480
agcacacccc ctcaccgtat tccagcaccg tgtccgtggg caccgcaaag acctacggcc   3540
agacgtcggc tgctacacga cctggacact gtggactcgc ggagaagcag cattgtggac   3600
ctgtcaaccc acttctcggt gcagctacac ctacaggcaa caacaaaaga cggaaactct   3660
gtagtggtaa cactacgcct ataatacatt taaaaggtga cagaaacagt ttaaaatgtt   3720
tacggtacag attgcgaaaa catagcgacc actatagaga tatatcatcc acctggcatt   3780
ggacaggtgc aggcaatgaa aaaacaggaa tactgactgt aacataccat agtgaaacac   3840
aaagaacaaa atttttaaat actgttgcaa ttccagatag tgtacaaata ttggtgggat   3900
acatgacaat gtaatacata tgctgtagta ccaatatgtt atcacttatt tttttatttt   3960
gcttttgtgt atgcatgtat gtgtgctgcc atgtcccgct tttgccatct gtctgtatgt   4020
gtgcgtatgc atgggtattg gtatttgtgt atattgtggt aataacgtcc cctgccacag   4080
cattcacagt atatgtattt tgtttttttat tgcccatgtt actattgcat atacatgcta   4140
```

-continued

```
tattgtcttt acagtaattg tataggttgt tttatacagt gtattgtaca ttgtatattt   4200
tgttttatac cttttatgct ttttgtattt ttgtaataaa agtatggtat cccaccgtgc   4260
cgcacgacgc aaacgggctt cggtaactga cttatataaa acatgtaaac aatctggtac   4320
atgtccacct gatgttgttc ctaaggtgga gggcaccacg ttagcagata aaatattgca   4380
atggtcaagc cttggtatat ttttgggtgg acttggcata ggtactggca gtggtacagg   4440
gggtcgtaca gggtacattc cattgggtgg gcgttccaat acagtggtgg atgttggtcc   4500
tacacgtccc ccagtggtta ttgaacctgt gggccccaca gacccatcta ttgttacatt   4560
aatagaggac tccagtgtgg ttacatcagg tgcacctagg cctacgttta ctggcacgtc   4620
tgggtttgat ataacatctg cgggtacaac tacacctgcg gttttggata tcacaccttc   4680
gtctacctct gtgtctattt ccacaaccaa ttttaccaat cctgcatttt ctgatccgtc   4740
cattattgaa gttccacaaa ctggggaggt ggcaggtaat gtatttgttg gtacccctac   4800
atctggaaca catgggtatg aggaaatacc tttacaaaca tttgcttctt ctggtacggg   4860
ggaggaaccc attagtagta ccccattgcc tactgtgcgg cgtgtagcag gtccccgcct   4920
ttacagtagg gcctaccaac aagtgtcagt ggctaaccct gagtttctta cacgtccatc   4980
ctctttaatt acatatgaca acccggcctt tgagcctgtg gacactacat taacatttga   5040
tcctcgtagt gatgttcctg attcagattt tatggatatt atccgtctac ataggcctgc   5100
tttaacatcc aggcgtggga ctgttcgctt tagtagatta ggtcaacggg caactatgtt   5160
tacccgcagc ggtacacaaa taggtgctag ggttcacttt tatcatgata taagtcctat   5220
tgcaccttcc ccagaatata ttgaactgca gcctttagta tctgccacgg aggacaatga   5280
cttgtttgat atatatgcag atgacatgga ccctgcagtg cctgtaccat cgcgttctac   5340
tacctccttt gcattttta aatattcgcc cactatatct tctgcctctt cctatagtaa   5400
tgtaacggtc cctttaacct cctcttggga tgtgcctgta tacacgggtc ctgatattac   5460
attaccatct actacctctg tatggcccat tgtatcaccc acggcccctg cctctacaca   5520
gtatattggt atacatggta cacattatta tttgtggcca ttatattatt ttattcctaa   5580
gaaacgtaaa cgtgttccct atttttttgc agatggcttt gtggcggcct agtgacaata   5640
ccgtatatct tccacctcct tctgtggcaa gagttgtaaa taccgatgat tatgtgactc   5700
ccacaagcat attttatcat gctggcagct ctagattatt aactgttggt aatccatatt   5760
ttagggttcc tgcaggtggt ggcaataagc aggatattcc taaggtttct gcataccaat   5820
atagagtatt tagggtgcag ttacctgacc caaataaatt tggtttacct gatactagta   5880
tttataatcc tgaaacacaa cgtttagtgt gggcctgtgc tggagtggaa attggccgtg   5940
gtcagccttt aggtgttggc cttagtgggc atccatttta taataaatta gatgacactg   6000
aaagttccca tgccgccacg tctaatgttt ctgaggacgt tagggacaat gtgtctgtag   6060
attataagca gacacagtta tgtattttgg gctgtgcccc tgctattggg gaacactggg   6120
ctaaaggcac tgcttgtaaa tcgcgtcctt tatcacaggg cgattgcccc cctttagaac   6180
ttaaaaacac agttttggaa gatggtgata tggtagatac tggatatggt gccatggact   6240
ttagtacatt gcaagatact aaatgtgagg taccattgga tatttgtcag tctatttgta   6300
aatatcctga ttatttacaa atgtctgcag atccttatgg ggattccatg tttttttgct   6360
tacggcgtga gcagcttttt gctaggcatt tttggaatag agcaggtact atgggtgaca   6420
ctgtgcctca atccttatat attaaaggca caggtatgcc tgcttcacct ggcagctgtg   6480
tgtattctcc ctctccaagt ggctctattg ttacctctga ctcccagttg tttaataaac   6540
```

-continued

```
catattggtt acataaggca cagggtcata acaatggtgt ttgctggcat aatcaattat   6600

ttgttactgt ggtagatacc actcccagta ccaatttaac aatatgtgct tctacacagt   6660

ctcctgtacc tgggcaatat gatgctacca aatttaagca gtatagcaga catgttgagg   6720

aatatgattt gcagtttatt tttcagttgt gtactattac tttaactgca gatgttatgt   6780

cctatattca tagtatgaat agcagtattt tagaggattg gaactttggt gttccccccc   6840

ccccaactac tagtttggtg gatacatatc gttttgtaca atctgttgct attacctgtc   6900

aaaaggatgc tgcaccggct gaaaataagg atccctatga taagttaaag ttttggaatg   6960

tggatttaaa ggaaaagttt tctttagact tagatcaata tccccttgga cgtaaatttt   7020

tggttcaggc tggattgcgt cgcaagccca ccataggccc tcgcaaacgt tctgctccat   7080

ctgccactac gtcttctaaa cctgccaagc gtgtgcgtgt acgtgccagg aagtaatatg   7140

tgtgtgtgta tatatatata catctattgt tgtgtttgta tgtcctgtgt ttgtgtttgt   7200

tgtatgattg cattgtatgg tatgtatggt tgttgttgta tgttgtatgt tactatattt   7260

gttggtatgt ggcattaaat aaaatatgtt ttgtggttct gtgtgttatg tggttgcgcc   7320

ctagtgagta acaactgtat ttgtgtttgt ggtatgggtg ttgcttgttg ggctatatat   7380

tgtcctgtat ttcaagttat aaaactgcac accttacagc atccatttta tcctacaatc   7440

ctccattttg ctgtgcaacc gatttcggtt gcctttggct tatgtctgtg gttttctgca   7500

caatacagta cgctggcact attgcaaact ttaatctttt gggcactgct cctacatatt   7560

ttgaacaatt ggcgcgcctc tttggcgcat ataaggcgca cctggtatta gtcattttcc   7620

tgtccaggtg cgctacaaca attgcttgca taactatatc cactccctaa gtaataaaac   7680

tgcttttagg cacatatttt agtttgtttt tacttaagct aattgcatac ttggcttgta   7740

caactacttt catgtccaac attctgtcta cccttaacat gaactataat atgactaagc   7800

tgtgcataca tagtttatgc aaccgaaata ggttgggcag cacatactat acttttc      7857
```

<210> SEQ ID NO 3
<211> LENGTH: 7931
<212> TYPE: DNA
<213> ORGANISM: Homo sapiens

<400> SEQUENCE: 3

```
cttaataaca atcttagttt aaaaaagagg agggaccgaa aacggttcaa ccgaaaacgg     60

ttatatataa accagcccaa aaaattagca gacgaggcat tatggaaagt aaagatgcct    120

ccacgtctgc aacatctata gaccagttgt gcaagacgtt taatctttct ttgcacactc    180

tgcaaattca gtgcgtgttt tgcaggaatg cactgaccac cgcagagata tatgcatatg    240

cctataagaa cctaaaggtt gtgtggcgag acaactttcc ctttgcagcg tgtgcctgtt    300

gcttagaact gcaagggaaa attaaccaat atagacactt taattatgct gcatatgcac    360

ctacagtaga agaagaaacc aatgaagata ttttaaaagt gttaattcgt tgttacctgt    420

gtcacaagcc gttgtgtgaa atagaaaaac taaagcacat attgggaaag gcacgcttca    480

taaaactaaa taaccagtgg aagggtcgtt gcttacactg ctggacaaca tgcatggaag    540

acttgttacc ctaaaggata tagtactaga cctgcagcct cctgaccctg tagggttaca    600

ttgctatgag caattagaag acagctcaga agatgaggtg gacaaggtgg acaaacaaga    660

cgcacaacct ttaacacaac attaccaaat actgacctgt tgctgtggat gtgacagcaa    720

cgtccgactg gttgtggagt gcacagacgg agacatcaga caactacaag accttttgct    780

gggcacacta aatattgtgt gtcccatctg cgcaccaaaa ccataacaag gatggcggac    840
```

-continued

```
gattcaggta cagaaaatga ggggtcgggg tgtacaggat ggtttatggt agaagccata    900
gtagagcaca ctacaggtac acaaatatca gaagatgagg aagaggaggt ggaggacagt    960
gggtatgaca tggtggactt tattgatgac aggcatatta cacaaaattc tgtggaagca   1020
caggcattgt ttaataggca ggaggcggat gctcattatg cgactgtgca ggacctaaaa   1080
cgaaagtatt taggcagtcc atatgtaagt cctataagca atgtagctaa tgcagtagaa   1140
agtgagataa gtccacggtt agacgccatt aaacttacaa cacagccaaa aaaggtaaag   1200
cgacggctgt ttgaaacacg ggaattaacg gacagtggat atggctattc tgaagtggaa   1260
gctgcaacgc aggtagagaa acatggcgac ccggaaaatg gggggagatgg tcaggaaagg   1320
gacacaggga gggacataga gggtgagggg gtggaacata gagaggcgga agcagtagac   1380
gacagcaccc gagagcatgc agacacatca ggaatattag aattactaaa atgtaaggat   1440
atacgatcta cattacatgg taagtttaaa gactgctttg ggctgtcatt tgttgattta   1500
attaggccat ttaaaagtga tagaaccaca tgtgccgatt gggtggttgc aggatttggt   1560
atacatcata gcatagcaga tgcatttcaa aagttaattg agccattaag tttatatgca   1620
catatacaat ggcttacaaa tgcatgggga atggtactat tagtattaat aaggtttaaa   1680
gtaaataaga gcagatgtac cgtggcacgt acattaggta cgttattaaa tatacctgaa   1740
aatcacatgt taattgagcc tcctaaaata caaagtggcg tacgagccct gtattggttt   1800
aggacaggca tttcaaatgc aagtacagtt ataggggagg cgccggaatg gataacgcgc   1860
cagaccgtta ttgaacatag tttggctgac agtcaattta aattaactga aatggtgcag   1920
tgggcatatg ataatgatat ttgtgaagaa agtgagatag catttgaata tgcacagcgt   1980
ggagactttg actccaatgc aagggccttt ttaaatagta atatgcaggc taaatatgta   2040
aaagattgtg caattatgtg cagacattat aaacatgcag aaatgaaaaa gatgtctatt   2100
aaacaatgga ttaagtatag ggtactaaa gttgacagtg taggtaactg gaagccaatt   2160
gtgcagtttc taagacatca aaacatagaa tttattccat ttttaagcaa actaaaatta   2220
tggctgcacg gaacgcccaa aaaaaattgt atagccattg tagggccacc tgacactggg   2280
aagtcgtgct tttgcatgag tttaattaag tttttggggg gaacagttat tagttatgtt   2340
aattcctgca gccatttctg gctacagcca ctaacggatg caaaagtggc attattggat   2400
gatgccacac aaccatgttg gacatatatg gatacatata tgagaaacct attagatggt   2460
aatcctatga gcatagatag aaaacataga gcattaacat taattaagtg tccaccgcta   2520
ctggttacat caaatataga cattagcaaa gaggagaaat acaaatattt acatagtaga   2580
gttaccacat ttacatttcc aaatccattc ccctttgaca gaaatgggaa tgcagtatat   2640
gaactatcag atgcaaactg gaaatgtttc tttgaaagac tgtcgtccag cctagacatt   2700
gaggattcag aggacgagga agatggaagc aatagccaag cgtttagatg cgtgccagga   2760
tcagttgtta gaactttatg aagaaaacag tattgatata cacaaacaca ttatgcattg   2820
gaaatgcata cgattggaaa gtgtattact acacaaagca aaacaaatgg gcctgagcca   2880
catcgggtta caagtagtac caccattaac tgtgtcagag actaaaggac ataatgctat   2940
tgaaatgcaa atgcatttag aatccttagc aaaaactcag tatggtgtgg aaccttggac   3000
attacaggac accagttatg aaatgtggct aacaccaccc aaacggtgct ttaaaaaaca   3060
gggaaatact gtggaggtaa aatttgatgg ctgtgaagac aatgtaatgg agtatgtggt   3120
atggacacat atatacctgc aggacaacga ctcatgggta aaagtaacta gttccgtaga   3180
tgccaagggc atatattata catgtggaca atttaaaaca tattatgtaa attttaataa   3240
```

-continued

```
agaggcacaa aagtatggta gtaccaatca ttgggaagta tgttatggca gcacagttat   3300
atgttctcct gcatctgtat ctagcactgt acgagaagta tccattgctg aacctactac   3360
atacaccccc gcacagacca ccgcccctac agtgtccgcc tgcaccacgg aagacggcgt   3420
gtcggcgccg cctaggaagc gagcacgtgg accgtccact aacaacaccc tgtgtgtggc   3480
caacatcaga tccgtggaca gtacaatcaa caacatcgtc actgacaatt acaacaagca   3540
ccaaagaagg aacaactgtc acagtgcagc tacgcctata gtgcaactgc aaggtgattc   3600
caattgttta aaatgtttta gatatagact gaatgacaaa tataaacatt tgtttgaatt   3660
agcatcttca acgtggcatt gggcctcacc tgaggcacca cataaaaatg caattgtaac   3720
attaacatat agcagtgagg aacaacgtca gcaattttta aacagtgtaa aaataccacc   3780
caccattagg cataaggtgg ggtttatgtc attacattta ttgtaaccat tacacctgta   3840
tatatgtata tgtgtacata acatacgtgt atggaggtag tgcctgtaca aattgctgca   3900
gcaacaacta caacattgat attgcctgtt gttattgcat ttgcagtatg tattcttagt   3960
attgtactta taatattaat atctgatttt gtagtatata catctgtgct ggtactaaca   4020
cttcttttat atttgctttt gtggctttta ttaacaaccc ctttgcaatt ctttttacta   4080
acactgtgtg tgtgctattt tcctgccttt tatatacaca tatacattgt gcaaacgcaa   4140
caataatggt gatgttaacc tgtcacttaa atgatggtga tacatggttg tttctgtggt   4200
tgtttactgc atttgttgta gctgtacttg gattgttgtt actacattac agggctgtac   4260
atggtactga aaaaactaaa tgtgctaagt gtaaatcaaa ccgcaatact actgtggatt   4320
atgtgtatat gtcacatggt gataatggag attatgtgta catgaactag agtaaacctt   4380
ttttatacag tgtgtggtgt acgttagtta tatataatga aacctagggc acgcagacgt   4440
aaacgtgcgt cagccacaca actatatcaa acatgcaagg ccactggtac atgtccccca   4500
gatgtaattc ctaaagttga acatactact attgcagatc aaatattaaa atggggaagc   4560
ttaggggttt tttttggtgg gttaggtatt ggtacagggg ctggtagtgg cggtcgtgca   4620
gggtatatac ccttgggaag ctctcccaag cctgctatta ctgggggggcc agcagcacgt   4680
ccgccagtgc ttgtggagcc tgttgcccct tccgatccct ccattgtgtc cttaattgag   4740
gagtctgcta ttattaatgc tggtgcacct gaggtggtac cccctacaca gggtggcttt   4800
actataacat catctgaatc gactacacct gctattttag atgtgtctgt taccaatcac   4860
actaccacta gtgtgtttca aaatcccctg tttacagaac cgtctgtaat acagccccaa   4920
ccacctgtgg aggccagtgg tcacatactt atatctgccc caacaataac atcccaacat   4980
gtagaagaca ttccactaga cacttttgtt gtatcctcta gtgatagtgg acctacatcc   5040
agtactcctc ttcctcgtgc ttttcctcgg cctcgggtgg gtttgtatag tcgtgcctta   5100
cagcaggtac aggttacgga ccccgcgttt ttgtccacgc cacagcgatt ggtaacttat   5160
gacaaccctg tctatgaagg agaagatgta agtttacaat ttacccatga gtctatccac   5220
aatgcacctg atgaagcatt tatggatatt attagactac atagaccagc tataacgtcc   5280
agacggggtc ttgtgcgttt tagtcgcatt gggcaacggg ggtccatgta cacacgcagt   5340
ggacaacata taggtgcccg catacattat tttcaggaca tttcaccagt tacacaagct   5400
gcagaggaaa tagaactgca ccctctagtg gctgcagaaa atgacacgtt tgatatttat   5460
gctgaaccat ttgaccctat ccctgaccct gtccaacatt ctgttacaca gtcttatctt   5520
acctccacac ctaataccct ttcacaatcg tggggtaata ccacagtccc attgtcaatc   5580
cctagtgact ggtttgtgca gtctgggcct gacataactt ttcctactgc atctatggga   5640
```

-continued

```
acacccttta gtcctgtaac tcctgcttta cctacaggcc ctgtttttat tacaggttct   5700
gacttctatt tgcatcctac atggtacttt gcacgcagac gccgtaaacg tattccctta   5760
ttttttacag atgtggcggc ctagcgacag cacagtatat gtgcctcctc ccaaccctgt   5820
atccaaggtt gttgccacgg atgcgtatgt taaacgcacc aacatatttt atcatgccag   5880
cagttctaga ctccttgctg tgggacatcc atattactct atcaaaaaag ttaacaaaac   5940
agttgtacca aaggtgtctg gatatcaata tagagtgttt aaggtagtgt tgccagatcc   6000
taacaagttt gcattacctg attcatccct gtttgacccc actacacagc gtttagtatg   6060
ggcgtgcaca gggttggagg taggcagggg tcaaccttta ggcgttggtg ttagtgggca   6120
tccattgcta aacaaatatg atgatgtaga aaatagtggt gggtatggtg gtaatcctgg   6180
tcaggataat agggttaatg taggtatgga ttataaacaa acccagctat gtatggtggg   6240
ctgtgctcca ccgttaggtg aacattgggg taagggtaca caatgttcaa atacctctgt   6300
acaaaatggt gactgccccc cgttggaact tattaccagt gttatacagg atggggacat   6360
ggttgataca ggctttggtg ctatgaattt tgcagactta caaaccaata aatcggatgt   6420
tccccttgat atttgtggaa ctgtctgcaa atatcctgat tatttgcaaa tggctgcaga   6480
cccttatggt gataggttgt ttttttattt gcgaaaggaa caaatgtttg ctagacactt   6540
ttttaatagg gccggtactg tgggggaacc tgtgcctgat gacctgttgg taaaaggggg   6600
taataacaga tcatctgtag ctagtagtat ttatgtacat acacctagtg gctcattggt   6660
gtcttcagag gctcaattat ttaataaacc atattggctt caaaaggctc agggacataa   6720
caatggtatt tgctggggaa accacttgtt tgttactgtg gtagatacca cacgcagtac   6780
aaatatgaca ctatgtgcat ctgtgtctaa atctgctaca tacactaatt cagattataa   6840
ggaatacatg cgccatgtgg aggagtttga tttacagttt atttttcaat tgtgtagcat   6900
tacattatct gcagaagtca tggcctatat acacacaatg aatccttctg ttttggagga   6960
ctggaacttt ggtttatcgc ctccaccaaa tggtacactg gaggatactt atagatatgt   7020
acagtcacag gccattacct gtcagaaacc cacacctgaa aaagaaaaac aggatcccta   7080
taaggatatg agtttttggg aggttaactt aaaagaaaag ttttcaagtg aattagatca   7140
gtttcccctt ggacgtaagt tttattgcca aagtggatat cgaggacgga cgtctgctcg   7200
tacaggtata aagcgcccag ctgtgtctaa gccctctaca gcccccaaac gaaaacgtac   7260
caaaaccaaa aagtaatata tgtgtgtcag tgtgttgtgt tatttatatg ttgttgtagt   7320
gtgtatatgt ttcttgtatt gtgtatatgt gtatatgttt gtgtatatgt gtatgttatg   7380
tatgttatgt tgttatgtat gtttgtgtgt ttagtgtgtg tatatatttg tggaatgtgt   7440
atgtatgttt ttgtgcaata aacaattatt atgtgtgtcc tgttacaccc agtgactaag   7500
ttgtgttttg cacgcgccgt ttgtgttgcc ttcatattat attatatata tttgtaatat   7560
acctatacta tgttaccccc ccccacttgc aaccgttttc ggttgccctt acatacactt   7620
acctcaaatt tgttataacg tgttttgtac taatcccata tgttgtgtgc caaggtacat   7680
attgccctgc caagtatctt gccaacaaca cacctggcca gggcgcggta ttgcatgact   7740
aatgtacaat aaacctgtcg gtttgtacaa tgttgtggat tgcagccaaa ggttaaaagc   7800
atttttggct tctagctgaa catttttgta cccttagtat attatgcaca atacccacaa   7860
aatgagtaac ctaaggtcac acacctgcaa ccggtttcgg ttacccacac cctacatatt   7920
tccttcttat a                                                        7931
```

-continued

<210> SEQ ID NO 4
<211> LENGTH: 7808
<212> TYPE: DNA
<213> ORGANISM: Homo sapiens

<400> SEQUENCE: 4
aacaattatc ttgtaaaaac tagggtgtaa ccgaaaaggg ttatgaccga aaacggtgca 60
tataaaagtg cagtggtaaa agtatagaag aacaccatgt tcgaagacaa gagggaaaga 120
ccacgaacgc tgcatgaatt atgtgaagct ttgaacgttt ctatgcacaa tatacaggta 180
gtgtgtgtgt attgtaaaaa ggaattatgt agagcagatg tatataatgt agcatttact 240
gaaattaaga ttgtatatag ggataataat ccatatgcag tatgcaaaca atgtttactg 300
ttttattcaa aaattagaga gtatagacgt tatagcaggt ctgtgtatgg tactacatta 360
gaggcaatta ctaaaaaaag cttatatgat ttatcgataa ggtgtcatag atgtcaaaga 420
ccacttgggc ctgaagaaaa gcaaaaattg gtggacgaaa aaaaaaggtt ccatgaaata 480
gcgggacgtt ggacggggca atgcgctaat tgctggcaac gtacacgaca acgtaacgaa 540
acccaagtgt aataaagcca tgcgtggtaa tgtaccacaa ttaaaagatg tagtattgca 600
tttaacacca cagactgaaa ttgacttgca atgctacgag caatttgaca gctcagagga 660
ggaggatgaa gtagataata tgcgtgacca gctaccagaa agacgggctg gacaggctac 720
gtgttacaga attgaagctc cgtgttgcag gtgttcaagt gtagtacaac tggcagtgga 780
aagcagtgga gacacccttc gcgttgtaca gcagatgtta atgggcgaac taagcctggt 840
ttgcccgtgt tgtgcgaaca actagcaacg gcgatggact gtgaaggtac agaggatgag 900
ggggcggggt gtaatgggtg gttttttgtt gaagcaatag tagaaaaaaa aacaggagat 960
aatgtttcgg atgatgagga tgaaaatgca gatgatacag gatctgattt aataaacttt 1020
atagatagtg aaactagtat ttgcagtcag gcggaacagg agacagcacg ggcgttgttt 1080
caggcccaag aattacaggc aaacaaagag gctgtgcatc agttaaaacg aaagtttcta 1140
gtcagcccgc gaagcagccc attaggagac attacaaatc aaaacaacac acacagccat 1200
agtcaggcaa acgagtcaca agttaaaagg agattactgg acagttatcc ggacagcgga 1260
tatggcaata cacaagtgga aactgtggaa gcaacgttgc aggtagatgg gcaacatggc 1320
ggttcacaga acagtgtgtg tagtagcggg gggggcagtg ttatggatgt ggaaacaaca 1380
gaaagctgtg caaatgtaga actaaacagt atatgtgaag tattaaaaag cagtaatgca 1440
aaagcaacgt taatggcaaa atttaaagag ttgtatggta ttagttataa tgagttggta 1500
cgggtgttta aaagtgataa aacatgttgt atagattggg tttgtgcatt gtttggcgtt 1560
tccccaatgg tagcagaaaa tttaaaaaca ctaattaagc cattttgcat gtactaccat 1620
atacaatgtt tatcatgtga ttggggcacc attgtattaa tgctaattag gttttcatgt 1680
gcaaaaaaca gaacaacaat tgctaagtgt ttaagtacat tagtaaatat cccacaatca 1740
caaatgttta tagaaccacc aaaattacgt agtacacctg tggcattata tttttataga 1800
acaggcatat caaacattag caatacatat ggagagacac ctgaatggat tacacgacaa 1860
acgcaactac aacatagttt tgaggatagt acctttgaat tatcacaaat ggtgcaatgg 1920
gcatttgacc atgaagtatt agatgatagt gaaatagcat ttcattatgc acaattagca 1980
gatatagata gtaatgctgc agcgttttta aagagtaatt gccaagcaaa atatgtaaaa 2040
gattgtggga ccatggcacg gcattacaaa cgagcacaaa gaaaatcatt atctatgtca 2100
gcctggataa ggtatagatg tgatagagca aaggatggag gcaactggag agaaattgct 2160
aaatttttaa gatatcaagg tgtaaacttt atgtccttta ttcaaatgtt taaacagttt 2220

-continued

```
ttaaaaggaa caccaaaaca caattgcata gtcatatatg gcccaccaaa cacaggcaag   2280
tcattatttg caatgagcct aatgaagttt atgcaagggt ccattatttc atatgtaaac   2340
tctggtagtc atttttggtt acagccacta gaggatgcta aaatagcatt gttagatgat   2400
gctacgtatg ggtgttggac atatattgat cagtatttaa gaaacttttt agatggtaat   2460
ccatgtagta tagatagaaa acataggagt ttaatacaat tagtatgtcc accattacta   2520
ataacgtcaa acataaatcc acaagaggat gcaaacctaa tgtatttaca tacaagggta   2580
acagtattaa agtttttaaa tacatttcca tttgataaca atgggaatgc tgtgtataca   2640
ttgaatgatg aaaattggaa aaattttttt tccaccacat ggtccagatt agatttggag   2700
gaggaagagg acaaagaaaa tggagaccct atgccaccgt ttaaatgtgt gccaggagaa   2760
aatactagac tgttatgaac tggacagtga taaattagta gatcaaatta actattggac   2820
attgttacga tatgaagctg ctatgtttta tgcagcacgg gaaagaaact tacgaacaat   2880
caatcaccag gtagtaccag caacaacagt atcaaaacaa aaggcctgtc aagcaattga   2940
aatgcacatg gccttacaat cgcttaacaa atcagactat aacatggaac catggacaat   3000
gcgggagaca tgttatgaac tatggtgtgt ggctcccaag caatgtttca aaaagggggg   3060
cataactgta acagttatat ttgatggaaa taaggacaat gcaatggact atacaagctg   3120
gaaatttata tatatatatg ataatgataa gtgggtaaag acaaatggaa atgtggacta   3180
tacgggtata tattacactg taaattcaaa aaaagaatat tatgtacagt ttaaagatga   3240
agccaaaata tatggggcac aacagtggga ggtctatatg tatggtactg taataacatg   3300
tcctgaatat gtatctagta cctgcagcga cgcgttatcc actactacaa ctgttgaaca   3360
actatcaaac accccaacga ccaatcccct taccacctgc gtgggcgcca aagaagccca   3420
gacacaacag cgaaaacgac agcgacttac tgagcccgac tcctccacaa tctccccact   3480
gtccgtggac aatacaaaca accaaataca ctgtggaagt ggaagcacta acactggagg   3540
gcaccaaagt gcaactcaga ctgcgtttat agtgcattta aaaggtgata caaattgttt   3600
aaaatgtttt agatacagat ttacaaaaca caaagggtta tataaaaacg tatcctcaac   3660
ctggcattgg accagtaata ctaaaacagg cattgttacc attgtgtttg acagtgcaca   3720
tcaacgggaa acatttataa aaaccattaa agtacccccca agtgtaacac tgtcattggg   3780
aattatgaca ctgtaactag tgtaatatat gtattgtaca tatatactgt cacaagccaa   3840
tatgtgctgc taattgtata gacatattgt aaccattgca gtgtttatta ttttgctatt   3900
tgtgctttgc ttgtgtgtgt gtcttgtgtt gtgttgtttg ttgccgctac tgctgtccca   3960
atacgtgttt gcagctgcct tattattaat tttatgtttt tggtttgttg ttgcaacatc   4020
ccaattaact acattttttg tatatttgat ttttttttac ttaccttgtt tacttttaca   4080
tctatataca tttttacttt tgcaataaac ttgttatatt tttgtgatta aatatggtgg   4140
ctacacgtgc acggcgtcgg aagcgagcat ctgtaacaca attatattct acatgcaaag   4200
ctgctggtac atgtcctcct gatgttgtga ataaggttga aggtactaca ttggccgata   4260
aaatattaca gtggagtggg ttgggtatat ttttgggtgg cctaggtatt ggtactgggt   4320
ctggatctgg ggggcgtact ggatatatcc ctttaggtgg tgggggtcgc ccaggcgtgg   4380
tggatattgc tcctgcaagg ccacctatta taattgacct atggcaccat actgaacctt   4440
ctatagtaaa tttggttgag gactctagta ttattcagtc tgggtctcct atacctacct   4500
ttactggtac cgatggcttt gaaattactt catcttccac aacaacccct gctgtgttgg   4560
acatcacccc atctgctggt actgtacatg tttctagtac taacattgaa aatcctttat   4620
```

-continued

```
atattgaacc tccatccatt gaggctccac aatctggaga agtgtcagat atatatttac   4680
tagtacacta ctctggtact catgggtatg aagaaatacc tatggaagtg tttgcatcca   4740
atgtcagtac tggtactgaa cctattagca gcacacctac tccaggggtt agtcgcatag   4800
ctgctccccg cttgtatagt aagtcctaca cacaggttaa agttacaaat cctgatttta   4860
ttagtaagcc atccacattt gttacattta ataatcctgc ttttgagcct attgacacat   4920
ccataacttt tgaggaacct gatgctgttg cacctgatcc tgattttctg gatattatta   4980
cactgcaccg ccctgccctt acatctcgta gaggcacagt acgctttagt aggttaggtc   5040
aaaaggccac catgcgcact cgtagtggca aacaaattgg tgctcgtgta cattattatc   5100
atgatattag tagaattgca ccagctgatg aacttgaaat gcagccttta ctttcacctt   5160
ctaataatta tagttatgac atttatgctg atttagatga agctgaaaca ggttttatac   5220
agcccacaca caccacacct atgtcacact cctctttgtc taggcagttg ccctccttat   5280
cttcatctat gtcttcatct tatgcaaatg ttactattcc attttcaact acatattctg   5340
ttcctattca tacagggcct gatgtggtat tgcccacatc tcctacagta tggccttatg   5400
ttccccacac ttccattgac accaagcatt ctattgttat actaggtggg gattactatt   5460
tgtggcccta tacacattta ctacgcaaac gccgtaaacg tataccctat ttttttacag   5520
atggcattgt ggcgcactaa tgacagcaag gtgtatttgc cacctgcacc tgtgtctcga   5580
attgtgaata cagaagaata tatcacacgc accggcatat attactatgc aggcagttcc   5640
agactaataa cattaggaca tccctatttt ccaataccta aaacctcaac gcgtgctgct   5700
attcctaaag tatctgcatt tcaatacagg gtatttaggg tacagttacc agatcctaac   5760
aagtttggac tcccggatcc aaatttatat aatccagaca cagataggtt ggtgtggggt   5820
tgtgtgggcg ttgaggtggg cagaggacag ccccttggtg ttggccttag tggtcatccc   5880
ttatttaata aatatgatga cacagaaaat tcacgcatag caaatggcaa tgcacaacaa   5940
gatgttagag ataacacatc tgttgacaac aaacagactc agttatgtat aataggctgt   6000
gctccaccta ttggggaaca ctggggtatt ggcactacat gcaaaaacac acctgtacct   6060
ccaggagact gcccccccct ggaacttgta tcctctgtca ttcaggatgg cgatatgatt   6120
gatacagggt ttggagctat ggatttcgct gccctacagg ccaccaaatc agacgtccct   6180
ttggatattt cacagtctgt ttgtaaatat cctgattatt taaaaatgtc tgcagacaca   6240
tatggtaatt ccatgttttt tcatttacgc agggagcaaa tctttgctag gcactattat   6300
aataaacttg taggtgttgg ggaagacatt cctaacgatt attatattaa gggtagtggt   6360
aatggccgtg accctataga aagttatata tactctgcta ctcccagtgg gtctatgata   6420
acatctgatt ctcaaatttt taataagcct tattggctcc accgtgcgca gggtcacaat   6480
aatggcattt gctggaacaa tcagcttttt attacctgtg ttgatactac cagaagtaca   6540
aatttaacta ttagcactgc cactgctgcg gtttccccaa catttactcc aagtaacttt   6600
aagcaatata ttaggcatgg ggaagagtat gaattgcaat ttatttttca attatgtaaa   6660
attactttaa ctacagaggt aatggcttat ttacacacaa tggatcctac cattcttgaa   6720
cagtggaatt ttggattaac attacctccg tctgctagtt tggaggatgc atataggttt   6780
gttagaaatg cagctactag ctgtcaaaag gacacccctc cacaggctaa gccagatcct   6840
ttggccaaat ataaattttg ggatgttgat ttaaaggaac gattttcttt agatttagac   6900
caatttgcat tgggtcgcaa gtttttgttg caggttggcg tacaacgcaa gcccagacca   6960
ggccttaaac gcccggcctc atcggcatcc tcttcctctt cctcttcagc caaacgtaaa   7020
```

```
cgtgttaaaa agtaatgtat gttagttttt gtatgcttgt gcacactgtt gtatgcctgt    7080

atgtatatgt ttgtgtatgt actgtatgtg tttttgtgtg tgtgtgtgtt gttgttcctg    7140

tatgtatgag ttatgtatgt ttattattaa taaactatgt ggtgtgtgtg tgtgtgtttt    7200

tgcatgactg catttgtatg acatgtacgg gtgtatgtgg gtattacatt atccccgtag    7260

gtcaagggtg gtgtttcggt ggcgtcccta ttgccctacc cattttttgc agcacaacag    7320

tttatatttg tgctatttag ttatactttg tagcttccat tttgttacag ctgcagccat    7380

tttgagtgca accgatttcg gttcgtgtac ttttagtata tttgccaagt tttaaaccac    7440

aactgccagt tgtttttggc ataaaccatc atttttttat gacatagtgc atacatccgc    7500

ccgcccacgc cttgtacttg gcgcgcctta ccggcgctag tcatacaacc tattagtcat    7560

ttgtacttta acaattgttg gcacactgtt ttccgcccta taataattta actgcttata    7620

ggcatgtatt ttttggcata ttttatctta ctaattgcat agttggcagg tcaaatacta    7680

tgtttttagt gccaagtttc tatcctactt ataaaccatc ttactcatat gcaggtgtgc    7740

tacacaaatg tgttacctaa ccgatttgtg ttctgcctat gcttgcaaca ttttttctta    7800

taacattt                                                             7808
```

<210> SEQ ID NO 5
<211> LENGTH: 7824
<212> TYPE: DNA
<213> ORGANISM: Homo sapiens

<400> SEQUENCE: 5

```
ctaaactata atgccaaatc ttgtaaaaac tagggtgtaa ccgaaaacgg tctgaccgaa      60

accggtgcat atataaagca gacatttttt ggtaggctac tgcaggacta tgttccagga     120

cgcagaggag aaaccacgga cattgcatga tttgtgtcag gcgttggaga catctgtgca     180

tgaaatcgaa ttgaaatgcg ttgaatgcaa aaagactttg cagcgatctg aggtatatga     240

ctttgtattt gcagatttaa gaatagtgta tagagatgga aatccatttg cagtatgtaa     300

agtgtgctta cgattgctat ctaaaataag tgagtataga cattataatt attcgctata     360

tggagacaca ttagaacaaa cactaaaaaa gtgtttaaat gaaatattaa ttagatgtat     420

tatttgtcaa agaccattgt gtccacaaga aaaaaaaagg catgtggatt taaacaaaag     480

gtttcataat atttcgggtc gttggacagg gcgctgtgca gtgtgttgga gaccccgacg     540

tagacaaaca caagtgtaac ctgtaacaac gccatgagag gaaacaaccc aacgctaaga     600

gaatatattt tagatttaca tcctgaacca actgacctat tctgctatga gcaattatgt     660

gacagctcag acgaggatga ataggcttg gacgggccag atggacaagc acaaccggcc      720

acagctaatt actacattgt aacttgttgt tacacttgtg gcaccacggt tcgtttgtgt     780

atcaacagta caacaaccga cgtacgaacc ctacagcagc tgcttatggg cacatgtacc     840

attgtgtgcc ctagctgtgc acagcaataa acaccatctg caatggatga ccctgaaggt     900

acaaacgggg taggggcggg ctgtactggc tggtttgagg tagaagcggt aatagaacga     960

agaacaggag ataatatttc agatgatgag gacgaaacag cagacgatag tggtacagat    1020

ttaatagagt ttatagatga ttcagtacaa agtactacac aggcagaagc agaggcagcc    1080

cgagcgttgt ttaatgtaca ggaaggggtg gacgatataa atgctgtgtg tgcactaaaa    1140

cgaaagtttg cagcatgctc agaaagtgct gtagaggact gtgtggaccg ggctgcaaat    1200

gtgtgtgtat cgtggaaata taaaaataaa gaatgcacac acagaaaacg aaaaattatt    1260

gagctagaag acagcggata tggcaatact gaagtggaaa ctgagcagat ggcacaccag    1320
```

-continued

```
gtagaaagcc aaaatggcga cgcagactta aatgactcgg agtctagtgg ggtgggggct   1380
agttcagatg taagcagtga aacggatgta gacagttgta atactgttcc attacaaaat   1440
attagtaata ttctacataa cagtaatact aaagcaacgc tattatataa attcaaagaa   1500
gcttatggag taagttttat ggaattagtt agaccattta aaagtgataa aacaagctgt   1560
acagattggt gtataacagg gtatggaata agtccctccg tagcagaaag tttaaaagta   1620
ctaattaaac agcacagtat atatacacac ctacaatgtt taacgtgtga cagaggaatt   1680
atattattat tgttaattag atttaaatgt agcaaaaata gattaactgt ggcaaaatta   1740
atgagtaatt tactatcaat tcctgaaaca tgtatgatta tcgagccacc aaaattacga   1800
agtcaagcat gtgccttata ttggtttaga acagcaatgt caaatataag tgatgtgcaa   1860
gggacaacac cagaatggat agatagatta acagtgttac agcatagctt taatgatgat   1920
atatttgatt taagtgaaat gatacaatgg gcatatgata atgacattac agatgatagt   1980
gacattgcat ataaatatgc acagttagca gatgttaata gtaatgcagc agcatttta    2040
agaagcaatg cacaagcaaa aatagtaaaa gactgtggcg ttatgtgcag acattataaa   2100
agagcagaaa agcgtggtat gacaatggga caatggatac aaagtaggtg tgaaaaaaca   2160
aatgatggag gtaattggag accaatagta caatttttaa gatatcaaaa tattgaattt   2220
acagcatttt tagttgcatt taaacagttt ttacaaggtg taccaaaaaa aagttgtatg   2280
ttactgtgtg gcccagcaaa tacagggaaa tcatattttg gaatgagttt aatacatttt   2340
ttaaaaggat gcattatttc atatgtaaat tccaaaagtc atttttggtt gcagccatta   2400
tcagatgcta aactaggtat gatagatgat gtaacagcca taagctggac atatatagat   2460
gattatatga gaaatgcatt agatggtaac gacatttcaa tagatgtaaa acatagggca   2520
ttagtacaat taaaatgtcc accattaata attacctcaa atacaaatgc aggcaaagat   2580
tcacgatggc catatttgca cagtagacta acagtatttg aatttaacaa tccatttcca   2640
tttgatgcaa atggtaatcc agtgtataaa ataaatgatg aaaattggaa atcctttttc   2700
tcaaggacgt ggtgcaaatt aggcttaata gaggaagagg acaaggaaaa cgatggagga   2760
aatatcagca cgtttaagtg cagtgcagga caaaatccta gacatatacg aagctgataa   2820
aaatgattta acatcacaaa ttgaacattg gaaactaata cgcatggagt gtgctataat   2880
gtatacagcc agacaaatgg gaatatcaca tttgtgccac caggtggtgc cgtcattggt   2940
agcatcaaag actaaagcgt ttcaagtaat tgaactgcaa atggcattag agacattaaa   3000
tgcatcacca tataaaacag atgaatggac attgcaacaa acaagcttag aagtgtggtt   3060
atcagagcca caaaaatgct ttaaaaaaaa aggcataaca gtaactgtac aatatgacaa   3120
tgataaagca aacacaatgg attatacaaa ttggagtgaa atatatatta ttgaggaaac   3180
aacatgtact ttggtagcag gagaagttga ctatgtgggg ttgtattata tacatggcaa   3240
tgaaaagacg tattttaaat attttaaaga ggatgcaaaa aagtactcta aaacacaatt   3300
atgggaggta catgtgggta gtcgggtaat tgtatgtcct acatctatac ctagtgatca   3360
aatatccact actgaaactg ctgacccaaa gaccaccgag gccaccaaca acgaaagtac   3420
acaggggaca aagcgacgac gactcgattt accagactcc agagacaaca cccagtactc   3480
cacaaagtat acagactgcg ccgtggacag tagaccacga ggaggaggac tacacagtac   3540
aactaactgt acatacaaag ggcggaacgt gtgtagttct aaagtttcac ctatcgtgca   3600
tttaaaaggt gacccaaata gtttaaaatg tttaagatat agattaaaac catttaaaga   3660
cttatactgt aatatgtcat ccacatggca ttggaccagt gatgacaaag gtgacaaagt   3720
```

-continued

```
aggaattgtt actgtaacat acacaacgga aacacaacga caactgtttt taaacactgt   3780
taaaatacca cccactgtgc aaataagtac tggtgttatg tcattgtaat tgtattgtac   3840
aattactgta tgtaaaccac aagccaatat gtgctgctaa gtgtatatac aatgatatta   3900
cctatttttg ttgtttgttt tatactgttt ttatgcttgt gcattttttt gcggccattg   3960
gtgctatcta tttctatata tgcttggttg ctggtgttgg tgttgctgct ttgggtgtct   4020
gtggggtcgg ctctacgaat ttttttctgt tacttaatat ttttatatat accaatgatg   4080
tgtattaatt ttcatgcaca atacttaacc caacaagact aactgtatac tggttctgca   4140
catggtggta tggtattgta aatatttact gttgtgtgtg ttgtttttat tatttttata   4200
catttactaa taaatacttt tatattttta gcactgtctt attatgagac acaaacggtc   4260
tacaaggcgc aagcgtgcat ctgctacaca actttaccaa acatgcaagg cctcaggcac   4320
ctgcccacct gatgttatac ccaaagttga aggcactact atagcagatc aaatattacg   4380
atatggtagc ttaggggtgt tttttggagg tttaggcatt ggtacagggt cgggtacagg   4440
tggcaggact ggatatgtgc cccttggtag taccccaccg tctgaggcta tacctttaca   4500
gcccatacgt cccccagtta ccgttgatac tgtggggcct ttggattctt ctattgtatc   4560
tttaatagag gaatctagtt ttatagacgc cggtgcacca gccccatcaa ttcccactcc   4620
atctggtttt gatattacca cctctgcaga tactacacct gcaatactta atgtttcctc   4680
tattggagaa tcatctatac aaactgtttc tacacattta aatccctcct ttactgagcc   4740
atccgtactc cgccctcctg cacctgcaga ggcctctgga catttaatat tttcctctcc   4800
tactgttagc acacatagtt atgaaaacat accaatggat acctttgtta tttctactga   4860
cagtggcaat gtcacgtcta gcacacccat tccagggtct cgccctgtgg cacgccttgg   4920
tttatacagt cgcaacaccc aacaagttaa ggttgttgac cctgcttttt taacatctcc   4980
tcatagactt gtaacatatg ataatccagc atttgaaggc tttaaccctg aggacacatt   5040
gcagtttcaa catagtgaca tatcgcctgc tcctgatcct gattttctag atattgttgc   5100
attacacaga cctgcattaa cctctcgcag ggtactgta cgttatagta gggttgggca   5160
aaaggctaca cttcgtactc gcagtggaaa gcaaataggg gctaaagtac attactacca   5220
agacttaagt cccatacagc ctgtccagga acaggtacaa cagcagcaac aatttgaatt   5280
acaatcttta aatacttctg tttctcccta tagtattaat gatggacttt atgatattta   5340
tgctgacgat gctgatacta tacatgattt tcagagtcct ctgcactcac atacgtcctt   5400
tgccaccaca cgtaccagta atgtgtccat accattaaat actggatttg acactcctct   5460
tgtgtcattg gaacctggtc cagacattgc atcttctgta acatctatgt ctagtccatt   5520
tattcctata tctccactaa ctccttttaa taccataatt gtggatggtg ctgattttat   5580
gttgcaccct agctatttta ttttgcgtcg cagacgtaaa cgttttccat atttttttgc   5640
agatgtccgt gtggcggcct agtgaggcca ctgtgtacct gcctcctgtg cctgtgtcta   5700
aggttgtaag cactgatgaa tatgtgtcac gcacaagcat ttattattat gctggcagtt   5760
ccagactttt ggctgttggc aatccatatt tttccatcaa aagtcccaat aacaataaaa   5820
aagtattagt tcccaaggta tcaggcttac agtatagggt ctttagggtg cgtttacctg   5880
atcccaataa atttggtttt cctgatacat ctttttataa ccctgataca caacgtttgg   5940
tctgggcatg tgtaggcctt gaaataggta ggggacagcc attgggtgtt ggcgtaagtg   6000
gtcatcctta tttaaataaa tttgatgaca ctgaaaccag taacagatat cccgcacagc   6060
cagggtctga taacagggaa tgcttatcta tggattataa acaaacacaa ttatgtttaa   6120
```

-continued

```
ttggctgtaa acctcccact ggtgagcatt ggggtaaagg tgttgcctgt aacaataatg   6180
cagctgctac tgattgtcct ccattggaac tttttaattc tattattgag gatggtgaca   6240
tggtagatac agggtttgga tgcatggact ttggtacatt gcaggctaat aaaagtgatg   6300
tgcctattga tatttgtaac agtacatgca aatatccaga ttatttaaaa atggccagtg   6360
aaccttatgg ggatagtttg ttcttttttc ttagacgtga gcagatgttt gttagacact   6420
tttttaatag ggctggaaaa cttggcgagg ctgtcccgga tgacctttat attaaagggt   6480
ccggtaatac tgcagttatc caaagtagtg catttttcc aactcctagt ggctctatag   6540
ttacctcaga atcacaatta tttaataagc cttattggct acagcgtgca caaggtcata   6600
acaatggcat ttgctggggc aatcagttat ttgttaccgt ggttgatacc actcgtagca   6660
ctaatatgac attatgcact gaagtaacta aggaaggtac atataaaaat gataatttta   6720
aggaatatgt acgtcatgtt gaagaatatg acttacagtt tgtttttcag ctttgcaaaa   6780
ttacactaac tgcagagata atgacatata tacatactat ggattccaat attttggagg   6840
actggcaatt tggtttaaca cctcctccgt ctgccagttt acaggacaca tatagatttg   6900
ttacctccca ggctattact tgccaaaaaa cagcaccccc taaagaaaag gaagatccat   6960
taaataaata tactttttgg gaggttaact taaaggaaaa gtttctgca gatctagatc   7020
agtttccttt gggacgaaag tttttattac aatcaggcct taaagcaaag cccagactaa   7080
aacgttcggc ccctactacc cgtgcaccat ccaccaaacg caaaaaggtt aaaaaataat   7140
tgttgtggta cttacactat tttattatac atgtttgttt gttttatgta tgtgttgtct   7200
gtttgtttat gtttgtgtat atgttgtatg tgttatgtgt catgtttgtg tacatgttct   7260
atgtccttgt cagtttcctg tttctgtata tatgtaataa actattgtgt gtattgtaaa   7320
ctatttgtat tgtttgggtg tatctatgag taaggtgctg tccctaaatt gccctaccct   7380
gccctgccta ttatgcatac ctatgtaata gtatttgtat gatatgtatt tttatagtttt  7440
taacagtact gcctccattt tactttacct ccattttgtg catgtaaccg atttcggttg   7500
ctggcacaaa cgtgtttttt ttaaactaca atttaaacaa tacagttaat cctttccctt   7560
cctgcactgc ttttgcctat acttgcatat gtgactcata tatacatgca gtgcagttgc   7620
aaaatgttta attatactca tagtttaaac atgcttatag gcacatattt taacttactt   7680
tcaatgctta agtgcagttt tggcttgcac aatagtttgt tatgccaaac tatgtcttgt   7740
aaaagtgact cactaacatt tattgccagg tgtggactaa ccgttttggg tcacattgtt   7800
catgtttcaa cattttatat aata                                          7824
```

<210> SEQ ID NO 6
<211> LENGTH: 7844
<212> TYPE: DNA
<213> ORGANISM: Homo sapiens

<400> SEQUENCE: 6

```
gaaagtttca atcatacttt tatatattgg gagtgaccga aaagggttta agaccgaaaa     60
cggtacatat aaaaggcagc ttattctgtg tggacatatc catggagcca caattcaaca    120
atccacagga acgtccacga agcctgcacc acttgagtga ggtattagaa atacctttaa    180
ttgatcttag attatcatgt gtatattgca aaaaagaact aacacgtgct gaggtatata    240
attttgcatg cactgaatta aaattagtgt atagggatga ttttccttat gcagtgtgca    300
gagtatgttt attgttttat agtaaagtta gaaaatatag gtattatgac tattcagtgt    360
atggagctac actagaaagt ataactaaaa aacagttatg tgatttatta ataaggtgct    420
```

-continued

```
acagatgtca aagtccgtta actccggagg aaaagcaatt gcattgtgac agaaaaagac    480
gatttcatct aatagcacat ggttggaccg ggtcatgttt ggggtgctgg agacaaacat    540
ctagagaacc tagagaatct acagtataat catgcatggt aaagtaccaa cgctgcaaga    600
cgttgtatta gaactaacac ctcaaacaga aattgaccta cagtgcaatg agcaattgga    660
cagctcagag gatgaggatg aggatgaagt agaccatttg caggagcggc cacagcaagc    720
tagacaagct aaacaacata cgtgttacct aatacacgta ccttgttgtg agtgtaagtt    780
tgtggtgcag ttggacattc agagtaccaa agaggacctg cgtgttgtac aacagctgct    840
tatgggtgcg ttaacagtaa cgtgcccact ctgcgcatca agtaactaac tgcaatggcg    900
tcacctgaag gtacagatgg ggaggggaag ggatgttgtg gatggtttga agtagaggca    960
attgtagaaa aaaaaacagg agataaaata tcagatgatg aaagtgacga ggaggatgaa   1020
atagatacag atttagatgg atttatagac gattcatata tacaaaatat acaggcagac   1080
gcagaaacag tcaacaattg ttgcaagtac aaacagcaca tgcagataaa cagacgttgc   1140
aaaaactaaa acgaaagtat atagctagtc cattaaggga tattagtaat cagcaaactg   1200
tgtgccggga aggagtaaaa cggaggctta ttttatcaga cctacaagac agcgggtatg   1260
gcaatacatt ggaaactctg gaaacaccag aacaggtaga tgaagaggta cagggacgtg   1320
ggtgcgggaa tacacaaaat ggaggctcac aaaacagtac ctatagtaac aatagtgagg   1380
actctgtaat acatatggat attgatagaa acaatgaaac gccaacacaa caattgcagg   1440
acttgtttaa aagtagcaat ttacaaggta aattatatta taaatttaaa gaagtgtatg   1500
gtattccatt ttcagaattg gtgcgtacgt ttaaaagtga tagtacatgt tgcaatgatt   1560
ggatatgtgc tatatttggt gttaatgaaa cattagccga ggcactaaaa actataataa   1620
aaccacactg tatgtattat catatgcaat gtttaacatg tacatggggg gttatagtaa   1680
tgatgctaat tagatataca tgtggcaaaa acagaaaaac aattgcaaaa gcattaagct   1740
caatattaaa tgtaccacag gagcaaatgt taattcaacc accaaaaata cgaagtcctg   1800
ctgtagcttt atatttttat aaaacagcaa tgtcaaatat tagtgatgtg tatggagaca   1860
caccagaatg gatacaaaga caaacacaat tgcaacacag tttacaggat agtcaatttg   1920
aattatctaa aatggtgcag tgggcatttg ataatgaagt aacagatgat agccaaattg   1980
cgtttcaata tgcacaatta gcagatgtag acagcaatgc acaagccttt ttaaaaagca   2040
atatgcaggc aaaatatgta aaggattgtg gaataatgtg tagacattat aaaagggcac   2100
aacagcaaca aatgaatatg tgccagtgga taaagcacat atgtagtaaa acagatgaag   2160
ggggtgattg gaaacccatt gtacaatttt taagatatca aggggtcgat ttcatttcat   2220
ttctaagtta ctttaaatta tttctacaag gaacacctaa acataactgt ttggtacttt   2280
gtggaccgcc aaatacaggt aaatcatgct ttgctatgag tcttataaag tttttttcaag   2340
ggtctgtcat ttcatttgtg aattcacaaa gccacttttg gttgcagcca ttagacaatg   2400
ctaaacttgg gttgttggat gatgcaacag aaatatgttg gaaatatata gacgattatt   2460
taaggaattt ggtagatgga aatcctataa gtttagatag aaaacataaa caattagtac   2520
aaataaaatg tccaccatta ctaattacaa ccaatataaa tcctatgcta gatgctaaat   2580
tacgatattt acacagtaga atgttagtgt ttcagtttca aaatccattt ccattagata   2640
ataatggtaa tcctgtatat gaattaagta atgtaaactg gaaatgtttc tttacaagga   2700
cgtggtccag attaaatttg gataacgacg aggacaaaga aaacaatgga gacgctttcc   2760
caacgtttaa atgcgtgcca gaacaaaata ctagactgtt ttgaaaaaag atagtagatg   2820
```

tattgcagat catatagaat attggaaagc tgtgcgacat gaaaatgtgc tatactataa 2880
agcaagagaa aatgacatta ctgtactaaa ccaccagatg gtgccttgtt tacaagtatg 2940
taaagcaaaa gcatgtagtg caatagaagt gcaaatagca ctggaatcat taagtacaac 3000
aatatataac aatgaagagt ggacattaag agacacatgc gaggaactat ggcttactga 3060
acctaaaaaa tgctttaaaa aagaaggaca acatatagaa gtatggtttg atggtagtaa 3120
aaacaattgt atgcaatatg tagcctggaa atatatatat tacaatggag attgtgggtg 3180
gcaaaaagtg tgttctgggg tagactatag aggtatatat tatgtacatg atggccacaa 3240
aacatactac acagactttg aacaagaggc caaaaaattt gggtgtaaaa acatatggga 3300
agtacatatg gaaaatgaga gtatttattg tcctgactct gtgtctagta cctgtagata 3360
caacgtatcc cctgttgaaa ctgttaacga atacaacacc cacaagacca ccaccaccac 3420
ctccacgtcc gtgggcaacc aagacgccgc agtatcccac agaccaggaa aacgacccag 3480
actacgggaa tcagaatttg actcctccag agagtcccac gcaaagtgtg tcacaacaca 3540
cacacacatc agcgacacag acaataccga cagtagaagt agaagtatca acaacaacaa 3600
ccaccctggt gataagacta cgcctgtagt acatttaaaa ggtgaaccta acagattaaa 3660
atgttgtaga tatcgatttc aaaaatataa aacattgttt gtggatgtaa catcaacata 3720
tcattggaca agtacagaca ataaaaatta tagcataatt acaattatat ataaggatga 3780
aacacaacga aacagctttt taagtcatgt aaaaattcca gtagtgtaca ggttagtttg 3840
ggacaaatga gttttccata aagtgctgta tatattgtat atacatttgt gttattgtaa 3900
cacacaaata cgtgaagtgt acctgccata cattgctgct acgcatatat attgcaacca 3960
ttgatttttg tgttattggt gtgtttgcgc tttgcttttg tgtttgtttg cttgtgtgtc 4020
atgttgtccc gcttttgcta tctgcctctg tgttttccag ttgtatatta ttaataatat 4080
tgttttggtt tgttatagcc acatcctttt ttaatacatt tataatattt ttgatatttt 4140
tttactgtcc tgtgctgtgt atatatttac atgctttgtg gataataaat aatatgtaaa 4200
tgtagtagta ctgttactac tatggttgcc caccgtgcca cacgacgcaa acgcgcatct 4260
gcaacacaac tatataaaac atgtaagttg tctggtacat gtccagagga tgttgttaat 4320
aaaatagagc aaaaaacatg ggctgataaa atattgcaat ggggaagttt atttacatat 4380
tttggaggcc ttggcattgg tacaggaact gggtctgggg gtcgtgcagg ctatgttcca 4440
ttggggtcta ggccttccac aatagttgat gtaactccgg cgcgaccacc tattgttgtg 4500
gaatccgtag ggcctacaga cccttccatt gttacattag ttgaggagtc cagtgttata 4560
gaatctggtg cagggattcc taattttact gggtctgggg gatttgaaat tacatcctca 4620
tcaacaacta cacctgccgt gttggatatt acaccaacct ctagtactgt acatgtcagt 4680
agtacccata taaccaatcc gttatttatt gatccccctg ttattgaggc cccacaaaca 4740
ggcgaggtgt ctggcaatat tttaattagc acacccacat ctggtataca tagctatgaa 4800
gaaataccta tgcaaacatt tgctgttcac ggttctggta cagaacctat tagtagtact 4860
cctattccag gctttaggcg tattgcagct cctagattat atagaaaagc atttcagcag 4920
gttaaggtaa ctgaccctgc atttcttgat agacctgcaa cattagtatc tgctgataat 4980
ccactttttg aaggtactga cacatcttta gctttttctc cgtcgggtgt ggctcctgac 5040
cctgatttta tgaatatagt agcattacat aggcctgcat ttactacacg taggggtggt 5100
gtacgtttta gtaggcttgg cagaaaggct actatacaaa cacgtagagg cacacaaata 5160
ggtgcccgtg tgcattatta ttatgatata agtcctattg cacaggctga ggaaattgaa 5220

-continued atgcagccat tattgtctgc aaataattca tttgatggcc tatatgatat ttatgcaaat 5280
atagatgatg aagcacctgg tttgtctagc cagtcagttg ctacaccttc tgcacactta 5340
cctataaagc cttccacatt gtcttttgct agtaacacca ctaatgtaac tgcccccttta 5400
ggtaatgtgt gggaaacacc attttattca ggtcctgaca tagtgttgcc tacaggcccc 5460
agtacgtggc cctttgttcc tcagtctcct tatgatgtta cccatgatgt atatatacag 5520
ggatcctcct ttgcattatg gcctgtgtat ttttttagac gtaggcgccg taaacgtatt 5580
ccctattttt ttgcagatgg cgacgtggcg gcctagtgaa aataaggtgt atctacctcc 5640
aacacctgtt tcaaaggttg tggcaacgga ttcctatgta aaacgcacta gtatatttta 5700
tcatgcaggc agttcacgat tgcttgccgt aggacatccc tattactctg tgactaagga 5760
caataccaaa acaaacattc ccaaagttag tgcatatcaa tatagggtat ttagggtacg 5820
gttgcccgac cctaataagt ttgggcttcc agatactaat atttataatc cggaccagga 5880
acggttagtg tgggcatgtg taggtttgga ggtaggccgc ggacagcctt taggtgctgg 5940
gctaagtggc catccattgt ttaataggct ggatgatact gaaagttcca atttagcaaa 6000
taataatgtt atagaagata gtagggacaa tatatcagtt gatggcaagc aaacacagtt 6060
gtgtattgtt ggatgtactc ccgctatggg tgaacattgg actaaaggtg ctgtgtgtaa 6120
gtccacacaa gttaccacag ggactgccc gcctcttgca ttaattaata cacctataga 6180
ggatggggac atgatagaca caggatttgg cgctatggac tttaaggtgt tgcaggaatc 6240
taaggctgag gtacctttag acattgtaca atccacctgt aaatatcctg actatttaaa 6300
aatgtctgca gatgcctatg gtgattctat gtggttttac ttacgcaggg aacaattatt 6360
tgccagacat tattttaata gggctggtaa agttggggaa acaatacctg cagagttata 6420
tttaaagggt agcaatggta gagaaccccc tccgagttct gtatatgttg ctacgcctag 6480
tgggtctatg attacgtctg aggcacagtt atttaataaa ccttattggt tgcaacgtgc 6540
ccaaggccat aataatggca tttgctgggg taatcaatta tttgttactg tagtagatac 6600
tactagaagt actaacatga ctattagtac tgctacagaa cagttaagta aatatgatgc 6660
acgaaaaatt aatcagtacc ttagacatgt ggaggaatat gaattacaat ttgtttttca 6720
attatgcaaa attactttgt ctgcagaggt tatggcatat ttacataata tgaatgctaa 6780
cctactggag gactggaata ttgggttatc ccgcgccagtg gccaccagcc tagaagataa 6840
atatagatat gttagaagca cagctataac atgtcaacgg gaacagccac caacagaaaa 6900
acaggaccca ttagctaaat ataaattttg ggatgttaac ttacaggaca gtttttctac 6960
agacctggat caatttccac tgggtagaaa atttttaatg caactgggca ctaggtcaaa 7020
gcctgctgta gctacctcta aaaagcgatc tgctcctacc tccacctcta caccagcaaa 7080
acgtaaaagg cggtagtgtg ttgttgtgtg tttgtgtaac tgtgtttgtg tgttgtatat 7140
atggtatgtt tgtgtatgtg ctttatttta tactttgtat gtgtatgttg tgtttgtgta 7200
aatgtttgtg tgaaatgttt gtgtgtgtat tcattgtatg tatgactgta tatatgtgta 7260
atgtttgtgt gtctgtaata aacatgaatg agtgctttta cgcgtggttg cataaactaa 7320
ggtgtgtcat tattgtggct tttgttttgt aagttattgt gtacagtgta ctatgtgtat 7380
tgtgcataca tatatatacc ataacatact ccattttgtt gtttttccgc catttgtac 7440
atgcaaccga attcggttgc atggcctagt gccattattt aaactaaaag gaattcggtt 7500
gcatggccta gtgccattat ttaaaccaaa aggccctttt cagcagaaca gttaatcctt 7560
tggcatattg ccgtttcctg tgttttatac ttgaattatg tacagtaccg caccctgtat 7620

-continued

```
tactcacagg tactatgact gccaactatg cttttatctg catactttag tgctgttggg   7680
cacacatttt tatacatgtg tctgcaactt tggtgttttg gcttgcagaa tacactatgt   7740
aggccaagta tctgtcagta tctgttttgc aaacatgtaa catacaatta ctcatttttt   7800
aaaaccgttt acggtcgtgc aaaaacaggt ttcttttaat tgtt                     7844
```

<210> SEQ ID NO 7
<211> LENGTH: 7824
<212> TYPE: DNA
<213> ORGANISM: Homo sapiens

<400> SEQUENCE: 7

```
gaaagtttca atcatacttt attatattgg gagtaaccga aatgggttta ggaccgaaaa     60
cggtacatat aaaaggcagc ctgttgtgcc tgtagatatc catggattcc atattcagca    120
atacacagga acgtccacga agcctgcacc atctgagcga ggtattacaa atacctttac    180
ttgatcttag attatcatgt gtatactgca aaaaggaact tacaagttta gagctatata    240
ggtttgcatg tattgagtta aaactagtat atagaaacaa ttggccatat gcagtatgta    300
gggtatgttt attgttttat agtaaggtta gaaaatatag gtactataaa tattcagtgt    360
atggggcaac attagaaagt ataactaaaa aacagttatc tgatttatca ataaggtgct    420
accgatgtca atgtccgtta acaccggagg aaaaacaatt gcactgtgaa cataaaagac    480
gatttcatta tatagcatat gcatggaccg ggtcatgttt gcagtgttgg agacatacga    540
gtagacaagc tacagaatct acagtataac catgcatggt aaagtaccaa cgttgcaaga    600
ggttatatta gaacttgcac cgcaaacgga aattgaccta caatgcaatg agcaattgga    660
cagctcagag gatgaggatg aggatgaaat agaccatttg ctggagcggc cacagcaagc    720
tagacaagct gaacaacata agtgttacct aattcacgta ccttgttgta agtgtgagtt    780
ggtggtgcag ttggacattc agagtaccaa agaggagcta cgtgtggtac aacagctgct    840
tatgggtgcg ttaacagtaa cgtgcccact ctgcgcatca tctaaataac tgcaatggca    900
tcacctgaag gtacagatgg ggaggggatg ggatgttgtg gatggtttca ggtagaagca    960
attgtagaaa gaaaaacggg ggatacaata tcagatgatg aaagcgagga ggagaatgaa   1020
acagatacag atgtagatgg atttatagac aatacactta taaacaatac acaggaagac   1080
agggagacag ctcaacaatt attgcaagta caaacagcac atgcagatgc acagacgttg   1140
caaaaactaa aacgaaagta tataggtagt ccccttaagtg atattagtaa tcagcaaact  1200
gtgtaccgag aggaagtaaa acgaaggcta atattatcag aagacagcgg gtatggcaat   1260
acattggaaa cattggaaac atcacaacag gtagaatacg aaaagggaaa tgggtgcggg   1320
agctcacaaa atggaggctc gcaaaacagt aattgtagtg agcactcggt atcaaatatg   1380
gatatagata caaatatgga aacaccaaca caccaattgc aggaactatt taaaagtagt   1440
aacgtacaag gaagattaca ttttaaattt aaagaagtgt atggagtgcc atatacagag   1500
ttggtgcgaa catttaaaag cgatagtaca tgttgtaacg attggatatg tgcaatattt   1560
ggcgttaatg aaacattagc agaggcgtta aaaactatac taaaaccaca atgtgtgtac   1620
tatcatatgc aatgcttaac atgttcatgg ggagtaattg taatgatgct aattagatat   1680
atatgtggaa aaaatagaaa aacaattaca aaatcgctaa gctcaatttt aaatgtacca   1740
caagagcaaa tgttaattca accaccaaaa ctacgaagtc ctgctgtagc attatatttt   1800
tataaaacag caatgtcaaa tattagtgag gtgtatgggg aaacaccaga atggatacaa   1860
agacagacac aattgcaaca cagtttacaa gacaatcaat ttgaattgtc taaaatggta   1920
```

-continued

```
cagtgggcat ttgataatga agtaacagat gatagccaaa ttgccttttt atatgcacaa   1980
ctagcagaca tagatagcaa tgcacaagca tttttaaaaa gtaatatgca agcaaaatat   2040
gtaaaggatt gtggaataat gtgtagacat tacaaaaggg cacagcaaca gcaaatgaat   2100
atgtgccagt ggataaagca tatatgtagt aaagtagatg aaggggggtga ttggaaaccc   2160
attgtgcaat ttttacgata tcaaggggtc gacttcattt catttttaag ttattttaaa   2220
ttatttttac aaggaacgcc taaacataat tgtttggtac tgtgtggacc accaaataca   2280
ggtaaatcat gttttgctat gagccttata aatttttttcc aagggtcagt catttcattt   2340
gttaattcac aaagccactt ttggttacag ccactagaca atgccaaatt aggtttgctg   2400
gatgatgcaa cagatacgtg ttggagatac atagatgatt atctaagaaa tttattagat   2460
gggaatccca taagtttaga taggaaacat aaacaattag tacaaataaa atgtcctcca   2520
gttattatta caactaatgt aaatcctatg caagatgcaa aattaagata tttacacagt   2580
agaatttcag tgtttaagtt tgaaaatcca tttccattag ataacaatgg taatcctgtg   2640
tatgaattaa gtaatgtaaa ttggaaatgt ttttttgaaa ggacatggtc cagattaaat   2700
ttggataacg acgaggacaa agaaaacaat ggagactcta tcccaacgtt tagatgcgtg   2760
ccagaacaaa atactagact gttatgaaaa agatagtaaa tgcattatag atcacataga   2820
ctattggaaa gctgtacgac atgaatatgt attatattat aaagcaagag aaaatgacat   2880
taatgtacta aaccaccaga tggtgccctc tttacaagtg tgtaaagcaa aagcatgtag   2940
tgcaatagaa ttacaaatag cactggaagc aataagtaac acaatatata aaaatgaaga   3000
gtggacatta cgtgatacat gtgatgaact gtggcgcacg gagcctaaaa actgttttaa   3060
aaaagaagga caacacatag aagtgtggtt tgatggtaac aaaaataatt gtatggaata   3120
tgtggtgtgg aaatttatat attataatgg agagtgtggg tggtgtaaag tgtcatcagg   3180
ggtggattac agaggcatat attatatgca tgatggccac aaaacatatt acacagactt   3240
tgaacaggag gccaaaaaat atgggtgtac aaacatatgg gaagtacata tggaaaccga   3300
gagtatttac tgtcctgact ctgtgtctag tacctgtaga tacaacgtac cccctgttga   3360
gactgttaac gaatacaaca accacaggac caccaccacc gcctccacct ttgtgggcgc   3420
ccaagacgcc gcggtatccc acagaccagg aaaacgaccc agagcaagtg aatcagaacc   3480
tgactcctcc agagagtcct acgcacactg tgtcacaaca gacacagaca tcagtaacaa   3540
cgccaacagt agaagtccac gtatcaacac acaaagccac tgtggtgata aaactacgcc   3600
tgtaatccat ttaaaaggtg aagctaatag attaaagtgt tgtagataca gatttcaaaa   3660
atataaaaca ttatttacag atgtaacaac aacatatcat tggacaagta cagataataa   3720
agacagtagt attattacaa tattatataa agatgaaaca caacgggaca cctttttaaa   3780
tgttgtaaaa ataccaccta gtgtacaggt tattttggga caaatgagtt gtccataaag   3840
tgttgtatat attgtatata catatgtgtt attgtaacac tggtacaggt gaagtgtaat   3900
tgccatacat tgctgctaag catatatatt gcacccatta attgtatttg gtatattatg   3960
tgttattgta acactgggaa aggtaacgtg taatcgccat atattgcaac cattgatttt   4020
tgtgtaattt gtgtgtttgc gctttgcttt tgtgtttgtc tgtgtgtgtg ccattttgtc   4080
ccgcttttgc tatctgcatc tttatttaca agttgtctta tactaattat tttatttttgg   4140
tttgttgtgg ctacatcatt ttttgatact tttatactgt ttttactatt tttttatata   4200
cctacactgt gtatatattg ccatgctttg tggttaataa accatttgta acagtagtaa   4260
tttttgctac tatggttgcc caccgtgcca cacgacgcaa acgcgcatct gccacacaat   4320
```

-continued

```
tatataaaac atgcaaatta tctggtacat gtcctgagga tgttattaat aaggtggagc   4380
aaaaaacatg ggctgatagg attttacaat ggggaagttt atttacatat tttggggggc   4440
ttggcattgg tactgggtct gggtcgggtg gtcgggcggg ctatgttccc ttaggctcta   4500
ggccttctac tatagttgat gtcactcctg cacgaccacc tattgtggtg gagtcagttg   4560
ggcctacaga tccttctatt gttacactgg tagaagaatc tagtgttatt aactcagggg   4620
ctggtgttcc caattttact gggtcagggg gatttgaagt tacatcctct tccacaacca   4680
cacctgctgt gttggatatt acacccacat ctagtactgt acatgtaagt agtactacta   4740
taacaaaccc actatatatt gatcctccag taattgaggc tccacaaact ggagaggtat   4800
ctggtaatat tttgattagc actcctacat ctggaataca tagctatgag gaaataccta   4860
tgcaaacatt tgctatacac ggtactggca acgaacctat tagtagtacc cctattccag   4920
gttttagacg ccttgctgct cccaggttat atagtagggc ttttcagcag gttagggtca   4980
ctgacccagc atttttggac aaccccacaa cattaatatc tgctgataat cctgtttttg   5040
aaggtgctga cacaacgttg accttttctc cctcgggtgt ggctcctgat cctgatttta   5100
tggatatagt tgcattacat aggcctgcat ttactacacg tagaacaggt gtgcgtttta   5160
gtaggctagg caaaaaggct accatgcaaa cacgtagggg tacgcaaata ggtgctcgtg   5220
tgcattatta ttatgatata agtcctattg cacaggctga tgaaattgaa atgcagccat   5280
tattgtctac agacaattca tttgatggcc tatatgatat ttatgcaaat attgatgatg   5340
aggcacccat ttcatttcgt cagtctggtg ctacaccttc tgcacaatta cctattaaac   5400
cttctacatt atcctttgct agtaacacag ctaatgttac tgccccttttg ggaaatgttt   5460
gggaaacacc attttattca ggtcctgata tagttttacc tacaggcccc agtacttggc   5520
ccttcgtacc tcagtctcct tctgatgtta cacatgatgt atatatacag ggagctacat   5580
ttgcactatg gcctgtatat tttttaaac gtaggcgccg taaacgtatt ccctattttt   5640
ttgcagatgg cgatgtggcg gcctagtgac aataaggtgt acctacctcc aacacctgtt   5700
tcaaaggttg tggcaacgga tacatatgta aaacgtacca gtatatttta tcatgcaggt   5760
agctctaggt tgcttgctgt tggccatcct tattactctg tttccaaatc tggtaccaaa   5820
acaaacatcc ctaaagttag tgcatatcag tatagagtgt ttagggtacg gttgcctgat   5880
cctaataagt ttggccttcc tgatccatct ttctataatc ctgaccagga acgtttggta   5940
tgggcctgtg taggtttgga ggtaggccga ggtcaacctt taggtgctgg gttaagtggt   6000
catccattat ttaataggct ggatgacact gaggtctcta atttagcagg taataatgtt   6060
atagaagata gccgggacaa tatatctgtt gattgtaaac aaacccagtt atgtattgtg   6120
ggatgtgcac cagcattagg ggaacattgg actaagggcg cggtgtgtaa gtctacacca   6180
ggtaatacag gggattgtcc acctcttgca ttagttaata ccccgataga ggacggtgac   6240
atggtggaca ccgggtttgg tgcaatggac tttaagctat tacaggaatc aaaggctgag   6300
gtgccattgg acattgtaca atctacatgt aaatatcctg attatttaaa aatgtctgca   6360
gatgcctatg gggattctat gtggttttac ttacgcaggg aacaattgtt tgccagacat   6420
tactttaata gggcaggtaa tgttggggaa gccattccta cagatttgta ttggaagggt   6480
ggcaatggca gggaccctcc tcccagttct gtatatgttg ctactcctag tgggtccatg   6540
attacctctg aggcccaatt atttaataaa ccttattggt tgcaacgtgc acagggccat   6600
aataatggca tatgctgggg taatcaggta tttgttactg ttgtggatac taccagaagc   6660
accaacatga ctattaatgc agctaaaagc acattaacta aatatgatgc ccgtgaaatc   6720
```

-continued

```
aatcaatacc ttcgccatgt ggaggaatat gaactacagt ttgtgtttca actttgtaaa   6780
ataaccttaa ctgcagaagt tatggcatat ttgcataata tgaataatac tttattagac   6840
gattggaata ttggcttatc cccaccagtt gcaactagct tagaggataa atataggtat   6900
attaaaagca cagctattac atgtcagagg gaacagcccc ctgcagaaaa gcaggatccc   6960
ctggctaaat ataagttttg ggaagttaat ttacaggaca gcttttctgc agacctggat   7020
cagtttcctt tgggtagaaa atttttaatg caactaggcc ctagaccccc tagacccaag   7080
gctagtgtat ctgcctctaa aaggcgggcg gctcctacct cttcctcttc ttcaccagct   7140
aaacgtaaaa aacgatagtt gtgtgttgtg tgttgtatgt attgtatggt tgtgcttgta   7200
ctgtatgttt ttgtgtatgt ttatgtattt tataattgtg tatgtgctat gtgtatgtat   7260
gactgtatgt atgtgtaatg ttttgtgtgt atgtaataaa catgcatggt tacttttacg   7320
cgtggttgca taaactaagg tgcggtagta tccttgggca gtgtgtgtca ggttaggtgg   7380
tgttccttac tgtttaatgt tatattaaat aggttgtttg tatgcactat agtaacacac   7440
caaactccat tttagtgctg tacgccattt tatgcatgca accgaattcg gttgcctagc   7500
cttttgtcct tatttaaacc caaaacgact tttcagcaaa acagttaatc ctttggcata   7560
ttgccgtttc ctgttgtatg attcaggtat gtacactgcc ttaccctgta ttactcacct   7620
gtatttctgt gccaactatg cttttatctg catactttgg cgctgttggg catatgtttt   7680
tatgcaggtg tttgcaatat attttgttgg cgtgtagccc ttattgtata agccaagtat   7740
ctgtcttgca aatatgtaac catatactta ctcattttac aaaaccgttt acggtcgtgc   7800
taaaacaggt ttcttttaat tgtt                                          7824
```

<210> SEQ ID NO 8
<211> LENGTH: 7700
<212> TYPE: DNA
<213> ORGANISM: Homo sapiens

<400> SEQUENCE: 8

```
actataatgt actattaaaa aaaagggtgt aaccgaaaac ggtttcaacc gaaatcggtg     60
catataaaag taggaaagca aaaaacgcta cagattggga aatgctgttt cccaattcag    120
aagaacgacc atacaagcta caagcgttat gtgacgaagt gaatatttct atacatgata    180
taaacctgga ctgtgtgttt tgccaacgtg gactgtacag atctgaggta tatgattttg    240
catttagtga tttgtgtatt gtatatagaa aggataaacc atatggtgta tgtcaaccgt    300
gtttaaaatt ttattctaaa attagagagt ataggcgata tagacaatca gtatatggca    360
ctacgttaga aaatttaact aacaaacagt tatgtaatat tttaataagg tgcggaaaat    420
gccaaaaacc attatgtcca ctggaaaagc aaaagcatgt agatgaaaaa aaacggtttc    480
atcaaatagc agaacagtgg accggacgct gtacacggtg ctggagacca tctgcaactg    540
tggtgtaaga tgcatggaaa aaaaacaacc ttgcaggaca ttactttaga cctgaaacca    600
acaaccgaaa ttgaccttac atgttacgag tcattggaca actcagagga tgaggatgaa    660
acagacagcc atctagacag acaagctgaa cgagagtgtt acagaatagt tactgactgc    720
acgaagtgtc agtgcacagt atgccttgcc attgaaagca acaaagctga tttaagagtg    780
atagaagagt tgcttatggg tacactaggt attgtgtgcc ccaactgttc cagaaaccta    840
taaaagaaga tggctgattc aggtaattgg gaagggaggt gtacgggatg gtttaatgta    900
gaagccattg tagaaagaaa aacaggggat ccaattccag aggatgaaaa ttatgatgga    960
ggggatacag atgagtcgga aatgggggat tttattgata atgcacatat accaaatata   1020
```

-continued

```
tatgcacaac aggaaattgc acaggcattg tatcagtcac agcaagcaaa tgcagacaat   1080
gaggctatac gtgttctaaa acgaaagttt acaggtagtc ctggcggtag cccagatatg   1140
aaaagagatg aattcataga caaacagctt agtccacaaa taaatgtatt gtcaataagt   1200
agcggtagaa gtacatctaa acgaagactg tttgaggagc aggacagtgg atatggcaat   1260
actgaagtgg aaacttacga gacagaggta ccgggacttg gggcaggggt agggtgttta   1320
caaaatgtta atgaagaagg caaccaaatt gtgtcgccac gtgaaagcag tagtgggtcc   1380
agtagcattt caaatatgga tatagaaaca gagagcacac ctataacaga tattacaaat   1440
ttattacaaa ggaataatgc aaaagcagca ttgctagcaa aatttaaaga agtatatggg   1500
ttaagttata tggaattagt tagaccatat aaaagtgata aaacacattg ccaagattgg   1560
gtgtgtgctg tgtttggtgt aataccctca cttgcagaaa gtttaaaatc cttactaaca   1620
cagtattgta tgtatataca tttgcagtgt ttaacatgta catggggcat aatagtgtta   1680
gtattagtaa gatttaagtg caataaaaat agactaacag tgcaaaaatt attaagtagt   1740
ttattaaatg taacacaaga acgcatgtta attgaacctc caagactacg aagtacacca   1800
tgtgcattat attggtatag aactagttta tcaaatatta gtgaaatagt aggagacaca   1860
cctgagtgga ttaaaagaca aacgttagtg cagcatagtt tagatgatag tcaatttgac   1920
ctatctcaaa tgatacagtg ggcatttgat aatgatataa cagacgactg tgaaatagca   1980
tataaatatg cattattagg caatgtagac agtaatgcag ctgcattttt aaaaagtaat   2040
gcacaagcaa aatatgtaaa agactgtggt acaatgtgca gacattataa agcagcagaa   2100
cgtaaacaaa tgtcaatggc acaatggata caacatagat gtgatttaac taatgatggt   2160
ggtaattgga aagatattgt gctattccta agatatcaaa atgtagaatt tatgcctttt   2220
ttaattacat taaaacaatt tttaaaaggt attcccaaac aaaactgtat agtattatat   2280
ggaccgccag atacaggaaa atcacatttt ggaatgagtt taattaaatt tatacaaggt   2340
gtagttattt cgtatgtaaa ttcaactagt catttttggt tatcaccctt agctgatgca   2400
aaaatggcat tattagatga tgcaacacct ggatgctgga cgtacataga caaatattta   2460
agaaatgcat tagatggtaa tcctatatgt ttagatagaa aacataaaaa tttattacaa   2520
gttaaatgcc ctccattact gataacatca aatacaaatc ctaaagcaga tgatacttgg   2580
aaatatttac atagtagaat taaggtgttt actttttttaa atccatttcc atttgacagt   2640
aatgggaacc cactatacca acttactaat gaaaactgga aagcattttt tacaaaaacg   2700
tggtcaaaac tagatttaac agaggacgac gacaaggaaa atgatggaga cactgtgcaa   2760
acgtttaagt gcgtgtcagg acgcaatcct agaactgtat gaacgtgaca gtgtacacct   2820
aagtgatcat attgatcatt ggaaacacgt gcgacatgaa aatgtattat tacataaagc   2880
acgtgaaatg ggactgcaaa ctgttaacaa tcaagcggtg ccaagccttg cagtatcacg   2940
atccaaaggg tataatgcaa ttgaaatgca aatagcacta gaaagtttaa atgaatcttt   3000
gtataacaca gaggaatgga cattgcaaca tacaagttgg gaactgtggg ttacagaacc   3060
taaacaatgt tttaaaaagg atggaaaaac agtagaggtt agatatgact gtgaaaagga   3120
caatagcatg caatatgtat tttggacaca tatatattgt tggtatgaag gggggtgggc   3180
aaaggtaggt agcaaaatag attataatgg tatatattat gaaacagatg atgaggaaaa   3240
ggtatactat acaagatttg atacagatgc aaaacggtac ggggtaaaag gcatatggga   3300
agtacatatg ggtggtcagg taatatgttg tgctcctgta tctagcgcct gtgaagtatc   3360
cattcctgaa attgttaacc cactgcacac cacaaccacc aacaccacca ccacctgcac   3420
```

-continued

```
caacgttgac accggtgtgc catcacggaa acggcaaaga cagtgtgact cggaccagag   3480
gcccctggat tgtttgcata acctacatcc caccacagag tcctgtaccc agtgtactac   3540
acataatgtt gcgccaatag tgcatttaaa aggtgacaaa aacagcttaa aatgttttag   3600
atatagattg cataaaggct attcacattt atttaaaaat gtaacaacaa catggcattg   3660
gaccaatact acaaatagta aatgtggtgt aataacatta atgtttacaa ctgtattgca   3720
acaacaacat tttttacaac atgtaaaaat accacaaact attgtagtta catcaggata   3780
catgtctttg taacattggt tacacagtat atatgattct ttgtatattt gtatttttgt   3840
tttgtgttgg cttttgtttg tgcttgtgtg tgtcgcttgc agtgtctgtg tatatttacc   3900
catggttatt ggtattgatt ataataacct ttatacatgt atcacaatca ttgttaaaag   3960
tatttttttt atatgttttg gtattttata ttcctatggc acttgtacat taccatgcta   4020
cattacaaat aacataaaca attttacata tataataaac tgcctaatat ttttagtgta   4080
ccatgcgtcg caagcgtgac acacacatac gaaaaaaacg tgcatctgca acacaattat   4140
ataaaacatg taaacaagca ggtacgtgcc ctcctgatgt aattcccaag gttgaaggta   4200
gtactatagc tgataatata ttaaaatatg gtagtattgg agtttttttt gggggattgg   4260
gaataggtag tgggtctgga tcaggggggc gtactggata cgttccatta tctacaggca   4320
caccatctaa accagttgaa attccattac aacctatacg accatcagtt gttacgtctg   4380
ttgggccttc agattcttct attgtttcat tagtggaaga atcaagtttt atagagtcag   4440
gtatacctgg tcctacatct atagtgcctt ctacttcagg gtttgatatt acaacttctg   4500
taaacagtac acctgctatt atagatgtat ctgctattag tgatactaca caaatatctg   4560
ttacaacatt taaaaatcca acctttactg acccatctgt gttgcaacct cctccaccct   4620
tagaagcctc tggcagactt ttattttcaa atgacactgt aactacccat tcatatgaaa   4680
atatacctct tgacacattt gtagttacaa cagaccacaa tagtattgtt agtagtacgc   4740
ccatcccagg gaggcaacct gctgcacgct taggattata tggacgtgca atacaacagg   4800
ttaaggttgt agaccctgcg tttttaacta cgcctacacg tttagtaaca tatgacaacc   4860
ctgcctttga aggcctgcag gatacaacat tagagtttca gcacagtgac ttgcataatg   4920
ctcctgattc tgatttttta gatattgtaa aattacatag gcctgcttta acctctagaa   4980
aaacaggcat acgtgttagt agattgggac aacgtgcaac actttctact agaagtggca   5040
aacgtatagg tgctaaagta catttttatc atgatataag tcctatacct actaatgata   5100
ttgaaatgca acctttagtt acaccacaaa cacctagtat agtaactggt agtagtatta   5160
atgatgggtt atatgatgtg tttttagaca atgatgtaga agagactgta ctacaacaaa   5220
catatacacc tacaagtata catagtaata gtttagttag tagtgatatt tctactgcaa   5280
ctgcaaatac aactattcct tttagtactg ggttagacac acatcctggt ccagatattg   5340
ctttaccact accttctaca gaaactattt ttacaccaat agtgccatta cagcctgctg   5400
gtcctatata tatttatggg tcaggtttta tattacaccc tagttattat ttgttaaagc   5460
gcaaacgtaa acgtctgtca tattctttta cagatgtggc gacctactga tgcaaaggta   5520
tacctgcccc ctgtgtctgt gtctaaggtt gtaagcacag atgaatatgt aacaagaaca   5580
aatatatatt attatgcagg tagcacacgt ttgttggctg tgggacaccc atattttcct   5640
atcaaggatt ctcaaaaacg taaaaccata gttcctaaag tttcaggttt gcaatacagg   5700
gtgtttaggc ttcgtttacc agatcctaat aaatttggat ttccagatgc atccttttat   5760
aatcctgata aggagcgcct agtatgggcc tgttctggtg tggaggttgg acgtggacaa   5820
```

```
cccttaggta taggtactag tggcaatcca tttatgaata aattagatga tactgaaaat   5880
gctcctaaat acattgctgg acaaaataca gatggtagag aatgtatgtc agtggattat   5940
aaacaaacac agttgtgtat tttaggttgt aggcctccct taggggaaca ttggggtcca   6000
ggcacgccat gtacttcaca aactgttaat actggtgatt gtcccccact ggaattaaag   6060
aacaccccta tacaggatgg tgatatgata gatgttggct ttggagccat ggattttaaa   6120
gctttacaag caaataaaag tgatgtacct attgatattt ctaacactac ctgtaaatac   6180
ccagattatt taggcatggc tgctgatccc tatggtgatt ccatgtggtt ttatcttcgt   6240
agggaacaaa tgtttgttcg acacttattt aacagggctg gtgataccgg tgataaaatc   6300
ccagatgacc taatgattaa aggcacaggc aatactgcaa caccatccag ttgtgttttt   6360
tatcctacac ctagtggttc catggtttct tcagatgcac agttgtttaa taaaccttat   6420
tggttgcaaa aggcacaggg acaaaataat ggtatttgtt ggcataatca attattttta   6480
actgttgtag atactactag aagcactaat ttttctgtat gtgtaggtac acaggctagt   6540
agctctacta caacgtatgc caactctaat tttaaggaat atttaagaca tgcagaagag   6600
tttgatttac agtttgtttt tcagttatgt aaaattagtt taactactga ggtaatgaca   6660
tatatacatt ctatgaattc tactatattg gaagagtgga atttggtct taccccacca    6720
ccgtcaggta ctttagagga aacatataga tatgtaacat cacaggctat tagttgccaa   6780
cgtcctcaac ctcctaaaga aacagaggac ccatatgcca agctatcctt ttgggatgta   6840
gatcttaagg aaaagtttc tgcagaatta gaccagtttc ctttgggaag aaaattttta    6900
ttacaacttg gtatgcgtgc acgtcctaag ttacaagctt ctaaacgttc tgcatctgct   6960
accacaagtg ccacacctaa gaaaaaacgt gctaaacgta tttaataagt gtaatgtgta   7020
tgtgttgttt gttgtatgtt acatgtgttt tgtatgtttg tttgttgtat gttaactgtt   7080
tactaatact gtgtgtatgt ttatgtacat gtgtataact gtttgtttat atatatgtat   7140
gtatttgtgt gtatgtgtat gtgtatgtgt atgtgtagta atgtttgtat gtatgtttaa   7200
taaagtttat atgtgtgttg tgtgggtggt ttacttgact actgtgcttc cattttgtat   7260
agtcgccatt ttacatgcat taaggtaaaa agggcaaccg atttcggttg cacagtaaaa   7320
catgttttaa tgtgttttgc tgttgtagca aaatagttgt actgtttttg gcttcctgca   7380
ggcaacttgg cagggtttgt ttccttaaca tgttcatccc acgcaaggtt ataaaggtaa   7440
aaggcgccac ctggcagtta ctcatttgtc tgcaattatt taaacaatgt cttgcacaca   7500
catttttac ccaccctatc ataaaattgc ttttaagcac atacctatac tatgtacaca    7560
gtgtactctt ggcagaacat tgttttttaa atgccaagta attgttttat aaatgagtaa   7620
taacgtgtta ctcatactgc acctaaaaag ttaaacctat ttggatcaca caaatgccaa   7680
tttatttctt attacaaata                                               7700
```

<210> SEQ ID NO 9
<211> LENGTH: 7905
<212> TYPE: DNA
<213> ORGANISM: Homo sapiens

<400> SEQUENCE: 9

```
cttataacat tttacaatca taatttaaaa aaagggaggc accgaaaacg gtcacgaccg     60
aaaacggtgt atataaaacc atgcaaaagt tgcttgccca tacggaatgg cgcgatttcc    120
caatcctgca gaacggccat acaaattgcc tgacctgtgc acggcgctgg acactacatt    180
gcacgacatt acaatagact gtgtctattg taaaacacag ctacagcaaa cagaggtata    240
```

-continued

```
tgaatttgca tttagtgatt tatttatagt atatagaaac ggggagccat atgctgcatg    300
ccaaaaatgt attaaatttc atgctaaagt aagggaacta cggcattatt cgaactcggt    360
gtatgcaaca actttggaaa gcataactaa taccaagtta tataatttat caataaggtg    420
catgagttgc ctgaaaccat tgtgtccagc agaaaaatta aggcatgtta ataccaaaag    480
aagatttcac caaatagcag gaagctatac aggacagtgc cgacactgct ggaccagcaa    540
ccgggaggac cgcagacgta tacgaagaga aacacaagta taaatataaa tatgcatgga    600
ccacggccga cattgcaaga gattgtttta gatttatatc catacaatga aatacagccg    660
gtcgaccttg tatgtcacga gcaattagaa gattcagaca atgaaacaga tgaacccgac    720
catgtagtta atcaccaaca acaactacta gccagacggg aagaaccaca gcgtcacaaa    780
atacagtgta tgtgttgtaa gtgtaatact acactgcact tagtagtaga agcctcacaa    840
gagaacctgc gatctctact gcagctgttt atggagacac tgtcatttgt gtgtccctgg    900
tgtgcatcgg gaacccagta acctgcaatg gccaattgtg aaggtacaga tggggatggg    960
tcgggatgta acggatggtt cctagtacag gcaatagtag ataaacaaac gggcgacact   1020
gtgtcagagg acgaggacga aaatgcaaca gatacaggtt cagacttggc agactttatt   1080
gatgatacta cagatatttg tgtacaggca gagcgcgaga cagcacaggt actgtataat   1140
atgcaagagg cccaaaggga tgcacaatca gtgcgtgcct taaaacgaaa gtatggaggg   1200
agcaatctaa ataaaagtcc ttgtgcaaaa ccgccaggcg tacataggga acaaagggta   1260
acactacaag agctcccggt aaacatatgc aataaacagg caagaacaaa cgtgtattca   1320
gtaccagaca gcggctatgg caatatggaa gtggaaacag ctgaagtgga ggtaactgta   1380
gtaaataata caaatgggga agaggaaggg gaaaatggcg gggaaaatgg cggcagcata   1440
cgggaggagt gcagtagtgt agacagtgct attgatagtg agaatcaaga tccacagtca   1500
cctactgcac agctaaaaac agtattacag gctaataacc aaaaagccat actactatca   1560
caatttaaac acacatatgg attagcattt aacgacctgg tacgtacatt taaaagtgat   1620
aaaaccatat gtactgactg ggtagcagca atatgtggag taaatcccac catagcagaa   1680
ggctttaaaa cactaattca gccatatgcg ttatatacac atatacagtg tttggatacc   1740
aaatatggag tgtatatact actattaatt agatataaat gtggaaaaaa caggataaca   1800
gtaggcaaag gattaagtaa attattacat gtgccagaaa gttgtatgct aattgaacca   1860
cctaaattgc gtagccctgt tgcagcactg tattggtata gaactggaat gtctaatata   1920
agtgaagtgt caggtactac gccagaatgg atacagcgat taacagtaat acagcatgga   1980
atagatgaca gtgtatttga cctgtctgat atggtacaat gggcatttga taatgatgta   2040
acagaagaca gtgacatagc atatggatat gcattattag cagatagtaa tagtaatgct   2100
gcagcatttt taaaaagtaa ctgccaggca aaatatgtac gcgactgtgc tacaatgtgc   2160
agacattata aaagggcaca aaaaaaacaa atgactatgg cgcaatggat taggtttaga   2220
tgtgataaat gtgacgatgg gggcgactgg cgaccaatag tgcaatttct aaggtatcaa   2280
ggggtagaat ttataacctt tttgtgtgca tttaaggagt ttttaaaggg caccccaaag   2340
aaaaattgca tagtaataca gggaccacca aacacaggca agtcatactt ttgtatgagt   2400
ttaatgcact ttttacaagg tacagtaatt tcatatgtaa attccactag tcatttttgg   2460
ttagagccac ttgcagatgc aaaggtagca atgttggatg atgccacagg cacatgctgg   2520
tcatatttcg atacgtatat gagaaatgca ttagatggaa atcctataag ccttgacaga   2580
aaacatagac atttaataca aattaagtgt ccacccatat taataacatc caataccaat   2640
```

-continued

```
cctgtagagg aaaataggtg gccataccta actagcagac taacagtgtt tacatttcct   2700
aatgcattcc catttgacca aaacaggaat ccagtgtaca caatcaataa taaaaactgg   2760
aaaagttttt tccaaaagac ttggtgcaaa ttagacttgc agcaggacga ggatgaagga   2820
gacaatgatg gaaacactat cccaacgttt aaatgcgtta caggagaaaa tactagaaca   2880
ttatgaacag gacagtaaac taatatatga tcaaatcaat tattggaaat atgtgcgact   2940
ggaaaatgca atattttatg cagcacggga acgtggcatg catactatag accaccaggt   3000
ggtgccacca ggcactactt caaaagcaaa agcatatcaa gctattgaac tgcagatggc   3060
cctagagagc cttgcacaaa ctgactttaa taaagaggag tggacattaa aggacacaag   3120
taatgaaatg tggcagacaa agccaaaaca atgttttaaa aaaaaaggtg ttacagtgga   3180
ggtgtggtac gatggaaaca aggacaattc tatgcattat gtagtgtggg gagcaatata   3240
ttataaaaca catacagaca cgtggtgtaa aacagaaggg tatgtggatt actggggtat   3300
atattatgtg cacgagcagc ataagacata ttatgaagtg tttaagcagg atgcacaaat   3360
gtatgggact agcggaaaat gggaagtgca ttgtaatggc aacataattc attgtcctga   3420
ctctatgtac agtaccagtg acgacacagt acccactact gagcttactg cagaactaca   3480
acacaccacc ccggcccata ccgccgcaac aaccccatgc accaaaaaaa ctaagtcggc   3540
gccgtcttgc aagtgtggag tctccagacc ctcagaaaca gacggagtgt tcgtggacct   3600
tgttacaagt aaaggctgca acaaacgacg gcaccagtgt tgtggtgaca ctacacctat   3660
agtgcattta aaaggtgaca aaaatggttt aaagtgtctt aggtatcgat tgcgaaaatt   3720
taattcattg tatgaaaata tttcatgtac ttggcattgg atagggggca agggaagtaa   3780
acatacaggt atactaactg taacatatac tactgaagca caacgccaaa aatttttgga   3840
aactgttaga attccaccta gtgtacatgt atctgtggga tatatgacat tgtaacagca   3900
catgctgtat gtatattgta tacatatcaa tgattgcatt ggtgtttttg gtgtggtttg   3960
ctgtatgctt atatatatgt tgcagtgtcc cgcttttgcc gtctgtgcat ttgtgtgcgt   4020
atatgtggct acttttattt gtgtttattg ttgtacatac cacaccattg caaatgtttt   4080
gtatatattt actatttttt atattgccta tgtggttttt acacatcctt tcagtatatg   4140
cttaagttgt gttgctgcat agtgtattgt acattacttg tttttacatt tatattgtac   4200
caataaacat ggtttctagc cgtgcgtcca ggcgtaagcg tgcatctgca acagacatat   4260
ataaaacctg caagcaatca ggcacatgtc cgcctgatgt tgttaataag gtggagggta   4320
ccacactggc tgataggttt ttacaatggg ctagtttagg tatttttttg ggtggtttgg   4380
gaatcggtac gggtactggt actgggggcc gcacagggta cattcctttg gggggtaggc   4440
ctagtacagt tgtagatgtt accccctgcac gtcctcctgt ggttatagaa cctgtaggac   4500
ctacagaacc ttctattgtt cagttggtag aggaatctag tgttgtttcc tctggtacac   4560
ccatccctac ttttacaggc acatctgggt ttgaaattac atcttctgca accacaacac   4620
ctgctgtatt agatattacc cctgcttctg ggtctgttca aattagtacc actagttata   4680
ccaatcctgc atttgctgat ccatcgttaa ttgaggttcc acaaacaggt gaggtgtcag   4740
gcaatatatt tgttactact ccaacatctg gaacacatgg atatgaagaa attcctatgc   4800
aggtttttgc ctcacatgga acaggcacag aacctattag tagtactcct gttcctggtg   4860
ttagtcgtgt ggcaggccca cgtttatata gtagggccta tcatcaggtt cgtgttaata   4920
attttgattt tgtaacccgc ccttcatctt ttgtaacatt tgacaatcca gcttttgagc   4980
ctggtgatac atccttaaca tttgaacctg ctgacacagc tcctgatcca gattttctgg   5040
```

-continued

```
acattgttcg tttacatcgg cctgctttaa cctcacgacg cggaacagta cgctttagta   5100
ggcttggtaa aaaggccaca atgtttaccc ggcggggtac acaaattggg gcacaggttc   5160
attattatca tgatattagt aacattactg caacagaaga cattgagatg caacctttac   5220
ttacctctga atctacagat ggtttatatg atatatatgc agatgcagat atagataatg   5280
caatgttaca tactacttct catacaggtt ctacaggacc taggtcccat ctttcatttc   5340
cttctatacc ttctacagtg tctacaaaat atagtaatac aaccattcca tttactactt   5400
cttgggacat acctgtaacc actggccctg acatagtttt acctactgca tcccccaatt   5460
tgccctttgt ccctcctaca tctatagata ccacagttgc aatagccatt cagggctcca   5520
attattattt attgccttta ttatattatt ttctaaagaa acgtaaacgt attccctatt   5580
tttttacaga tggctttgtg gcggtctagt gacaacacgg tgtatttgcc acccccttct   5640
gtggcgaagg ttgtcaatac agatgattat gtaacacgta caggcatata ttattatgct   5700
ggaagctctc gcttattaac agtagggcat ccttatttta aggtacctgt aaatggtggc   5760
cgcaagcagg aaatacctaa ggtgtctgca tatcagtata gggtatttag ggtatcccta   5820
cctgatccta ataagtttgg ccttccggat ccttcccttt ataatcctga cacacaacgc   5880
ctggtatggg cctgtatagg tgtggaaatt ggtagaggcc agccattggg cgttggcgtt   5940
agtggacatc ctttatataa tagattggat gatactgaaa attctcattt ttcctctgct   6000
gttagtacac aggacagtag ggacaatgtg tctgtggact ataagcaaac acagttatgt   6060
attataggct gtgttcctgc tatgggagag cactgggcta agggcaaggc ctgtaagtcc   6120
actcaacagg gcgattgtcc accattagaa ttagttaata ctgcaattga ggatggcgat   6180
atgatagata caggctatgg tgccatggac tttcgtacat tgcaggaaac caaaagtgag   6240
gtaccactag atatttgcca atccgtgtgt aaatatcctg attatttgca gatgtctgct   6300
gatgtatatg ggacagtatg ttttttttgt ttgcgcaagg aacagttgtt tgccaggcac   6360
ttttggaata gaggtggcat ggtgggcgac acaatacctt cagagttata tattaaaggc   6420
acggatatac gtgagcgtcc tggtactcat gtatattccc cttccccaag tggctctatg   6480
gtctcttctg attcccagtt gtttaataag ccctattggt tgcataaggc ccagggacac   6540
aataatggca tttgttggca taaccagttg tttattactg tggtggacac tacacgtagt   6600
actaatttta cattgtctgc ctgcaccgaa acggccatac ctgctgtata tagccctaca   6660
aagtttaagg aatatactag gcatgtggag gaatatgatt tacaatttat atttcaattg   6720
tgtactatca cattaactgc tgacgttatg gcctacatcc atactatgaa tcctgcaatt   6780
ttggacaatt ggaatatagg agttacccct ccaccatctg caagcttggt ggacacgtat   6840
aggtatttac aatcagcagc tatagcatgt caaaaggatg ctcctacacc tgaaaaaaag   6900
gatccctatg acgatttaaa attttggaat gttgatttaa aggaaaagtt tagtacagaa   6960
ctagatcagt ttcctttggg gcgcaaattt ttactacagg taggggctcg cagacgtcct   7020
actataggcc ctcgcaaacg ccctgcgtca gctaaatcgt cttcctcagc ctctaaacac   7080
aaacggaaac gtgtgtccaa gtaatgtatg tatgttgtat gctgtgtatt attgtactat   7140
tacatatttg tgtttttatg ttgtatgctt gcacactgtt tacatatttg tgtttgtatg   7200
ttgtatgctt gcacactgta ctgtatatgt ttgtcctggt acatatttgt ggttgtatgt   7260
gtatatgttg cgtgctatgt gtatgtttta gaagtatgtg tgtatgtatg tttttgttaa   7320
taaagtatgt atggaggttt catttgtggt tgcaccctgt gactaaggtg ttgtccctgt   7380
tttacatata ataggagtgt gattaccaac atttcctaca taattttatg ccctacccta   7440
```

-continued

```
aggtgtgtgt ataccatttg tagtttatac atttatattt tatagtgggt tacctgtata   7500

cagcaacggc cattttgtgt gaaaccgttt tcggttgcat ttggctttgt accatcagtt   7560

acccttataa accttttgta tcagcaaaaa catgtcctgt aacctaagtt cacctacata   7620

cttggcacta ctaacagttt tagtggcgca cctacactta gtcatcatcc tgtccaggtg   7680

cactacaaca atgctttggc aaccttatgc acctccaccc tgtctaataa agtgctttta   7740

ggcatgtatt ttacctgttt ttacttacct aagagcatag ttggcctgta taacagcttt   7800

tacatccaag aatgtgtcgt ttggtgcaag ttatattttg tgactaatat ttttacagac   7860

ctgtgtgcaa ccgaaatagg ttgggcagac attcctatac tttta                   7905
```